(12) United States Patent
Lee et al.

(10) Patent No.: US 11,075,343 B2
(45) Date of Patent: Jul. 27, 2021

(54) ORGANIC LIGHT EMITTING COMPOUNDS AND ORGANIC LIGHT EMITTING DEVICES INCLUDING THE SAME

(71) Applicant: SFC CO., LTD., Cheongju-si (KR)

(72) Inventors: Se-jin Lee, Daejeon (KR); Taejung Yu, Yongin-si (KR); Seok-bae Park, Chungcheongnam-do (KR); Byung-sun Yang, Namwon-si (KR); Su-Jin Lee, Busan (KR); Bong-Hyang Lee, Busan (KR); Yeongtae Choi, Yongin-si (KR)

(73) Assignee: SFC CO., LTD., Cheongju-si (KR)

( * ) Notice: Subject to any disclaimer, the term of this patent is extended or adjusted under 35 U.S.C. 154(b) by 0 days.

(21) Appl. No.: 15/405,766

(22) Filed: Jan. 13, 2017

(65) Prior Publication Data
US 2017/0207397 A1    Jul. 20, 2017

(30) Foreign Application Priority Data

Jan. 18, 2016 (KR) .................. 10-2016-0006142
Oct. 14, 2016 (KR) .................. 10-2016-0133381

(51) Int. Cl.
| | | |
|---|---|---|
| H01L 51/00 | (2006.01) | |
| C09K 11/02 | (2006.01) | |
| C07D 491/048 | (2006.01) | |
| C07D 405/14 | (2006.01) | |
| C07D 405/10 | (2006.01) | |
| C07D 209/86 | (2006.01) | |
| C09K 11/06 | (2006.01) | |
| C07D 405/04 | (2006.01) | |
| H05B 33/20 | (2006.01) | |
| H01L 51/50 | (2006.01) | |

(52) U.S. Cl.
CPC ........ *H01L 51/0067* (2013.01); *C07D 209/86* (2013.01); *C07D 405/04* (2013.01); *C07D 405/10* (2013.01); *C07D 405/14* (2013.01); *C07D 491/048* (2013.01); *C09K 11/025* (2013.01); *C09K 11/06* (2013.01); *H01L 51/0052* (2013.01); *H01L 51/0054* (2013.01); *H01L 51/0071* (2013.01); *H01L 51/0072* (2013.01); *H01L 51/0073* (2013.01); *H05B 33/20* (2013.01); *C09K 2211/1007* (2013.01); *C09K 2211/1029* (2013.01); *C09K 2211/185* (2013.01); *H01L 51/0085* (2013.01); *H01L 51/5016* (2013.01); *H01L 2251/5384* (2013.01)

(58) Field of Classification Search
None
See application file for complete search history.

(56) References Cited

U.S. PATENT DOCUMENTS

| | | | | |
|---|---|---|---|---|
| 2015/0144938 A1* | 5/2015 | Lee | ..................... | H01L 51/0072 257/40 |
| 2016/0141522 A1* | 5/2016 | Ma | ..................... | H01L 51/0085 257/40 |
| 2017/0117486 A1* | 4/2017 | Cho | ..................... | H01L 51/0072 |
| 2018/0287073 A1* | 10/2018 | Ha | ..................... | H01L 51/50 |

FOREIGN PATENT DOCUMENTS

| | | |
|---|---|---|
| CN | 102056899 A | 5/2011 |
| CN | 104583202 A | 4/2015 |
| CN | 104795503 A | 7/2015 |
| KR | 10-2014-0025271 A | 3/2014 |
| KR | 10-2015-0111271 A | 10/2015 |
| KR | 10-2015-0141045 A | 12/2015 |
| KR | 10-2017-0056431 A | 5/2017 |
| WO | WO 2015/090504 A2 | 6/2015 |
| WO | WO-2017/06181 A1 * | 4/2017 |

OTHER PUBLICATIONS

Chinese Office Action dated Mar. 19, 2019 in counterpart Chinese Patent Application No. 201710031627.7 (13 pages in English and 11 pages in Chinese).
Korean Office Action dated Mar. 11, 2021 in counterpart Korean Patent Application No. 10-2016-0133381 (13 pages in Korean).

* cited by examiner

*Primary Examiner* — Jay Yang
(74) *Attorney, Agent, or Firm* — NSIP Law

(57) ABSTRACT

Disclosed is an organic light emitting compound represented by Formula 1:

$$HAr_1 - (L)_n - HAr_2 \qquad (1);$$

an organic light emitting device including the organic light emitting compound of Formula 1: and
an organic light emitting device including the organic light emitting compound of Formula 1 as a first compound and a second compound represented by Formula 2:

$$HAr_3 - (L)_n - HAr_4 \qquad (2)$$

20 Claims, No Drawings

ORGANIC LIGHT EMITTING COMPOUNDS AND ORGANIC LIGHT EMITTING DEVICES INCLUDING THE SAME

CROSS-REFERENCE TO RELATED APPLICATIONS

This application claims priority from Korean Patent Application No. 10-2016-0006142, filed on Jan. 18, 2016, and Korean Patent Application No. 10-2016-0133381, filed on Oct. 14, 2016, each of which is incorporated by reference herein in its entirety.

BACKGROUND OF THE INVENTION

1. Field of the Invention

The present invention relates to organic light emitting devices with low driving voltage, high efficiency, and long life.

2. Description of the Related Art

Organic light emitting diodes are self-luminous devices and have the advantages of large viewing angle, high contrast, short response time, high luminance, low driving voltage, and excellent response speed characteristics. Another advantage of organic light emitting diodes is their ability to produce multiple colors.

The most important factor determining the luminescent properties (e.g., luminous efficiency) of an organic light emitting diode is a light emitting material. When a light emitting layer of an organic light emitting device uses a single light emitting material, intermolecular interaction or luminescence quenching occurs. The intermolecular interaction shifts the maximum emission to a longer wavelength and causes low color purity. The luminescence quenching leads to poor device efficiency. In an attempt to solve these problems, a host/dopant system was proposed. The two light emitting materials are co-deposited to form a light emitting layer with high color purity. In addition, the light emitting layer exhibits high luminous efficiency through energy transfer. If needed, two or more materials may be co-deposited to form a light emitting layer.

Fluorescent materials are widely used at present as materials for light emitting layers but extensive research is being conducted to develop phosphorescent materials, which are known to achieve improved luminous efficiency theoretically by a factor of up to 4 compared to fluorescent materials, based on the luminescence mechanism of organic light emitting layers.

For phosphorescent materials with high efficiency, however, stable host and dopant compounds are difficult to synthesize. Further, the application of phosphorescent materials to light emitting layers causes many problems associated with instability resulting from high energy barriers at the interfaces with the light emitting layers. Particularly, phosphorescent materials have high current efficiency but their high driving voltage leads to low power efficiency and considerably short device life. Under these circumstances, there is an urgent need to find a solution to the problems of phosphorescent materials.

SUMMARY OF THE INVENTION

Therefore, the present invention has been made in an effort to solve the above problems and is directed to providing organic light emitting compounds that ensure high efficiency, low driving voltage, and improved life characteristics of organic light emitting devices. The present invention is also directed to providing organic light emitting devices including the organic light emitting compounds.

The present invention provides an organic light emitting compound and an organic light emitting device including the organic light emitting compound wherein the organic light emitting compound is represented by Formula 1:

$$HAr_1-(L)_n-HAr_2 \quad (1)$$

The present invention also provides an organic light emitting device including a first electrode, a second electrode opposite to the first electrode, and at least one organic layer interposed between the first and second electrodes wherein the organic layer includes the organic light emitting compound represented by Formula 1 as a first compound and a second compound represented by Formula 2:

$$HAr_3-(L)_n-HAr_4 \quad (2)$$

Specific structures of the first compound represented by Formula 1 and the second compound represented by Formula 2 are described below.

The organic light emitting devices of the present invention exhibit low driving voltage, high efficiency, and long life. Due to these advantages, the organic light emitting devices of the present invention are useful in a variety of industrial applications, including displays and lighting systems.

DETAILED DESCRIPTION OF THE INVENTION

The present invention will now be described in more detail.

One aspect of the present invention is directed to an organic light emitting compound represented by Formula 1:

$$HAr_1-(L)_n-HAr_2 \quad (1)$$

wherein L represents a linker and is a single bond or is selected from substituted or unsubstituted $C_1$-$C_{30}$ alkylene groups, substituted or unsubstituted $C_2$-$C_{30}$ alkenylene groups, substituted or unsubstituted $C_2$-$C_{30}$ alkynylene groups, substituted or unsubstituted $C_2$-$C_{30}$ cycloalkylene groups, substituted or unsubstituted $C_2$-$C_{30}$ heterocycloalkylene groups, substituted or unsubstituted $C_6$-$C_{30}$ arylene groups, and substituted or unsubstituted $C_2$-$C_{30}$ heteroarylene groups, n is an integer from 1 to 3, provided that when n is equal to or greater than 2, the plurality of L groups are identical to or different from each other, $HAr_1$ is selected from the following structures 1 to 5:

Structure 1

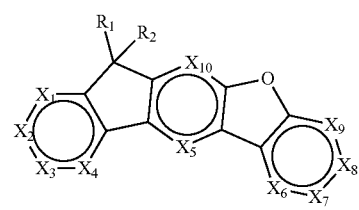

Structure 2

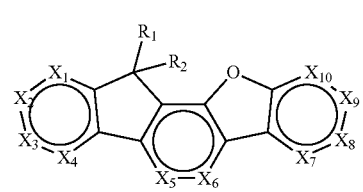

-continued

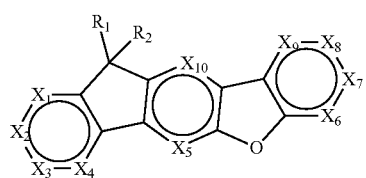
Structure 3

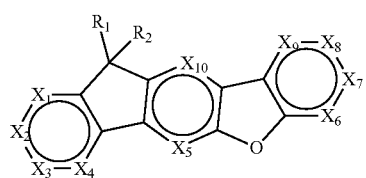
Structure 4

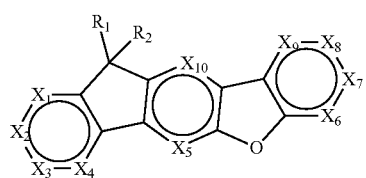
Structure 5 wherein $X_1$ to $X_{10}$ are identical to or different from each other and are each independently $CR_3$ or N, $R_1$ to $R_3$ are identical to or different from each other and are each independently selected from a hydrogen atom, a deuterium atom, substituted or unsubstituted $C_1$-$C_{30}$ alkyl groups, substituted or unsubstituted $C_2$-$C_{30}$ alkenyl groups, substituted or unsubstituted $C_2$-$C_{30}$ alkynyl groups, substituted or unsubstituted $C_2$-$C_{30}$ cycloalkyl groups, substituted or unsubstituted $C_2$-$C_{30}$ heterocycloalkyl groups, substituted or unsubstituted $C_5$-$C_{30}$ cycloalkenyl groups, substituted or unsubstituted $C_1$-$C_{30}$ alkoxy groups, substituted or unsubstituted $C_6$-$C_{30}$ aryloxy groups, substituted or unsubstituted $C_1$-$C_{30}$ alkylthioxy groups, substituted or unsubstituted $C_6$-$C_{30}$ arylthioxy groups, substituted or unsubstituted $C_1$-$C_{30}$ alkylamine groups, substituted or unsubstituted $C_6$-$C_{30}$ arylamine groups, substituted or unsubstituted $C_6$-$C_{50}$ aryl groups, substituted or unsubstituted $C_3$-$C_{50}$ heteroaryl groups containing O, N or S as a heteroatom, substituted or unsubstituted $C_1$-$C_{24}$ alkylsilyl groups, substituted or unsubstituted $C_6$-$C_{24}$ arylsilyl groups, substituted or unsubstituted germanium groups, substituted or unsubstituted boron groups, substituted or unsubstituted aluminum groups, a carbonyl group, a phosphoryl group, an amino group, a thiol group, a cyano group, a hydroxyl group, a nitro group, halogen groups, a selenium group, a tellurium group, an amide group, an ether group, and an ester group, with the proviso that $R_1$ to $R_2$ are optionally linked together to form a ring and one of $X_1$ to $X_{10}$ is a carbon atom linked to L, and $HAr_2$ is a substituted or unsubstituted $C_2$-$C_{30}$ heteroaryl group or a substituted or unsubstituted $C_2$-$C_{30}$ condensed polycyclic heteroaromatic group.

More specifically, $HAr_2$ in Formula 1 may be selected from, but not limited to, the following structures:

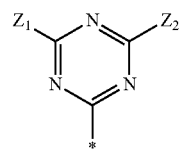
D1

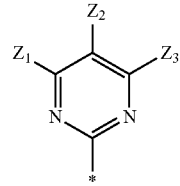
D2

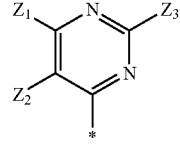
D3

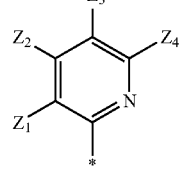
D4

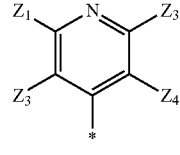
D5

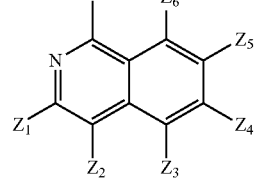
D6

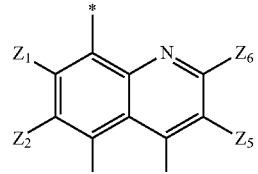
D7

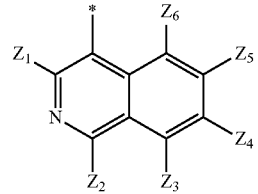
D8

-continued
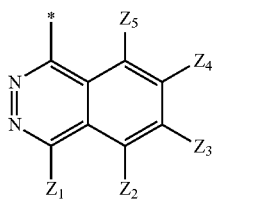
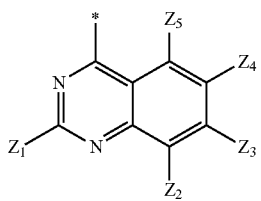
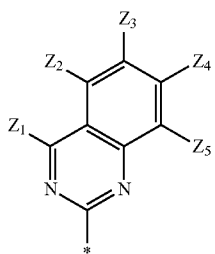
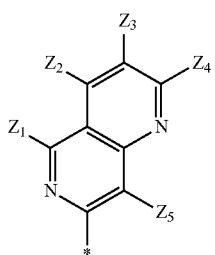
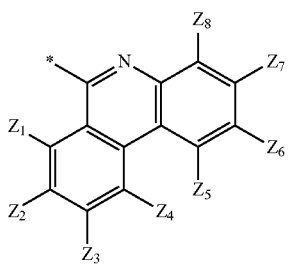
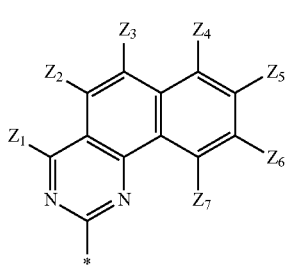
-continued
D9 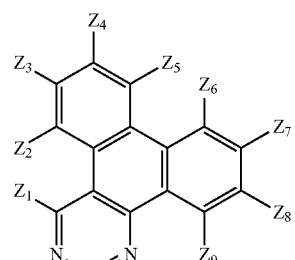
D10
D11 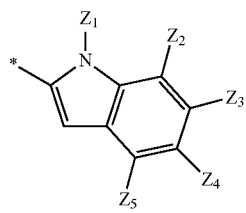
D12 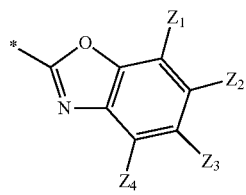
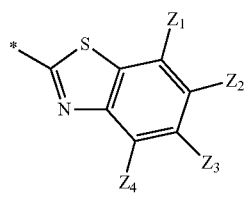
D13 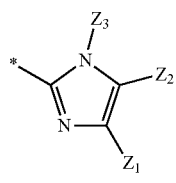
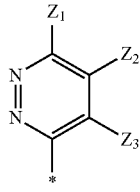
D14
D15
D16
D17
D18
D19
D20
D21 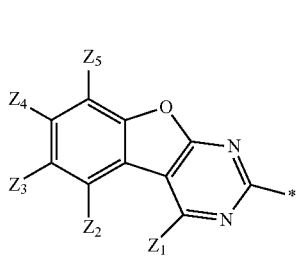

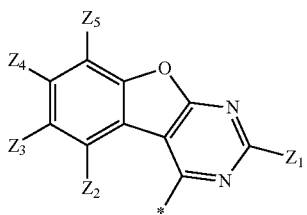
D22

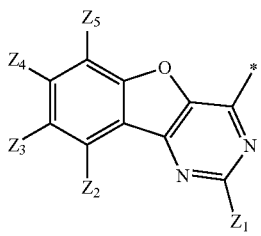
D23

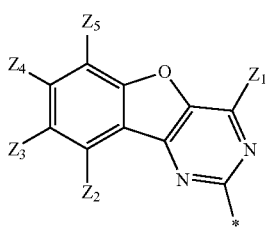
D24

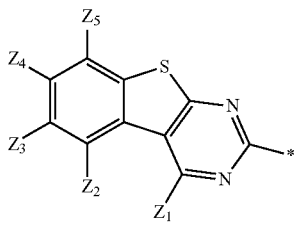
D25

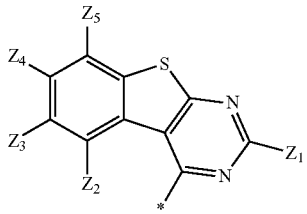
D26

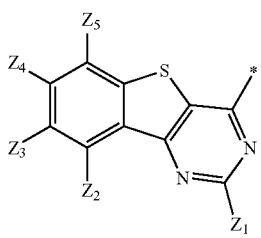
D27

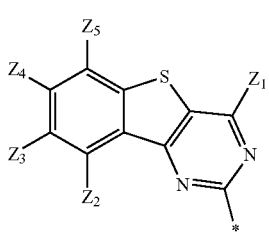
D28

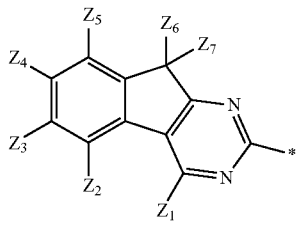
D29

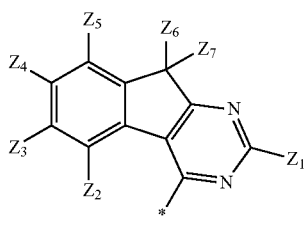
D30

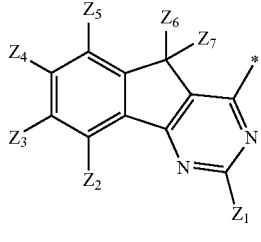
D31

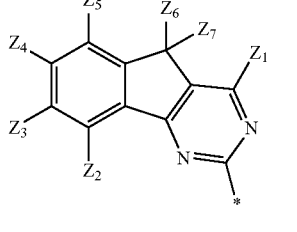
D32

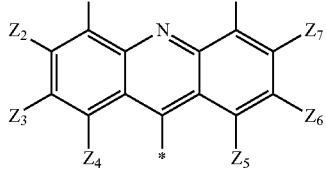
D33 wherein $Z_1$ to $Z_9$ are identical to or different from each other and have the same meanings as $R_1$ to $R_3$ and the asterisk (*) represents a site at which $HAr_2$ is linked to L.

The term "substituted" in the definition of "substituted or unsubstituted" used herein refers to substitution with at least one substituent selected from the group consisting of deuterium, a cyano group, halogen groups, a hydroxyl group, a nitro group, $C_1$-$C_{24}$ alkyl groups, $C_1$-$C_{24}$ halogenated alkyl groups, $C_2$-$C_{24}$ alkenyl groups, $C_2$-$C_{24}$ alkynyl groups, $C_1$-$C_{24}$ heteroalkyl groups, $C_6$-$C_{24}$ aryl groups, $C_7$-$C_{24}$ arylalkyl groups, $C_2$-$C_{24}$ heteroaryl groups, $C_2$-$C_{24}$ heteroarylalkyl groups, $C_1$-$C_{24}$ alkoxy groups, $C_1$-$C_{24}$ alkylamino groups, $C_1$-$C_{24}$ arylamino groups, $C_1$-$C_{24}$ heteroarylamino groups, $C_1$-$C_{24}$ alkylsilyl groups, $C_6$-$C_{24}$ arylsilyl groups, and $C_6$-$C_{24}$ aryloxy groups.

In the "substituted or unsubstituted $C_1$-$C_{30}$ alkyl groups", "substituted or unsubstituted $C_5$-$C_{50}$ aryl groups", etc., the number of carbon atoms in each alkyl or aryl group is considered as the number of carbon atoms constituting the unsubstituted alkyl or aryl moiety and the number of carbon atoms in the substituent(s) is excluded therefrom.

Specific examples of the alkyl groups used in the present invention include methyl, ethyl, propyl, isobutyl, sec-butyl, tert-butyl, pentyl, iso-amyl, hexyl, heptyl, octyl, stearyl, trichloromethyl, and trifluoromethyl groups. At least one hydrogen atom of each alkyl group may be substituted with a deuterium atom, a halogen atom, a hydroxyl group, a nitro group, a cyano group, a trifluoromethyl group, a silyl group (herein referred to as an "alkylsilyl group"), a substituted or unsubstituted amino group (—NH$_2$, —NH(R) or —N(R')(R''), in which R, R', and R'' are each independently a $C_1$-$C_{24}$ alkyl group (the —NH(R) and —N(R')(R'') are referred to as "alkylamino groups"), an amidino group, a hydrazine group, a hydrazone group, a carboxyl group, a sulfonic acid group, a phosphoric acid group, a $C_1$-$C_{24}$ alkyl group, a $C_1$-$C_{24}$ halogenated alkyl group, a $C_2$-$C_{24}$ alkenyl group, a $C_2$-$C_{24}$ alkynyl group, a $C_1$-$C_{24}$ heteroalkyl group, a $C_5$-$C_{24}$ aryl group, a $C_6$-$C_{24}$ arylalkyl group, a $C_3$-$C_{24}$ heteroaryl group or a $C_3$-$C_{24}$ heteroarylalkyl group.

Specific examples of the alkoxy groups used in the present invention include methoxy, ethoxy, propoxy, isobutyloxy, sec-butyloxy, pentyloxy, iso-amyloxy, and hexyloxy groups. The alkoxy groups may be substituted with the same substituents as in the alkyl groups.

Specific examples of the halogen groups used in the present invention include fluoro (F), chloro (Cl), and bromo (Br) groups.

The aryloxy groups used in the present invention refer to —O-aryl radicals in which the aryl group is as defined above. Specific examples of the aryloxy groups include phenoxy, naphthoxy, anthracenyloxy, phenanthrenyloxy, fluorenyloxy, and indenyloxy. At least one hydrogen atom of each aryloxy group may be substituted.

Specific examples of the silyl groups used in the present invention include trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl.

The aryl groups used in the present invention are organic radicals derived from aromatic hydrocarbons by removal of a hydrogen atom. Such aryl groups include 5- to 7-membered, preferably 5- or 6-membered single or fused ring systems. When the aryl group is substituted, the substituent may be fused with an adjacent substituent to form a ring.

Specific examples of the aryl groups include aromatic groups, such as phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, crycenyl, naphthacenyl, and fluoranthenyl groups.

Each aryl group may also be substituted with at least one substituent. More specifically, at least one hydrogen atom of each aryl group may be substituted with a deuterium atom, a halogen atom, a hydroxyl group, a nitro group, a cyano group, a silyl group, an amino group (—NH$_2$, —NH(R), —N(R')(R'') in which R, R' and R'' are each independently a $C_1$-$C_{10}$ alkyl group (the —NH(R) and —N(R')(R'') are referred to as "alkylamino groups")), an amidino group, a hydrazine group, a hydrazone group, a carboxyl group, a sulfonic acid group, a phosphoric acid group, a $C_1$-$C_{24}$ alkyl group, a $C_1$-$C_{24}$ halogenated alkyl group, a $C_1$-$C_{24}$ alkenyl group, a $C_1$-$C_{24}$ alkynyl group, a $C_1$-$C_{24}$ heteroalkyl group, a $C_6$-$C_{24}$ aryl group, a $C_6$-$C_{24}$ arylalkyl group, a $C_2$-$C_{24}$ heteroaryl group or a $C_2$-$C_{24}$ heteroarylalkyl group.

The heteroaryl groups used in the present invention may be selected from the following structures:

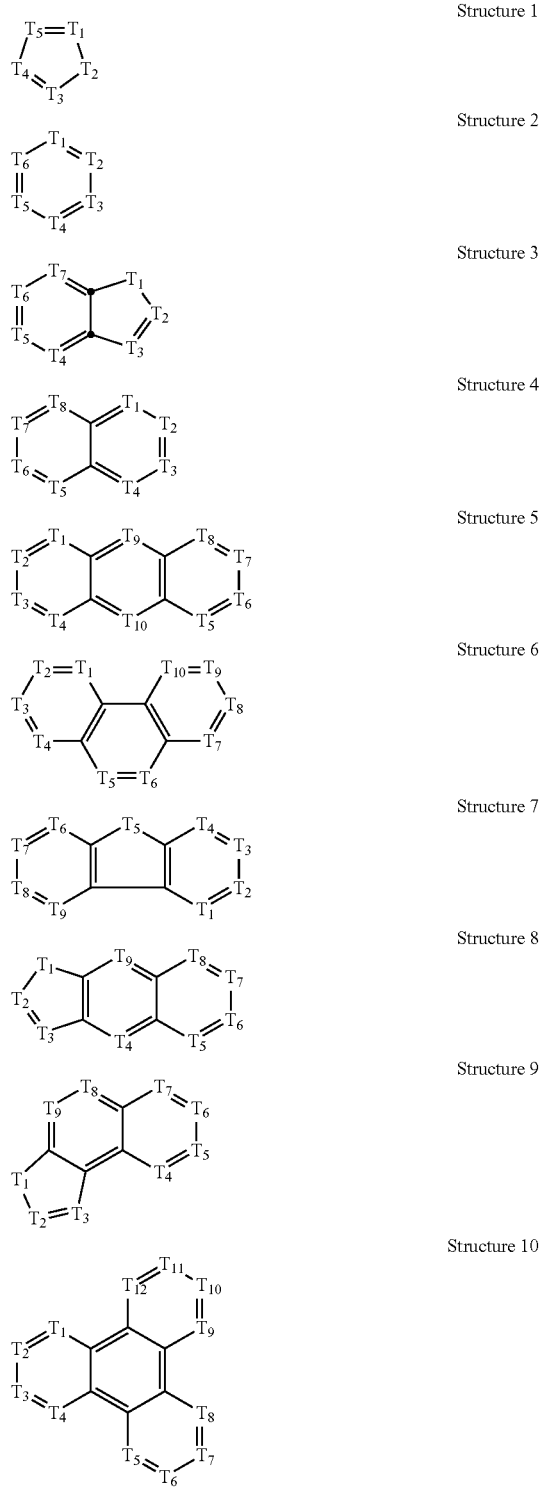

wherein $T_1$ to $T_{12}$ are identical to or different from each other and are each independently selected from $C(R_{101})$, $C(R_{102})(R_{103})$, N, $N(R_{104})$, O, and S, with the proviso that $T_1$ to $T_{12}$ are not simultaneously carbon atoms, $R_{101}$ to $R_{104}$ are identical to or different from each other and are each independently selected from hydrogen, deuterium, substituted or unsubstituted $C_1$-$C_{30}$ alkyl groups, substituted or unsubstituted $C_2$-$C_{30}$ cycloalkyl groups, substituted or unsubstituted $C_5$-$C_{30}$ aryl groups, and substituted or unsubstituted $C_2$-$C_{30}$ heteroaryl groups containing O, N, S or P as a heteroatom.

Due to resonance resulting from the migration of electrons, Structure 3 may also be represented by the following structure 3-1:

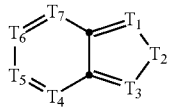

Structure 3-1 wherein $T_1$ to $T_7$ are as defined in Structures 1 to 10.

According to a preferred embodiment of the present invention, Structures 1 to 10 may be selected from the following structures:

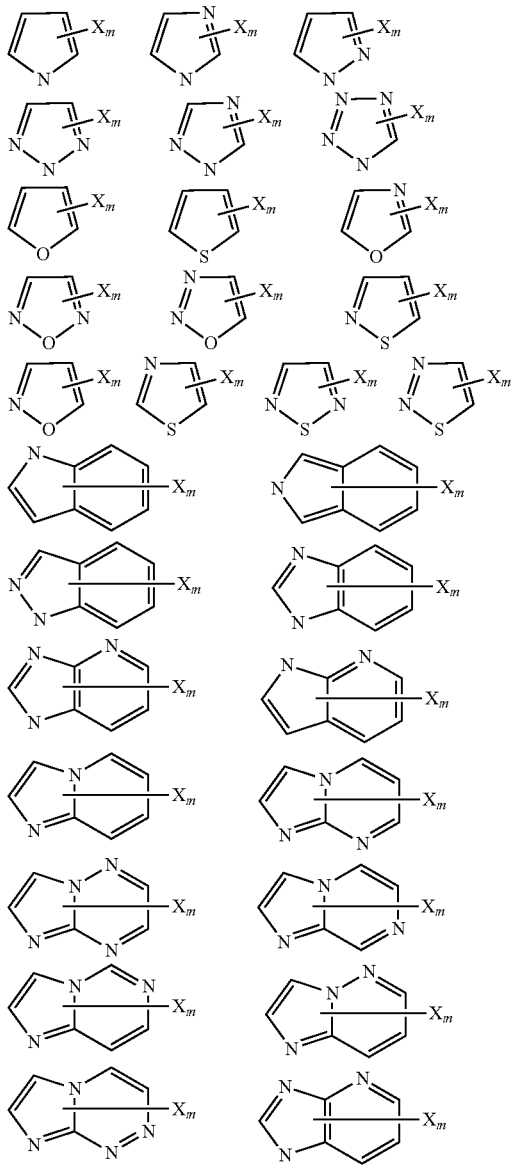

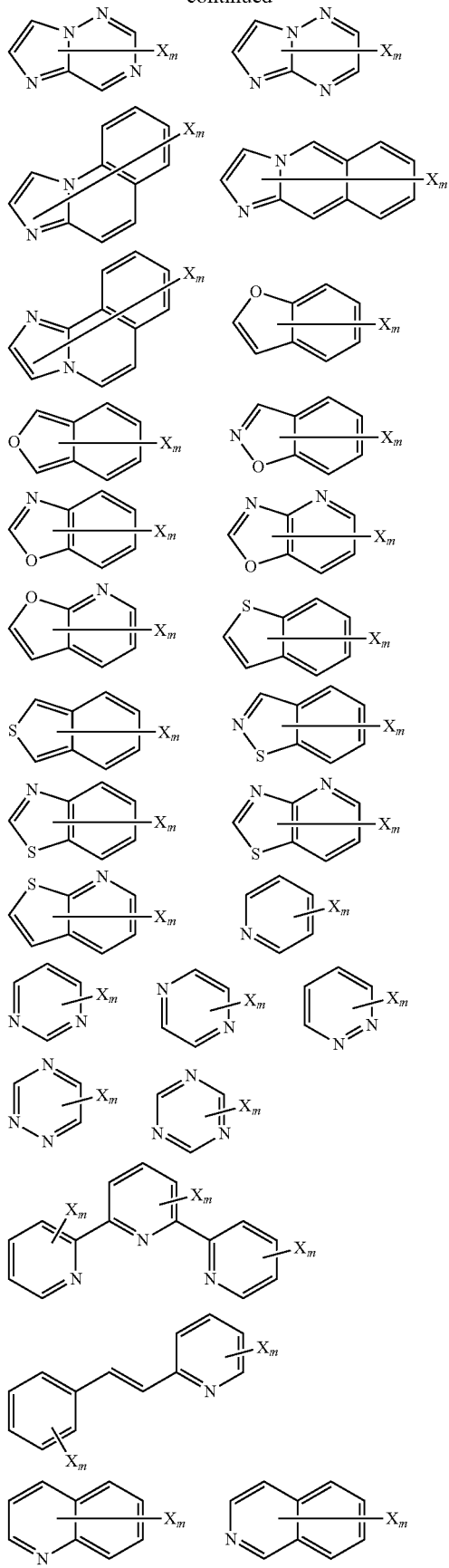

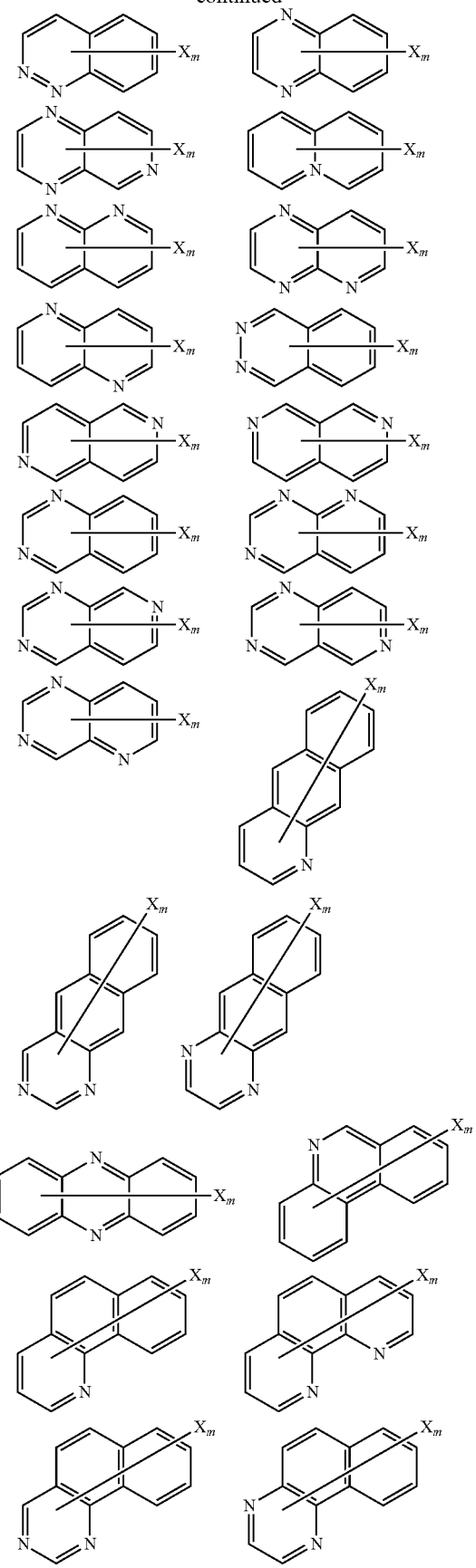
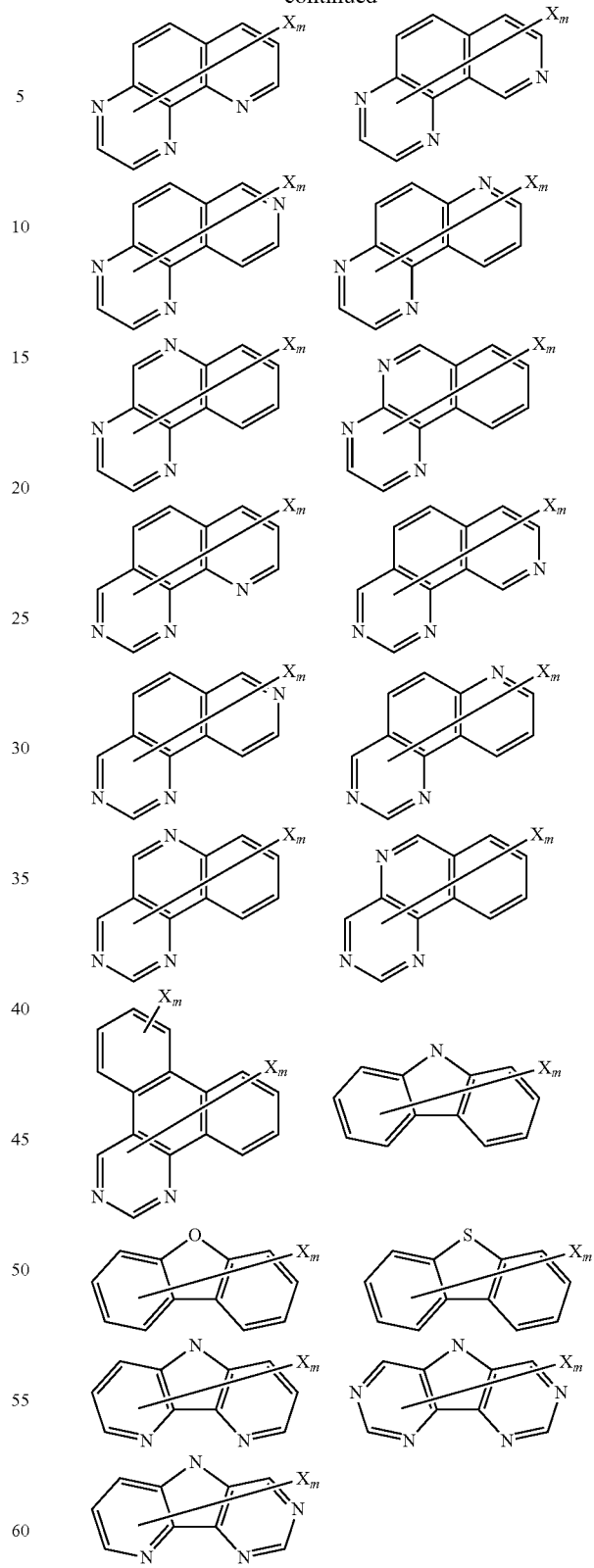
wherein X has the same meaning as $R_1$ to $R_{13}$ defined in Formula 1, m is an integer from 1 to 11, provided that when m is equal to or greater than 2, the plurality of X groups are identical to or different from each other.

The first compound represented by Formula 1 may be selected from Compounds E1 to E412, which are specifically described in the Examples section and claims that follow, but the scope of Formula 1 is not limited thereto.

A further aspect of the present invention is directed to an organic light emitting device including the organic light emitting compound of Formula 1. Specifically, the organic light emitting device includes a first electrode, a second electrode opposite to the first electrode, and at least one organic layer interposed between the first and second electrodes wherein the organic layer includes a light emitting layer, a hole transport layer between the light emitting layer and the first electrode, and an electron transport layer between the light emitting layer and the second electrode and wherein the light emitting layer includes the organic light emitting compound represented by Formula 1.

Another aspect of the present invention is directed to an organic light emitting device including a first electrode, a second electrode opposite to the first electrode, and at least one organic layer interposed between the first and second electrodes wherein the organic layer includes a light emitting layer, a hole transport layer between the light emitting layer and the first electrode, and an electron transport layer between the light emitting layer and the second electrode and wherein the light emitting layer includes the organic light emitting compound represented by Formula 1 and a second compound represented by Formula 2:

$$HAr_3 — (L)_n — HAr_4 \quad (2)$$

wherein L represents a linker and is a single bond or is selected from substituted or unsubstituted $C_1$-$C_{30}$ alkylene groups, substituted or unsubstituted $C_2$-$C_{30}$ alkenylene groups, substituted or unsubstituted $C_2$-$C_{30}$ alkynylene groups, substituted or unsubstituted $C_2$-$C_{30}$ cycloalkylene groups, substituted or unsubstituted $C_2$-$C_{30}$ heterocycloalkylene groups, substituted or unsubstituted $C_6$-$C_{30}$ arylene groups, and substituted or unsubstituted $C_2$-$C_{30}$ heteroarylene groups, n is an integer from 1 to 3, provided that when n is equal to or greater than 2, the plurality of L groups are identical to or different from each other, $HAr_3$ is selected from the following structures:

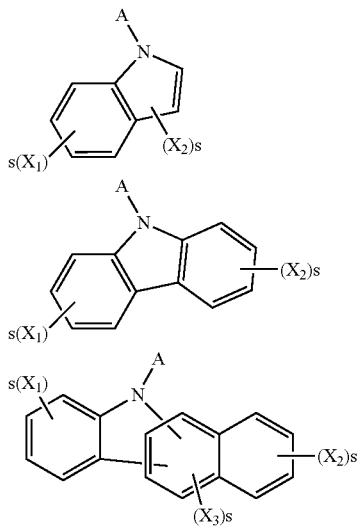

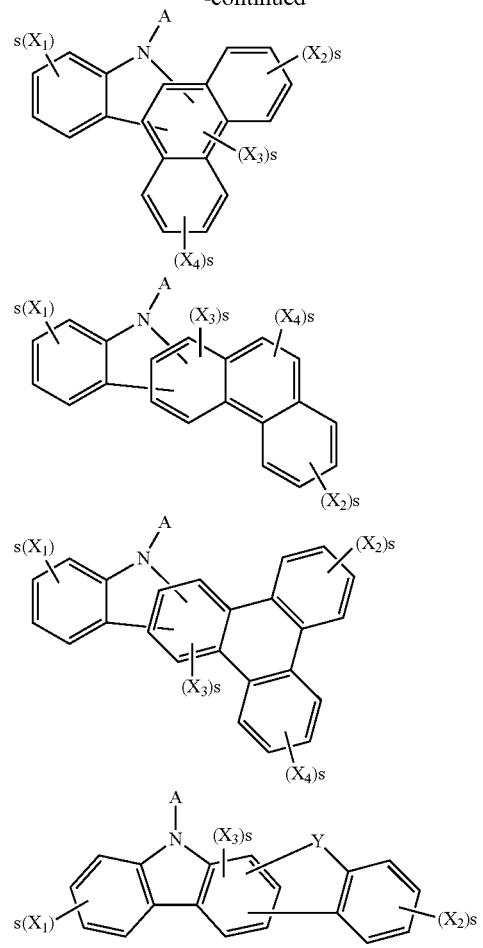

wherein Y is selected from N—$R_1$, $CR_2R_3$, $SiR_4R_5$, $GeR_6R_7$, O, S, and Se, $X_1$ to $X_4$ are each independently selected from hydrogen, deuterium, substituted or unsubstituted $C_1$-$C_{30}$ alkyl groups, substituted or unsubstituted $C_2$-$C_{30}$ alkenyl groups, substituted or unsubstituted $C_2$-$C_{30}$ cycloalkyl groups, substituted or unsubstituted $C_5$-$C_{30}$ cycloalkenyl groups, substituted or unsubstituted $C_1$-$C_{30}$ alkoxy groups, substituted or unsubstituted $C_6$-$C_{30}$ aryloxy groups, substituted or unsubstituted $C_1$-$C_{30}$ alkylthioxy groups, substituted or unsubstituted $C_5$-$C_{30}$ arylthioxy groups, substituted or unsubstituted $C_1$-$C_{30}$ alkylamine groups, substituted or unsubstituted $C_5$-$C_{30}$ arylamine groups, substituted or unsubstituted $C_5$-$C_{50}$ aryl groups, substituted or unsubstituted $C_3$-$C_{50}$ heteroaryl groups containing O, N or S as a heteroatom, substituted or unsubstituted silyl groups, substituted or unsubstituted germanium groups, substituted or unsubstituted boron groups, substituted or unsubstituted aluminum groups, a carbonyl group, a phosphoryl group, an amino group, a nitrile group, a hydroxyl group, a nitro group, halogen groups, a selenium group, a tellurium group, an amide group, and an ester group, with the proviso that $X_1$ to $X_4$ together with an adjacent group optionally forms an aliphatic, aromatic, heteroaliphatic or heteroaromatic fused ring and one of $X_1$ to $X_4$ is linked to L, s is an integer from 1 to 4, and A and $R_1$ to $R_7$ are each independently selected from hydrogen, deuterium, halogen atoms, a cyano group, substituted or unsubstituted $C_1$-$C_{20}$ alkyl groups, substituted or unsubstituted $C_3$-$C_{20}$ cycloalkyl groups, substituted or unsubstituted $C_1$-$C_{20}$ alkoxy groups, substituted or unsubstituted $C_6$-$C_{30}$ aryloxy groups, substituted or unsubstituted $C_1$-$C_{20}$ alkylthio groups, substituted or unsubstituted $C_6$-$C_{30}$ arylthio groups, substituted or unsubstituted $C_3$-$C_{50}$ alkylsilyl groups, substituted or unsubstituted $C_6$-$C_{50}$ arylsilyl groups, substituted or unsubstituted $C_6$-$C_{30}$ aromatic hydrocarbon groups, and substituted or unsubstituted $C_5$-$C_{30}$ heterocyclic groups, and $HAr_4$ is selected from the following structures:

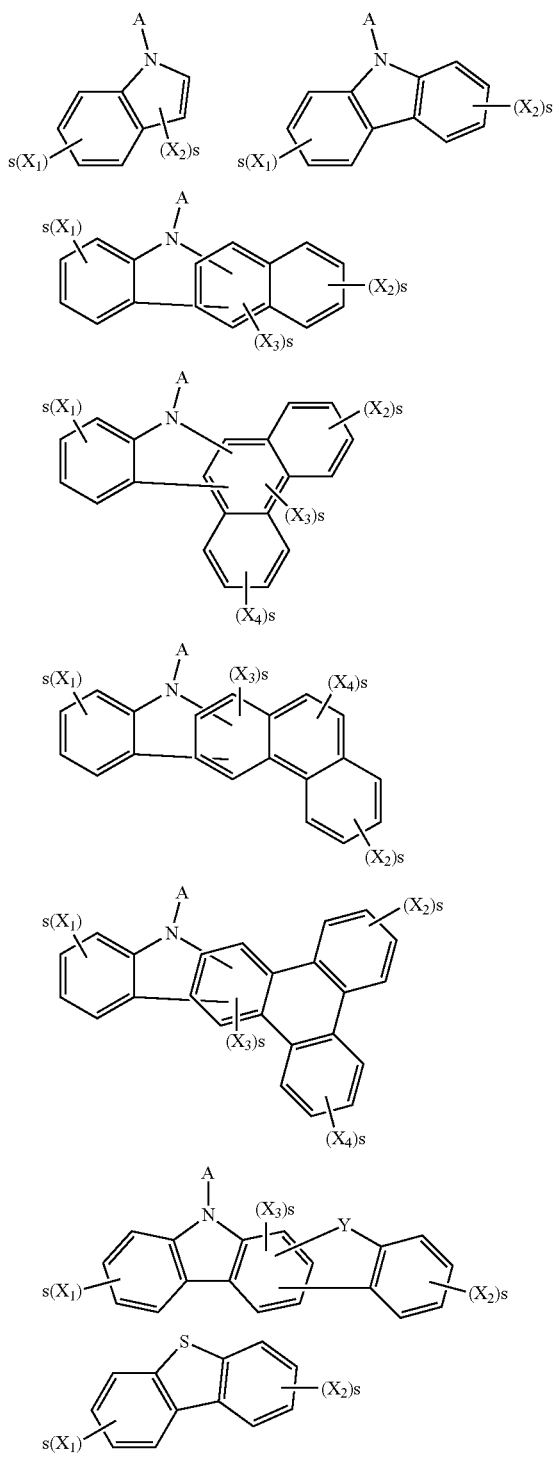

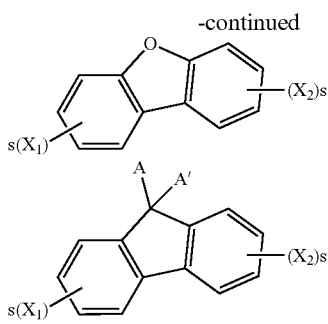

wherein Y, $X_1$ to $X_4$, s, A, and $R_1$ to $R_7$ are as defined above and A' has the same meaning as A and $R_1$ to $R_7$.

Each of A, A', $X_1$ to $X_4$, $R_1$ to $R_7$, $HAr_3$, $HAr_4$, and L may be further substituted with one or more substituents selected from $C_1$-$C_{60}$ alkyl groups, $C_5$-$C_{60}$ heteroaryl groups, $C_3$-$C_{60}$ cycloalkyl groups, $C_6$-$C_{60}$ aryl groups, $C_1$-$C_{60}$ alkoxy groups, $C_6$-$C_{30}$ aryloxy groups, $C_1$-$C_{20}$ alkylamino groups, $C_1$-$C_{20}$ alkylsilyl groups, $C_6$-$C_{30}$ arylsilyl groups, $C_1$-$C_{50}$ arylalkylamino groups, $C_2$-$C_{60}$ alkenyl groups, a cyano group, halogen groups, and deuterium.

The second compound represented by Formula 2 may be selected from Compounds H1 to H148, which are specifically described in the Examples section and claims that follow, but the scope of Formula 2 is not limited thereto.

According to one embodiment of the present invention, the light emitting layer of the organic light emitting device may further include a dopant compound, which may be mixed with the organic light emitting compound represented by Formula 1 in a weight ratio of 1:0.01-15.

According to a further embodiment of the present invention, the first compound, the second compound, and the dopant compound may be mixed in a weight ratio of 1:0.01-99:0.01-15. Within this range, satisfactory energy transfer and emission may occur.

A more detailed description will be given concerning the organic light emitting device of the present invention.

The organic light emitting device of the present invention includes an anode, a hole transport layer, a light emitting layer, an electron transport layer, and a cathode. The organic light emitting device of the present invention may optionally further include a hole injecting layer and an electron injecting layer. One or more intermediate layers may be further formed in the organic light emitting device. A hole blocking layer or an electron blocking layer may be further formed in the organic light emitting device. The device may further include one or more organic layers with various functions depending on the desired characteristics thereof.

A description will be given concerning a method for fabricating the organic light emitting device of the present invention. First, an electrode material for the anode is coated on a substrate to form the anode. The substrate may be any of those used in general organic light emitting devices. The substrate is preferably an organic substrate or a transparent plastic substrate that is excellent in transparency, surface smoothness, ease of handling, and waterproofness. A highly transparent and conductive metal oxide, such as indium tin oxide (ITO), indium zinc oxide (IZO), tin oxide ($SnO_2$) or zinc oxide (ZnO), is used as the anode material.

A material for the hole injecting layer is coated on the anode by vacuum thermal evaporation or spin coating to form the hole injecting layer. Then, a material for the hole transport layer is coated on the hole injecting layer by vacuum thermal evaporation or spin coating to form the hole transport layer.

The material for the hole injecting layer is not specially limited so long as it is usually used in the art. Example of such materials include 4,4',4"-tris(2-naphthyl(phenyl) amino)triphenylamine (2-TNATA), N,N'-di(1-naphthyl)-N, N'-diphenylbenzidine) (NPD), N,N'-diphenyl-N,N'-bis(3-methylphenyl)-1,1'-biphenyl-4,4'-diamine (TPD), and N,N'-diphenyl-N,N'-bis[4-(phenyl-m-tolylamino)phenyl] biphenyl-4,4'-diamine (DNTPD).

The material for the hole transport layer is not specially limited so long as it is commonly used in the art. Example of such materials include N,N'-bis(3-methylphenyl)-N,N'-diphenyl-[1,1-biphenyl]-4,4'-diamine (TPD) and N,N'-di (naphthalen-1-yl)-N,N'-diphenylbenzidine (α-NPD).

Subsequently, the organic light emitting layer is laminated on the hole transport layer. A hole blocking layer may be optionally formed on the organic light emitting layer by vacuum thermal evaporation or spin coating. The hole blocking layer blocks holes from entering the cathode through the organic light emitting layer. This role of the hole blocking layer prevents the life and efficiency of the device from deteriorating. A material having a very low highest occupied molecular orbital (HOMO) energy level is used for the hole blocking layer. The hole blocking material is not particularly limited so long as it has the ability to transport electrons and a higher ionization potential than the light emitting compound. Representative examples of suitable hole blocking materials include BAlq, BCP, and TPBI.

The electron transport layer is deposited on the hole blocking layer by vacuum thermal evaporation or spin coating, and the electron injecting layer is formed thereon. A metal for the cathode is deposited on the electron injecting layer by vacuum thermal evaporation to form the cathode, completing the fabrication of the organic light emitting device. As the metal for the cathode, there may be used, for example, lithium (Li), magnesium (Mg), aluminum (Al), aluminum-lithium (Al—Li), calcium (Ca), magnesium-indium (Mg—In) or magnesium-silver (Mg—Ag). The organic light emitting device may be of top emission type. In this case, a transmissive material, such as ITO or IZO, may be used for the cathode.

The material for the electron transport layer functions to stably transport electrons injected from the electron injecting electrode (i.e. the cathode). The material for the electron transport layer may be any known electron transport material, and examples thereof include, but are not limited to, quinoline derivatives, particularly, tris(8-quinolinolate)aluminum (Alq3), TAZ, Balq, beryllium bis(benzoquinolin-10-olate (Bebq2), ADN, and oxadiazole derivatives, such as PBD, BMD, and BND.

One or more layers selected from the hole injecting layer, the hole transport layer, the electron blocking layer, the light emitting layer, the hole blocking layer, the electron transport layer, and the electron injecting layer may be formed by a monomolecular deposition or solution process. According to the monomolecular deposition process, the material for each layer is evaporated under heat and vacuum or reduced pressure to form the layer in the form of a thin film. According to the solution process, the material for each layer is mixed with a suitable solvent, and then the mixture is formed into a thin film by a suitable method, such as ink-jet printing, roll-to-roll coating, screen printing, spray coating, dip coating or spin coating.

The organic light emitting devices of the present invention can be used in a variety of systems, such as flat panel displays, flexible displays, monochromatic flat panel lighting systems, white flat panel lighting systems, flexible monochromatic lighting systems, and flexible white lighting systems.

The present invention will be explained in more detail with reference to the following examples. However, these examples are provided to assist in understanding the invention and are not intended to limit the scope of the present invention.

Synthesis Example 1: Synthesis of Compound E1

Synthesis Example 1-(1): Synthesis of Intermediate 1-a

Intermediate 1-a was synthesized according to Reaction Scheme 1.

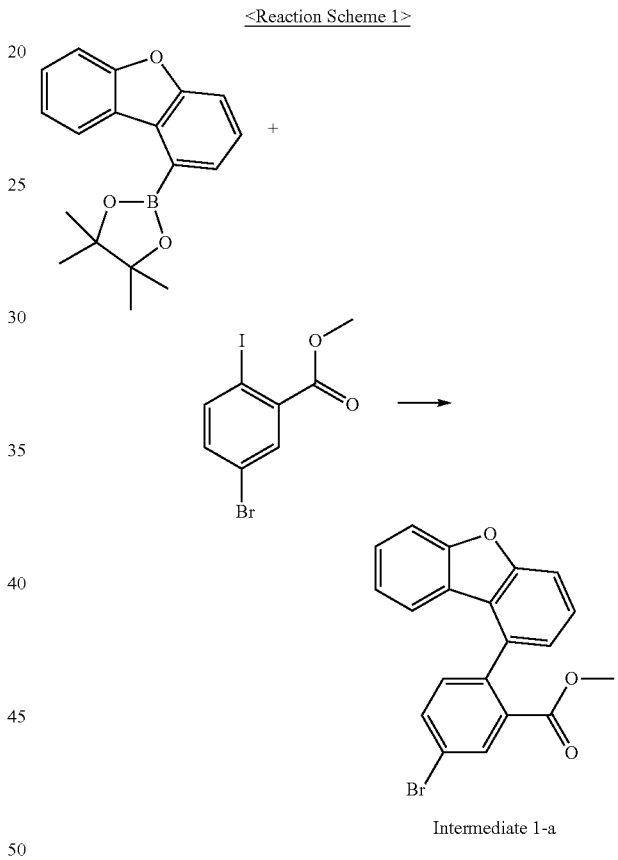

<Reaction Scheme 1>

Intermediate 1-a

Dibenzofuran-1-boronic acid pinacol ester (70 g, 238 mmol), methyl-5-bromo-2-iodobenzoate (80.1 g, 238 mmol), tetrakis(triphenylphosphine)palladium (5.4 g, 4.6 mmol), potassium carbonate (66 g, 474 mmol), toluene (400 mL), 1,4-dioxane (400 mL), and water (200 mL) were refluxed in a 1 L round bottom flask under a nitrogen atmosphere for 12 h. After completion of the reaction, the reaction mixture was allowed to stand for layer separation. The organic layer was concentrated under reduced pressure, purified by column chromatography, and dried, affording Intermediate 1-a (65.1 g, 72%).

Synthesis Example 1-(2): Synthesis of Intermediate 1-b

Intermediate 1-b was synthesized according to Reaction Scheme 2.

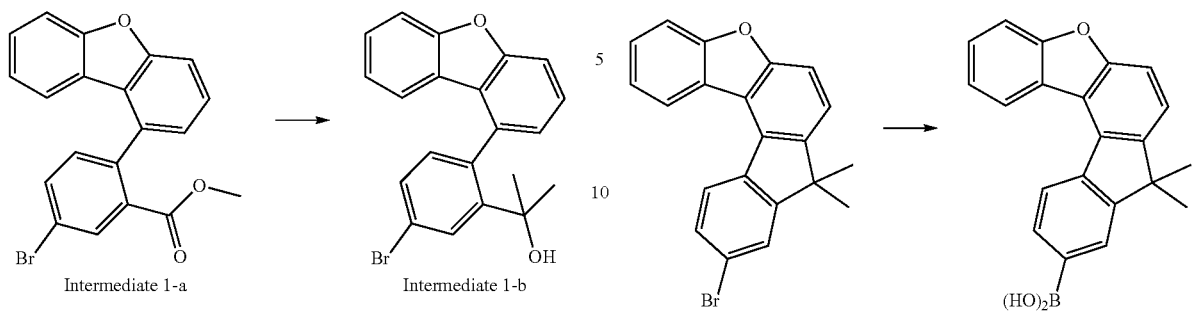

Intermediate 1-a (33.5 g, 110 mmol) was added to 150 mL of tetrahydrofuran in a 500 mL round bottom flask. After cooling to −10° C., 3 M methylmagnesium bromide (85 mL, 254 mmol) was slowly added dropwise to the reactor. The mixture was heated to 40° C. and stirred for 4 h. Thereafter, the temperature was lowered to −10° C. 70 mL of 2 N HCl was slowly added dropwise and 70 mL of an aqueous solution of ammonium chloride was added to the reactor. The temperature of the reactor was raised to room temperature. After completion of the reaction, the reaction mixture was washed with water and extracted with ethyl acetate. The organic layer was concentrated under reduced pressure, purified by column chromatography, and dried, affording Intermediate 1-b (27 g, 81%).

Synthesis Example 1-(3): Synthesis of Intermediate 1-c

Intermediate 1-c was synthesized according to Reaction Scheme 3.

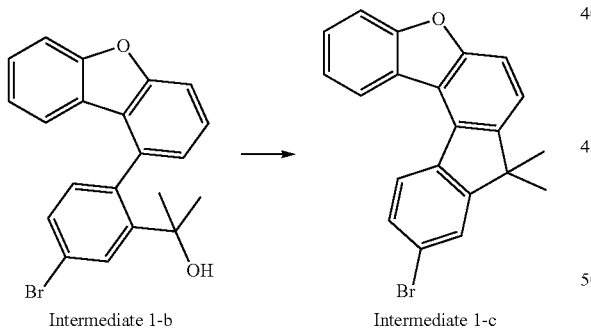

Intermediate 1-b (27 g, 89.2 mmol) and 70 mL of phosphoric acid were placed in a 500 mL round bottom flask under a nitrogen atmosphere and stirred at room temperature for 12 h. After completion of the reaction, the reaction mixture was extracted with ethyl acetate and water. The organic layer was concentrated, purified by column chromatography, and dried, affording Intermediate 1-c (17.6 g, 68%).

Synthesis Example 1-(4): Synthesis of Intermediate 1-d

Intermediate 1-d was synthesized according to Reaction Scheme 4.

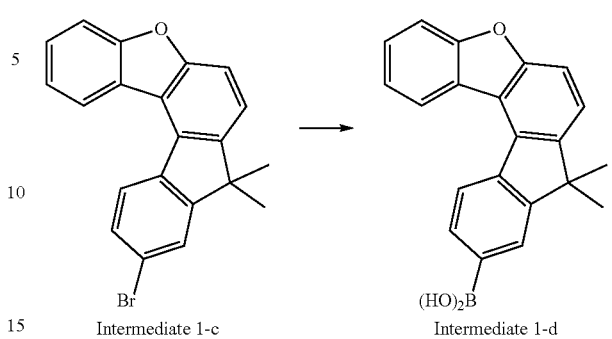

200 mL of tetrahydrofuran was added to Intermediate 1-c (17.6 g, 48.4 mmol) in a 100 mL round bottom flask under a nitrogen atmosphere. After cooling to −78° C., 1.6 M n-butyllithium (36.3 mL, 58.1 mmol) was slowly added dropwise to the reactor. After 1 h, trimethyl borate (7.0 mL, 62.9 mmol) was slowly added while maintaining the reactor at a low temperature. The mixture was stirred at room temperature. After completion of the reaction, the reaction mixture was allowed to stand for layer separation. The organic layer was concentrated under reduced pressure, recrystallized from hexane, and dried, affording Intermediate 1-d (13 g, 82%).

Synthesis Example 1-(5): Synthesis of Intermediate 1-e

Intermediate 1-e was synthesized according to Reaction Scheme 5.

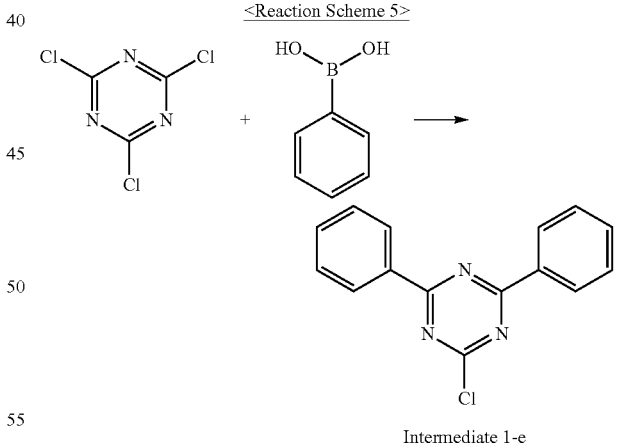

Cyanuric chloride (32 g, 174 mmol), 2-biphenylboronic acid (26 g, 212 mmol), tetrakis(triphenylphosphine)palladium (4.1 g, 3.5 mmol), potassium carbonate (73.4 g, 531 mmol), toluene (600 mL), and distilled water (200 mL) were stirred in a 2 L reactor at 100° C. for 12 h. After cooling to room temperature, the reaction mixture was extracted with ethyl acetate. The organic layer was concentrated under reduced pressure and purified by column chromatography, affording Intermediate 1-e (26.1 g, 56%).

Synthesis Example 1-(6): Synthesis of Compound E1

Compound E1 was synthesized according to Reaction Scheme 6.

<Reaction Scheme 6>

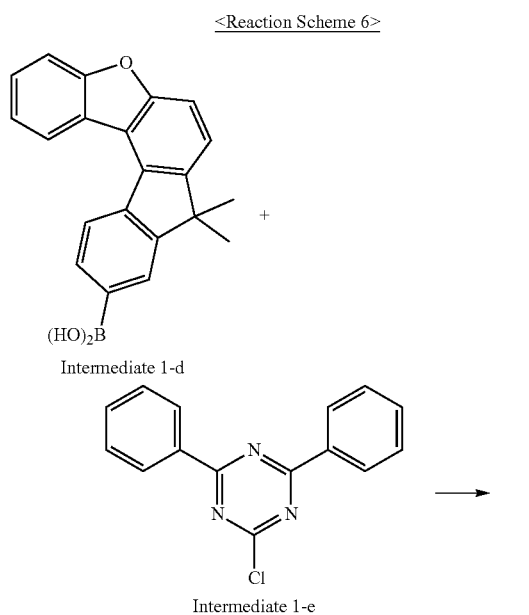

Intermediate 1-d

Intermediate 1-e

Compound E1

Intermediate 1-d (5 g, 15.2 mmol), Intermediate 1-e (4.5 g, 16.7 mmol), tetrakis(triphenylphosphine)palladium (0.3 g, 0.3 mmol), potassium carbonate (4.2 g, 30.4 mmol), toluene (25 mL), 1,4-dioxane (25 mL), and water (15 mL) were refluxed in a round bottom flask under a nitrogen atmosphere for 12 h. After completion of the reaction, the reaction mixture was allowed to stand for layer separation. The organic layer was concentrated under reduced pressure, purified by column chromatography, and dried, affording Compound E1 (6.8 g, 87%).

MS (MALDI-TOF): m/z 515.20[M$^+$]

Synthesis Example 2: Synthesis of Compound E19

Synthesis Example 2-(1): Synthesis of Intermediate 2-a

Intermediate 2-a was synthesized according to Reaction Scheme 7.

<Reaction Scheme 7>

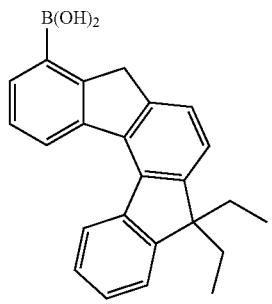

Intermediate 2-a

Intermediate 2-a (yield 57%) was synthesized in the same manner as in Synthesis Examples 1-(1) to 1-(4), except that methyl-2-iodobenzoate was used instead of methyl-5-bromo-2-iodobenzoate in Synthesis Example 1-(1) and ethylmagnesium bromide was used instead of methylmagnesium bromide in Synthesis Example 1-(2).

Synthesis Example 2-(2): Synthesis of Compound E19

Compound E19 was synthesized according to Reaction Scheme 8.

<Reaction Scheme 8>

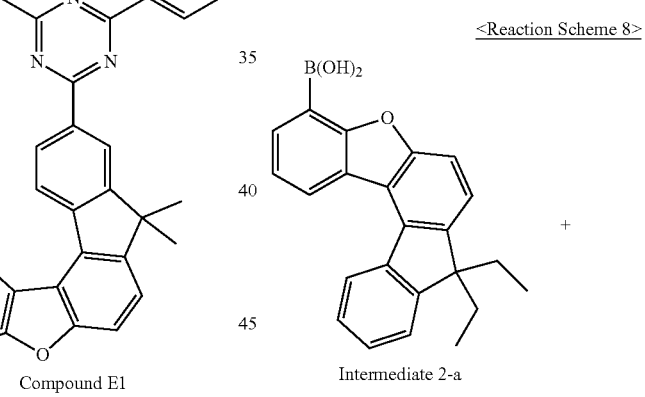

Intermediate 2-a

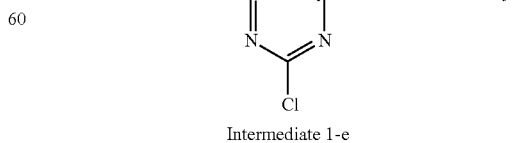

Intermediate 1-e

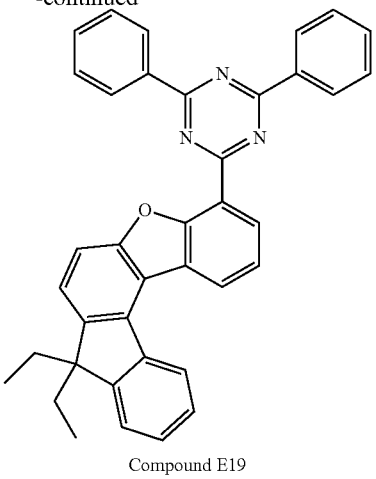

Compound E19

Compound E19 (yield 70%) was synthesized in the same manner as in Synthesis Example 1-(6), except that Intermediate 2-a was used instead of Intermediate 1-d.

MS (MALDI-TOF): m/z 543.23[M$^+$]

Synthesis Example 3: Synthesis of Compound E39

Synthesis Example 3-(1): Synthesis of Intermediate 3-a

Intermediate 3-a was synthesized according to Reaction Scheme 9.

<Reaction Scheme 9>

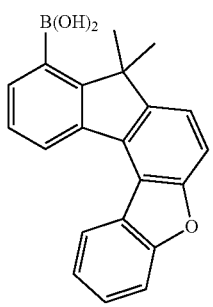

Intermediate 3-a

Intermediate 3-a (5.8 g, 74%) was synthesized in the same manner as in the synthesis of Intermediate 1-d, except that methyl-6-bromo-2-iodobenzoate was used instead of methyl-5-bromo-2-iodobenzoate in Synthesis Example 1-(1).

Synthesis Example 3-(2): Synthesis of Intermediate 3-b

Intermediate 3-b was synthesized according to Reaction Scheme 10.

<Reaction Scheme 10>

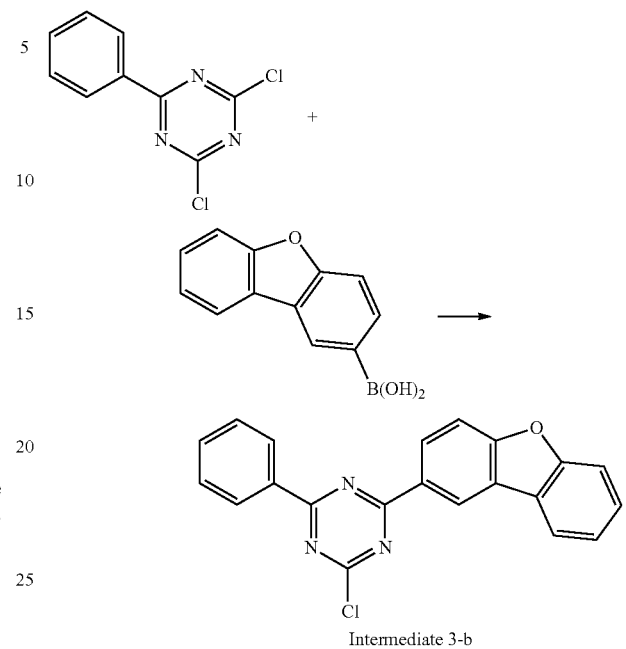

Intermediate 3-b 2,4-Dichloro-6-phenyl-1,3,5-triazine (50 g, 221 mmol), dibenzofuran-2-boronic acid (46.9 g, 221 mmol), tetrakis(triphenylphosphine)palladium (5.1 g, 4.4 mmol), potassium carbonate (61.2 g, 442 mmol), toluene (300 mL), 1,4-dioxane (300 mL), and water (200 mL) were refluxed in a 1 L round bottom flask under a nitrogen atmosphere for 12 h. After completion of the reaction, the reaction mixture was allowed to stand for layer separation. The organic layer was concentrated under reduced pressure, purified by column chromatography, and dried, affording Intermediate 3-b (25.3 g, 32%).

Synthesis Example 3-(3): Synthesis of Compound E39

Compound E39 was synthesized according to Reaction Scheme 11.

<Reaction Scheme 11>

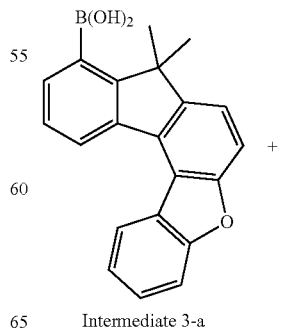

Intermediate 3-a

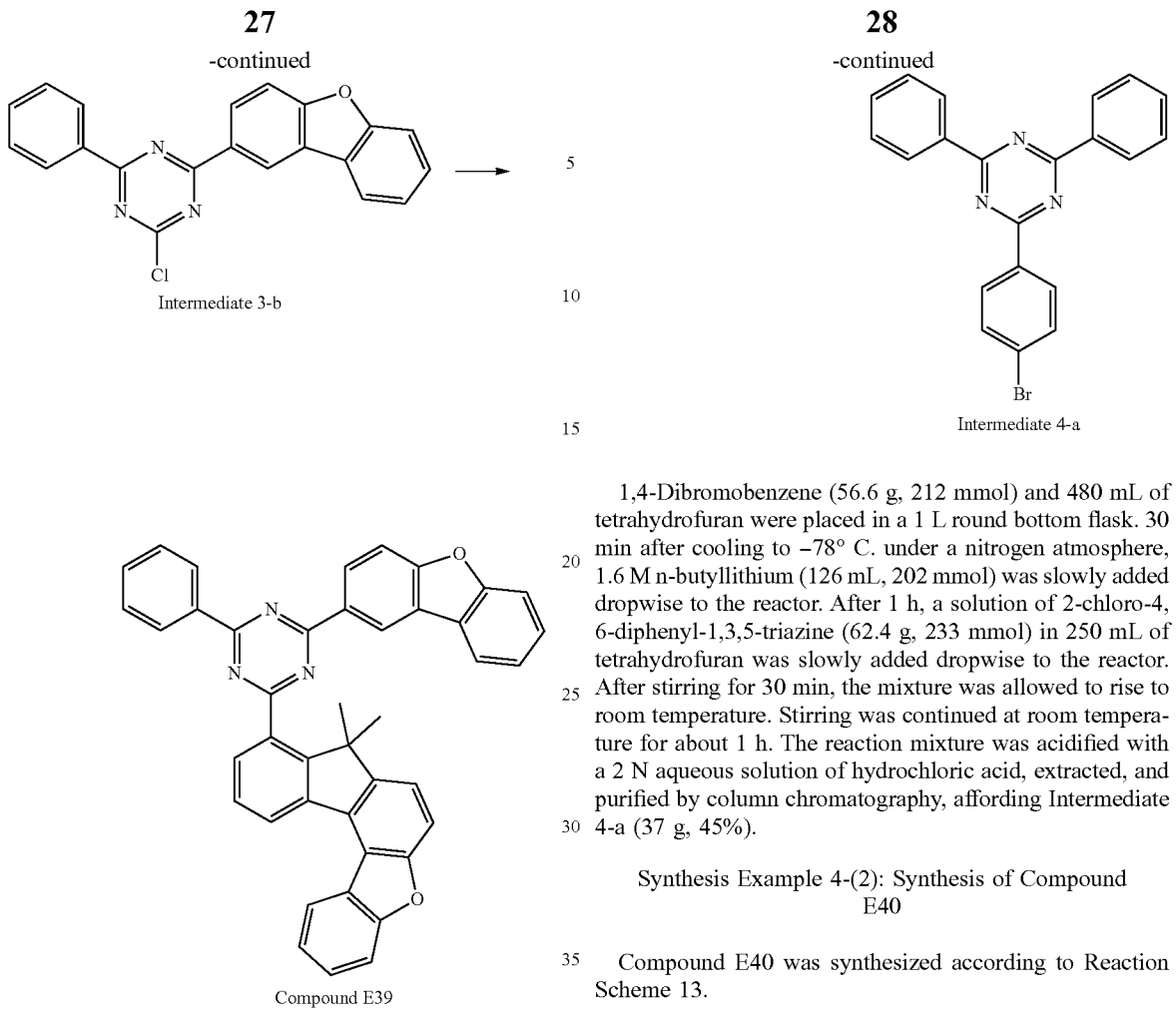

Compound E39 (5.1 g, 71%) was synthesized in the same manner as in Synthesis Example 1-(6), except that Intermediates 3-a and 3-b were used instead of Intermediates 1-d and 1-e, respectively.

MS (MALDI-TOF): m/z 605.21[M$^+$]

Synthesis Example 4: Synthesis of Compound E40

Synthesis Example 4-(1): Synthesis of Intermediate 4-a

Intermediate 4-a was synthesized according to Reaction Scheme 12.

1,4-Dibromobenzene (56.6 g, 212 mmol) and 480 mL of tetrahydrofuran were placed in a 1 L round bottom flask. 30 min after cooling to −78° C. under a nitrogen atmosphere, 1.6 M n-butyllithium (126 mL, 202 mmol) was slowly added dropwise to the reactor. After 1 h, a solution of 2-chloro-4,6-diphenyl-1,3,5-triazine (62.4 g, 233 mmol) in 250 mL of tetrahydrofuran was slowly added dropwise to the reactor. After stirring for 30 min, the mixture was allowed to rise to room temperature. Stirring was continued at room temperature for about 1 h. The reaction mixture was acidified with a 2 N aqueous solution of hydrochloric acid, extracted, and purified by column chromatography, affording Intermediate 4-a (37 g, 45%).

Synthesis Example 4-(2): Synthesis of Compound E40

Compound E40 was synthesized according to Reaction Scheme 13.

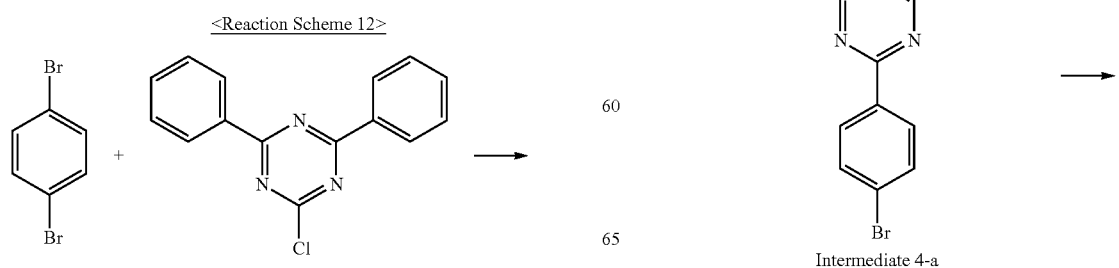

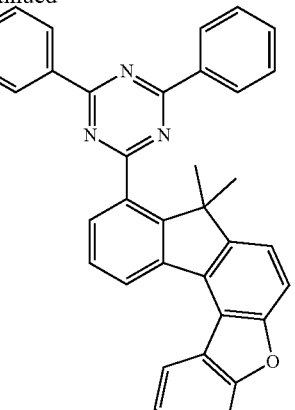

Compound E40

Compound E40 (4.3 g, 58%) was synthesized in the same manner as in Synthesis Example 1-(6), except that Intermediates 3-a and 4-a were used instead of Intermediates 1-d and 1-e, respectively.

MS (MALDI-TOF): m/z 591.23[M$^+$]

Synthesis Example 5: Synthesis of Compound E135

Synthesis Example 5-(1): Synthesis of Intermediate 5-a

Intermediate 5-a was synthesized according to Reaction Scheme 14.

<Reaction Scheme 14>

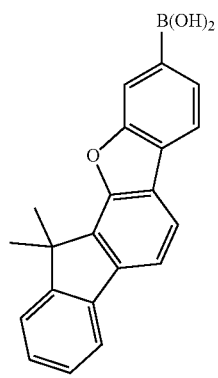

Intermediate 5-a

Intermediate 5-a (5.8 g, 74%) was synthesized in the same manner as in the synthesis of Intermediate 1-d, except that 3-bromodibenzofuran-7-boronic acid and methyl-2-bromobenzoate were used instead of dibenzofuran-1-boronic acid pinacol ester and methyl-5-bromo-2-iodobenzoate, respectively, in Synthesis Example 1-(1).

Synthesis Example 5-(2): Synthesis of Compound E135

Compound E135 was synthesized according to Reaction Scheme 15.

<Reaction Scheme 15>

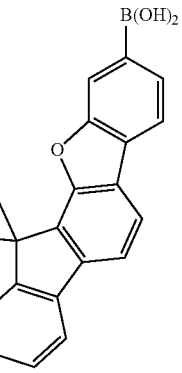

Intermediate 5-a

+

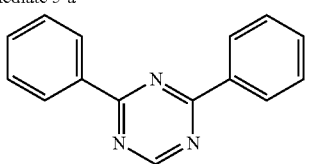

Intermediate 1-e

→

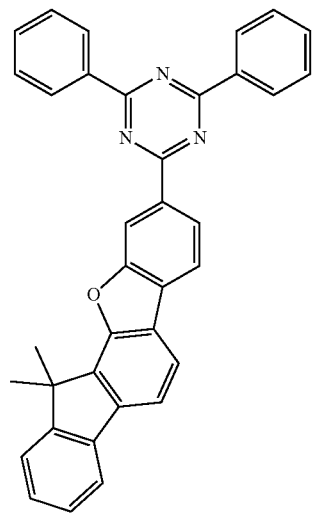

Compound E135

Compound E135 (6.1 g, 80%) was synthesized in the same manner as in Synthesis Example 1-(6), except that Intermediate 5-a was used instead of Intermediate 1-d.

MS (MALDI-TOF): m/z 515.20[M$^+$]

Synthesis Example 6: Synthesis of Compound E142

Synthesis Example 6-(1): Synthesis of Compound E142

Compound E142 was synthesized according to Reaction Scheme 16.

<Reaction Scheme 16>

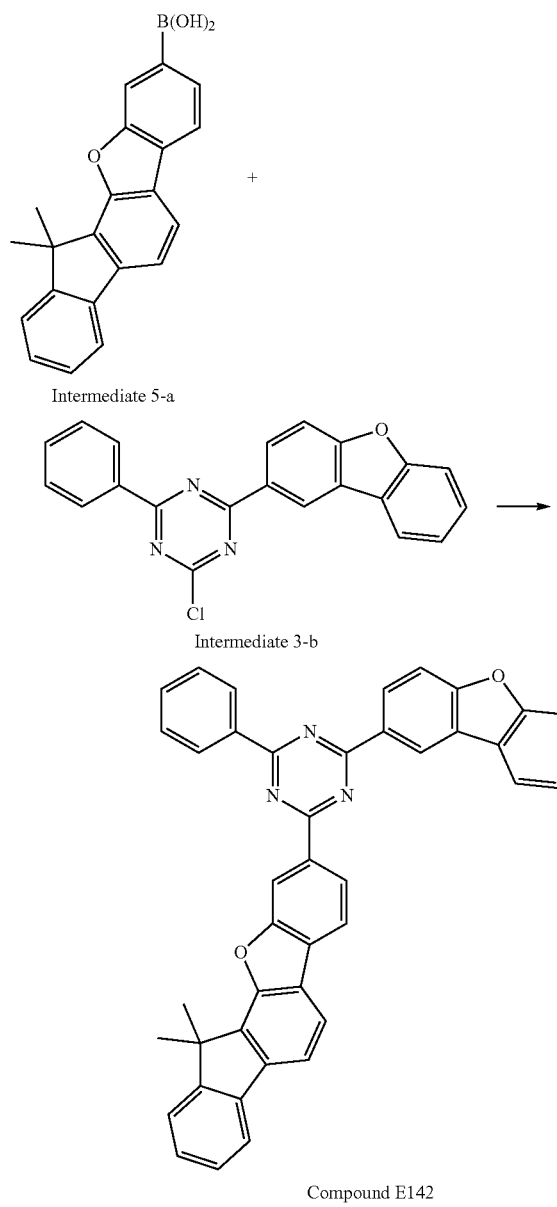

Compound E142 (5.7 g, 77%) was synthesized in the same manner as in Synthesis Example 1-(6), except that Intermediates 5-a and 3-b were used instead of Intermediates 1-d and 1-e, respectively.

MS (MALDI-TOF): m/z 605.21[M+]

Synthesis Example 7: Synthesis of Compound E154

Synthesis Example 7-(1): Synthesis of Intermediate 7-a

Intermediate 7-a was synthesized according to Reaction Scheme 17.

<Reaction Scheme 17>

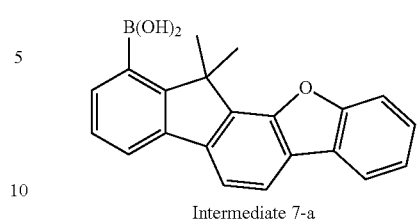

Intermediate 7-a

Intermediate 7-a (7 g, 81%) was synthesized in the same manner as in the synthesis of Intermediate 1-d, except that dibenzofuran-3-boronic acid and methyl-6-bromo-2-iodobenzoate were used instead of dibenzofuran-1-boronic acid pinacol ester and methyl-5-bromo-2-iodobenzoate, respectively, in Synthesis Example 1-(1).

Synthesis Example 7-(2): Synthesis of Compound E154

Compound E154 was synthesized according to Reaction Scheme 18.

<Reaction Scheme 18>

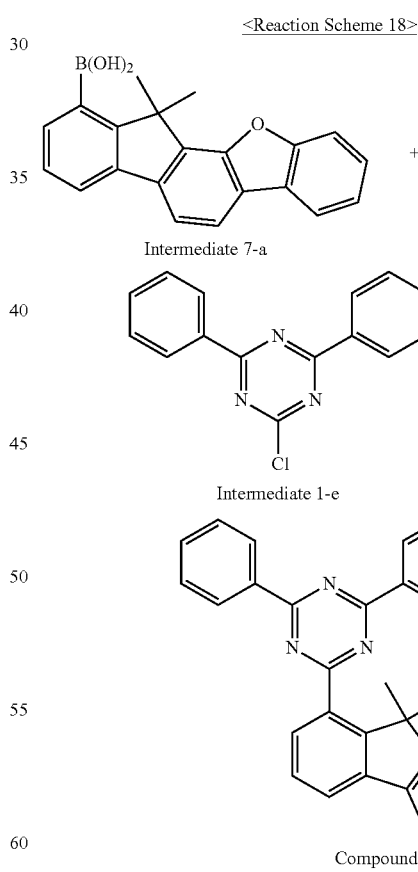

Compound E154 (5.7 g, 77%) was synthesized in the same manner as in Synthesis Example 1-(6), except that Intermediate 7-a was used instead of Intermediate 1-d.

MS (MALDI-TOF): m/z 515.20[M+]

Synthesis Example 8: Synthesis of Compound E158

Synthesis Example 8-(1): Synthesis of Intermediate 8-a

Intermediate 8-a was synthesized according to Reaction Scheme 19.

<Reaction Scheme 19>

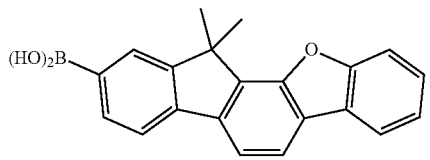

Intermediate 8-a

Intermediate 8-a (6.2 g, 74%) was synthesized in the same manner as in the synthesis of Intermediate 1-d, except that dibenzofuran-3-boronic acid and methyl-5-bromo-2-iodobenzoate were used instead of dibenzofuran-1-boronic acid pinacol ester and methyl-5-bromo-2-iodobenzoate, respectively, in Synthesis Example 1-(1).

Synthesis Example 8-(2): Synthesis of Compound E158

Compound E158 was synthesized according to Reaction Scheme 20.

<Reaction Scheme 20>

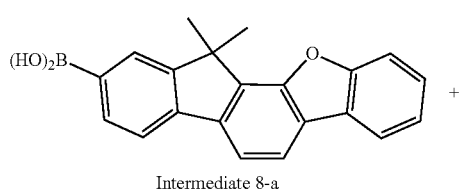

Intermediate 8-a

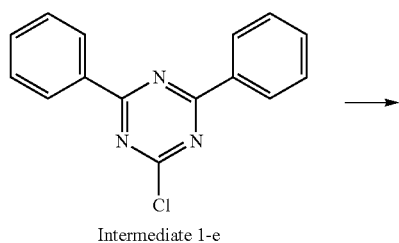

Intermediate 1-e

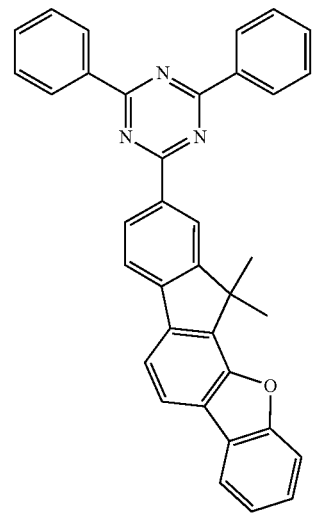

Compound E158

Compound E158 (6.6 g, 73%) was synthesized in the same manner as in Synthesis Example 1-(6), except that Intermediate 8-a was used instead of Intermediate 1-d.

MS (MALDI-TOF): m/z 515.20[M$^+$]

Synthesis Example 9: Synthesis of Compound E172

Synthesis Example 9-(1): Synthesis of Intermediate 9-a

Intermediate 9-a was synthesized according to Reaction Scheme 21.

<Reaction Scheme 21>

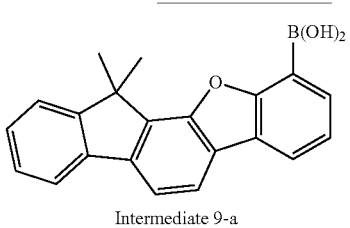

Intermediate 9-a

Intermediate 9-a (7.3 g, 85%) was synthesized in the same manner as in the synthesis of Intermediate 1-d, except that dibenzofuran-3-boronic acid and methyl-2-bromobenzoate were used instead of dibenzofuran-1-boronic acid pinacol ester and methyl-5-bromo-2-iodobenzoate, respectively, in Synthesis Example 1-(1).

Synthesis Example 9-(2): Synthesis of Intermediate 9-b

Intermediate 9-b was synthesized according to Reaction Scheme 22.

<Reaction Scheme 22>

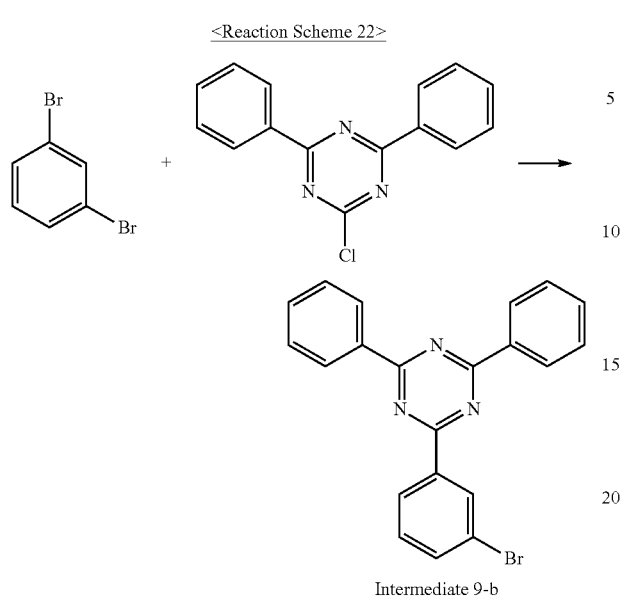

Intermediate 9-b

Intermediate 9-b (27 g, 58%) was synthesized in the same manner as in Synthesis Example 4-(1), except that 1,3-dibromobenzene was used instead of 1,4-dibromobenzene.

Synthesis Example 9-(3): Synthesis of Compound E172

Compound E172 was synthesized according to Reaction Scheme 23.

<Reaction Scheme 23>

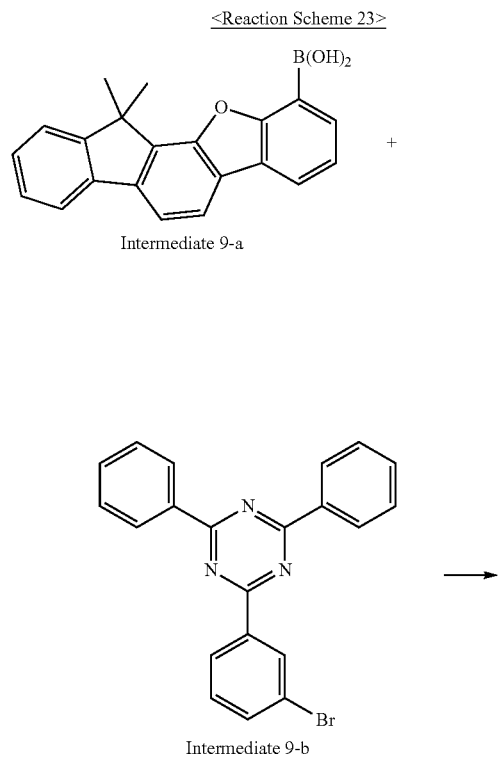

Intermediate 9-b

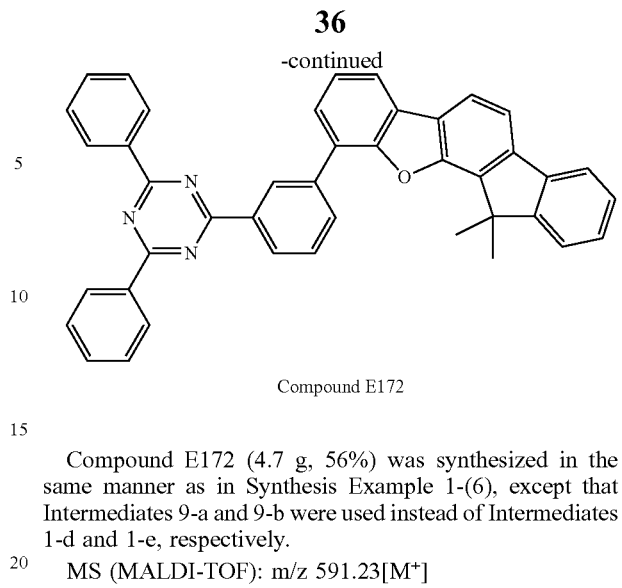

Compound E172

Compound E172 (4.7 g, 56%) was synthesized in the same manner as in Synthesis Example 1-(6), except that Intermediates 9-a and 9-b were used instead of Intermediates 1-d and 1-e, respectively.

MS (MALDI-TOF): m/z 591.23[M$^+$]

Synthesis Example 10: Synthesis of Compound H1

Synthesis Example 10-(1): Synthesis of Intermediate 10-a

Intermediate 10-a was synthesized according to Reaction Scheme 24.

<Reaction Scheme 24>

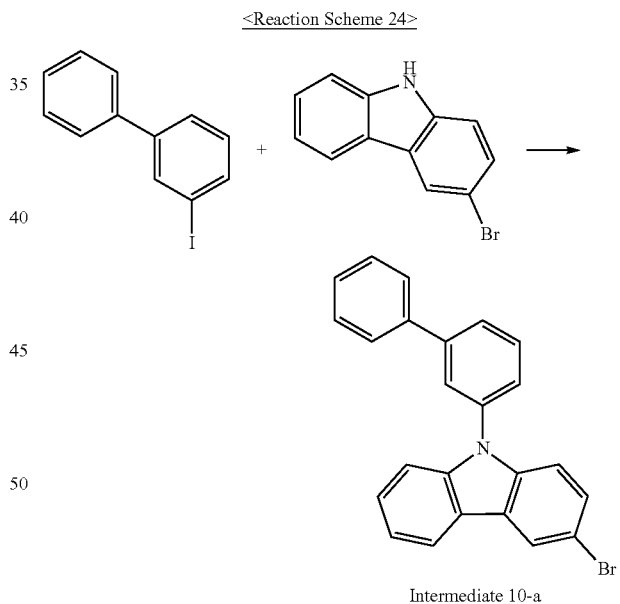

Intermediate 10-a

3-Iodobiphenyl (30 g, 107 mmol), 3-bromocarbazole (26.4 g, 107 mmol), tris(dibenzylideneacetone)dipalladium (2.0 g, 2.1 mmol), tri-tert-butylphosphonium tetrafluoroborate (3.1 g, 10.7 mmol), sodium tert-butoxide (20.5 g, 214 mmol), and xylene (300 mL) were refluxed in a round bottom flask under a nitrogen atmosphere for 12 h. After completion of the reaction, the reaction mixture was allowed to stand for layer separation. The organic layer was concentrated under reduced pressure, purified by column chromatography, and dried, affording Intermediate 10-a (31.9 g, 75%).

Synthesis Example 10-(2): Synthesis of Intermediate 10-b

Intermediate 10-b was synthesized according to Reaction Scheme 25.

<Reaction Scheme 25>

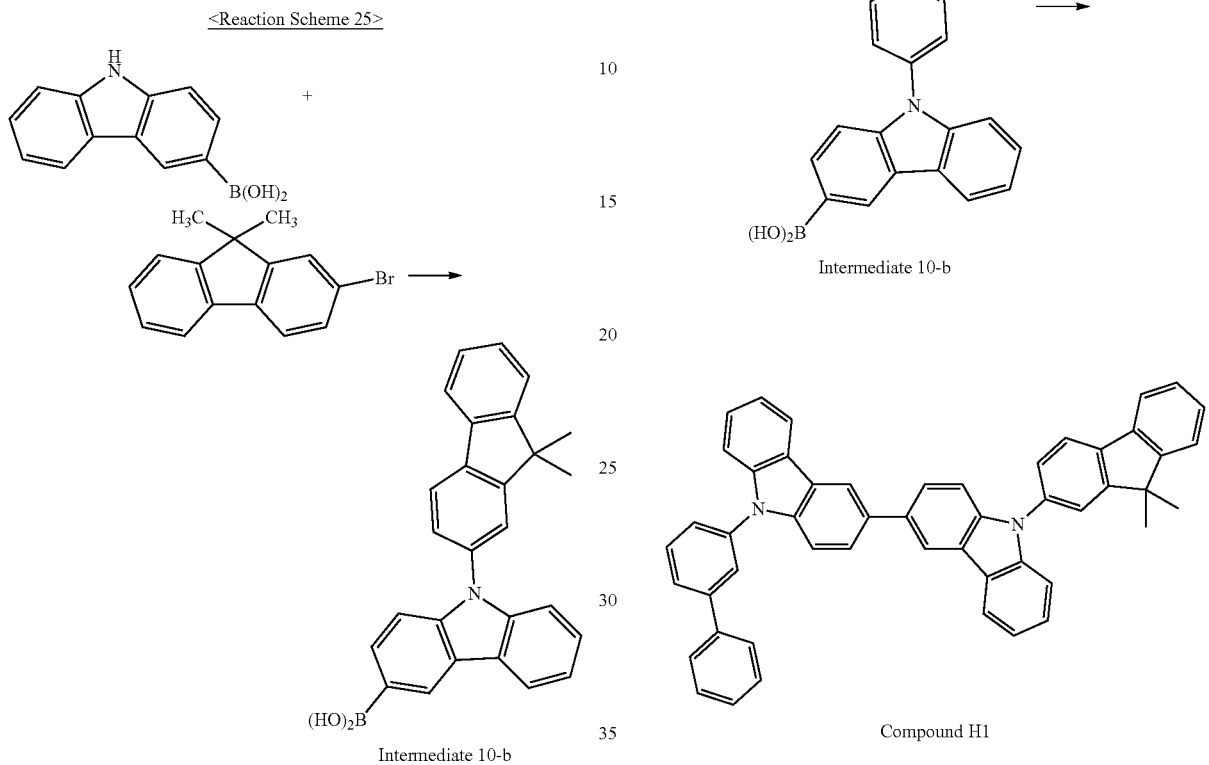

Intermediate 10-b

Intermediate 10-b (8.2 g, 59%) was synthesized in the same manner as in Synthesis Example 1-(6), except that carbazole-3-boronic acid and 2-bromo-9,9'-dimethylfluorene were used instead of Intermediates 1-d and 1-e, respectively.

Synthesis Example 10-(3): Synthesis of Compound H1

Compound H1 was synthesized according to Reaction Scheme 26.

<Reaction Scheme 26>

Intermediate 10-a

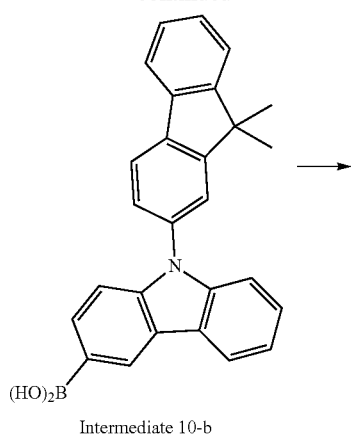

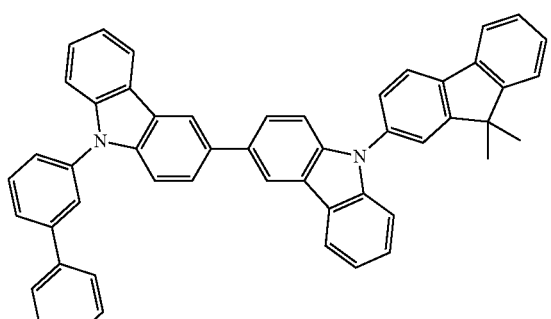

Compound H1

Compound H1 (11.3 g, 73%) was synthesized in the same manner as in Synthesis Example 1-(6), except that Intermediates 10-b and 10-a were used instead of Intermediates 1-d and 1-e, respectively.

MS (MALDI-TOF): m/z 676.29[M$^+$]

Synthesis Example 11: Synthesis of Compound H3

Synthesis Example 11-(1): Synthesis of Intermediate 11-a

Intermediate 11-a was synthesized according to Reaction Scheme 27.

<Reaction Scheme 27>

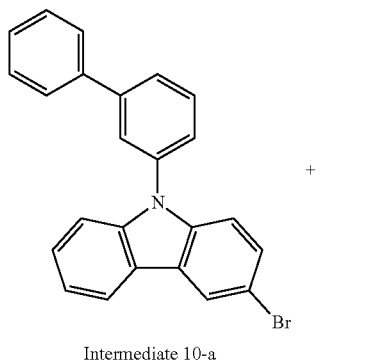

-continued

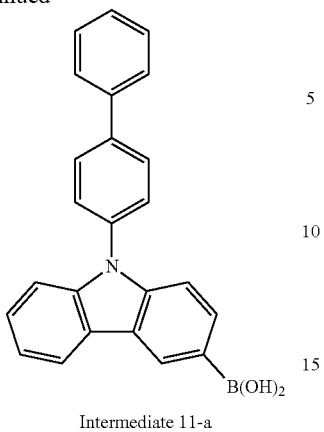

Intermediate 11-a

Intermediate 11-a (9.7 g, 63%) was synthesized in the same manner as in Synthesis Example 1-(6), except that carbazole-3-boronic acid and 4-bromobiphenyl were used instead of Intermediates 1-d and 1-e, respectively.

Synthesis Example 11-(2): Synthesis of Intermediate 11-b

Intermediate 11-b was synthesized according to Reaction Scheme 28.

<Reaction Scheme 28>

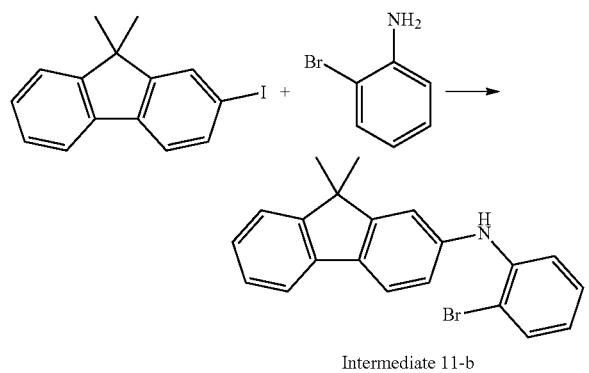

Intermediate 11-b 9,9-Dimethyl-2-iodofluorene (35.8 g, 112 mmol), 2-bromoaniline (23.5 g, 136 mmol), bis(dibenzylideneacetone)palladium (1.3 g, 1 mmol), 2,2'-bis(diphenylphosphino)-1,1'-binaphthalene (2.8 g, 4 mmol), sodium tert-butoxide (21.7 g, 226 mmol), and toluene (400 mL) were stirred at reflux in a 1 L round bottom flask as a rector overnight. After completion of the reaction, the reaction mixture was filtered, concentrated under reduced pressure, and purified by column chromatography, affording Intermediate 11-b (30 g, 74%).

Synthesis Example 11-(3): Synthesis of Intermediate 11-c

Intermediate 11-c was synthesized according to Reaction Scheme 29.

<Reaction Scheme 29>

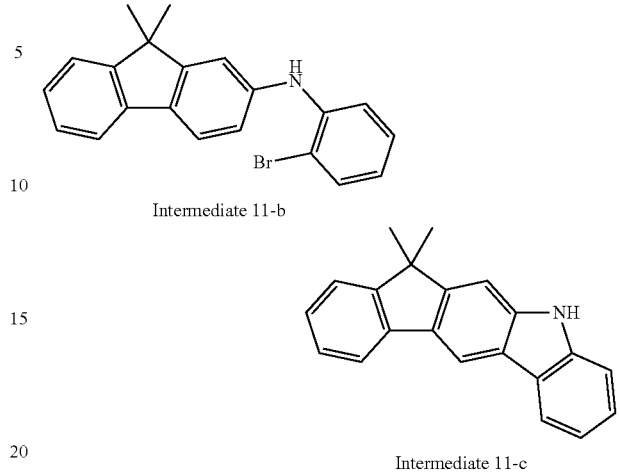

Intermediate 11-b

Intermediate 11-c

Intermediate 11-b (30.6 g, 84 mmol) and triphenylphosphine (43.8 g, 167 mmol) were placed in a 500 mL reactor and 250 mL of 1,2-dichlorobenzene was added thereto. The temperature of the reactor was raised to 120° C. Stirring was continued at 120° C. overnight. After completion of the reaction, the reaction solution was concentrated by heating and purified by column chromatography, affording Intermediate 11-c (21.2 g, 89%).

Synthesis Example 11-(4): Synthesis of Intermediate 11-d

Intermediate 11-d was synthesized according to Reaction Scheme 30.

<Reaction Scheme 30>

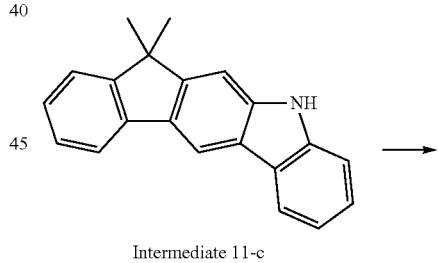

Intermediate 11-c

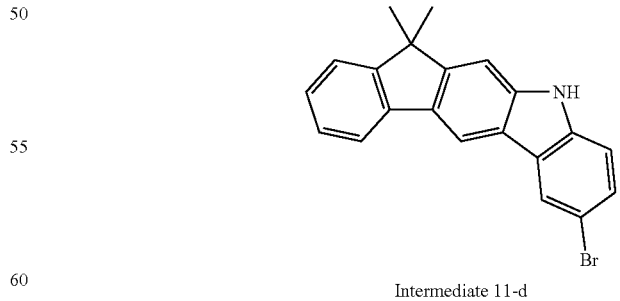

Intermediate 11-d

Intermediate 11-c (15.3 g, 0.054 mol) was dissolved in 100 mL of dimethylformamide in a 250 mL round bottom flask as a reactor. The solution was cooled to 0° C. To the solution was added dropwise a solution of N-bromosuccinic acid (10.6 g, 60 mmol) in 45 mL of dimethylformamide. The resulting mixture was stirred at room temperature overnight. After completion of the reaction, the reaction mixture was extracted with ethyl acetate, heptane, and water. The organic layer was concentrated under reduced pressure and purified by column chromatography, affording Intermediate 11-d (12.2 g, 62%).

Synthesis Example 11-(5): Synthesis of Intermediate 11-e

Intermediate 11-e was synthesized according to Reaction Scheme 31.

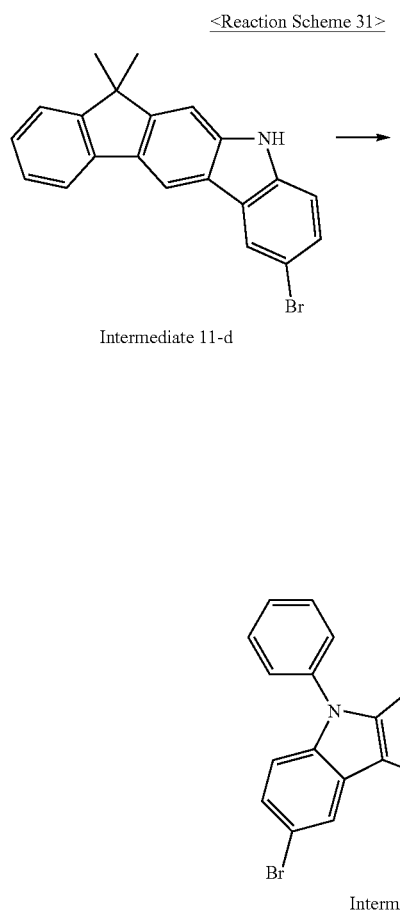

Intermediate 11-d (8.6 g, 23.6 mmol), iodobenzene (7.2 g, 35.4 mmol), bis(dibenzylideneacetone)palladium(0) (0.3 g, 0.5 mmol), tri-tert-butylphosphine tetrahydroborate (0.7 g, 2.4 mmol), sodium tert-butoxide (4.5 g, 47 mmol), and xylene (120 mL) were placed in a 250 mL round bottom flask as a reactor. The mixture was stirred at reflux at an elevated temperature overnight. The reaction solution was filtered, concentrated under reduced pressure, purified by column chromatography, and recrystallized from toluene and acetone, affording Intermediate 11-e (5.3 g, 51%).

Synthesis Example 11-(6): Synthesis of Compound H3

Compound H3 was synthesized according to Reaction Scheme 32.

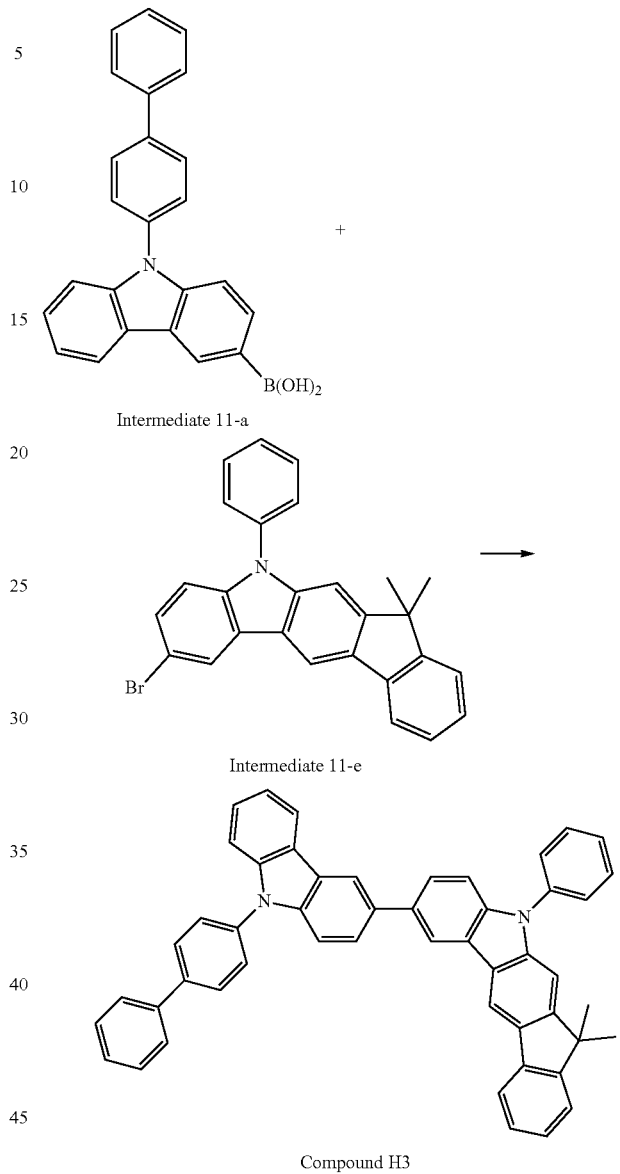

Compound H3 (7.8 g, 57%) was synthesized in the same manner as in the synthesis of Compound H1, except that Intermediates 11-a and 11-e were used instead of Intermediates 10-a and 11-b, respectively, in Synthesis Example 10-(1).

MS (MALDI-TOF): m/z 676.29[M$^+$]

Synthesis Example 12: Synthesis of Compound H19

Synthesis Example 12-(1): Synthesis of Intermediate 12-a

Intermediate 12-a was synthesized according to Reaction Scheme 33.

<Reaction Scheme 33>

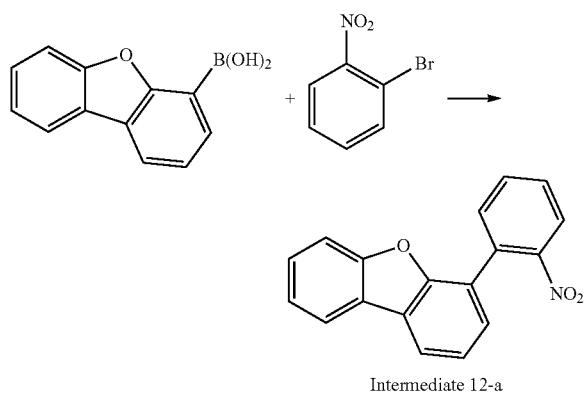

Intermediate 12-a

Intermediate 12-a (7.4 g, 57%) was synthesized in the same manner as in Synthesis Example 1-(6), except that dibenzofuran-1-boronic acid and 2-bromonitrobenzene were used instead of Intermediates 1-d and 1-e, respectively.

Synthesis Example 12-(2): Synthesis of Intermediate 12-b

Intermediate 12-b was synthesized according to Reaction Scheme 34.

<Reaction Scheme 34>

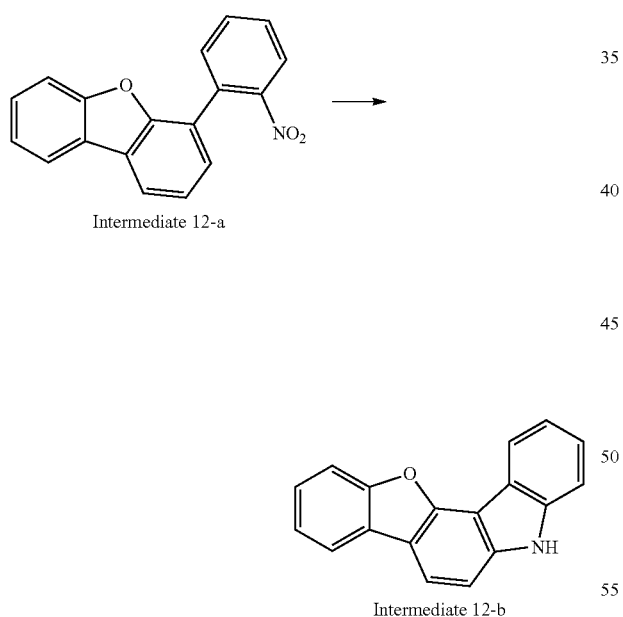

Intermediate 12-b (16 g, 60%) was synthesized in the same manner as in Synthesis Example 11-(3), except that Intermediate 12-a was used instead of Intermediate 11-b.

Synthesis Example 12-(3): Synthesis of Intermediate 12-c

Intermediate 12-c was synthesized according to Reaction Scheme 35.

<Reaction Scheme 35>

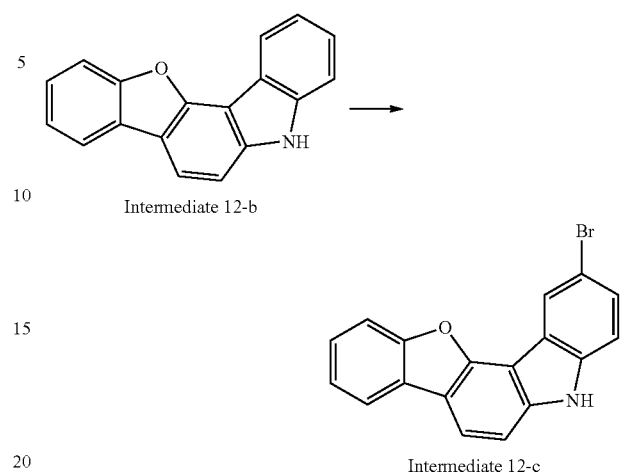

Intermediate 12-c (16.7 g, 80%) was synthesized in the same manner as in Synthesis Example 11-(4), except that Intermediate 12-b was used instead of Intermediate 11-c.

Synthesis Example 12-(4): Synthesis of Intermediate 12-d

Intermediate 12-d was synthesized according to Reaction Scheme 36.

<Reaction Scheme 36>

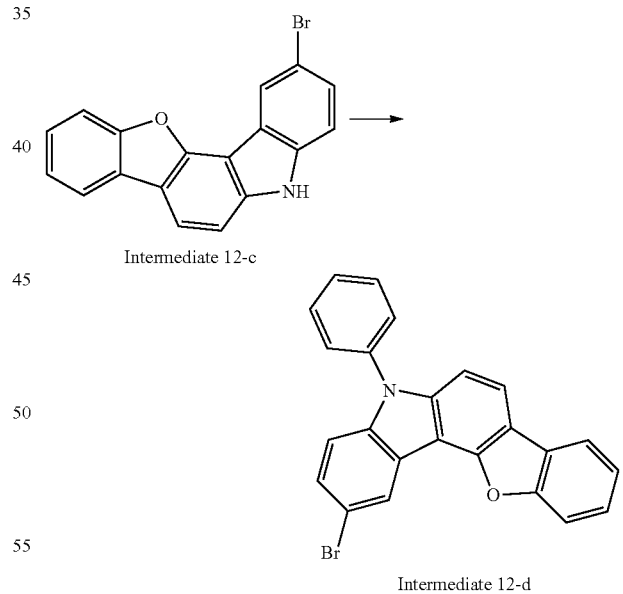

Intermediate 12-d (3.7 g, 51%) was synthesized in the same manner as in Synthesis Example 11-(5), except that Intermediate 12-c was used instead of Intermediate 11-d.

Synthesis Example 12-(5): Synthesis of Compound H19

Compound H19 was synthesized according to Reaction Scheme 37.

<Reaction Scheme 37>

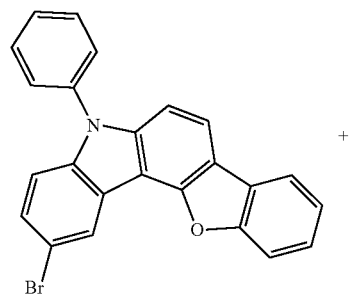

Intermediate 12-d

+

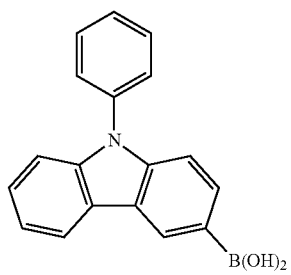

→

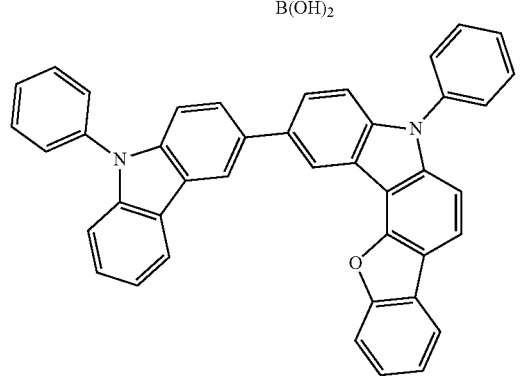

Compound H19

Compound H19 (6.4 g, 66%) was synthesized in the same manner as in the synthesis of Compound H1, except that Intermediate 12-d and N-phenylcarbazole-3-boronic acid were used instead of Intermediates 10-a and 10-b, respectively, in Synthesis Example 10-(1).

MS (MALDI-TOF): m/z 574.20[M⁺]

Synthesis Example 13: Synthesis of Compound H27

Synthesis Example 13-(1): Synthesis of Intermediate 13-a

Intermediate 13-a was synthesized according to Reaction Scheme 38.

<Reaction Scheme 38>

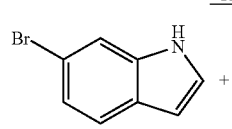

+

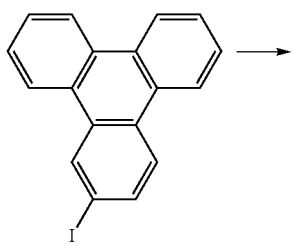

→

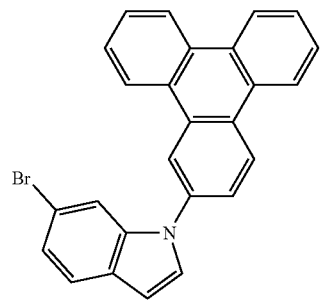

Intermediate 13-a

Intermediate 13-a (9.4 g, 71%) was synthesized in the same manner as in Synthesis Example 10-(1), except that 2-bromoindole and 1-iodotriphenylene were used instead of 3-bromocarb azole and 3-iodobiphenyl, respectively.

Synthesis Example 13-(2): Synthesis of Compound H27

Compound H27 was synthesized according to Reaction Scheme 39.

<Reaction Scheme 39>

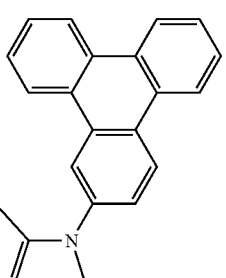

Intermediate 13-a

+

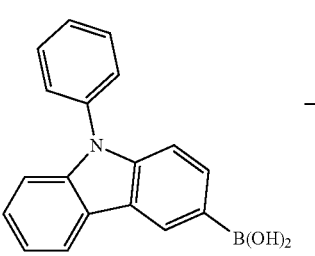

→

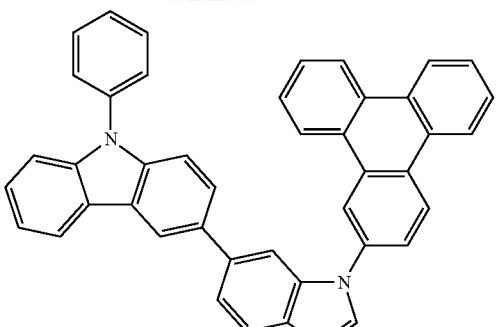

Compound H27

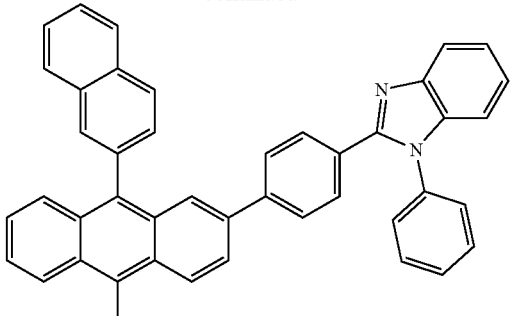

ET

Compound H27 (5.7 g, 62%) was synthesized in the same manner as in the synthesis of Compound H1, except that Intermediate 13-a and N-phenylcarbazole-3-boronic acid were used instead of Intermediates 10-a and 10-b, respectively, in Synthesis Example 10-(1).

MS (MALDI-TOF): m/z 584.23[M$^+$]

Examples 1-9: Fabrication of Organic Light Emitting Devices

ITO glass was patterned to have a light emitting area of 2 mm×2 mm, followed by cleaning. After the cleaned ITO glass was mounted in a vacuum chamber, the base pressure was adjusted to 1×10$^{-6}$ torr. HATCN (50 Å), NPD (900 Å), and one of Compounds E1-E173 were deposited on the ITO and doped with 7% of a green phosphorescent dopant (GD) to form a 300 Å thick light emitting layer. Thereafter, an ET: Liq (1:1) layer (300 Å), a Liq layer (10 Å), and an Al layer (1,000 Å) were formed in this order on the light emitting layer to fabricate an organic light emitting device. The luminescent properties of the organic light emitting device were measured at 0.4 mA.

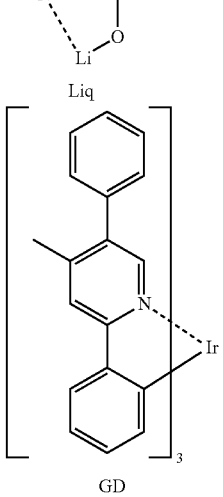

Liq

GD

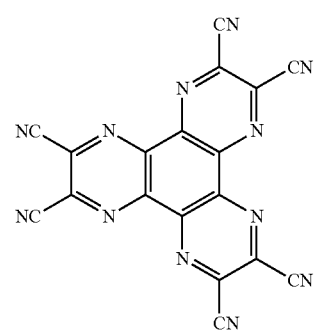

HATCN

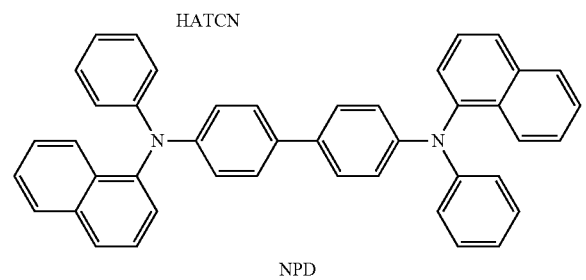

NPD

Example 10

An organic light emitting device was fabricated in the same manner as in Example 1, except that Compounds E1 and H1 (5:5, w/w) were deposited and doped with 7% of a green phosphorescent dopant (GD) to form a light emitting layer.

Example 11

An organic light emitting device was fabricated in the same manner as in Example 10, except that Compound E19 was used instead of Compound E1.

Example 12

An organic light emitting device was fabricated in the same manner as in Example 10, except that Compounds E39 and H3 were used instead of Compounds E1 and H1, respectively.

Example 13

An organic light emitting device was fabricated in the same manner as in Example 10, except that Compounds E40 and H3 were used instead of Compounds E1 and H1, respectively.

Example 14

An organic light emitting device was fabricated in the same manner as in Example 10, except that Compounds E135 and H19 were used instead of Compounds E1 and H1, respectively.

Example 15

An organic light emitting device was fabricated in the same manner as in Example 10, except that Compounds E142 and H19 were used instead of Compounds E1 and H1, respectively.

Example 16

An organic light emitting device was fabricated in the same manner as in Example 10, except that Compounds E154 and H27 were used instead of Compounds E1 and H1, respectively.

Example 17

An organic light emitting device was fabricated in the same manner as in Example 10, except that Compounds E158 and H27 were used instead of Compounds E1 and H1, respectively.

Example 18

An organic light emitting device was fabricated in the same manner as in Example 10, except that Compounds E172 and H27 were used instead of Compounds E1 and H1, respectively.

Comparative Example 1

For comparison, an organic light emitting device was fabricated in the same manner as in Examples 1-18, except that CBP was used instead of the inventive compounds. CBP is a phosphorescent host material well known in the art and its structure is as follows:

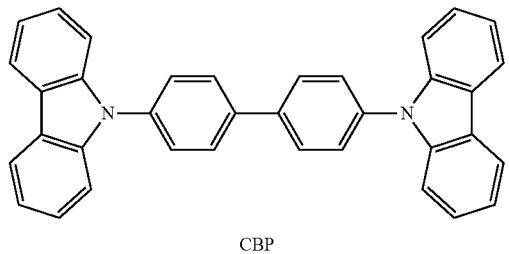 [SMILES: c1ccc2c(c1)c1ccccc1n2-c1ccc(-c2ccc(-n3c4ccccc4c4ccccc43)cc2)cc1 ; "CBP"]

CBP

Evaluation Example 1

The organic light emitting devices of Examples 1-18 and Comparative Example 1 were measured for driving voltage, luminance, color of light emission, and life. The results are shown in Table 1.

TABLE 1

|  | First host | Second host | wt:wt | Driving voltage (V) | Luminous efficiency (cd/A) | CIEx | CIEy | T95 (h) 6000 nit |
|---|---|---|---|---|---|---|---|---|
| Example 1 | Compound E1 |  | 1 | 3.5 | 44 | 0.334 | 0.628 | 60 |
| Example 2 | Compound E19 |  | 1 | 3.4 | 44 | 0.334 | 0.628 | 55 |
| Example 3 | Compound E39 |  | 1 | 3.6 | 42 | 0.329 | 0.631 | 50 |
| Example 4 | Compound E40 |  | 1 | 3.7 | 42 | 0.329 | 0.631 | 60 |
| Example 5 | Compound E135 |  | 1 | 3.5 | 43 | 0.334 | 0.629 | 50 |
| Example 6 | Compound E142 |  | 1 | 3.4 | 39 | 0.334 | 0.628 | 60 |
| Example 7 | Compound E154 |  | 1 | 3.5 | 43 | 0.334 | 0.629 | 60 |
| Example 8 | Compound E158 |  | 1 | 3.4 | 42 | 0.329 | 0.631 | 60 |
| Example 9 | Compound E172 |  | 1 | 3.7 | 40 | 0.327 | 0.632 | 50 |
| Example 10 | Compound E1 | Compound H1 | 5:5 | 3.8 | 55 | 0.328 | 0.633 | 240 |
| Example 11 | Compound E19 | Compound H1 | 5:5 | 3.8 | 60 | 0.330 | 0.632 | 235 |
| Example 12 | Compound E39 | Compound H3 | 5:5 | 3.9 | 58 | 0.338 | 0.626 | 280 |
| Example 13 | Compound E40 | Compound H3 | 5:5 | 4.0 | 65 | 0.330 | 0.632 | 270 |
| Example 14 | Compound E135 | Compound H19 | 5:5 | 4.2 | 62 | 0.326 | 0.634 | 240 |
| Example 15 | Compound E142 | Compound H19 | 5:5 | 4.4 | 60 | 0.330 | 0.631 | 250 |
| Example 16 | Compound E154 | Compound H27 | 5:5 | 4.0 | 63 | 0.330 | 0.632 | 260 |
| Example 17 | Compound E158 | Compound H27 | 5:5 | 4.4 | 57 | 0.327 | 0.633 | 250 |
| Example 18 | Compound E172 |  | 5:5 | 4.1 | 58 | 0.338 | 0.626 | 240 |
| Comparative Example 1 | CBP |  | 1 | 6.9 | 36 | 0.335 | 0.628 | 8 |

As can be seen from the results in Table 1, the organic light emitting devices including Compound 1 (Examples 1-9) and the organic light emitting devices including Compounds 1 and 2 (Examples 10-18) had low driving voltages, luminous efficiencies and, particularly, considerably improved life characteristics compared to the organic light emitting device of Comparative Example 1. These results demonstrate that the organic light emitting devices of Examples 1-18 are expected to be useful in a variety of industrial applications, including displays and lighting systems.

What is claimed is:
1. An organic light emitting compound represented by Formula 1:

$$HAr_1-(L)_n-HAr_2 \qquad (1)$$

wherein L represents a linker and is a single bond or is selected from substituted or unsubstituted $C_1$-$C_{30}$ alkylene groups, substituted or unsubstituted $C_2$-$C_{30}$ alkenylene groups, substituted or unsubstituted $C_2$-$C_{30}$ alkynylene groups, substituted or unsubstituted $C_2$-$C_{30}$ cycloalkylene groups, substituted or unsubstituted $C_2$-$C_{30}$ heterocycloalkylene groups, substituted or unsubstituted $C_6$-$C_{30}$ arylene groups, and substituted or unsubstituted $C_2$-$C_{30}$ heteroarylene groups, n is an integer from 1 to 3, provided that when n is equal to or greater than 2, the plurality of L groups are identical to or different from each other, $HAr_1$, is a group having the following structure 1:

Structure 1

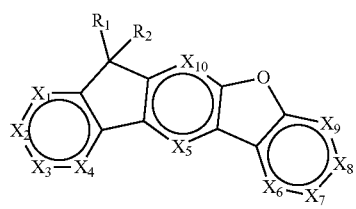

wherein $X_1$ to $X_{10}$ are identical to or different from each other and are each independently $CR_3$ or N, $R_1$ to $R_3$ are identical to or different from each other and are each independently selected from a hydrogen atom, a deuterium atom, substituted or unsubstituted $C_1$-$C_{30}$ alkyl groups, substituted or unsubstituted $C_2$-$C_{30}$ alkenyl groups, substituted or unsubstituted $C_2$-$C_{30}$ alkynyl groups, substituted or unsubstituted $C_2$-$C_{30}$ cycloalkyl groups, substituted or unsubstituted $C_2$-$C_{30}$ heterocycloalkyl groups, substituted or unsubstituted $C_5$-$C_{30}$ cycloalkenyl groups, substituted or unsubstituted $C_1$-$C_{30}$ alkoxy groups, substituted or unsubstituted $C_6$-$C_{30}$ aryloxy groups, substituted or unsubstituted $C_1$-$C_{30}$ alkylthioxy groups, substituted or unsubstituted $C_6$-$C_{30}$ arylthioxy groups, substituted or unsubstituted $C_1$-$C_{30}$ alkylamine groups, substituted or unsubstituted $C_6$-$C_{30}$ arylamine groups, substituted or unsubstituted $C_6$-$C_{50}$ aryl groups, substituted or unsubstituted $C_3$-$C_{50}$ heteroaryl groups containing O, N or S as a heteroatom, substituted or unsubstituted $C_1$-$C_{24}$ alkylsilyl groups, substituted or unsubstituted $C_6$-$C_{24}$ arylsilyl groups, substituted or unsubstituted germanium groups, substituted or unsubstituted boron groups, substituted or unsubstituted aluminum groups, a carbonyl group, a phosphoryl group, an amino group, a thiol group, a cyano group, a hydroxyl group, a nitro group, halogen groups, a selenium group, a tellurium group, an amide group, an ether group, and an ester group, with the proviso that one of $X_1$ to $X_{10}$ is a carbon atom linked to L, and $HAr_2$ is selected from the following structures:

D3

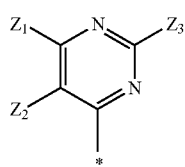

D5

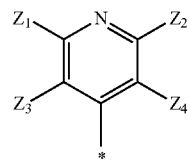

D6

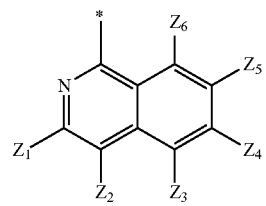

D7

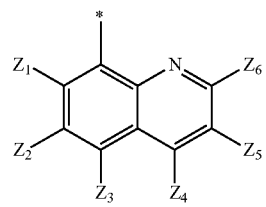

D8

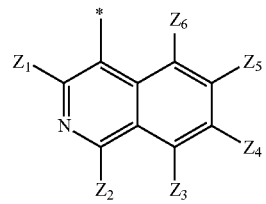

D9

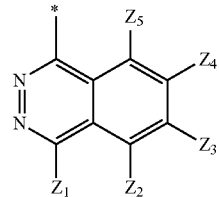

D10

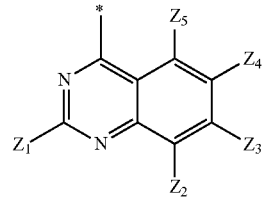

D11

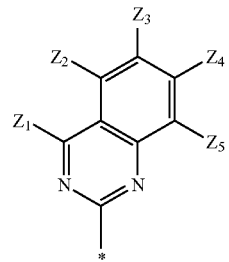

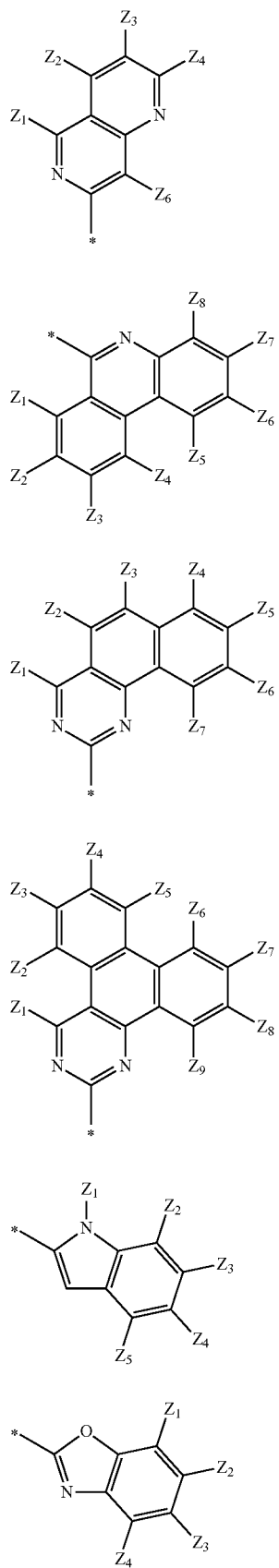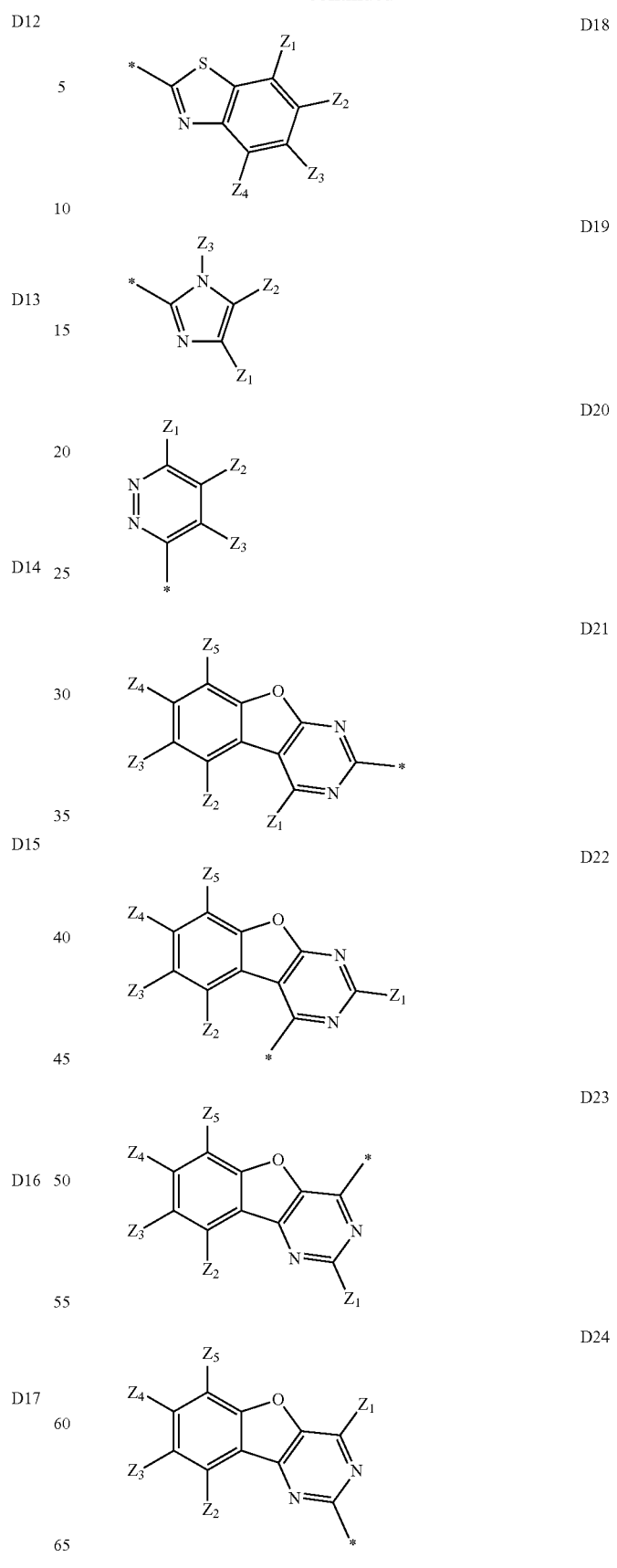

-continued

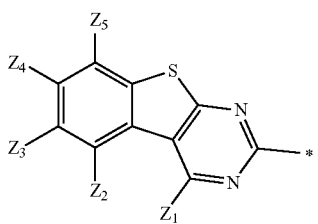
D25

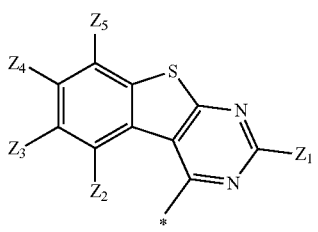
D26

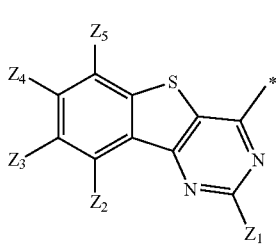
D27

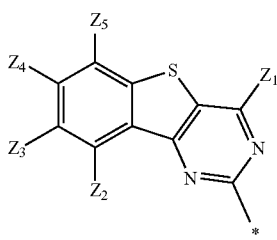
D28

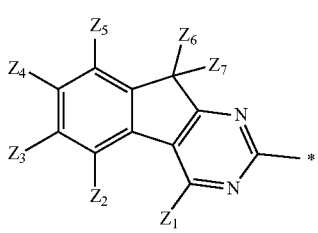
D29

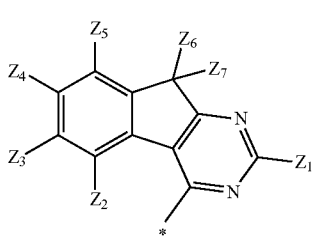
D30

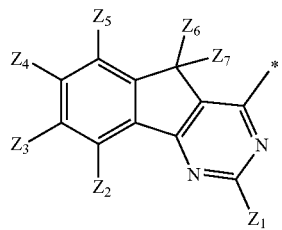
D31

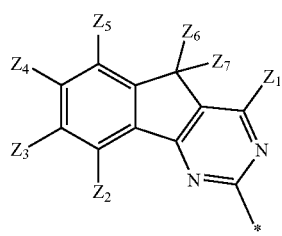
D32

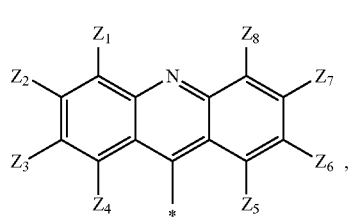
D33 and wherein $Z_1$ to $Z_9$ are identical to or different from each other and have the same meanings as $R_1$ to $R_3$ and the asterisk (*) represents a site at which $HAr_2$ is linked to L.

2. An organic light emitting device comprising a first electrode, a second electrode opposite to the first electrode, and at least one organic layer interposed between the first and second electrodes wherein the organic layer comprises the compound represented by Formula 1 according to claim 1.

3. The organic light emitting device according to claim 2, wherein the organic layer further comprises a light emitting layer comprising a phosphorescent dopant compound.

4. An organic light emitting device comprising a first electrode, a second electrode opposite to the first electrode, and at least one organic layer interposed between the first and second electrodes wherein the organic layer comprises (a) the compound represented by Formula 1 according to claim 1 as a first compound and (b) a second compound represented by Formula 2:

$$HAr_3\text{—}(L)_n\text{—}HAr_4 \qquad (2)$$

wherein L represents a linker and is a single bond or is selected from substituted or unsubstituted $C_1$-$C_{30}$ alkylene groups, substituted or unsubstituted $C_2$-$C_{30}$ alkenylene groups, substituted or unsubstituted $C_2$-$C_{30}$ alkynylene groups, substituted or unsubstituted $C_2$-$C_{30}$ cycloalkylene groups, substituted or unsubstituted $C_2$-$C_{30}$ heterocycloalkylene groups, substituted or unsubstituted $C_6$-$C_{30}$ arylene groups, and substituted or unsubstituted $C_2$-$C_{30}$ heteroarylene groups, n is an integer from 1 to 3, provided that when n is equal to or greater than 2, the plurality of L groups are identical to or different from each other, $HAr_3$ is selected from the following structures:

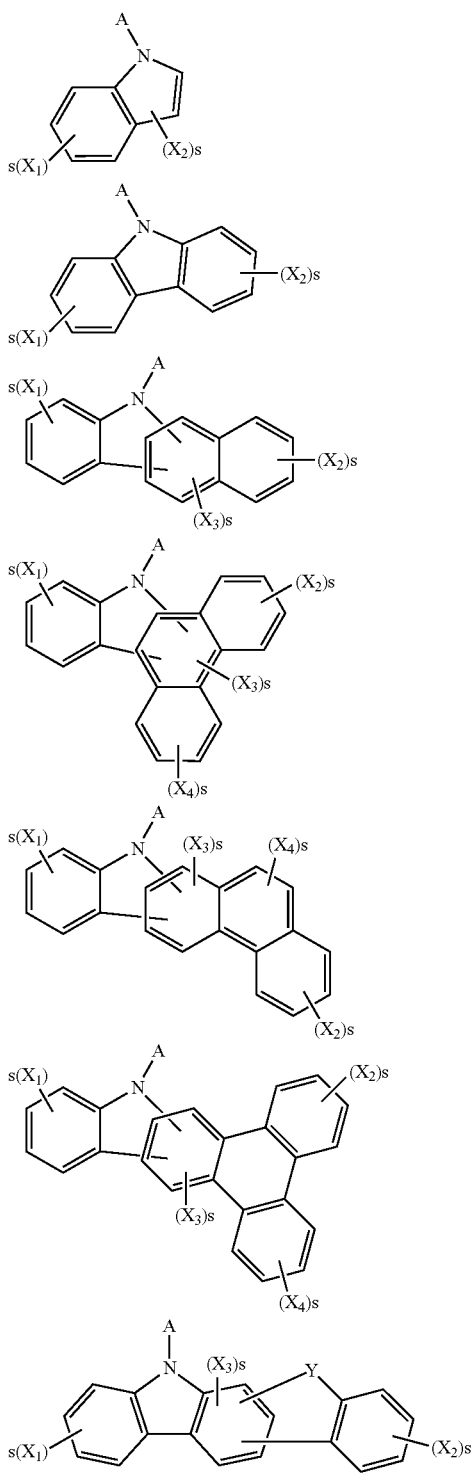

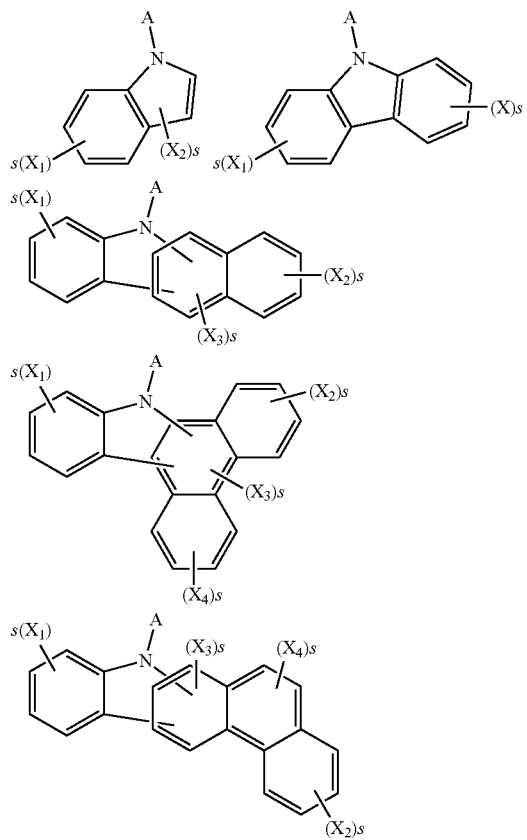

wherein Y is selected from N—$R_1$, $CR_2R_3$, $SiR_4R_5$, $GeR_6R_7$, O, S, and Se, $X_1$ to $X_4$ are each independently selected from hydrogen, deuterium, substituted or unsubstituted $C_1$-$C_{30}$ alkyl groups, substituted or unsubstituted $C_2$-$C_{30}$ alkenyl groups, substituted or unsubstituted $C_2$-$C_{30}$ cycloalkyl groups, substituted or unsubstituted $C_5$-$C_{30}$ cycloalkenyl groups, substituted or unsubstituted $C_1$-$C_{30}$ alkoxy groups, substituted or unsubstituted $C_6$-$C_{30}$ aryloxy groups, substituted or unsubstituted $C_1$-$C_{30}$ alkylthioxy groups, substituted or unsubstituted $C_5$-$C_{30}$ arylthioxy groups, substituted or unsubstituted $C_1$-$C_{30}$ alkylamine groups, substituted or unsubstituted $C_5$-$C_{30}$ arylamine groups, substituted or unsubstituted $C_5$-$C_{50}$ aryl groups, substituted or unsubstituted $C_3$-$C_{50}$ heteroaryl groups containing O, N or S as a heteroatom, substituted or unsubstituted silyl groups, substituted or unsubstituted germanium groups, substituted or unsubstituted boron groups, substituted or unsubstituted aluminum groups, a carbonyl group, a phosphoryl group, an amino group, a nitrile group, a hydroxyl group, a nitro group, halogen groups, a selenium group, a tellurium group, an amide group, and an ester group, with the proviso that $X_1$ to $X_4$ together with an adjacent group optionally forms an aliphatic, aromatic, heteroaliphatic or heteroaromatic fused ring and one of $X_1$ to $X_4$ is linked to L, s is an integer from 1 to 4, and A and $R_1$ to $R_7$ are each independently selected from hydrogen, deuterium, halogen atoms, a cyano group, substituted or unsubstituted $C_1$-$C_{20}$ alkyl groups, substituted or unsubstituted $C_3$-$C_{20}$ cycloalkyl groups, substituted or unsubstituted $C_1$-$C_{20}$ alkoxy groups, substituted or unsubstituted $C_6$-$C_{30}$ aryloxy groups, substituted or unsubstituted $C_1$-$C_{20}$ alkylthio groups, substituted or unsubstituted $C_6$-$C_{30}$ arylthio groups, substituted or unsubstituted $C_3$-$C_{50}$ alkylsilyl groups, substituted or unsubstituted $C_6$-$C_{50}$ arylsilyl groups, substituted or unsubstituted $C_6$-$C_{30}$ aromatic hydrocarbon groups, and substituted or unsubstituted $C_5$-$C_{30}$ heterocyclic groups, and $HAr_4$ is selected from the following structures:

-continued

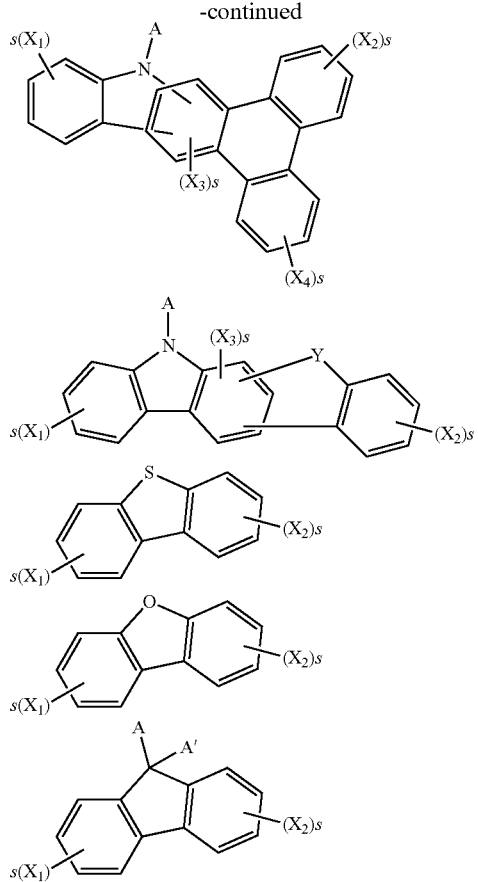

wherein Y, $X_1$ to $X_4$, s, A, and $R_1$ to $R_7$ are as defined above and A' has the same meaning as A and $R_1$ to $R_7$.

5. The organic light emitting device according to claim 4, wherein each of A, A', $X_1$ to $X_4$, $R_1$ to $R_7$, $HAr_3$, $HAr_4$, and L is further substituted with one or more substituents selected from $C_1$-$C_{60}$ alkyl groups, $C_5$-$C_{60}$ heteroaryl groups, $C_3$-$C_{60}$ cycloalkyl groups, $C_6$-$C_{60}$ aryl groups, $C_1$-$C_{60}$ alkoxy groups, $C_6$-$C_{30}$ aryloxy groups, $C_1$-$C_{20}$ alkylamino groups, $C_1$-$C_{20}$ alkylsilyl groups, $C_6$-$C_{30}$ arylsilyl groups, $C_1$-$C_{50}$ arylalkylamino groups, $C_2$-$C_{60}$ alkenyl groups, a cyano group, halogen groups, and deuterium.

6. The organic light emitting device according to claim 4, wherein the organic layer further comprises a light emitting layer, a hole transport layer between the light emitting layer and the first electrode, and an electron transport layer between the light emitting layer and the second electrode and wherein the light emitting layer comprises the first compound represented by Formula 1 and the second compound represented by Formula 2.

7. The organic light emitting device according to claim 6, wherein the light emitting layer further comprises a phosphorescent dopant compound.

8. The organic light emitting device according to claim 7, wherein the first compound, the second compound, and the dopant compound are mixed in a weight ratio of 1:0.01-99:0.01-15.

9. The organic light emitting device according to claim 4, wherein the second compound represented by Formula 2 is selected from a group consisting of Compounds H1 to H148:

Compound H1

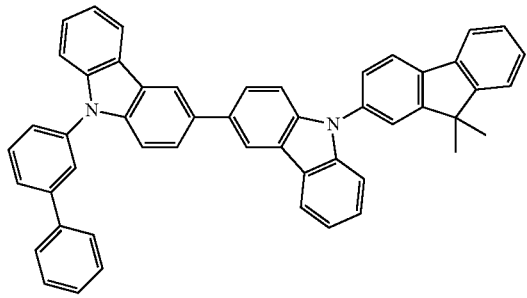

Compound H2

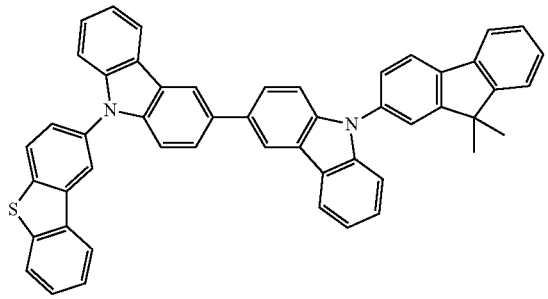

Compound H3

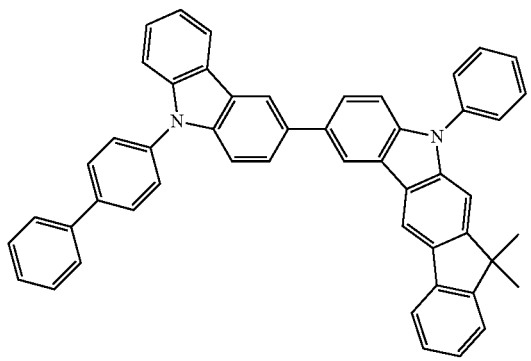

Compound H4

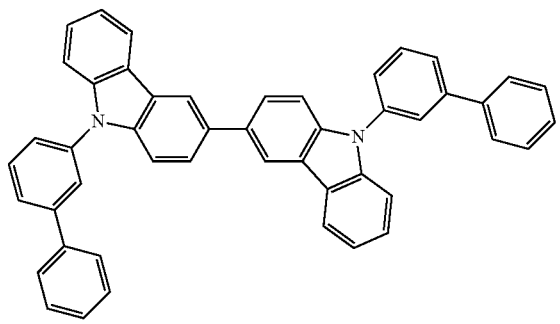

-continued
Compound H5
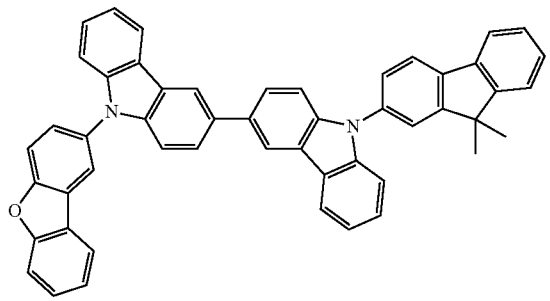
Compound H6
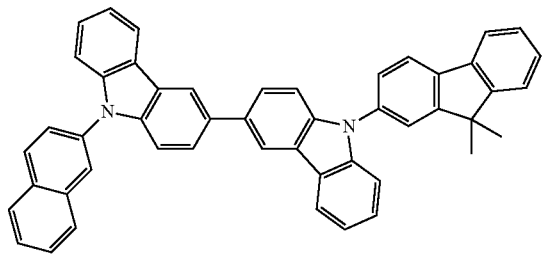
Compound H7
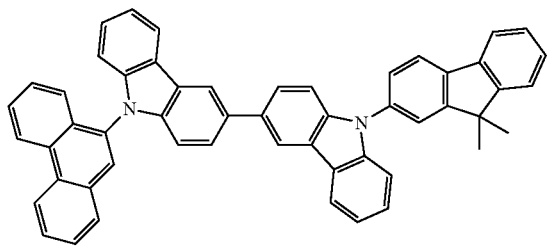
Compound H8
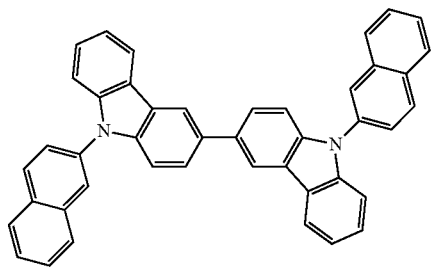
Compound H9
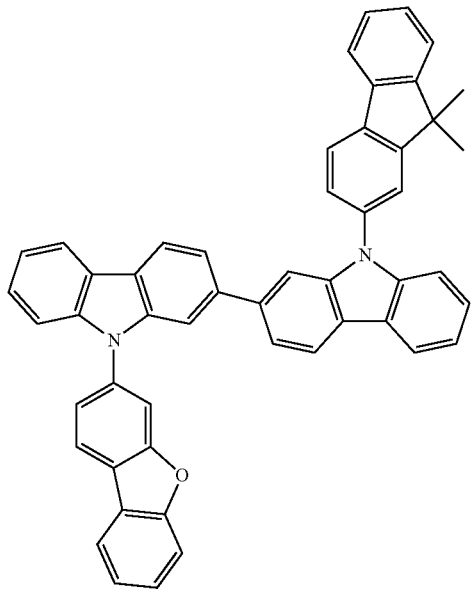
Compound H10
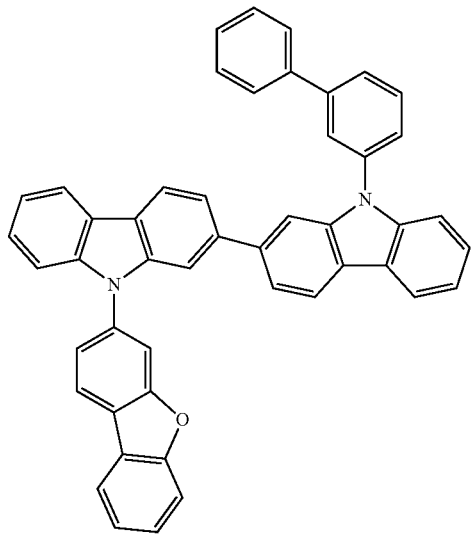

-continued
Compound H11
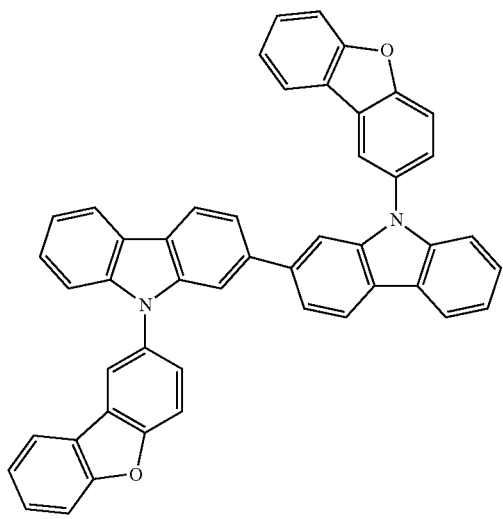
Compound H12
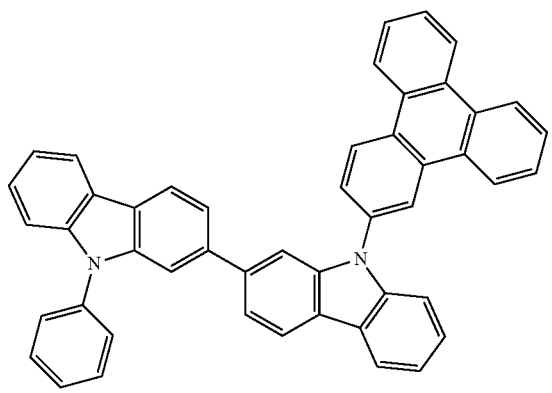
Compound H13
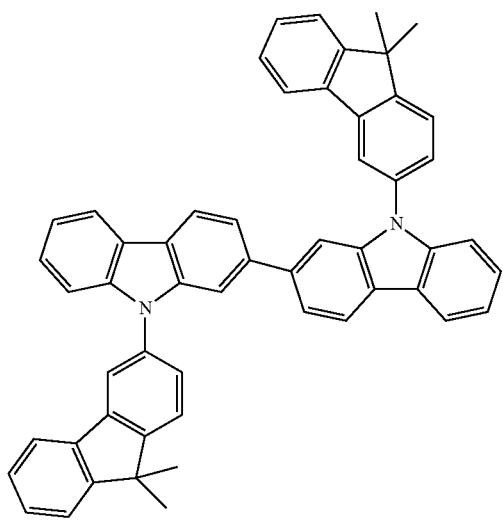
Compound H14
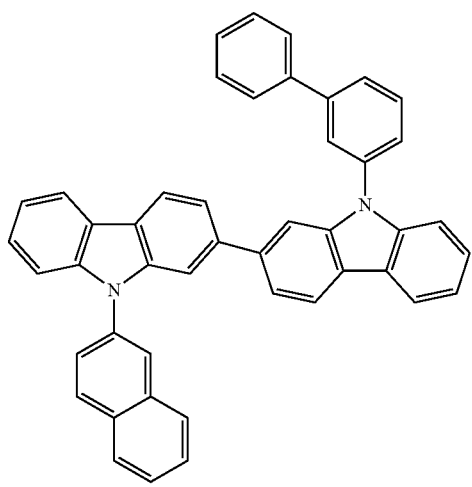
Compound H15
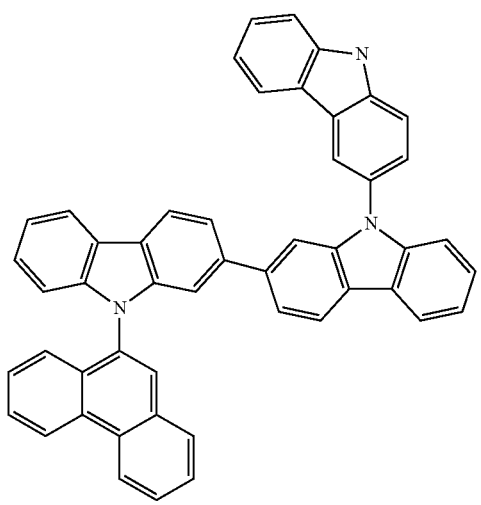
Compound H16
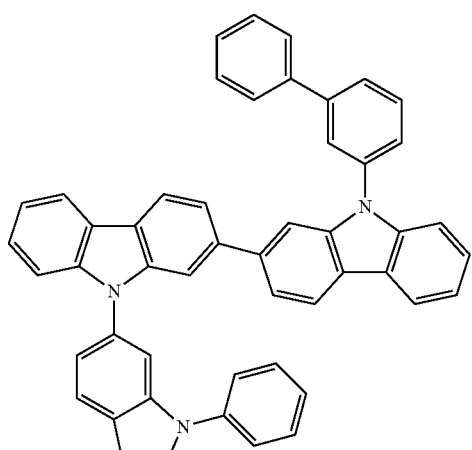

-continued
Compound H17
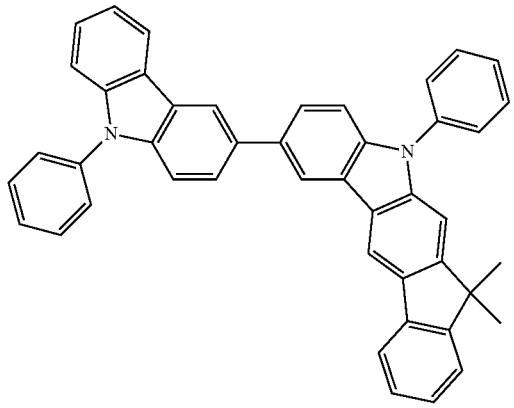
Compound H18
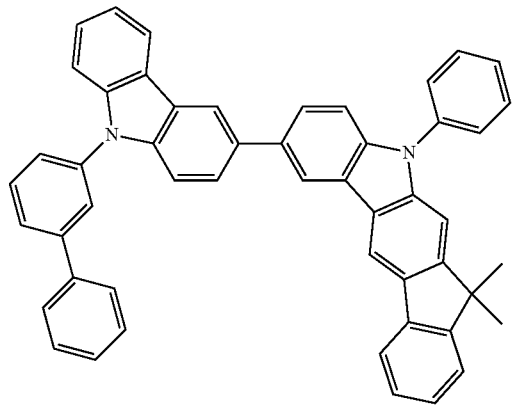
Compound H19
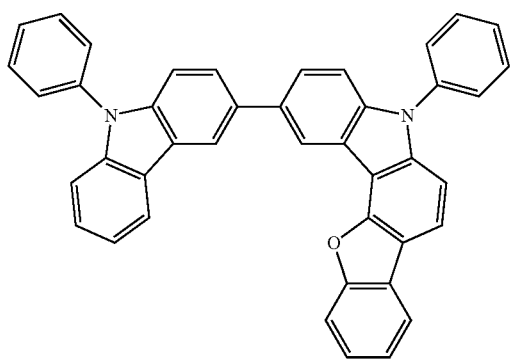
Compound H20
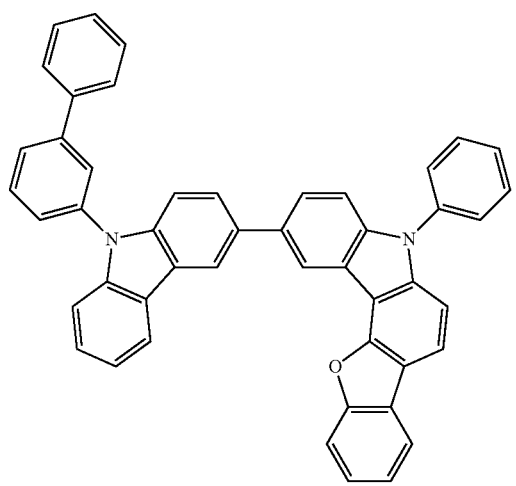
Compound H21
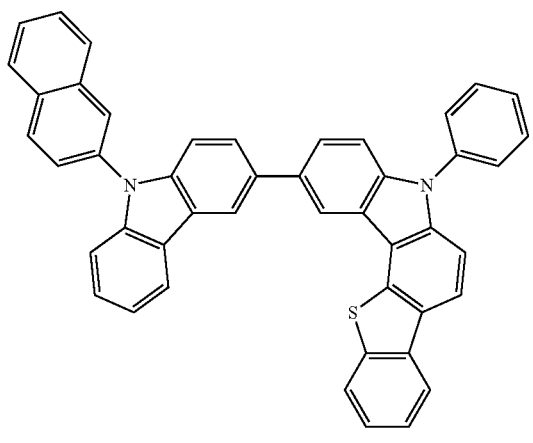
Compound H22
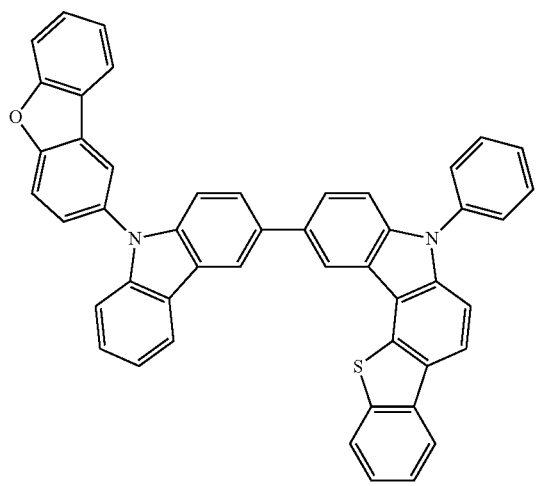

-continued
Compound H23
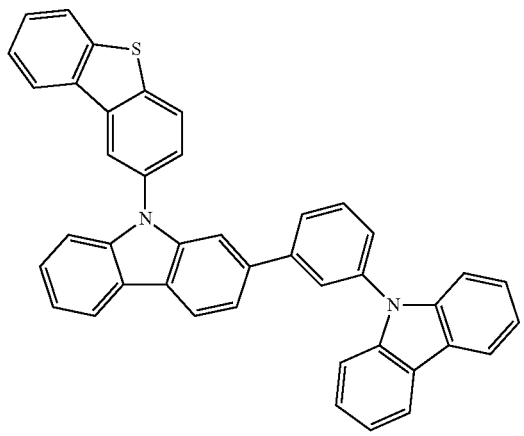
Compound H24
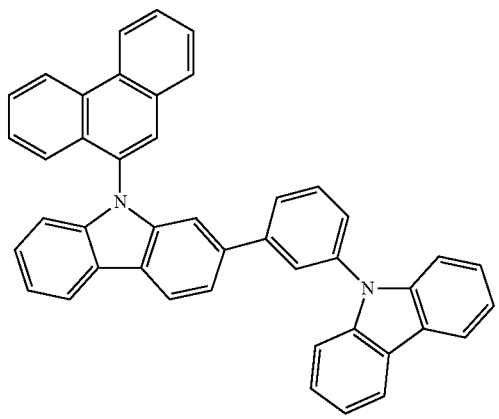
Compound H25
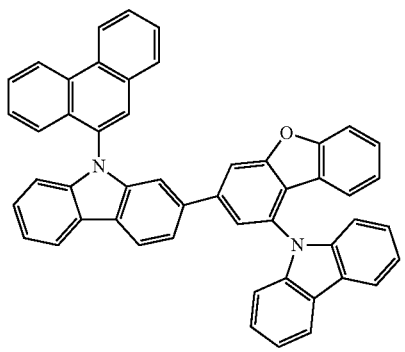
Compound H26
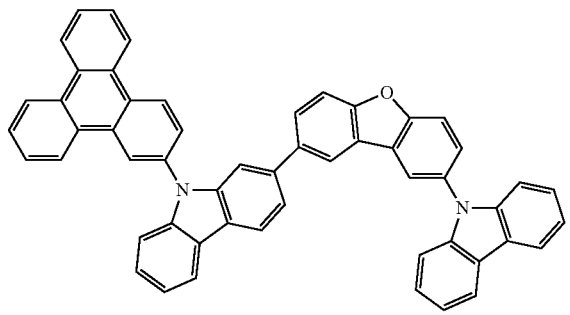
Compound H27
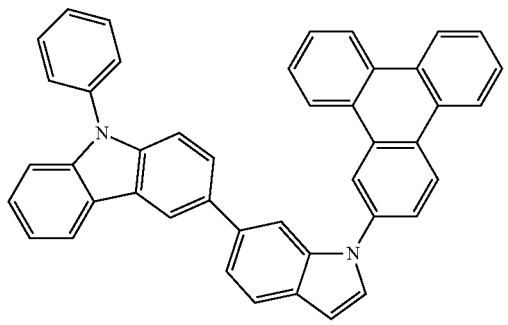
Compound H28
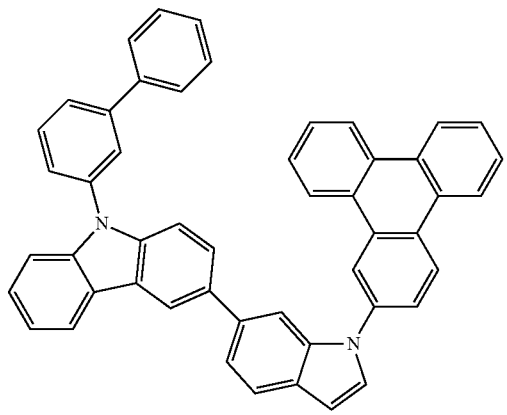

Compound H29
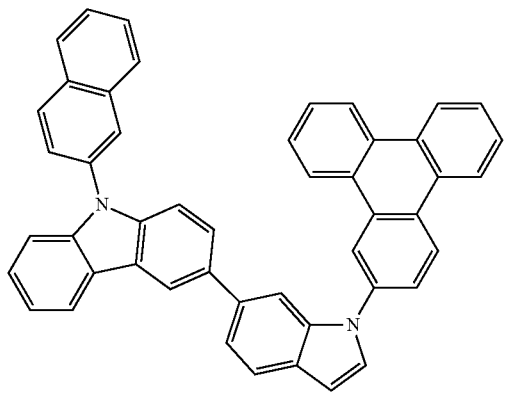
Compound H30
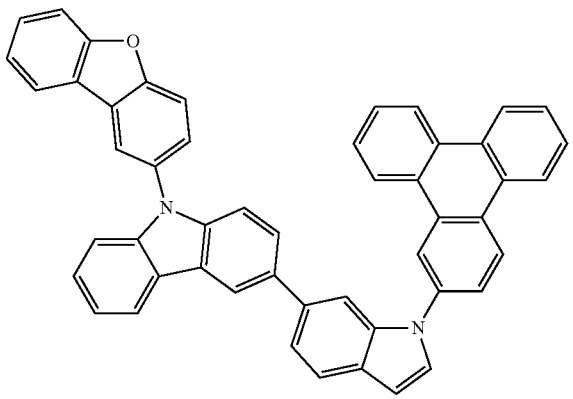
Compound H31
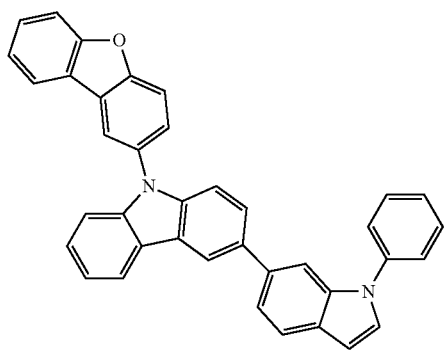
Compound H32
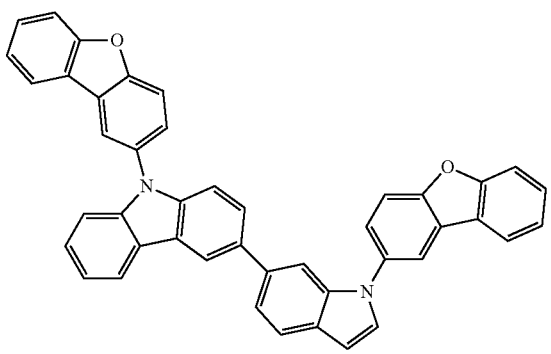
Compound H33
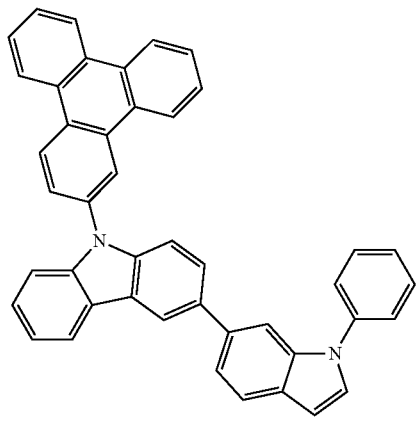
Compound H34
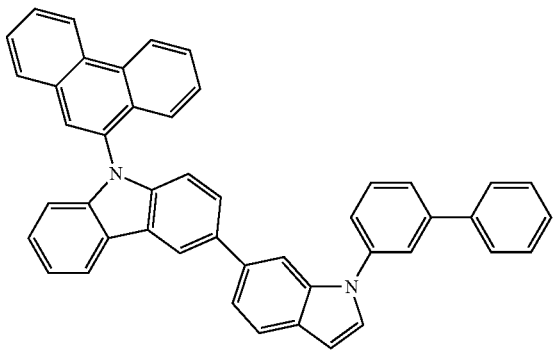
Compound H35
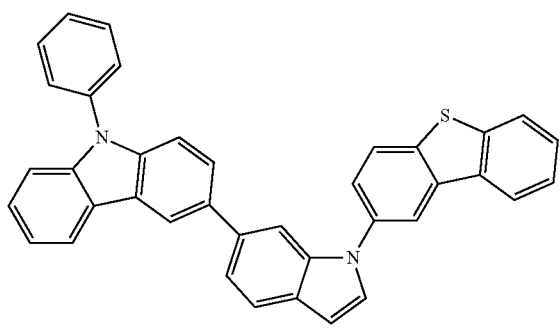
Compound H36
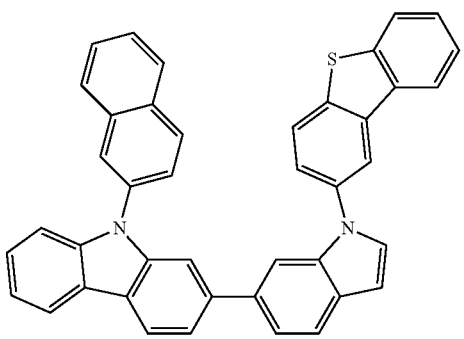

Compound H37
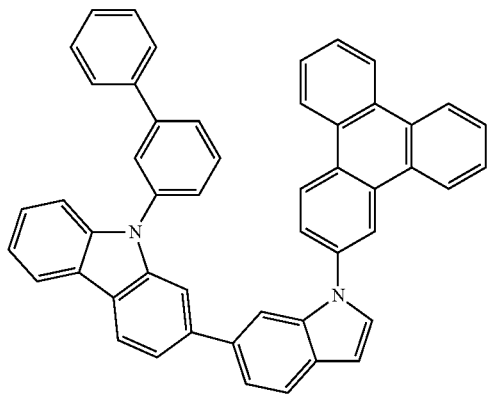
Compound H38
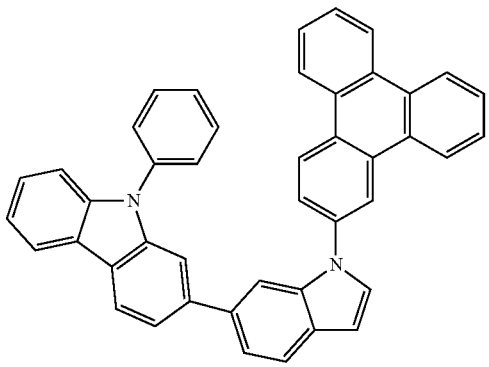
Compound H39
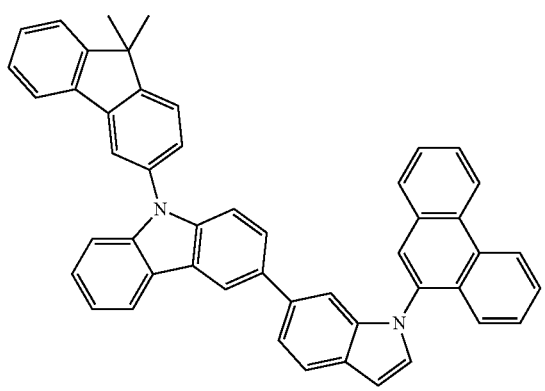
Compound H40
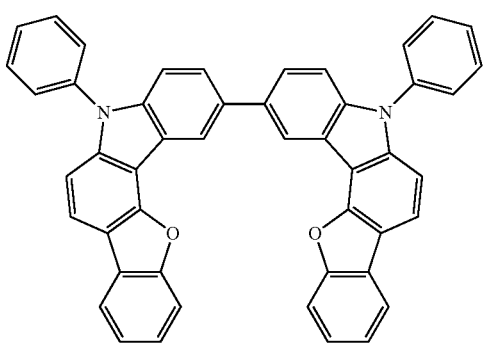
Compound H41
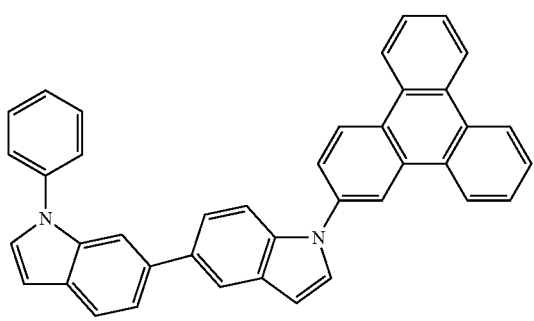
Compound H42
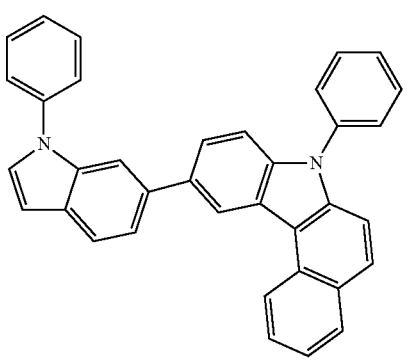
Compound H43
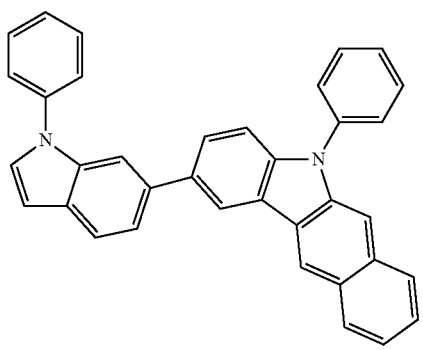
Compound H44
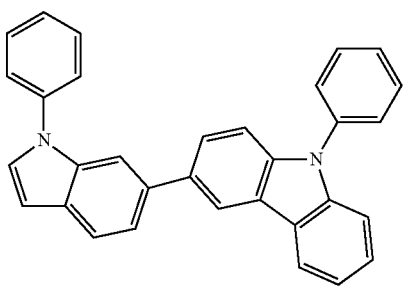

-continued
Compound H45
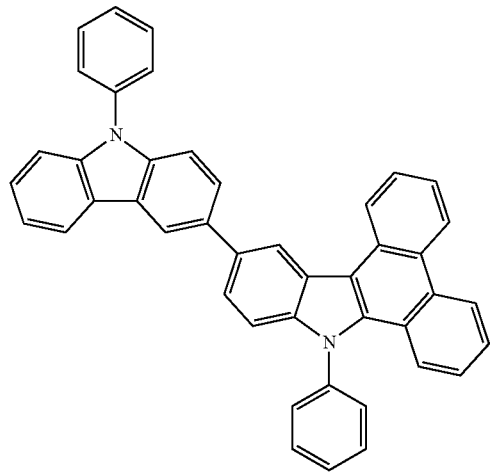
Compound H46
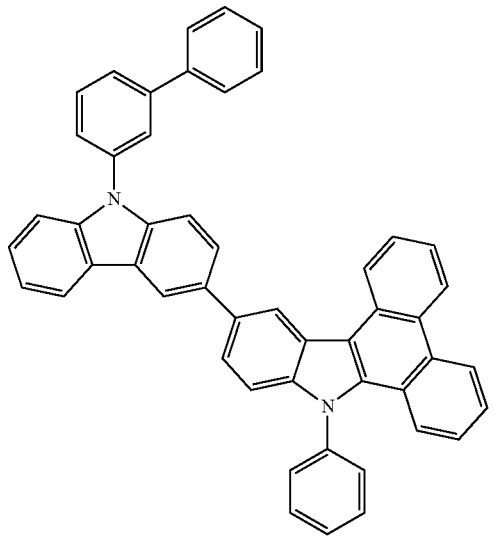
Compound H47
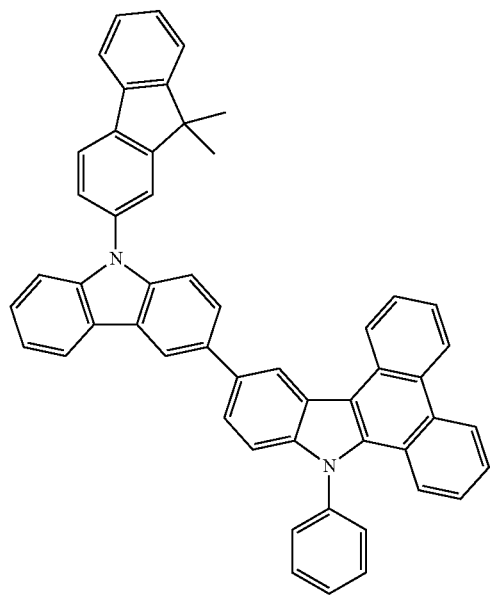
Compound H48
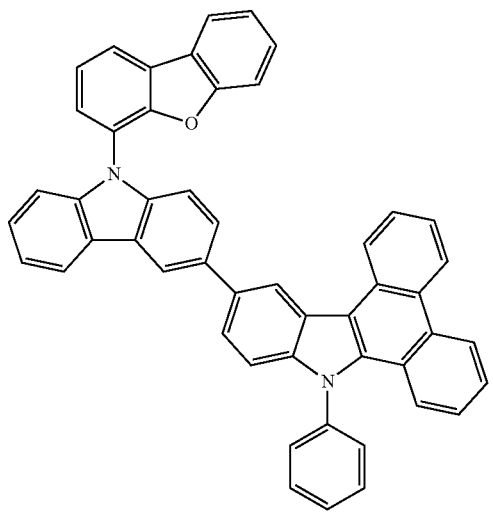
Compound H49
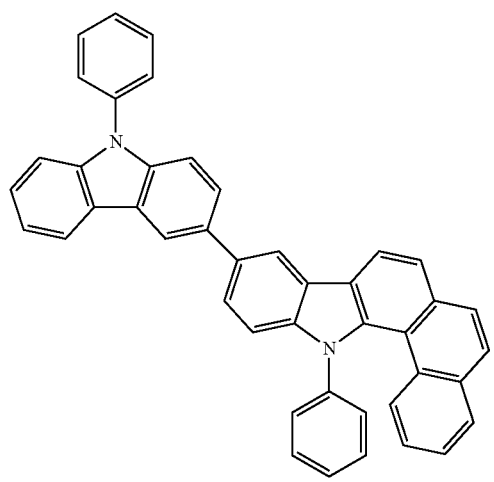
Compound H50
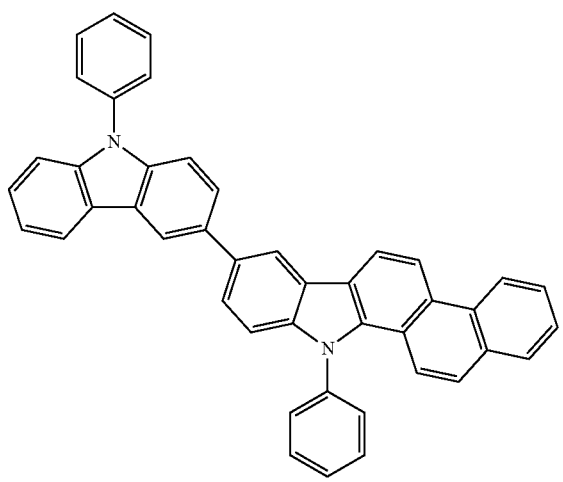

-continued
Compound H51
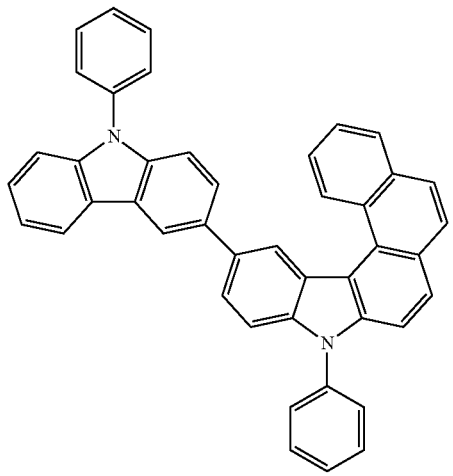
Compound H52
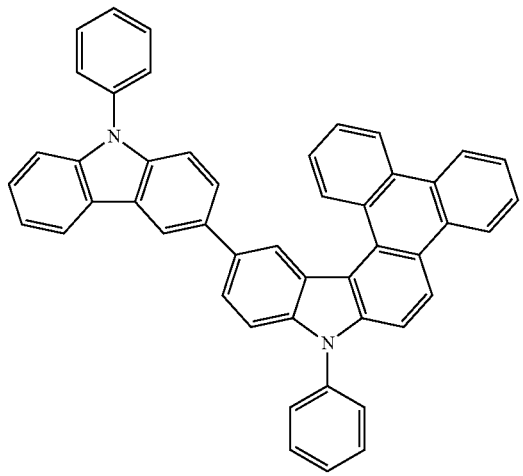
Compound H53
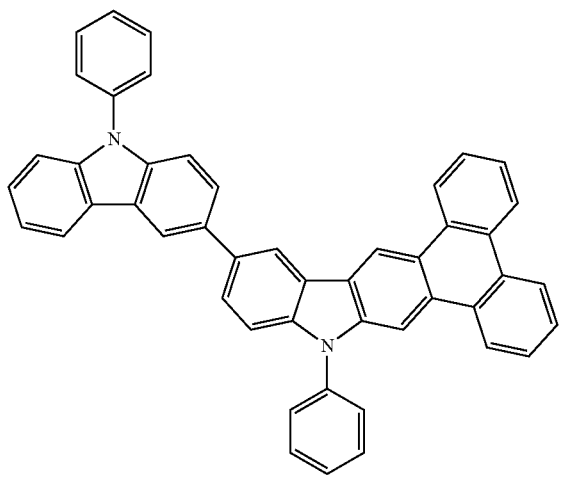
Compound H54
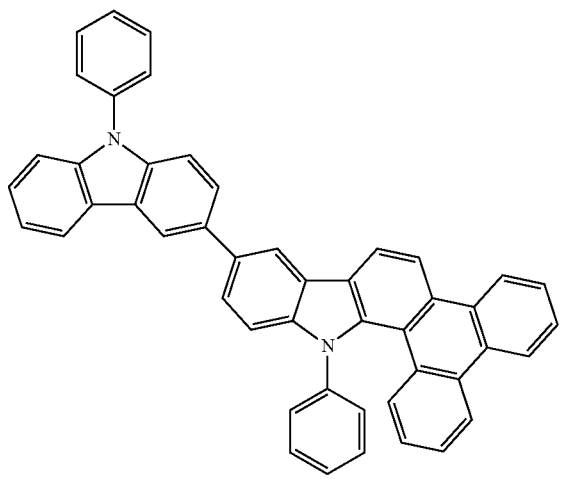
Compound H55
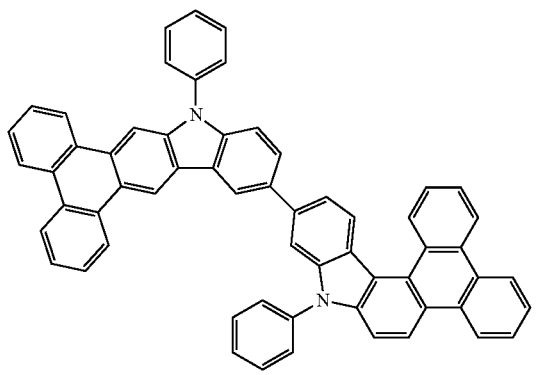
Compound H56
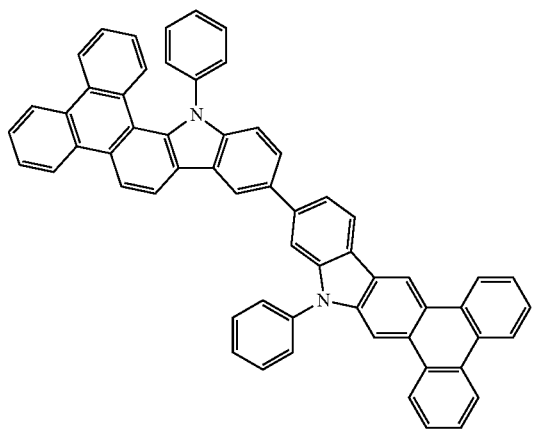

-continued
Compound H57
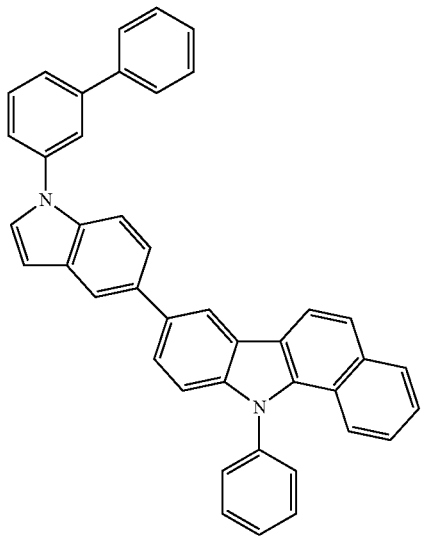
Compound H58
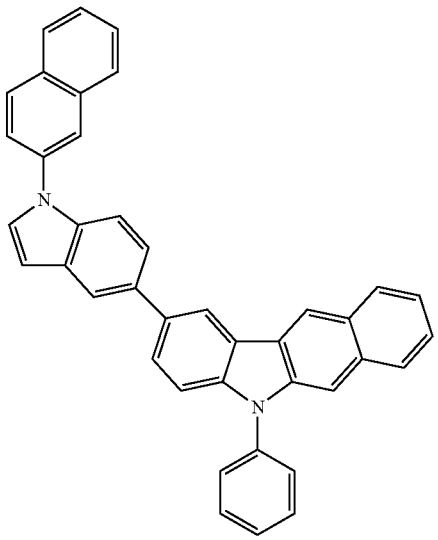
Compound H59
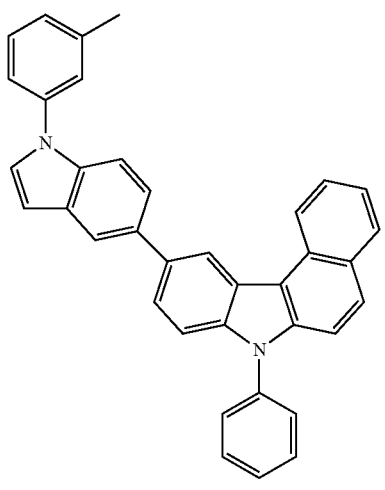
Compound H60
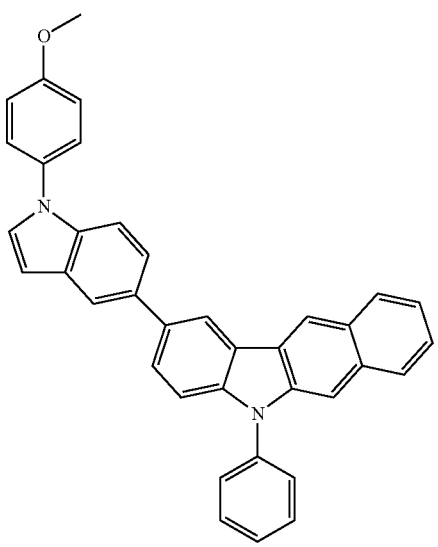
Compound H61
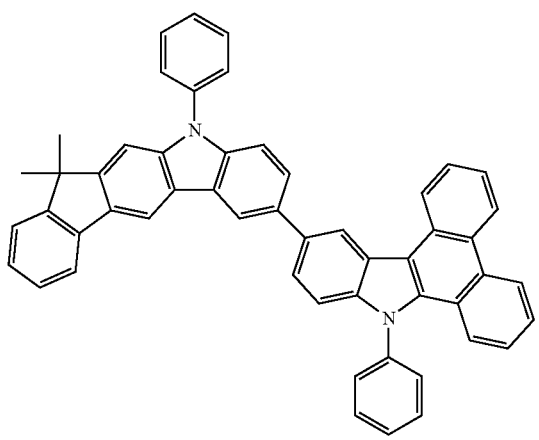
Compound H62
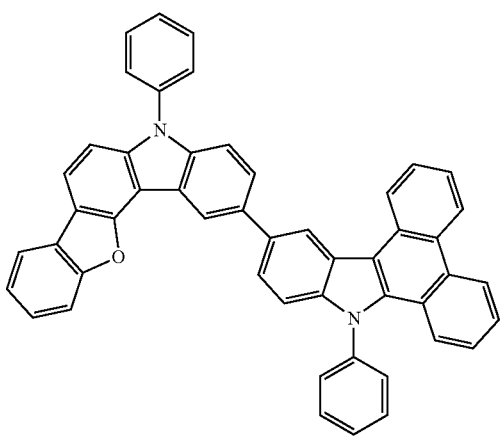

-continued
Compound H63
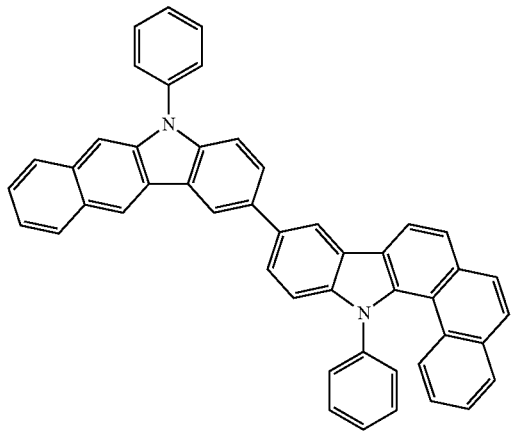
Compound H64
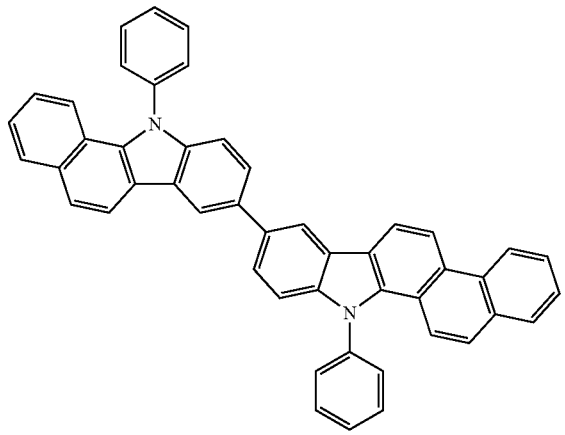
Compound H65
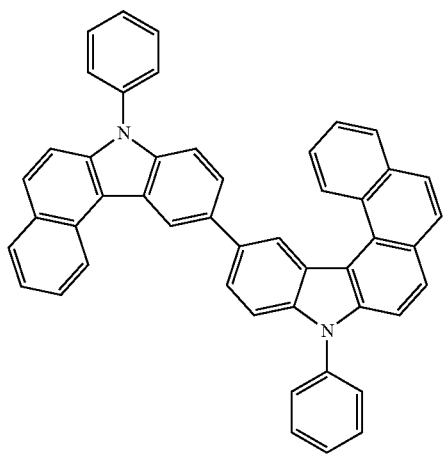
Compound H66
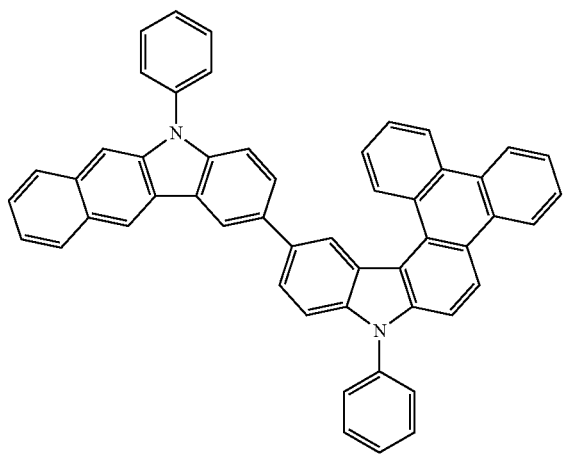
Compound H67
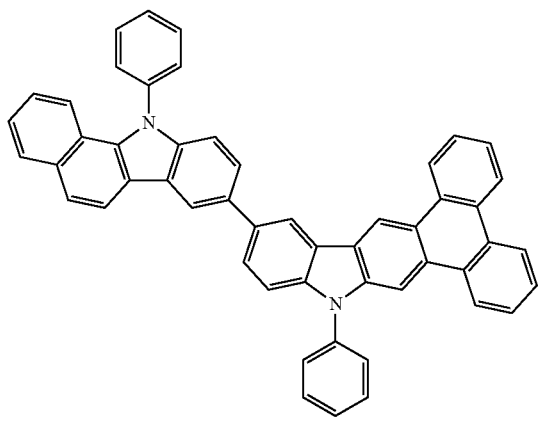
Compound H68
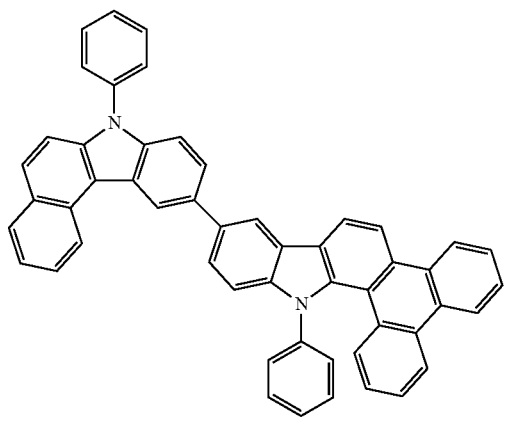

-continued
Compound H69
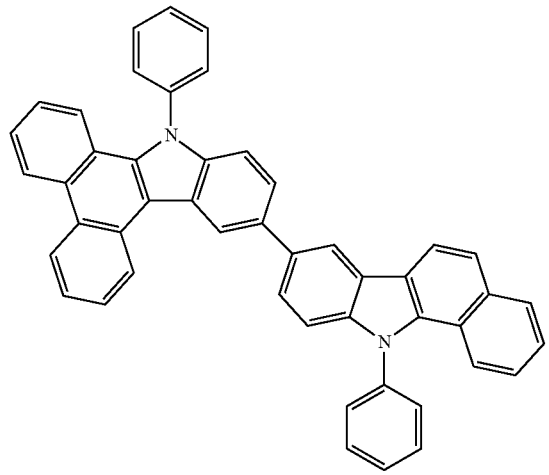
Compound H70
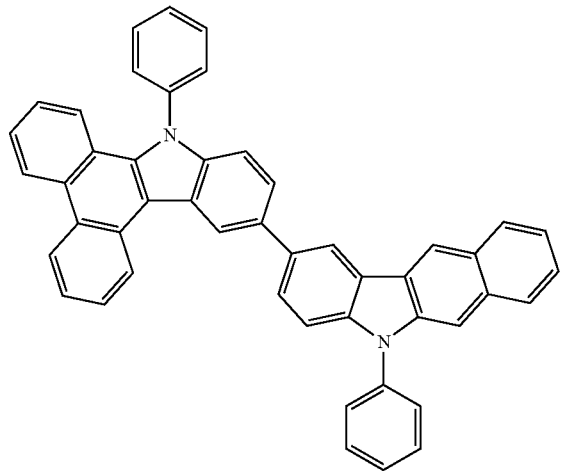
Compound H71
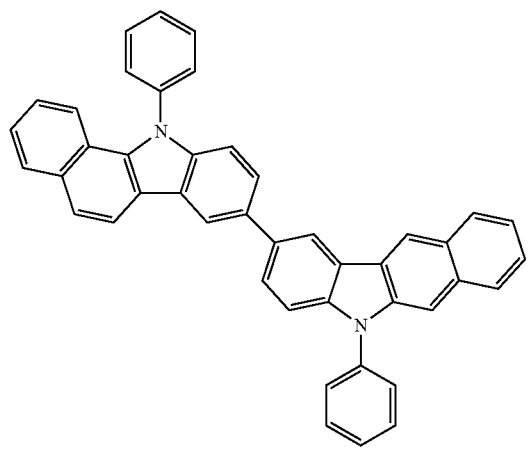
Compound H72
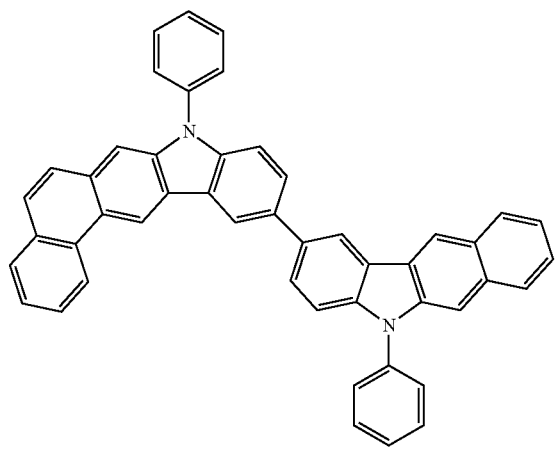
Compound H73
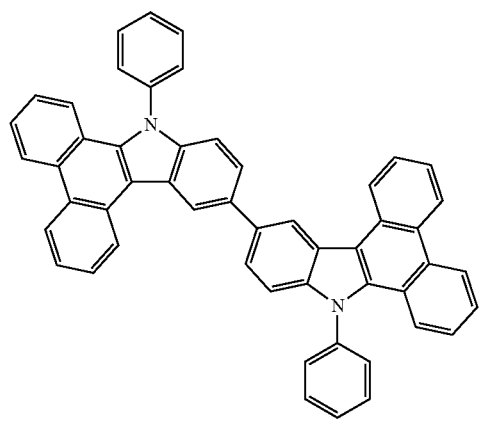
Compound H74
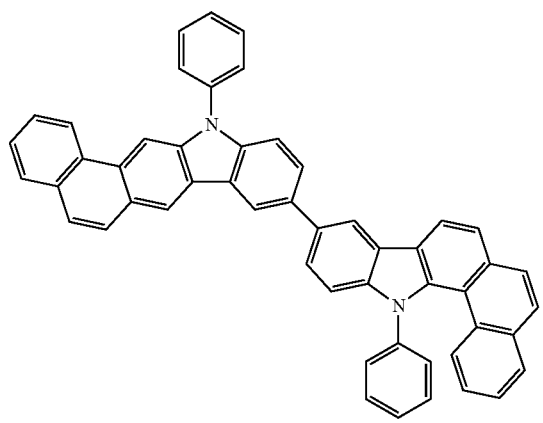

-continued
Compound H75
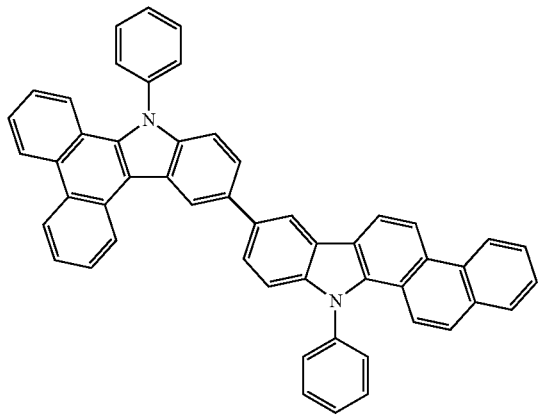
Compound H76
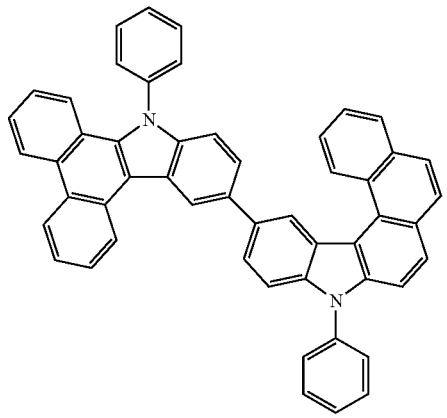
Compound H77
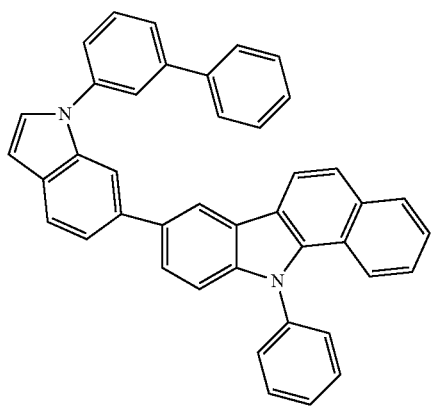
Compound H78
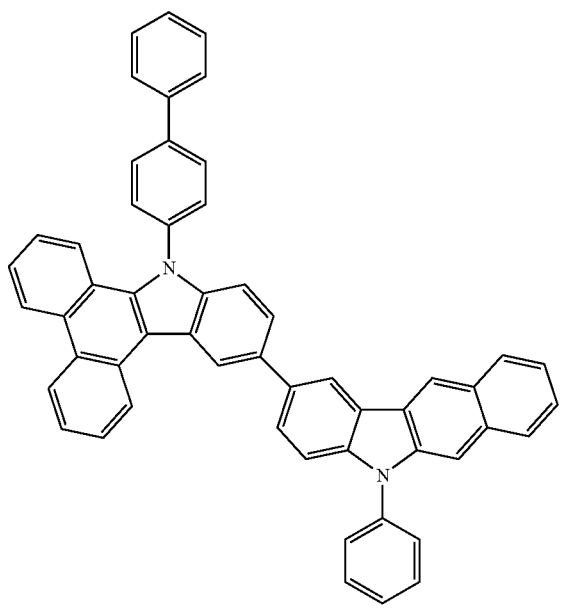
Compound H79
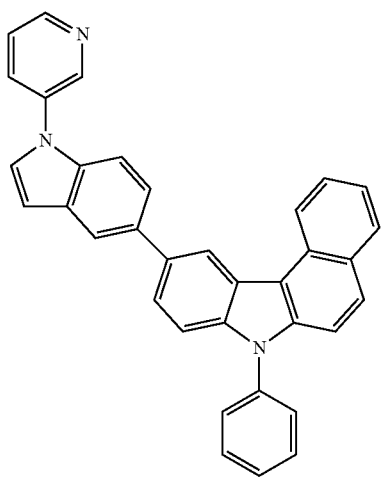
Compound H80
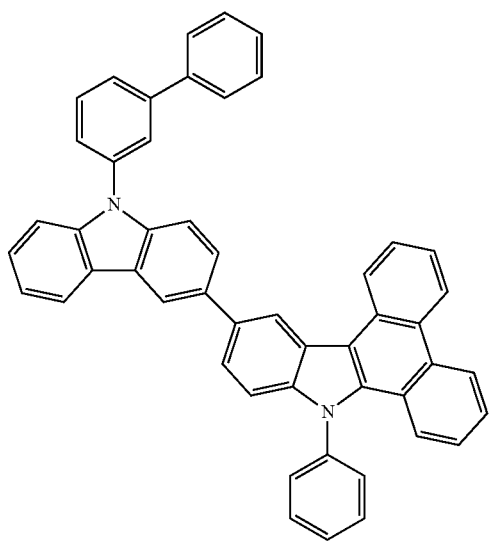

-continued
Compound H81
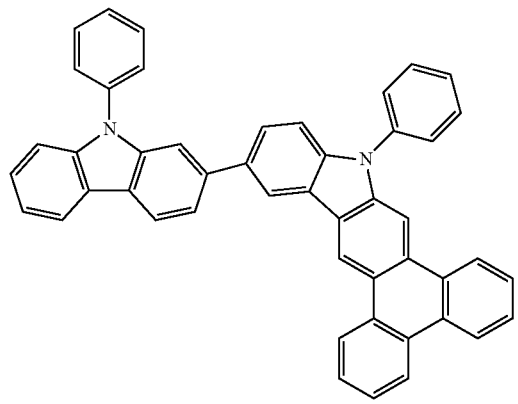
Compound H82
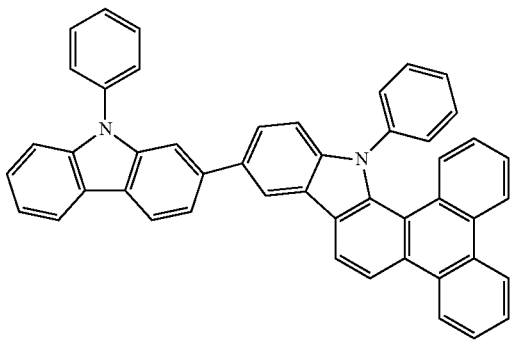
Compound H83
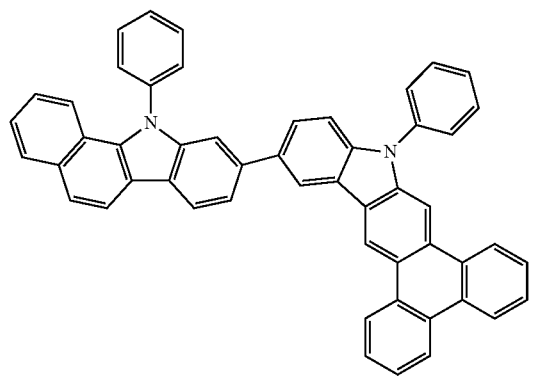
Compound H84
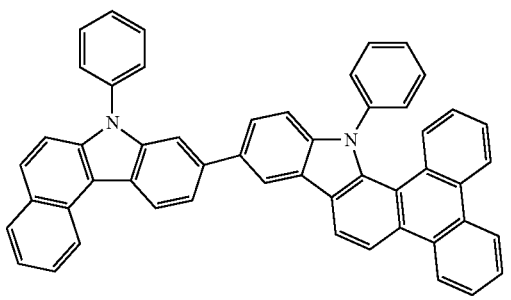
Compound H85
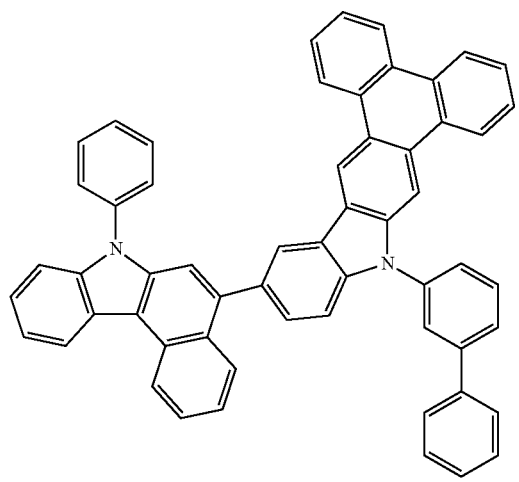
Compound H86
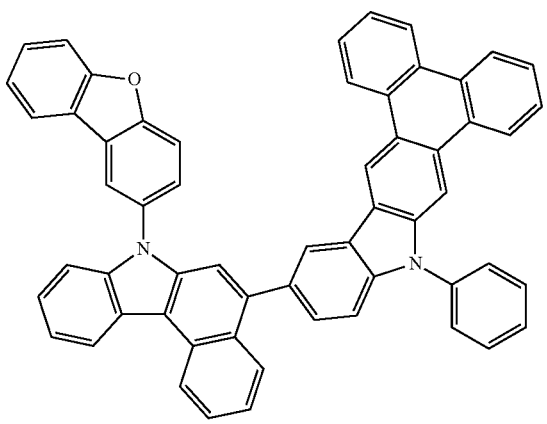

-continued
Compound H87
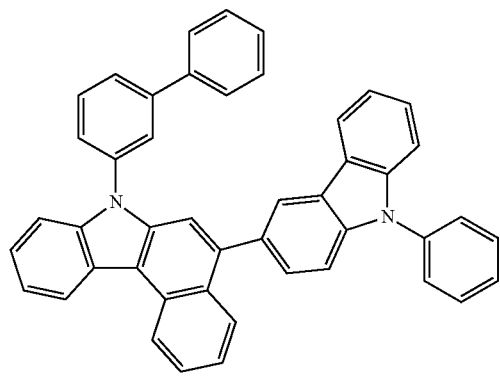
Compound H88
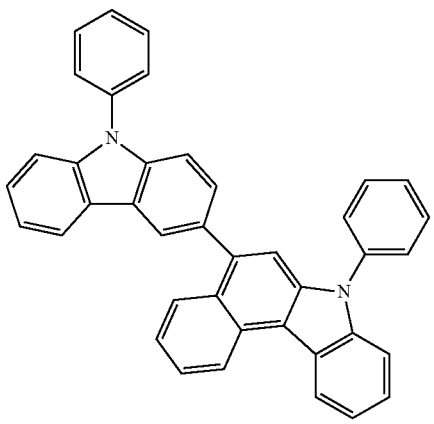
Compound H89
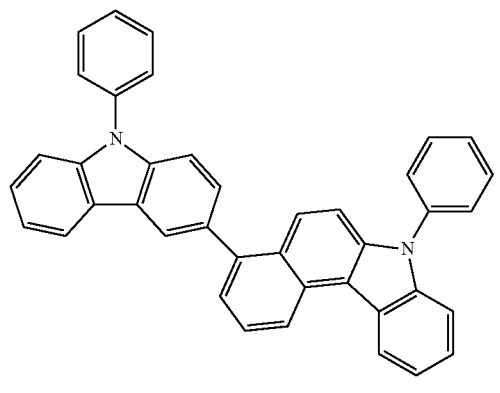
Compound H90
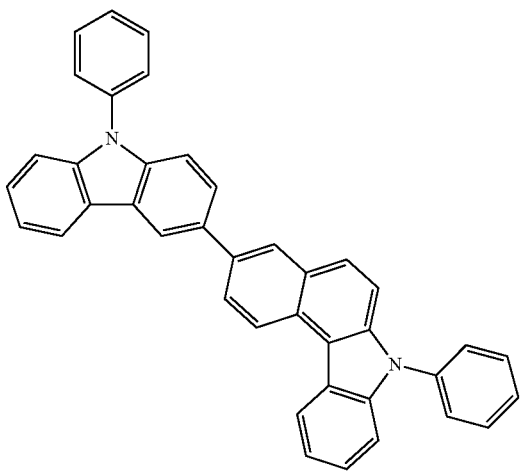
Compound H91
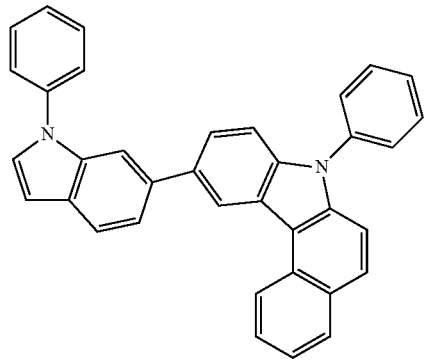
Compound H92
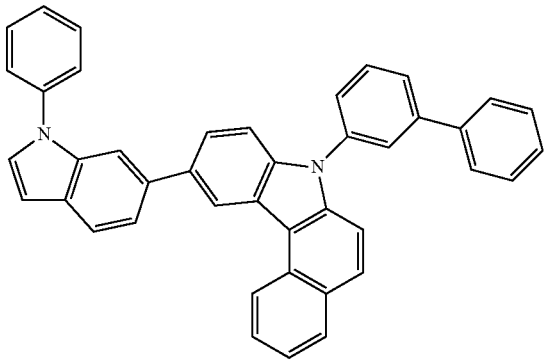

-continued
Compound H93
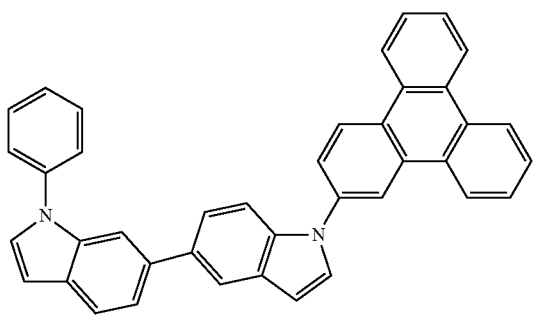
Compound H94
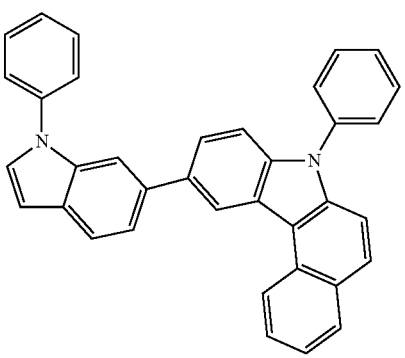
Compound H95
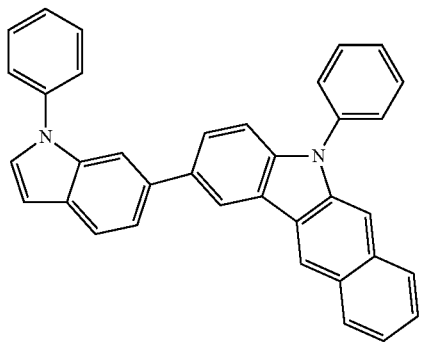
Compound H96
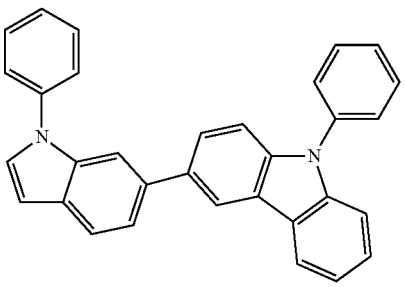
Compound H97
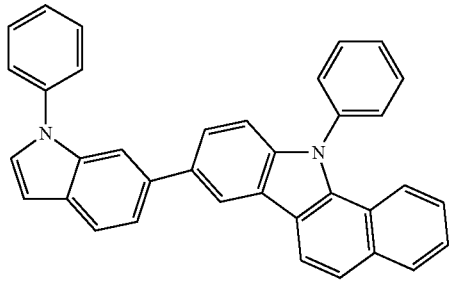
Compound H98
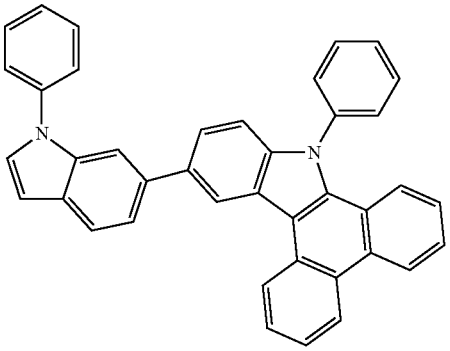
Compound H99
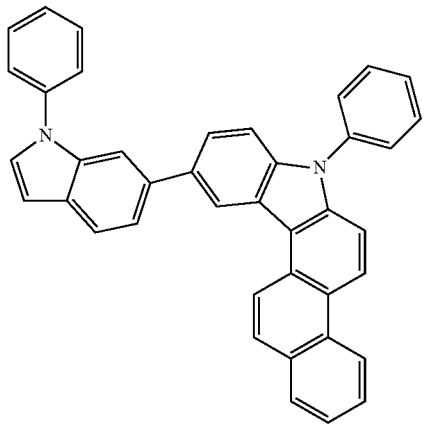
Compound H100
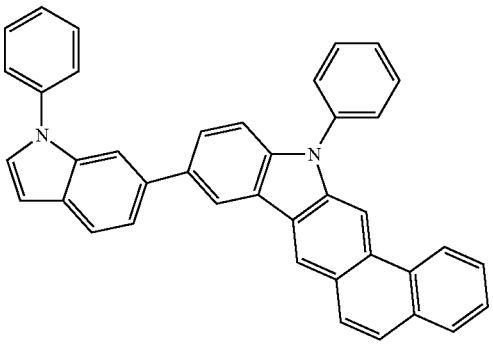

-continued
Compound H101
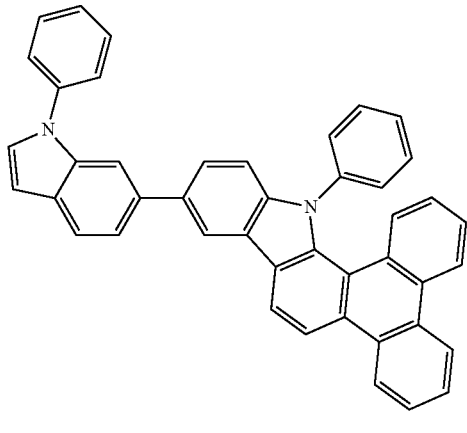
Compound H102
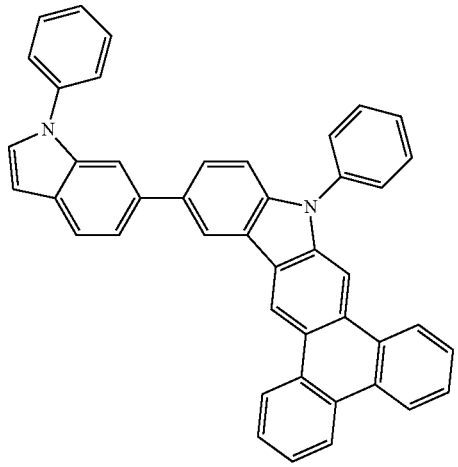
Compound H103
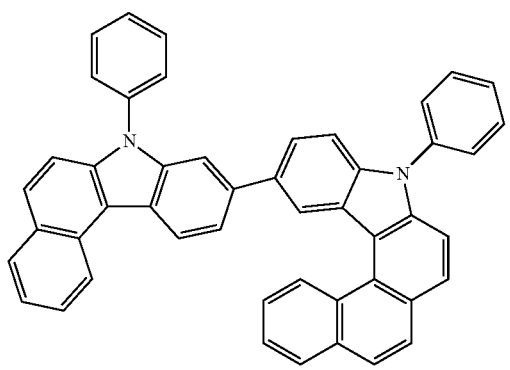
Compound H104
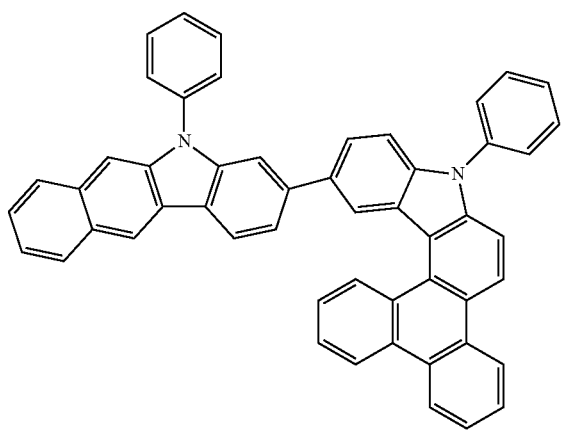
Compound H105
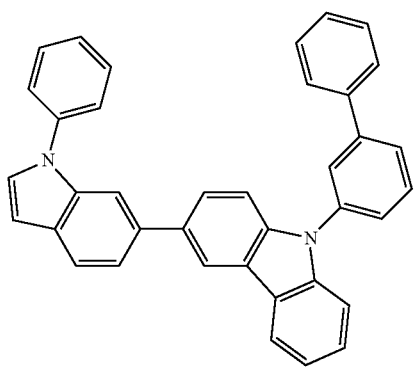
Compound H106
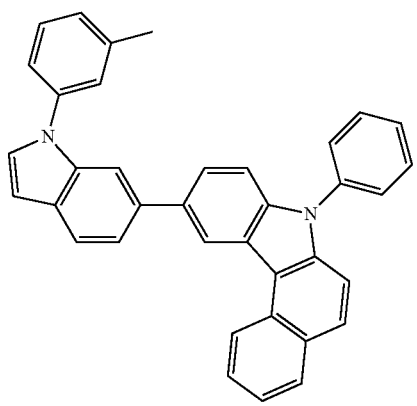

-continued
Compound H107
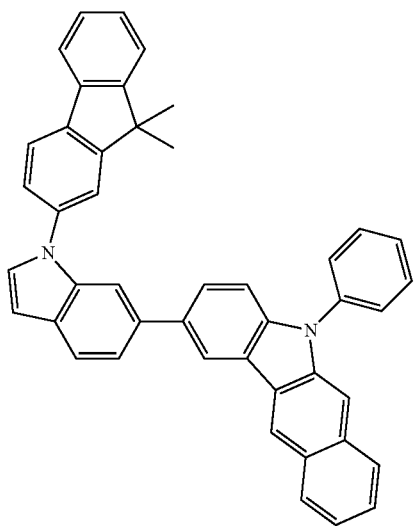
Compound H108
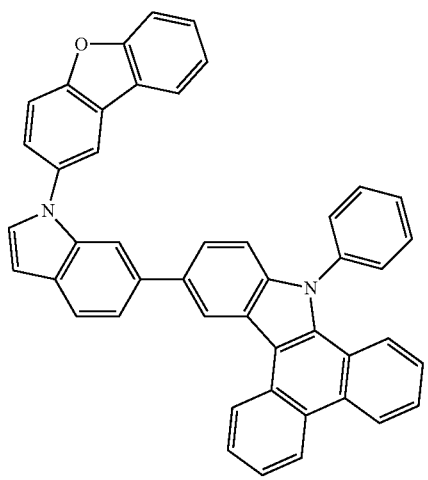
Compound H109
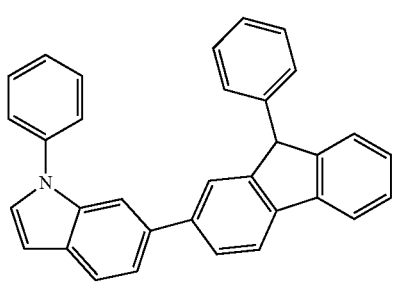
Compound H110
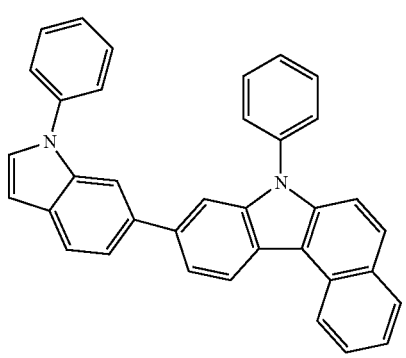
Compound H111
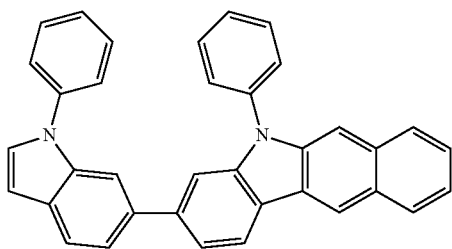
Compound H112
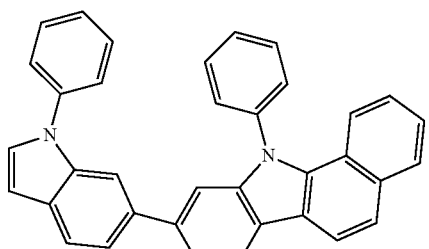

-continued
Compound H113
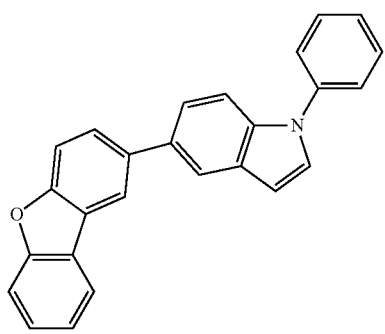
Compound H114
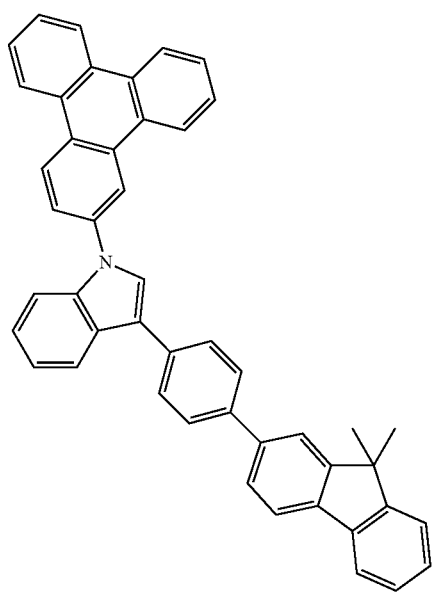
Compound H115
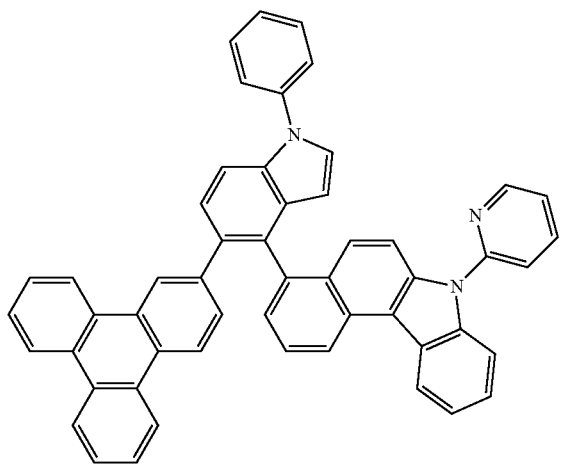
Compound H116
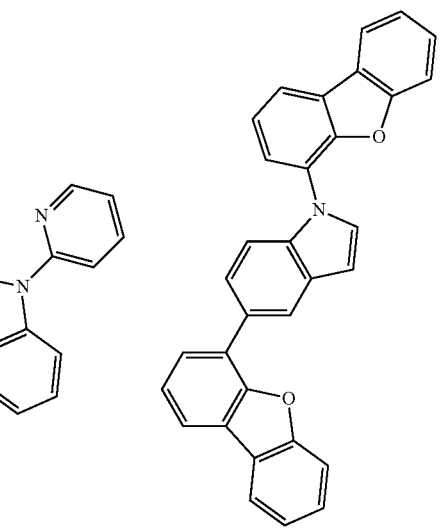
Compound H117
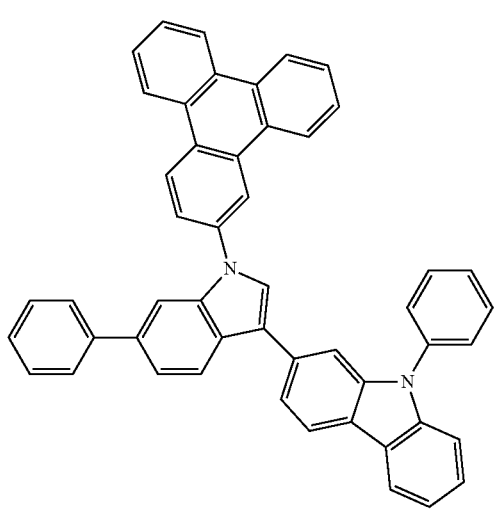
Compound H118
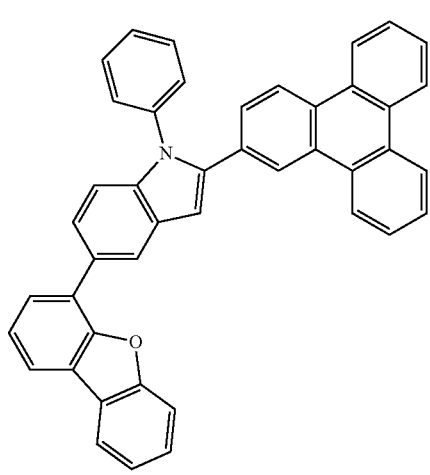

-continued
Compound H119
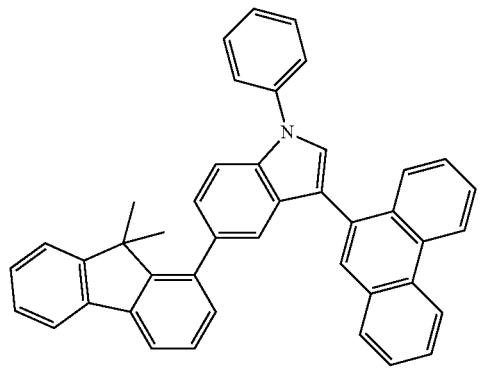
Compound H120
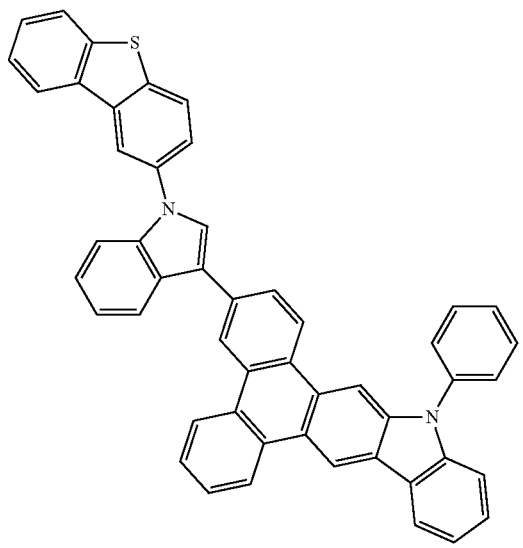
Compound H121
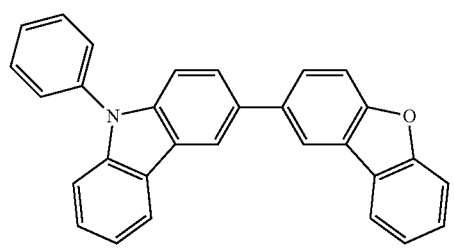
Compound H122
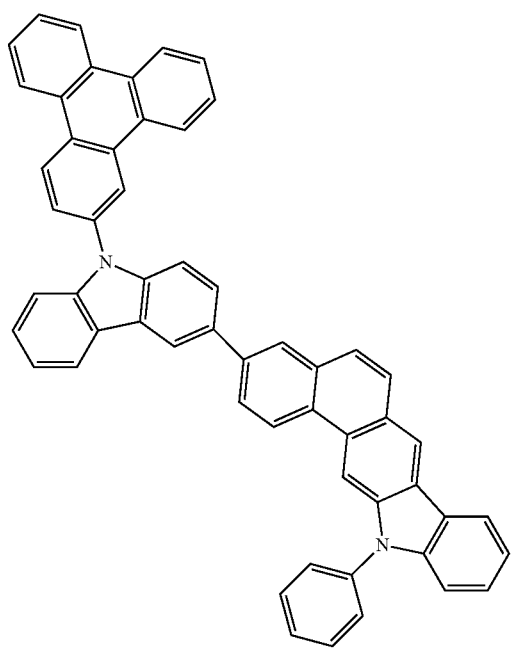

-continued
Compound H123
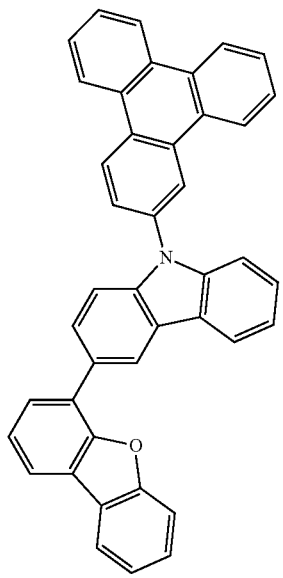
Compound H124
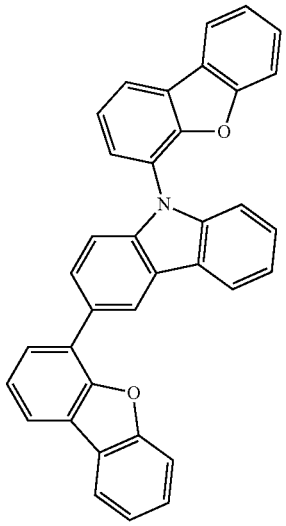
Compound H125
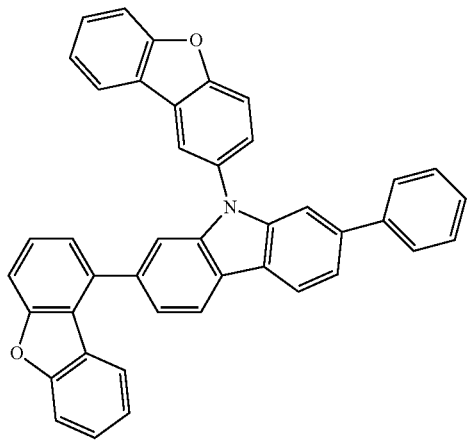
Compound H126
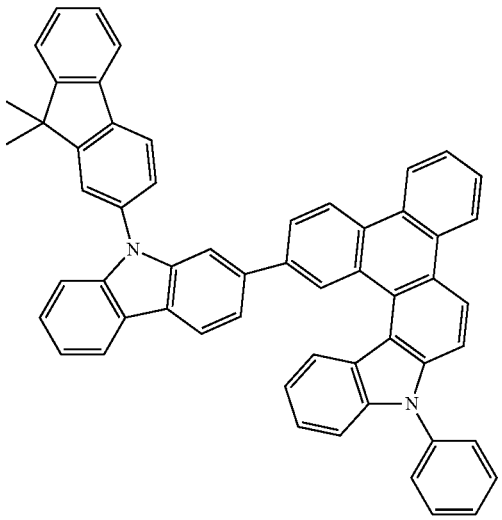
Compound H127
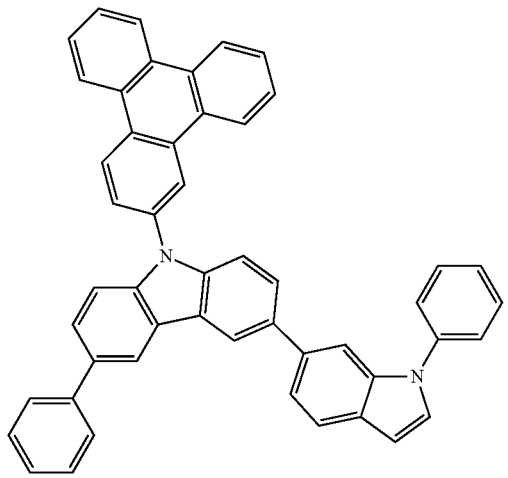
Compound H128
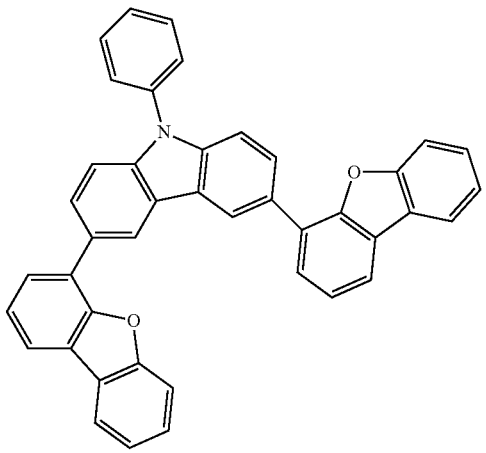

-continued
Compound H129
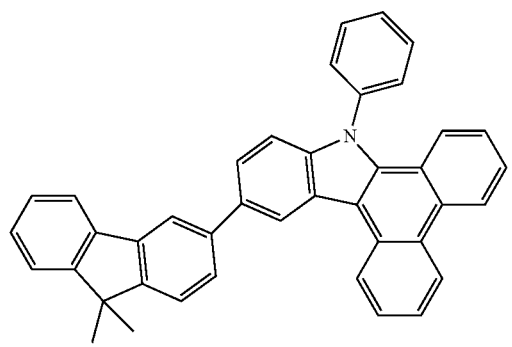
Compound H130
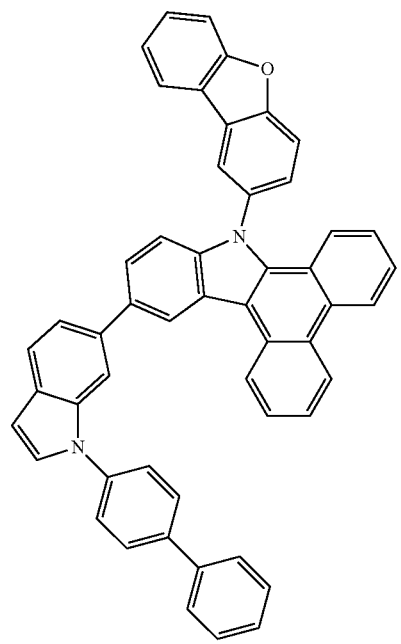
Compound H131
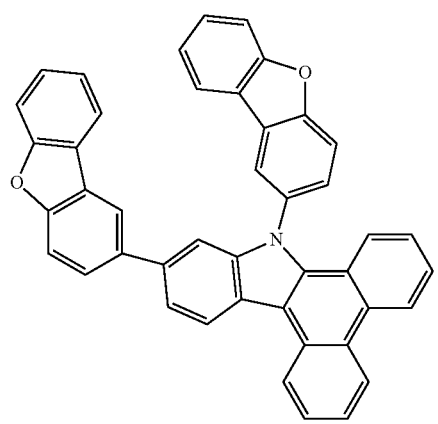
Compound H132
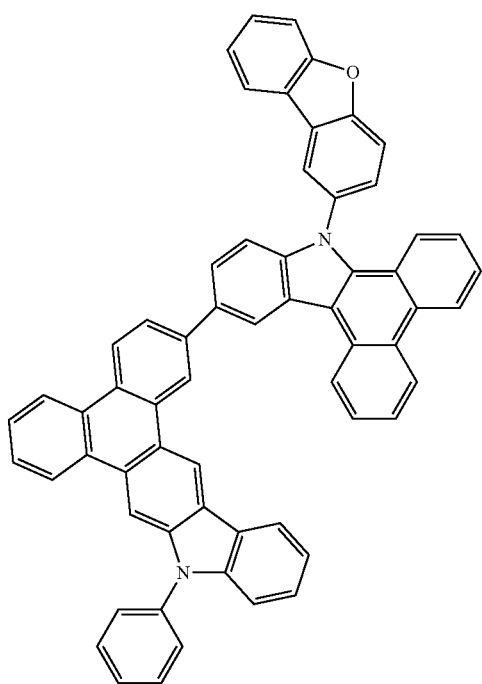

-continued
Compound H133
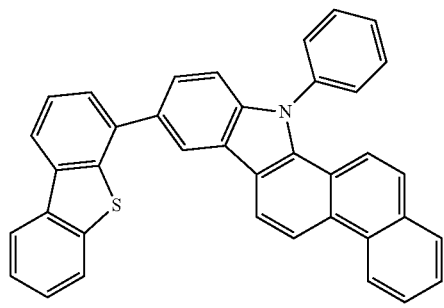
Compound H134
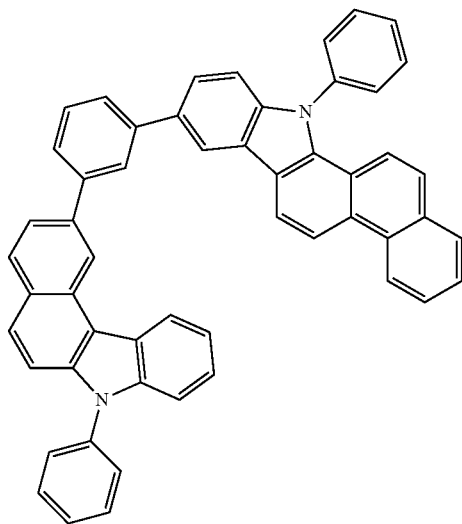
Compound H135
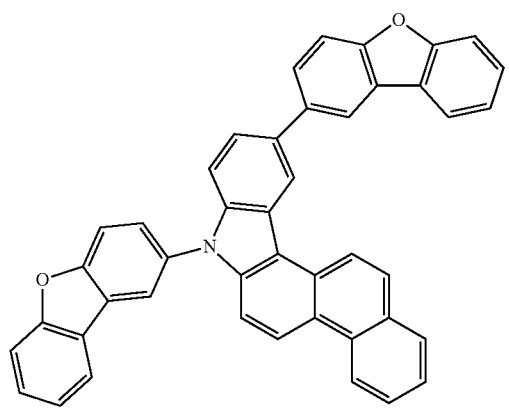
Compound H136
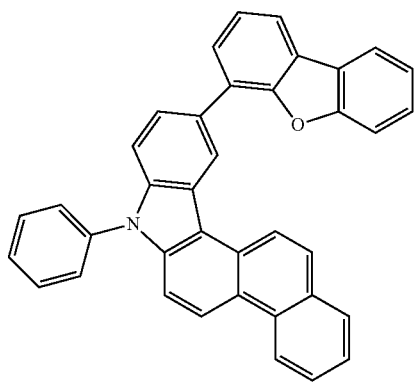
Compound H137
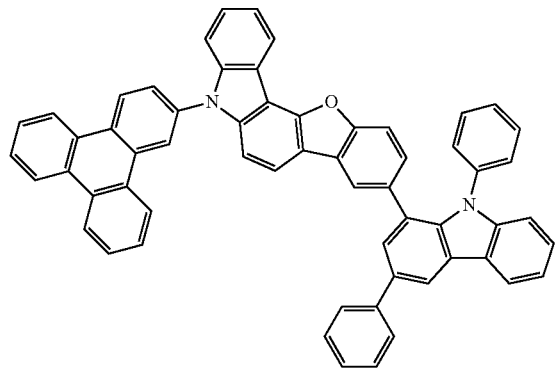
Compound H138
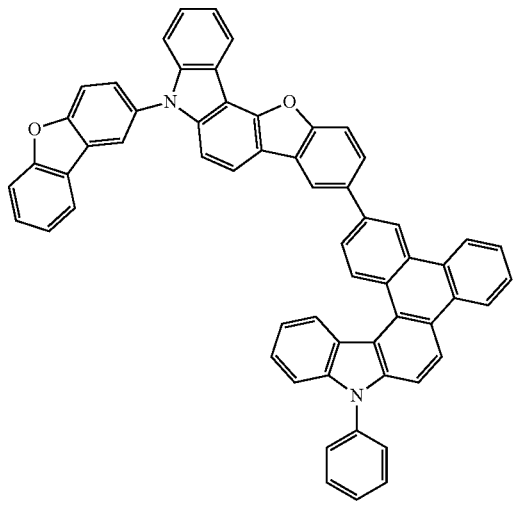

Compound H139
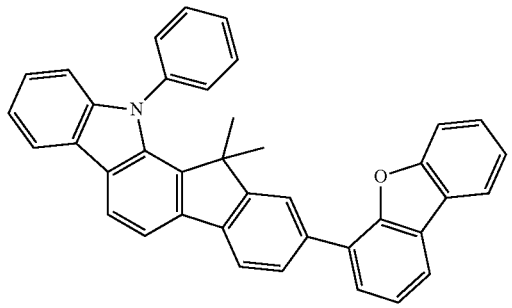
Compound H140
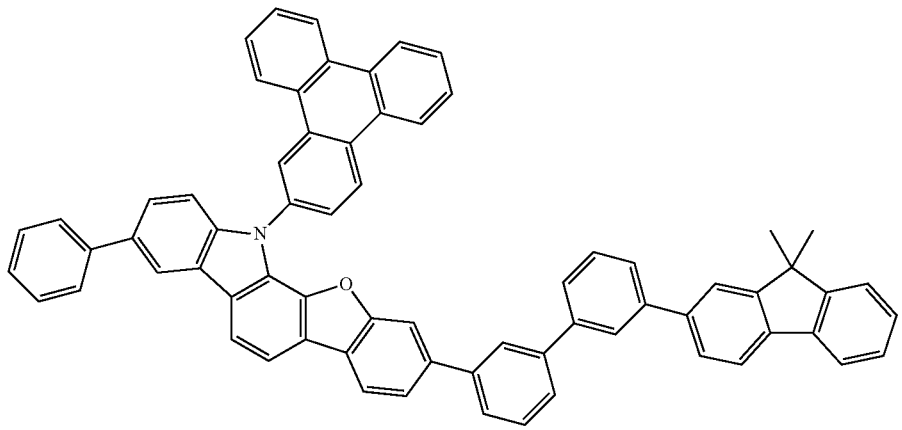
Compound H141
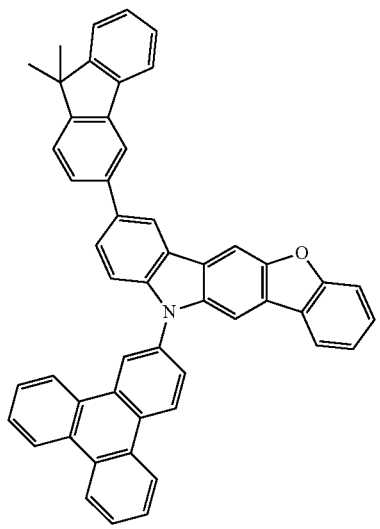
Compound H142
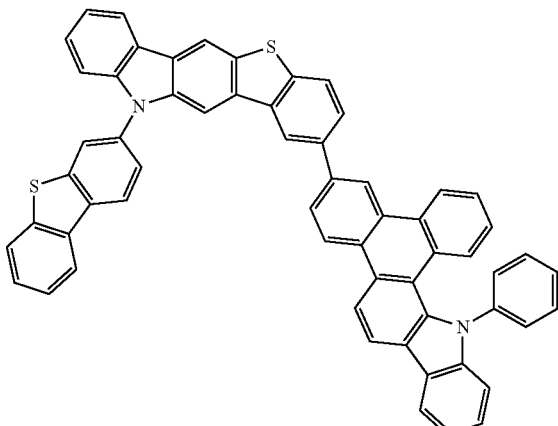
Compound H143
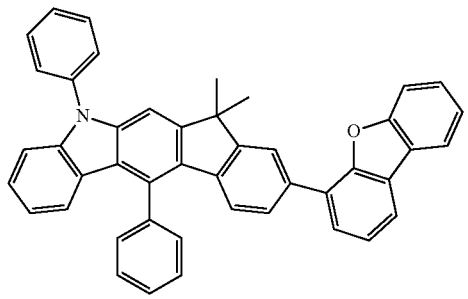
Compound H144
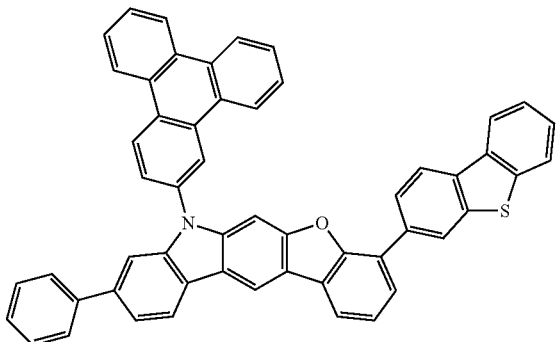

-continued
Compound H145
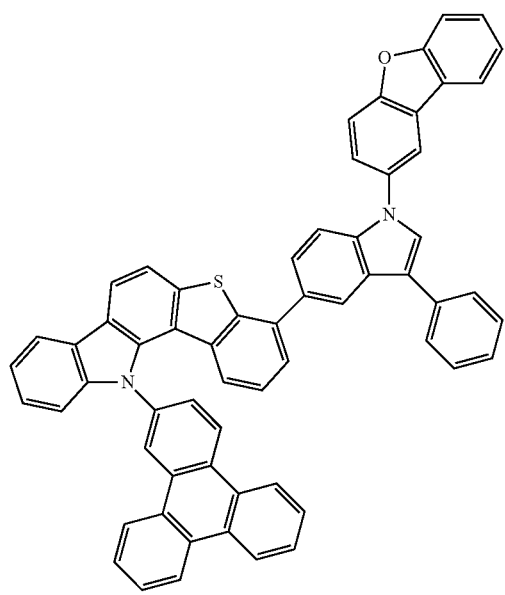
Compound H146
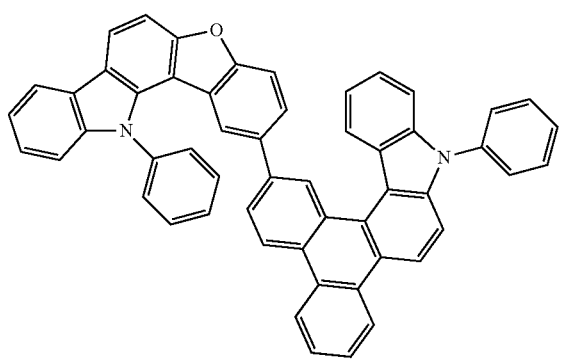
Compound H147
Compound H148
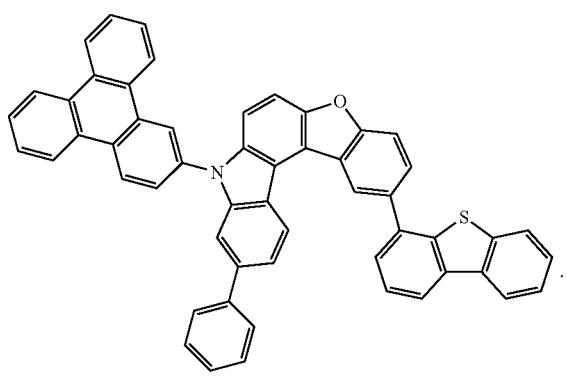
10. An organic light emitting compound selected from Compounds E1 to E412:
Compound E1
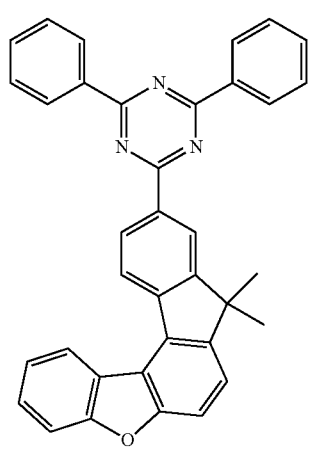
-continued
Compound E2
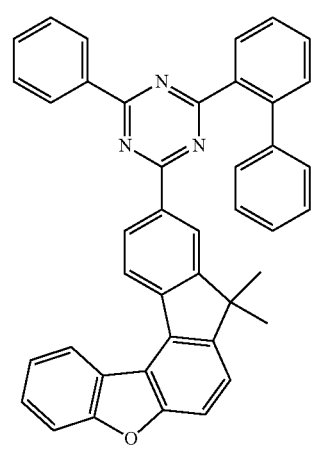

Compound E3
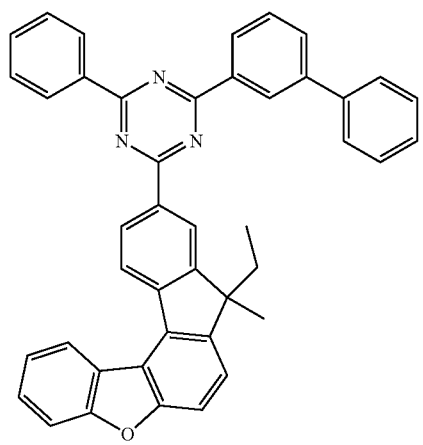
Compound E6
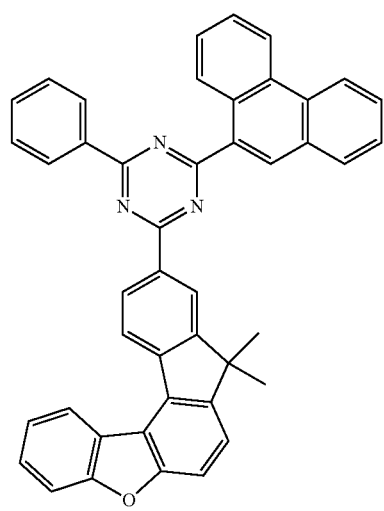
Compound E4
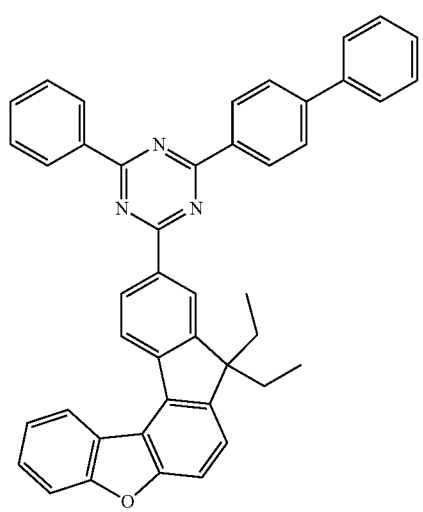
Compound E7
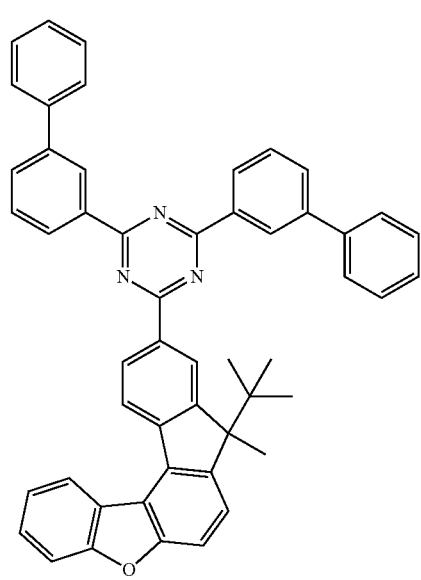
Compound E5
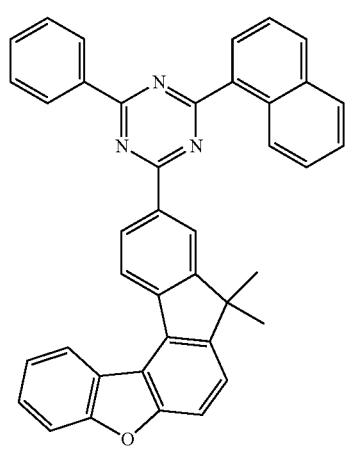
Compound E8
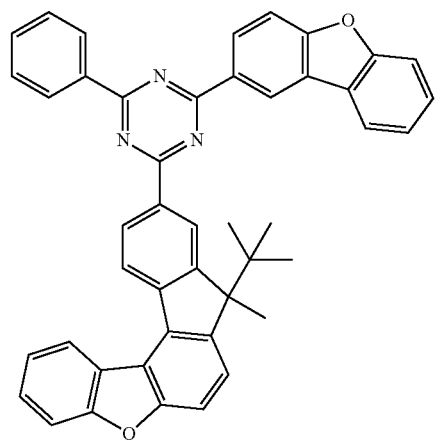

Compound E9
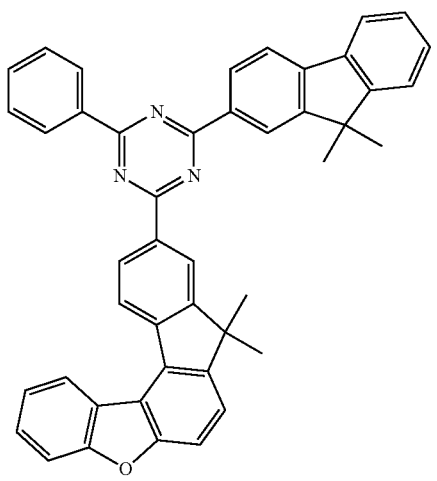
Compound E10
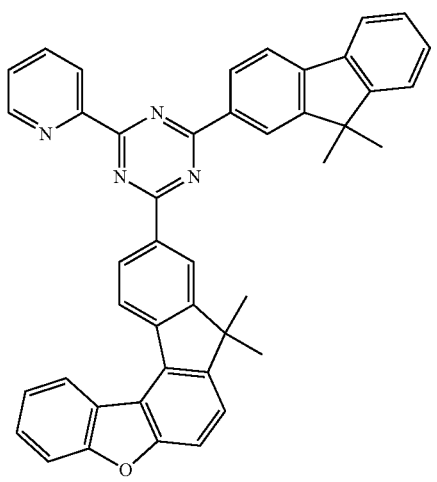
Compound E11
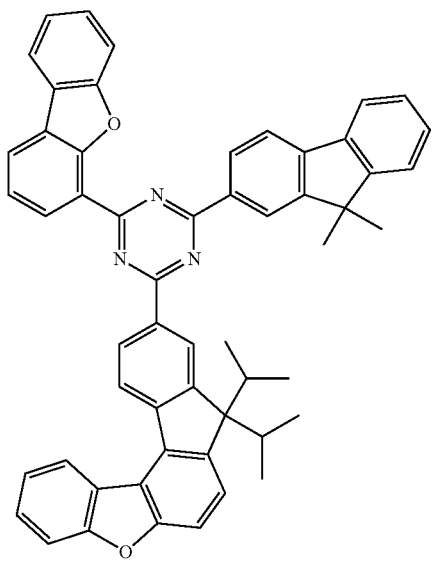
Compound E12
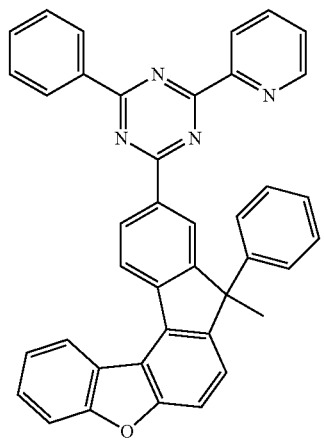
Compound E13
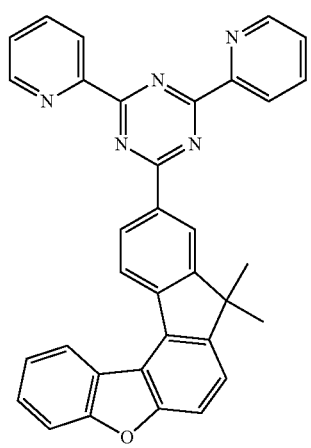
Compound E14
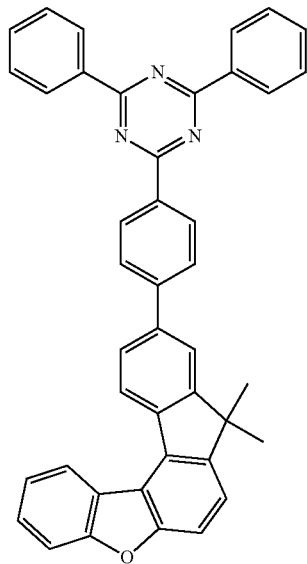

Compound E15
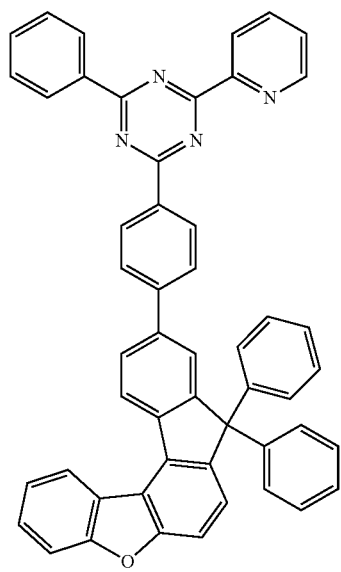
Compound E18
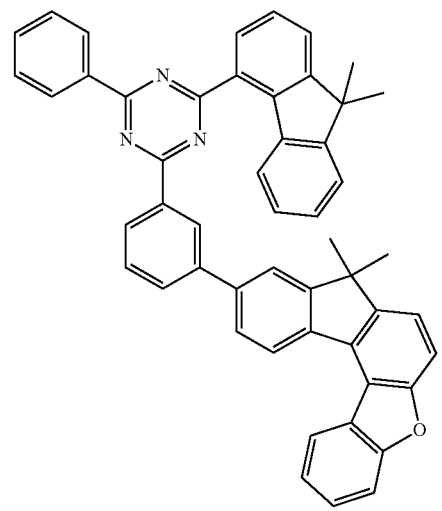
Compound E16
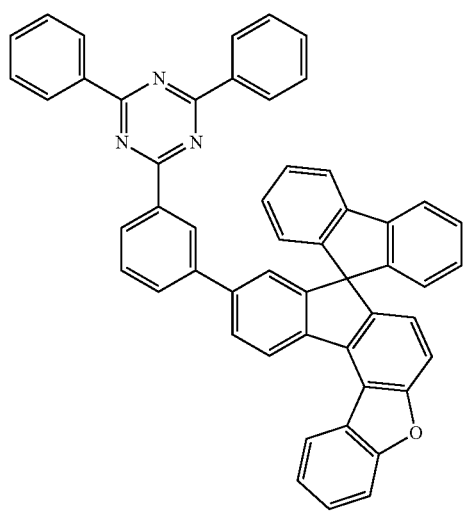
Compound E19
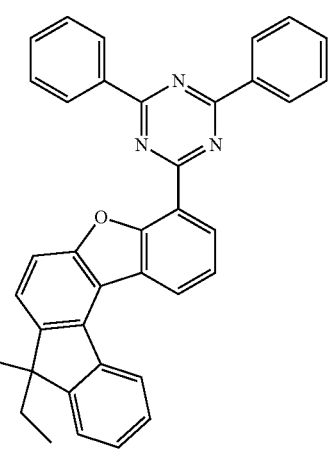
Compound E17
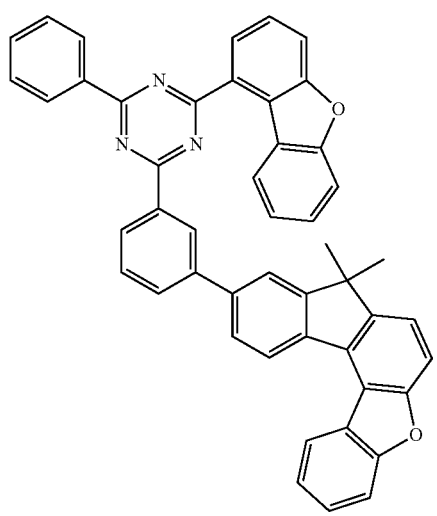
Compound E20
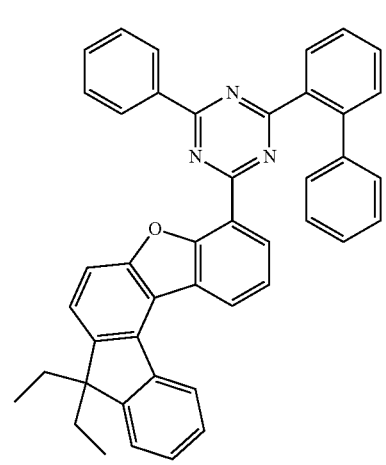

Compound E21
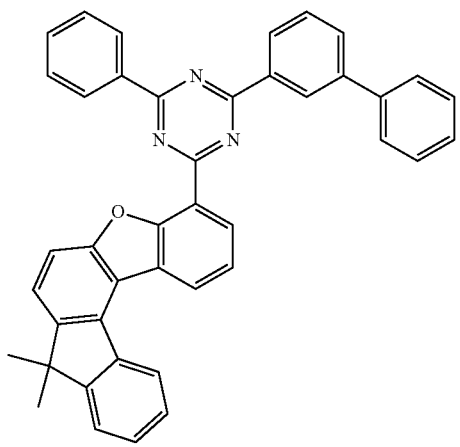
Compound E22
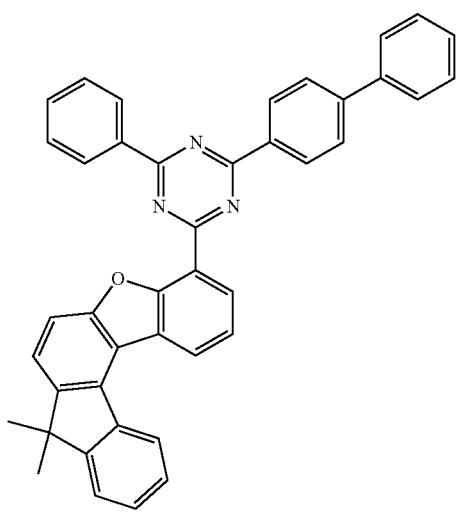
Compound E23
Compound E24
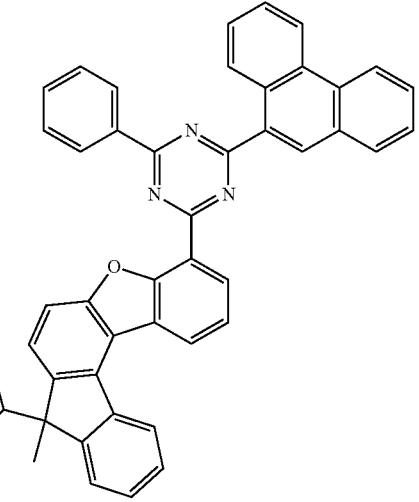
Compound E25
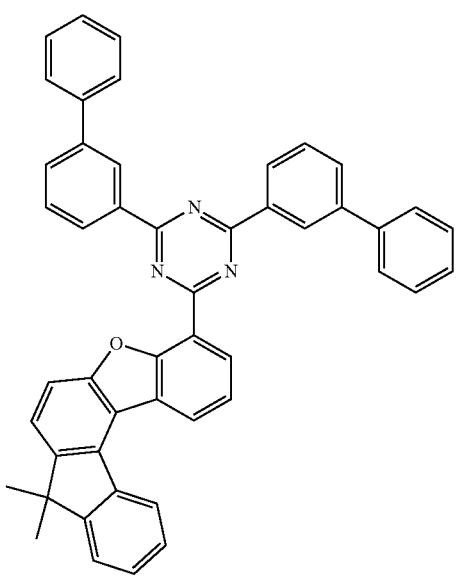
Compound E26
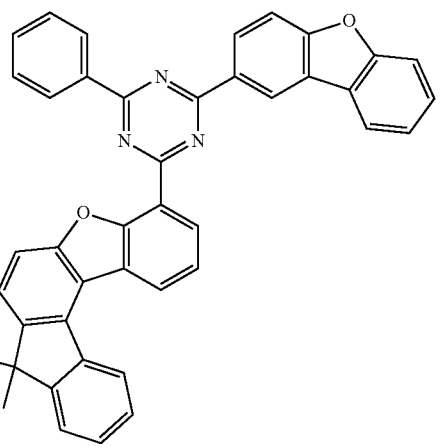

Compound E27
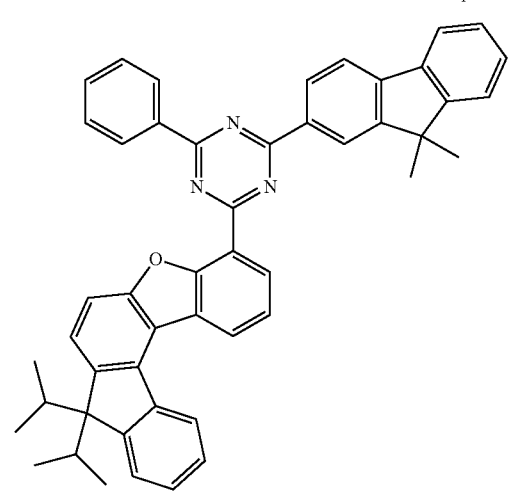
Compound E28
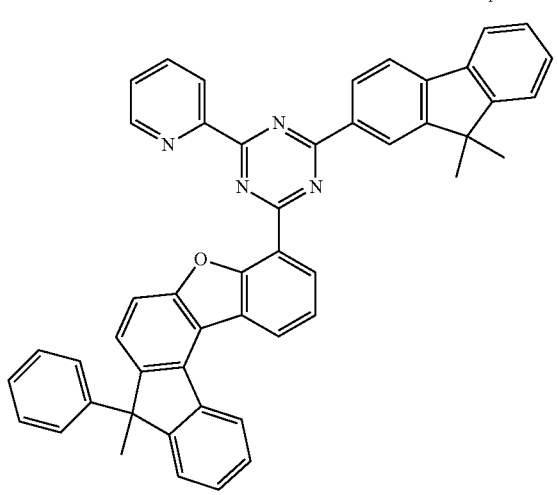
Compound E29
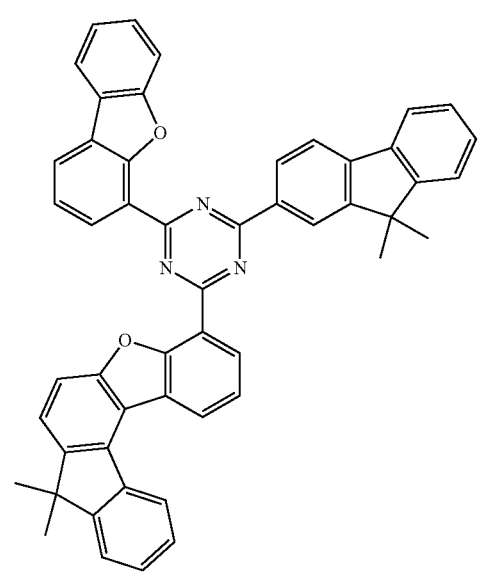
Compound E30
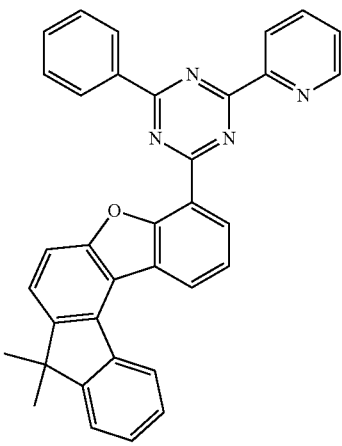
Compound E31
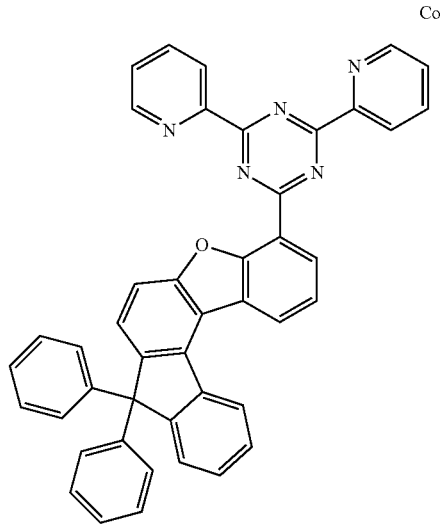
Compound E32
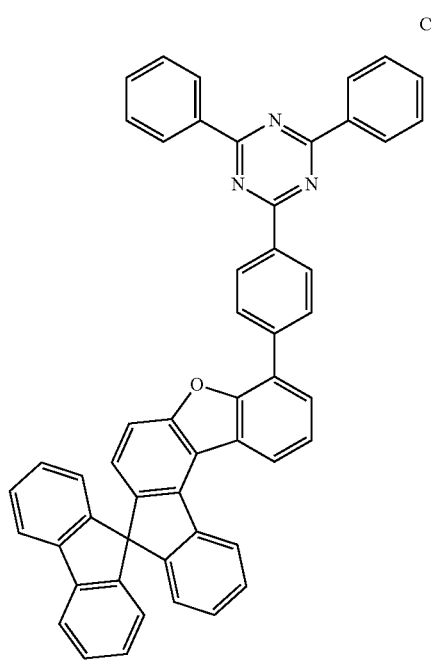

Compound E33
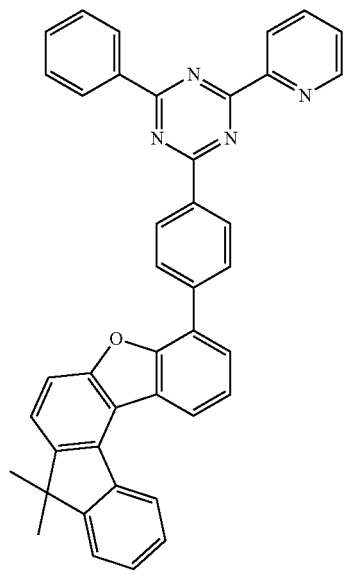
Compound E34
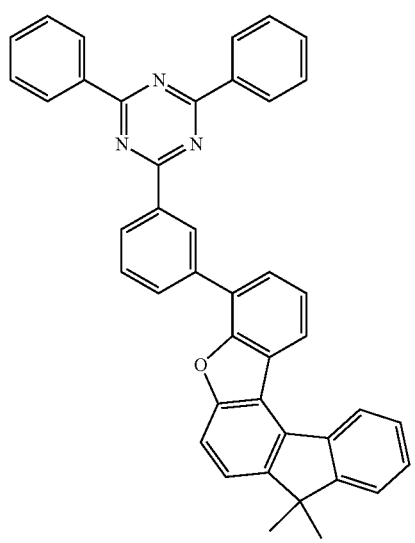
Compound E35
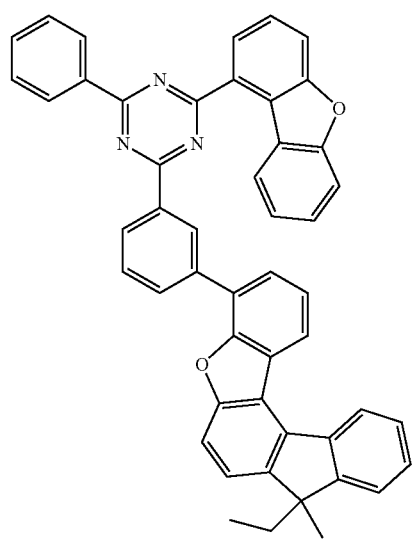
Compound E36
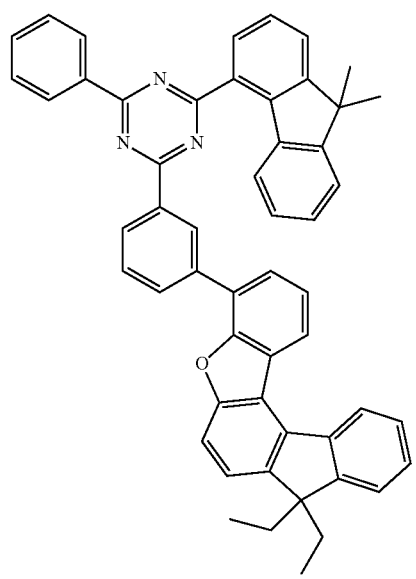
Compound E37
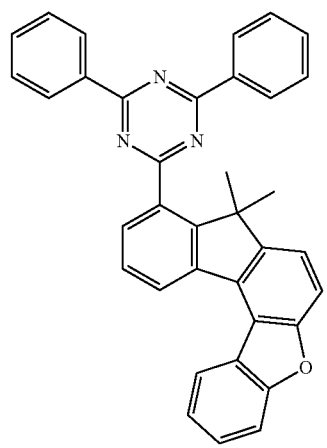

Compound E38
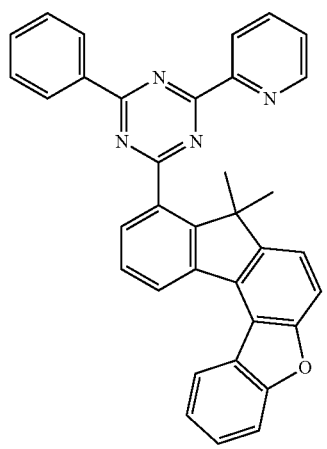
Compound E39
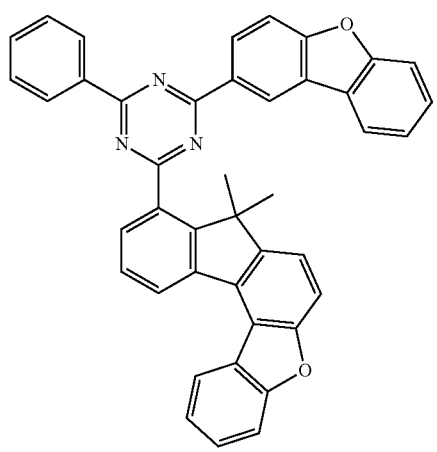
Compound E40
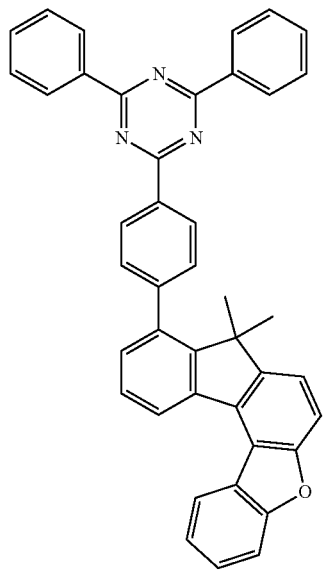
Compound E41
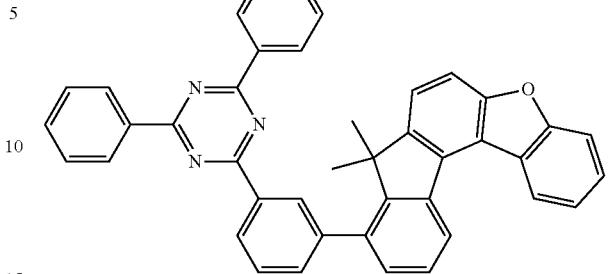
Compound E42
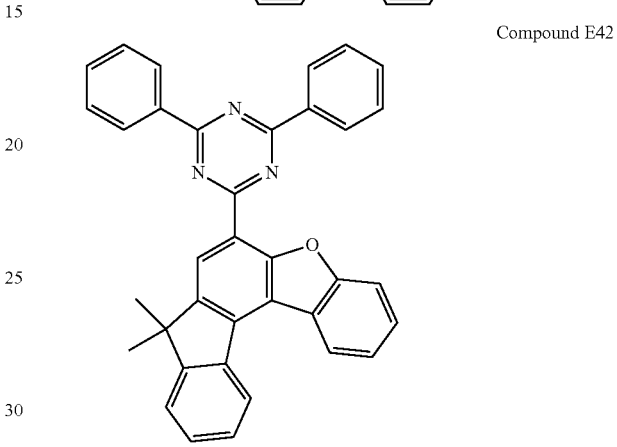
Compound E43
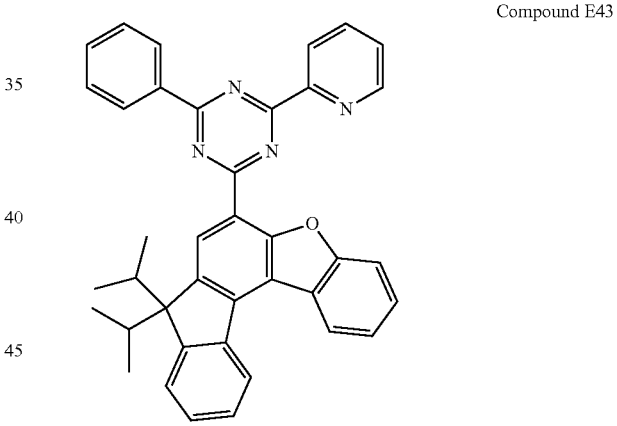
Compound E44
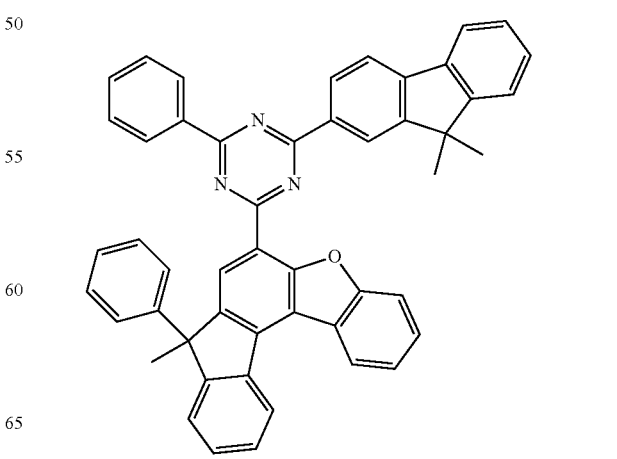

Compound E45
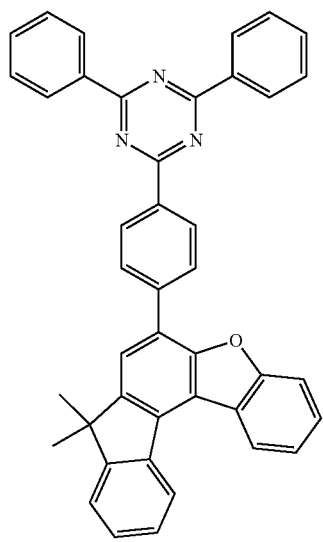
Compound E46
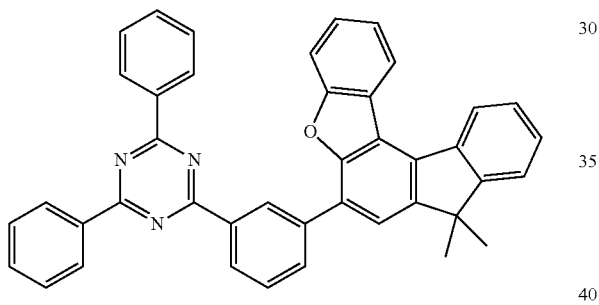
Compound E47
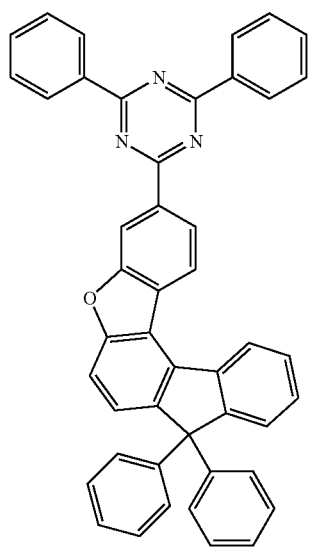
Compound E48
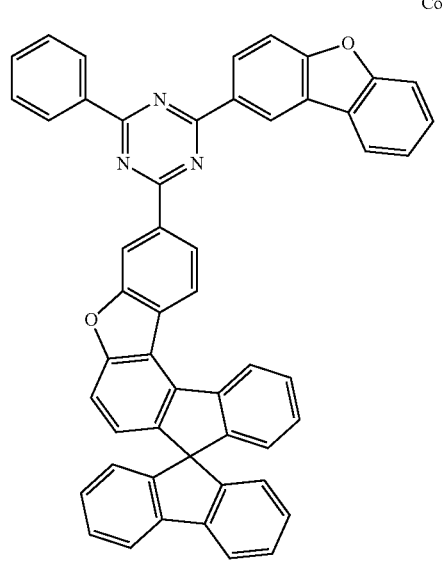
Compound E49
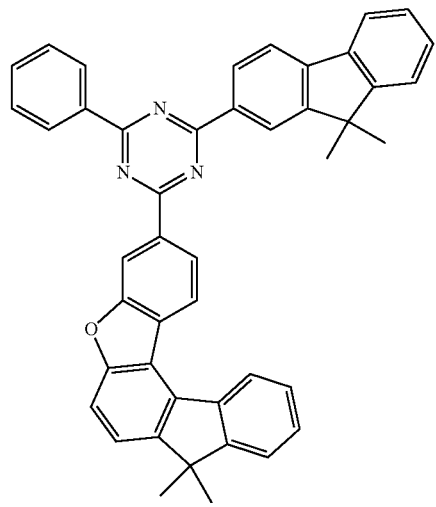

Compound E50
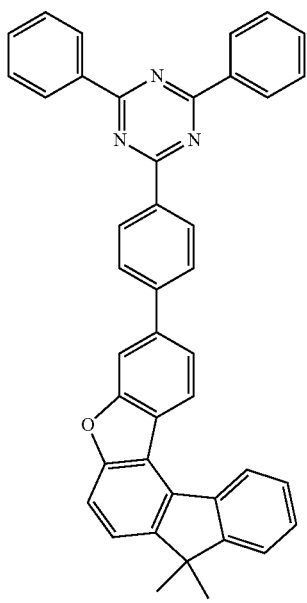
Compound E51
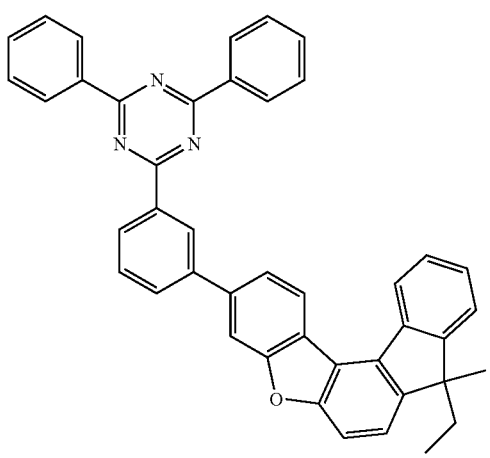
Compound E52
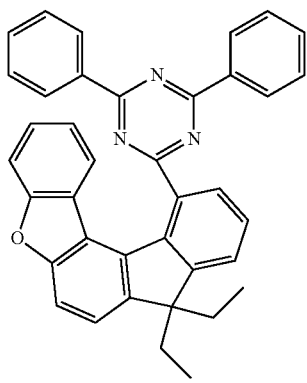
Compound E53
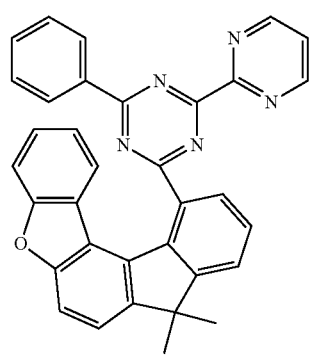
Compound E54
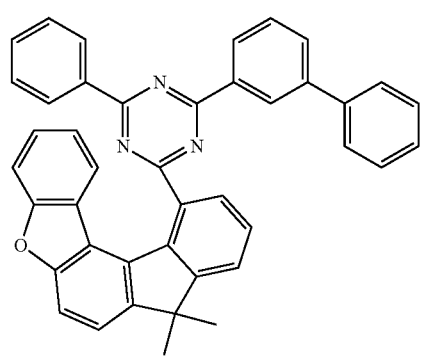
Compound E55
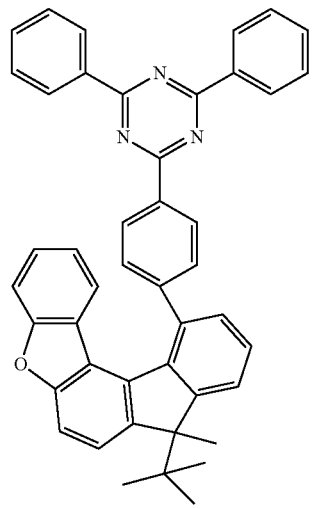

Compound E56
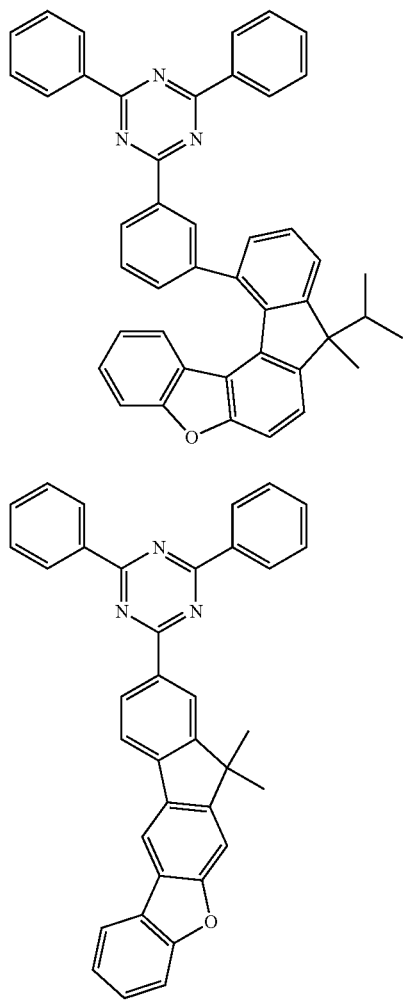
Compound E57
Compound E58
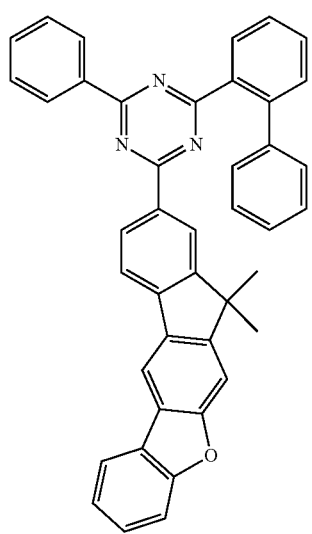
Compound E59
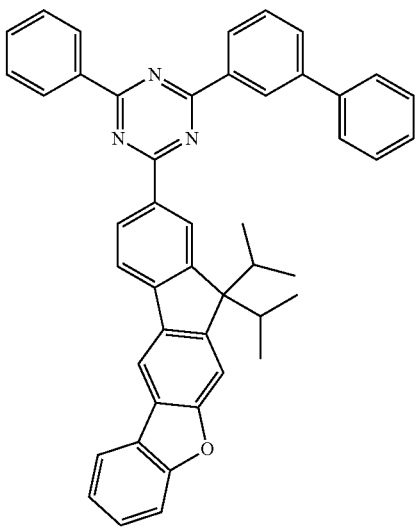
Compound E60
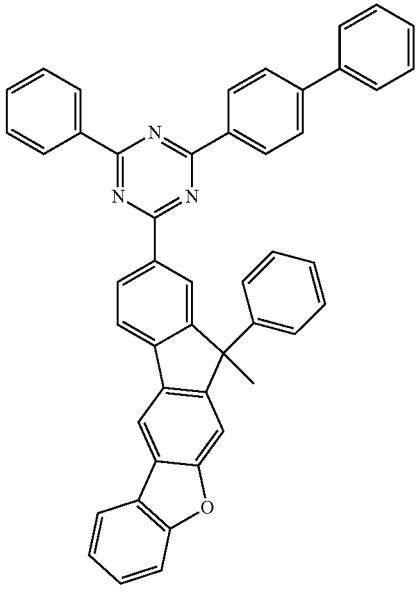

Compound E61
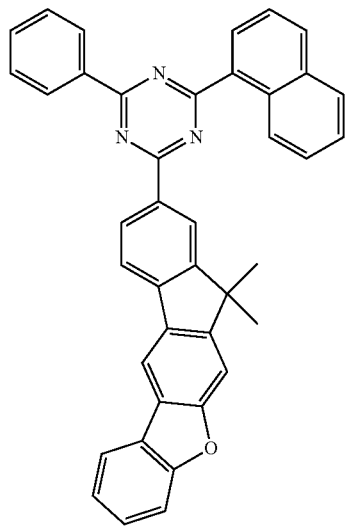
Compound E63
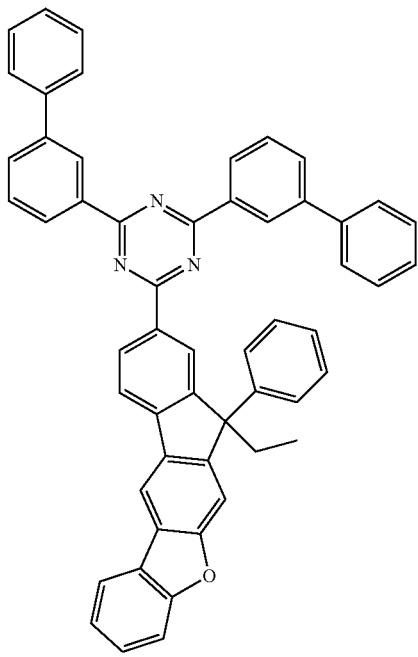
Compound E62
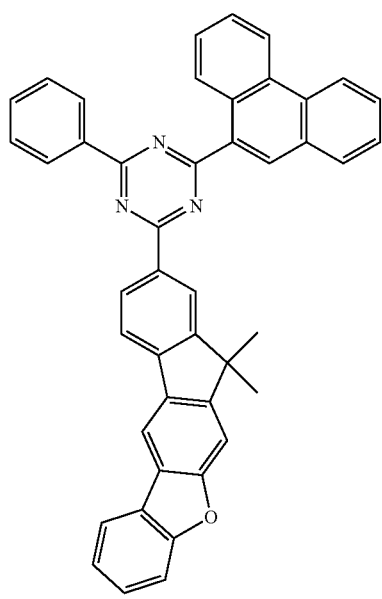
Compound E64
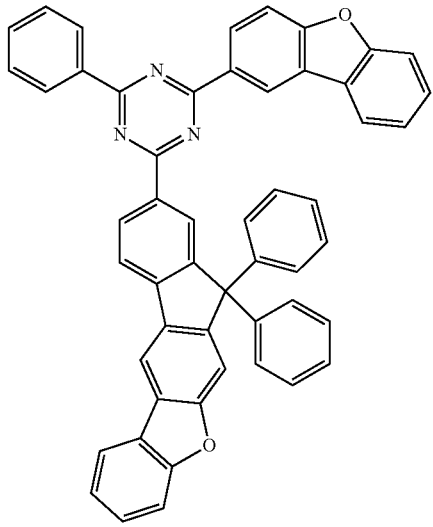

Compound E65
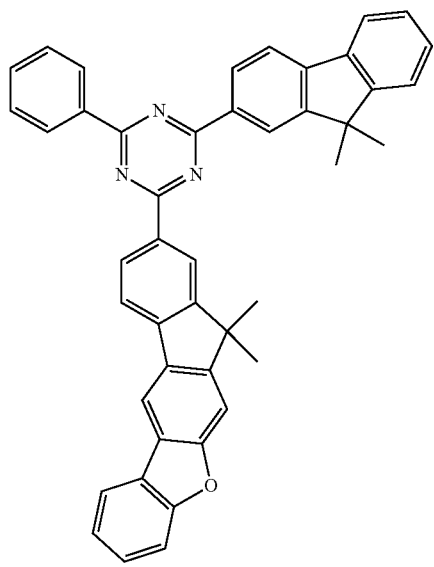
Compound E66
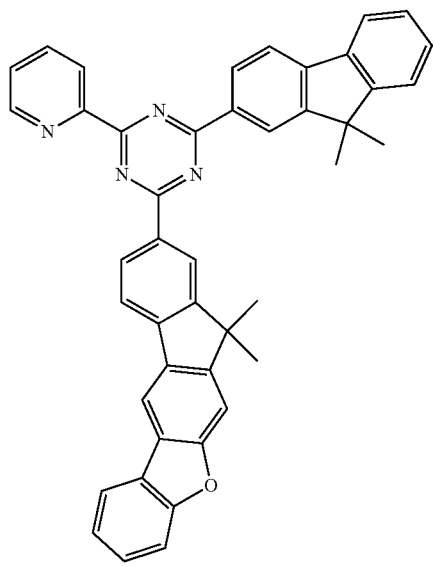
Compound E67
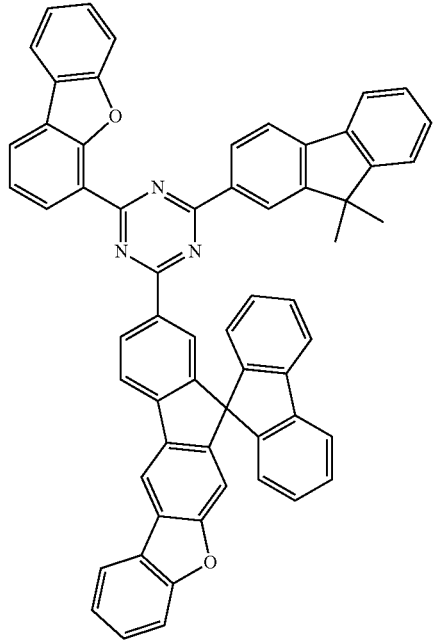
Compound E68
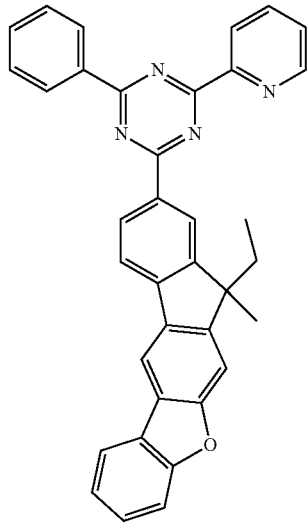

Compound E69
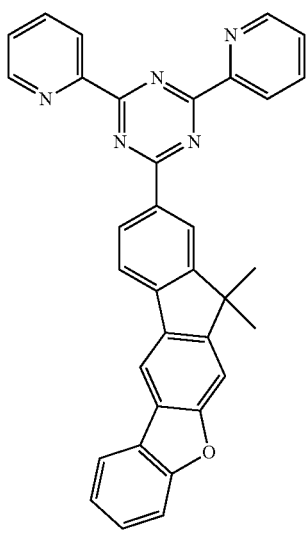
Compound E70
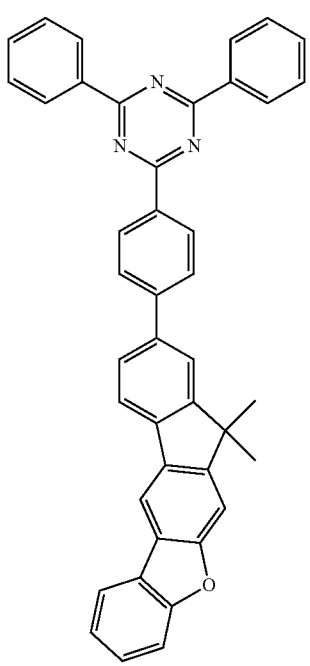
Compound E71
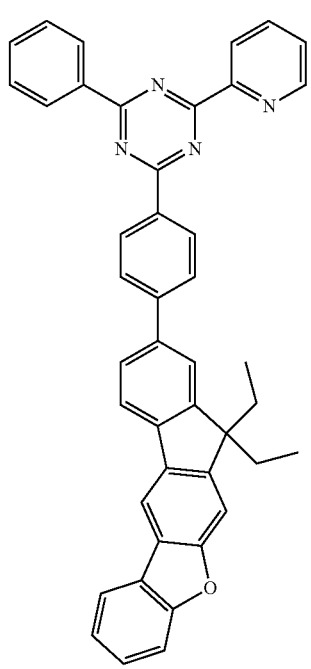
Compound E72
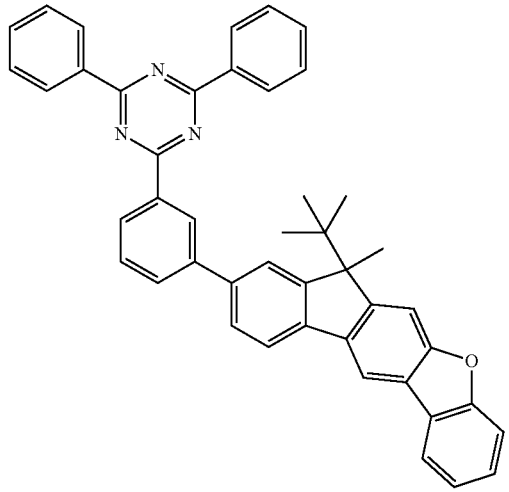

Compound E73
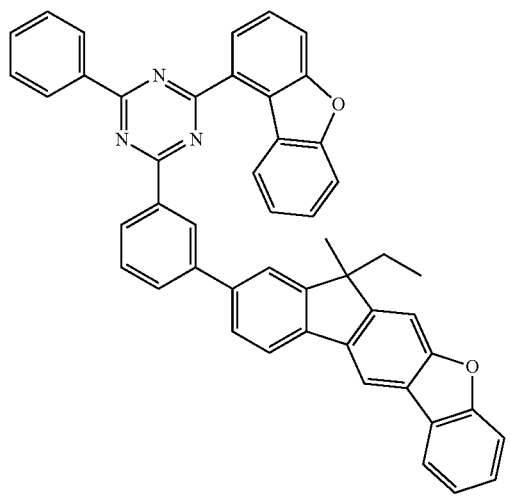
Compound E76
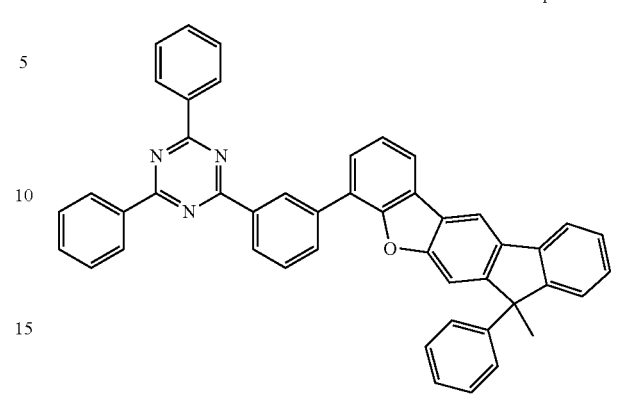
Compound E74
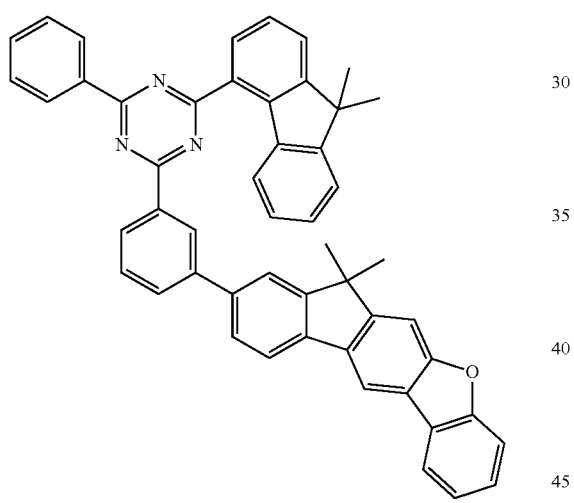
Compound E77
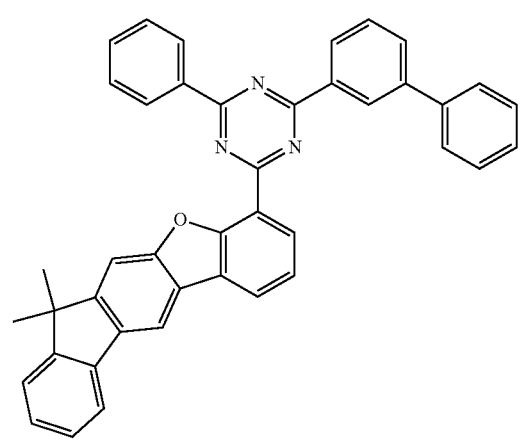
Compound E75
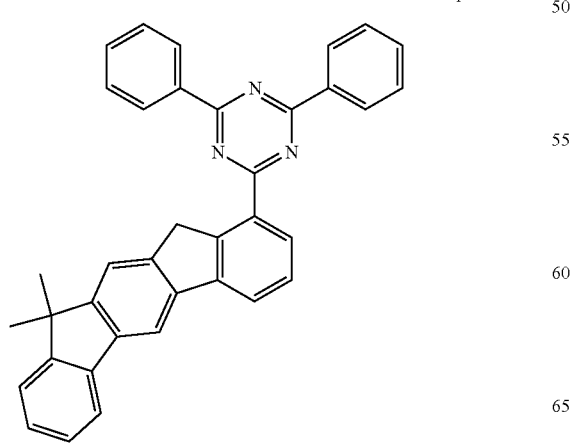
Compound E78
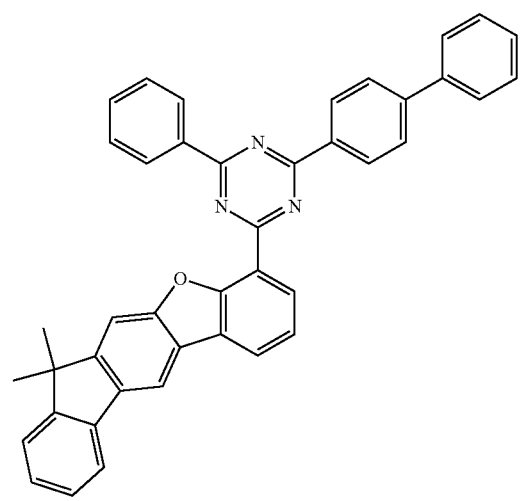

Compound E79
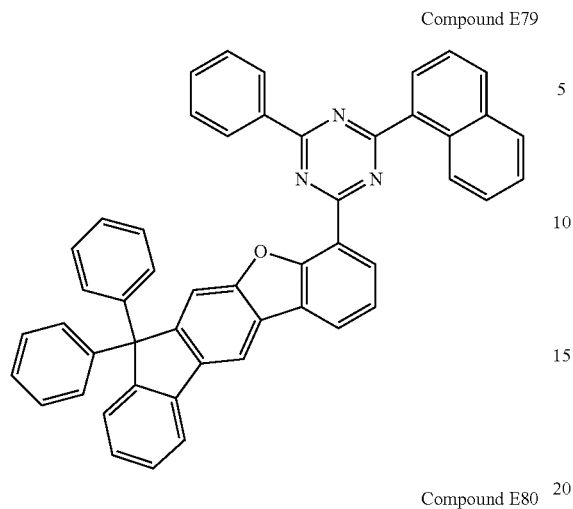
Compound E80
Compound E82
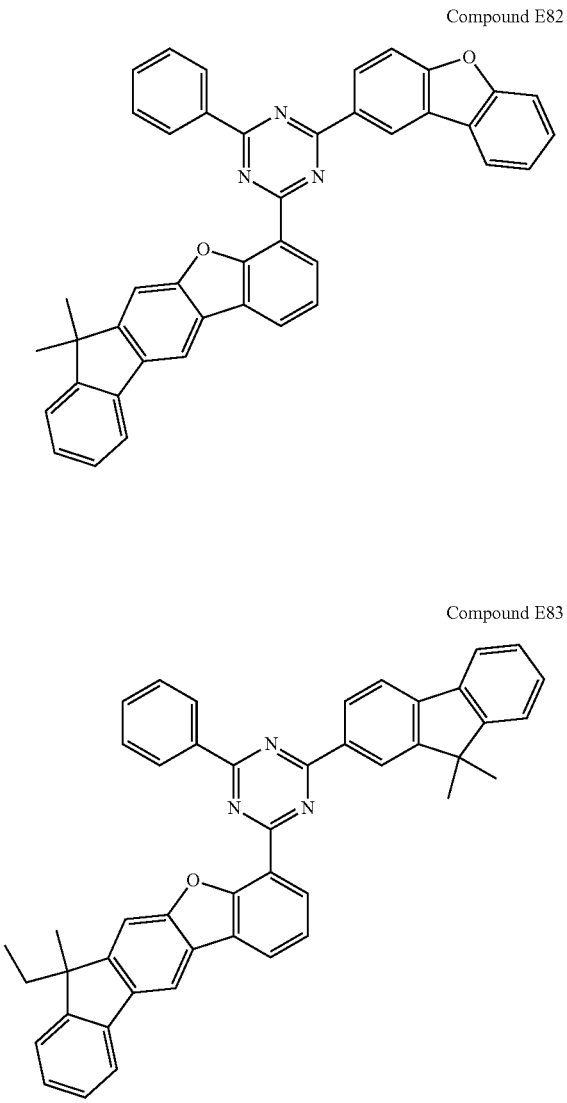
Compound E83
Compound E81
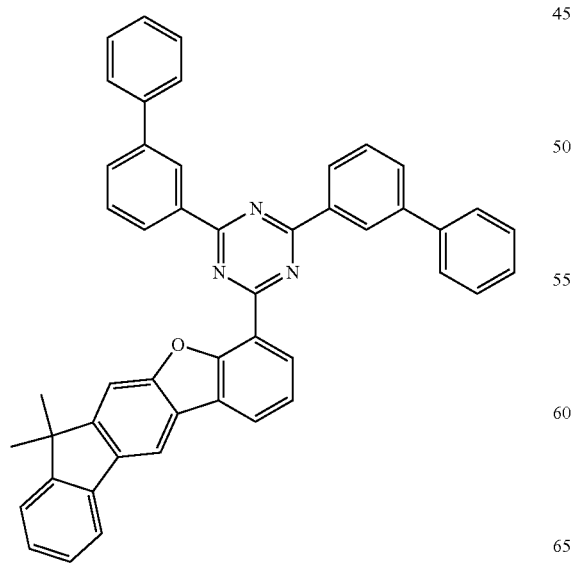
Compound E84
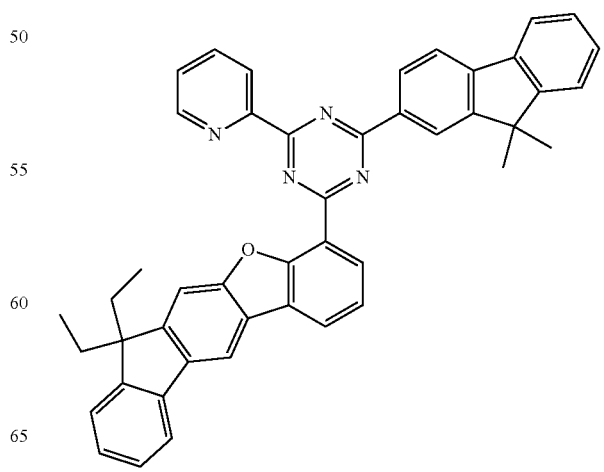

Compound E85
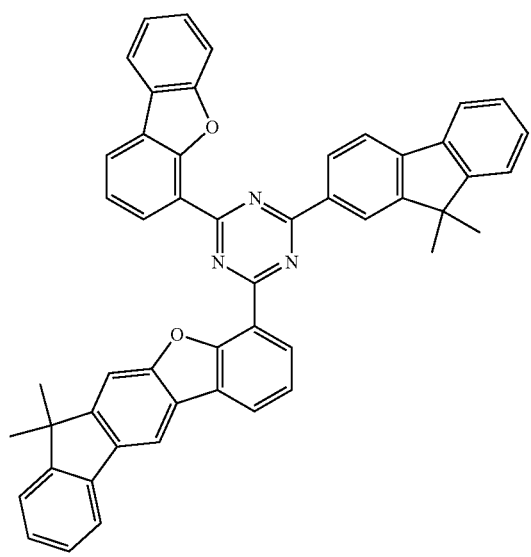
Compound E88
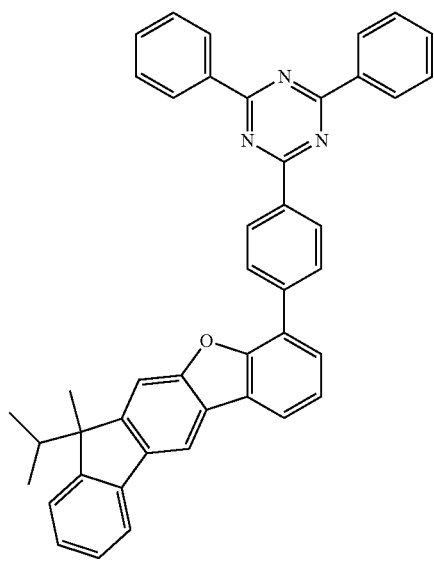
Compound E86
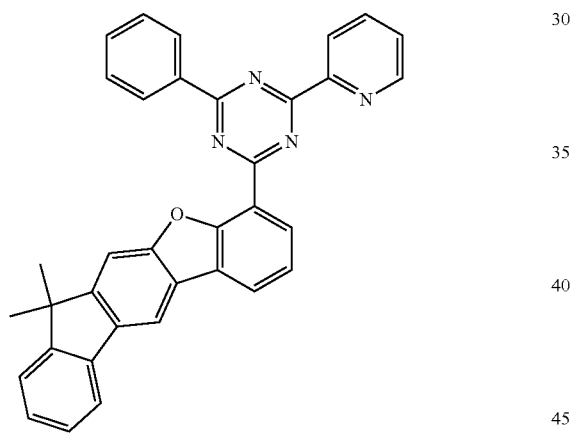
Compound E87
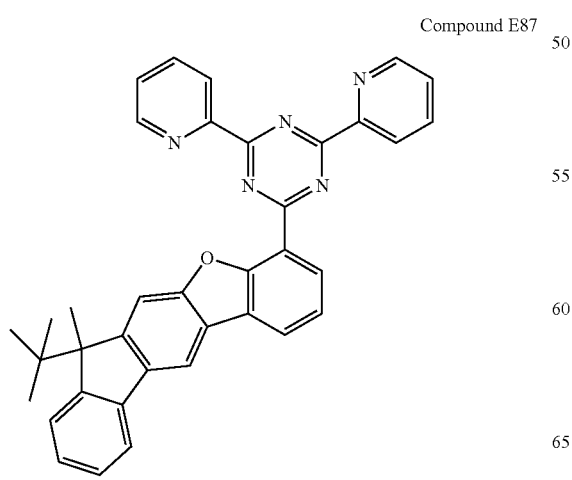
Compound E89
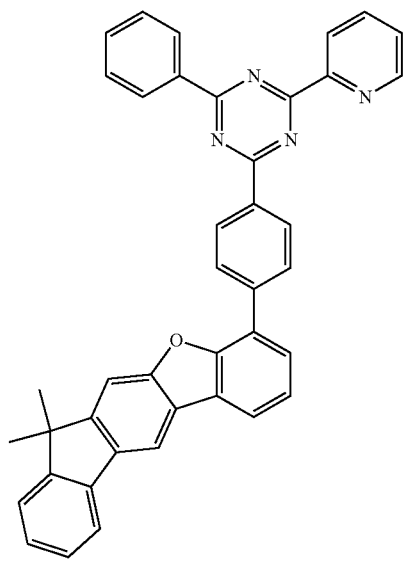

Compound E90
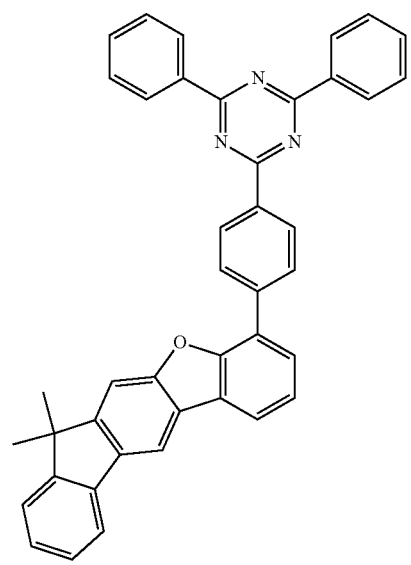
Compound E91
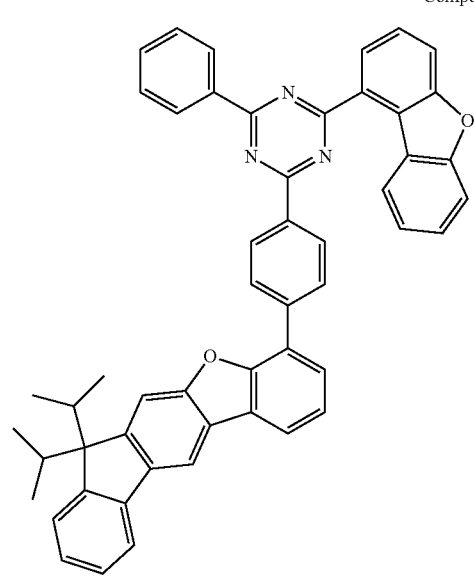
Compound E92
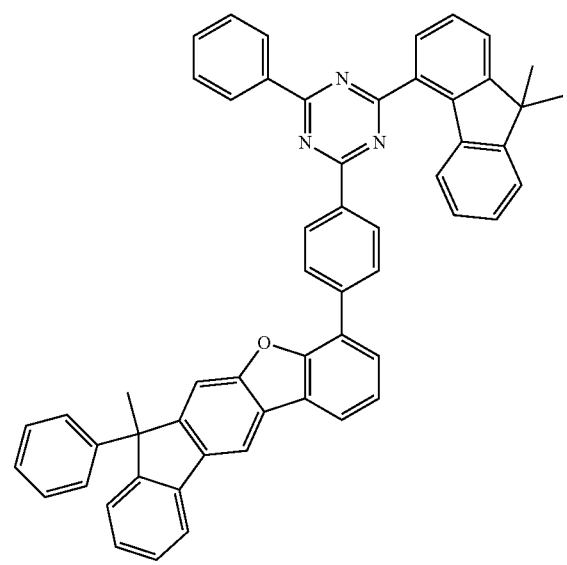
Compound E93
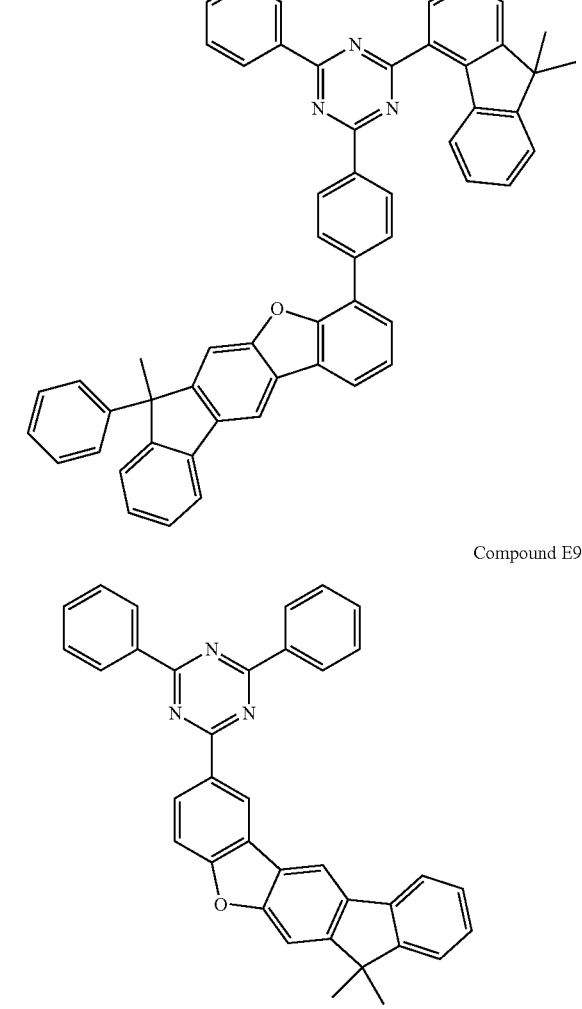
Compound E94
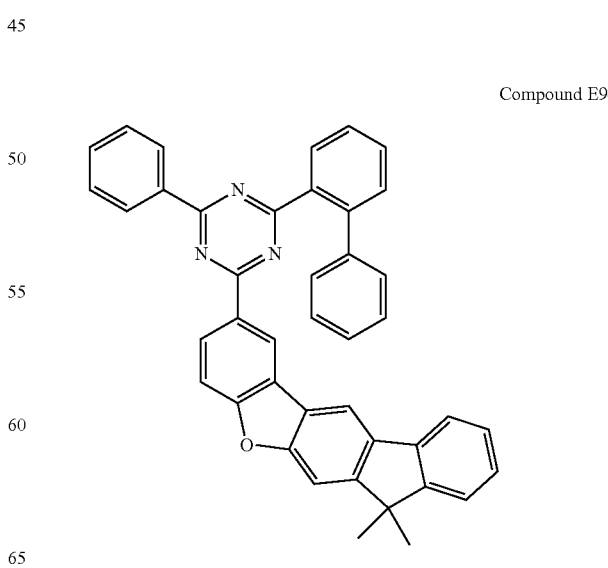

Compound E95
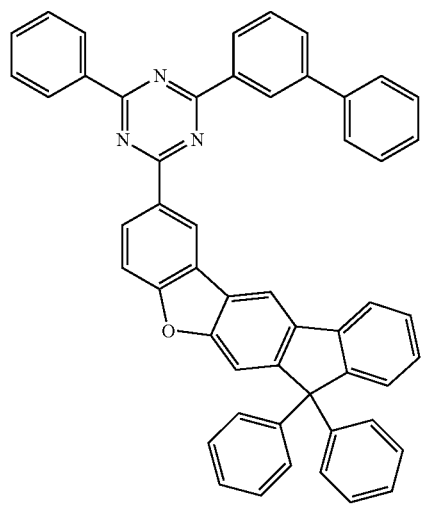
Compound E96
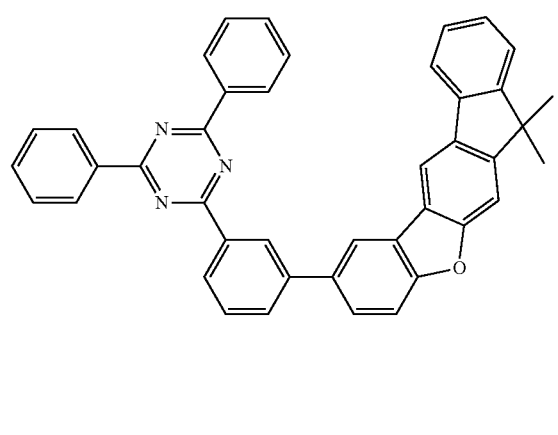
Compound E97
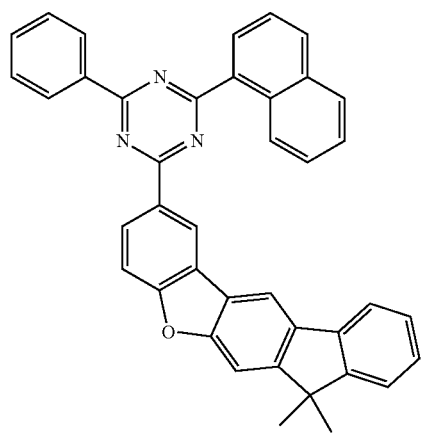
Compound E98
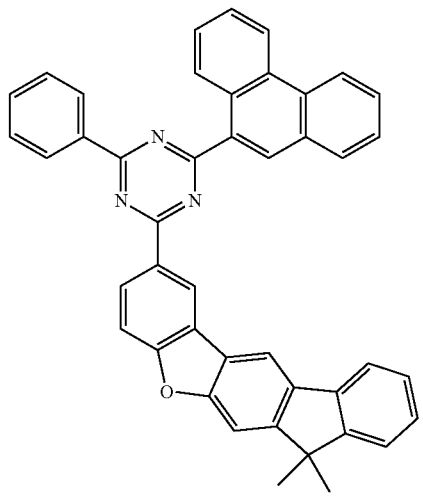
Compound E99
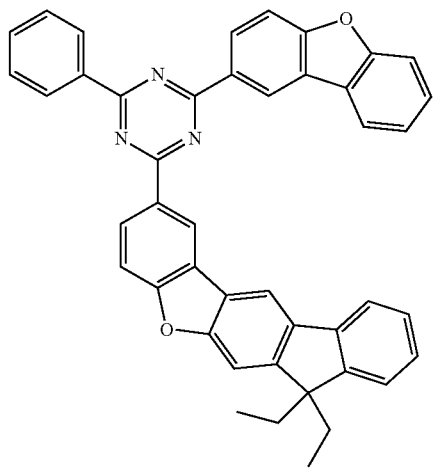
Compound E100

Compound E101
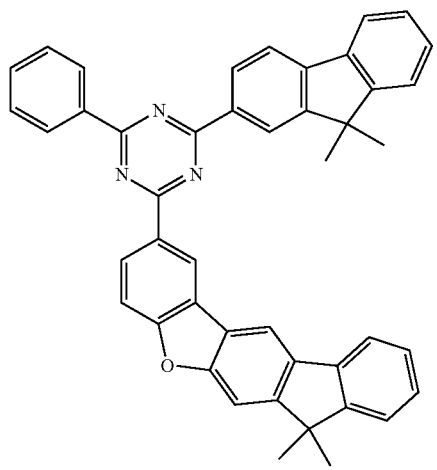
Compound E102
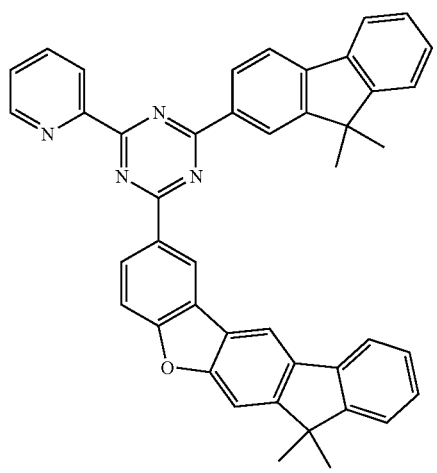
Compound E103
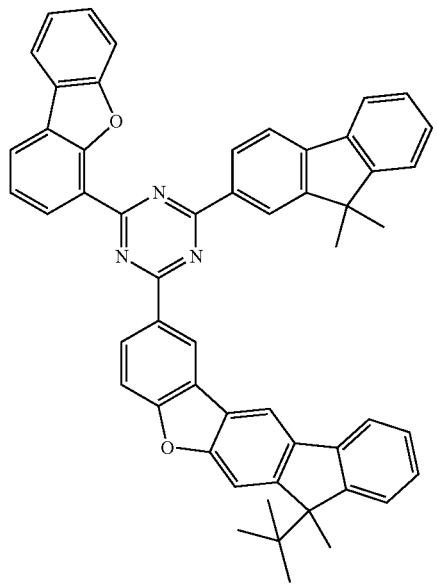
Compound E104
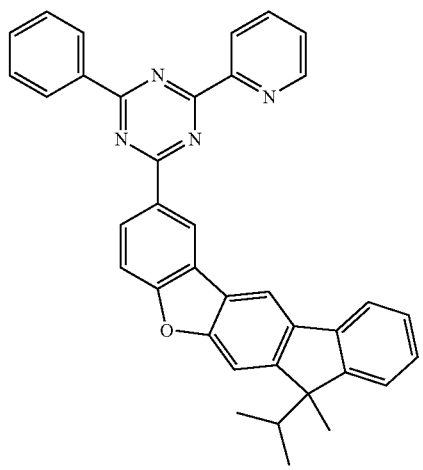
Compound E105
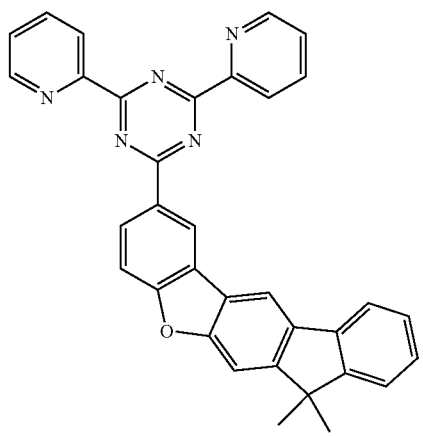
Compound E106
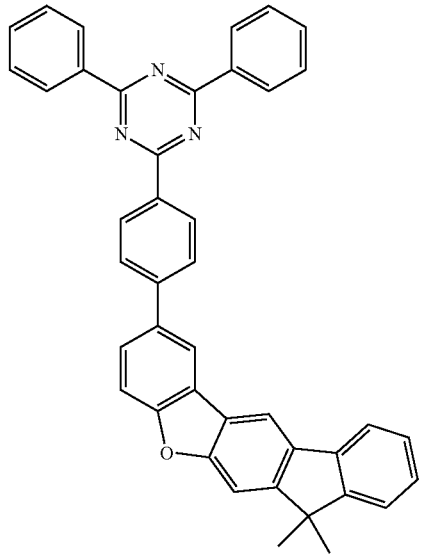

Compound E107
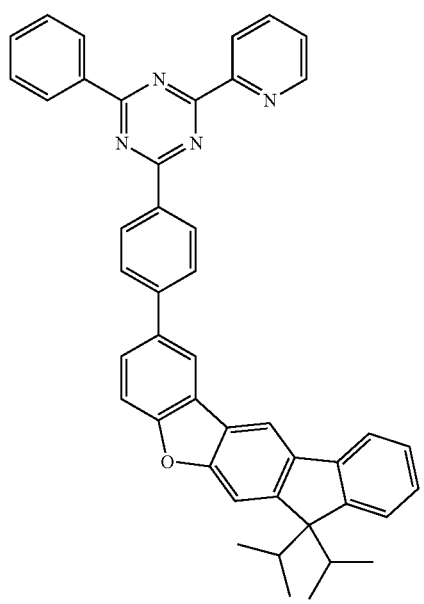
Compound E108
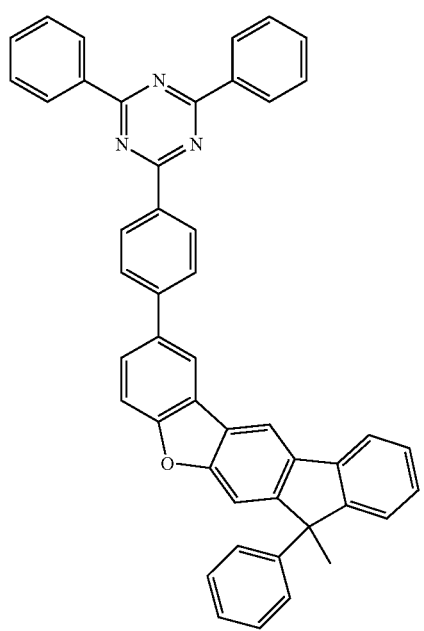
Compound E109
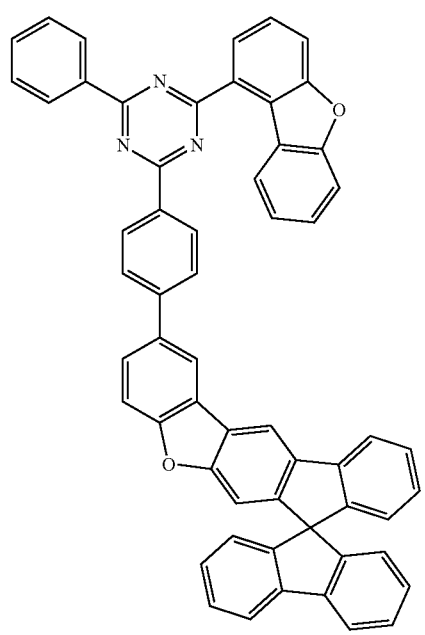
Compound E110
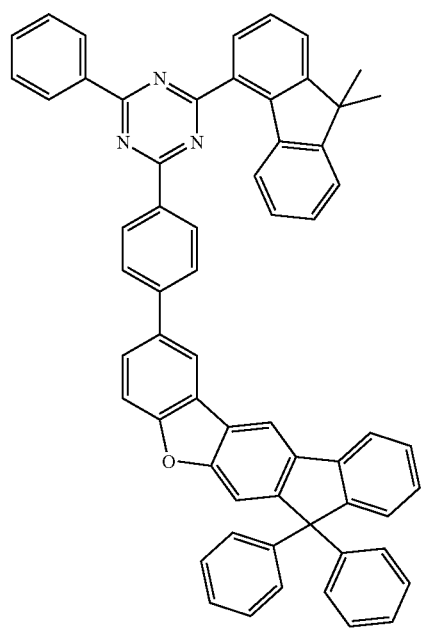

Compound E111
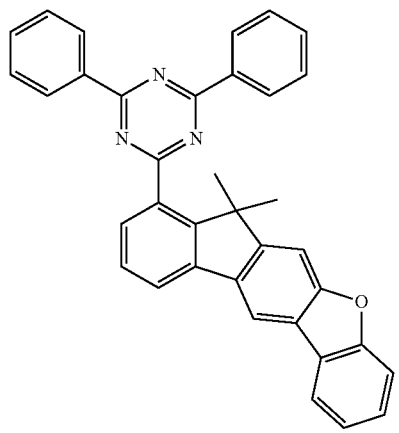
Compound E112
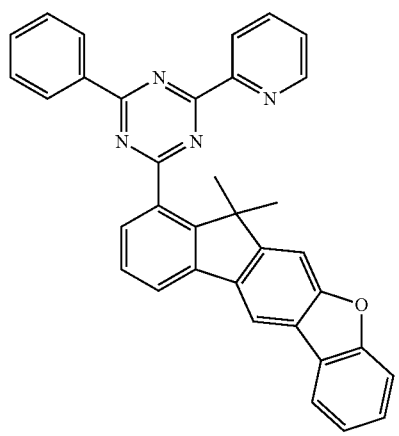
Compound E113
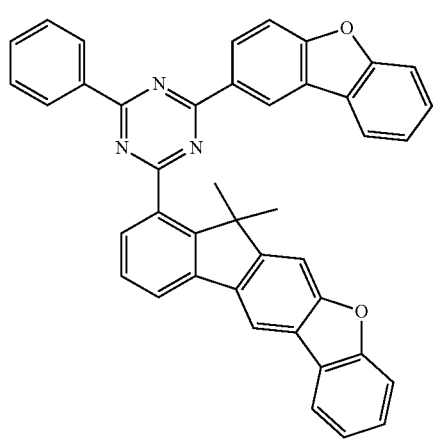
Compound E114
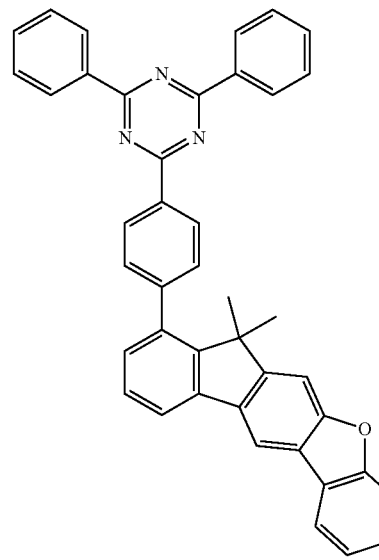
Compound E115
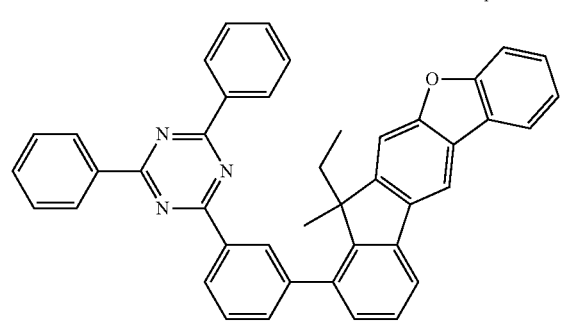
Compound E116
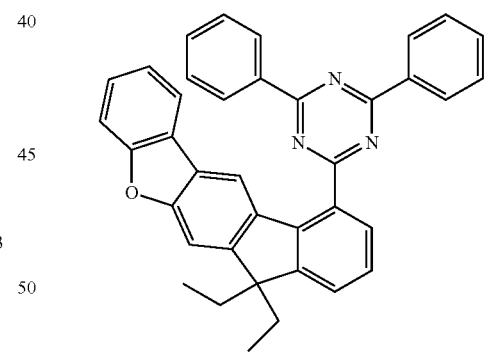
Compound E117
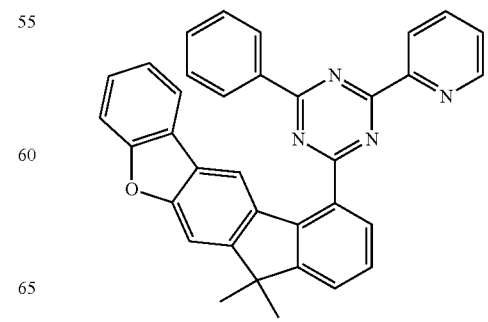

Compound E118
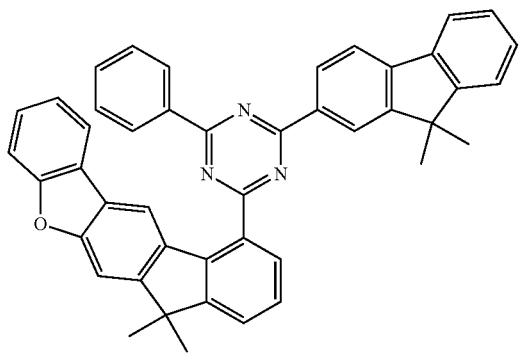
Compound E119
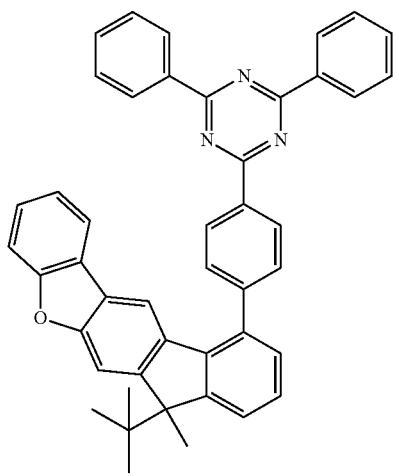
Compound E120
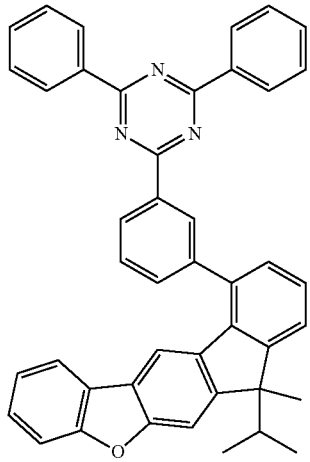
Compound E121
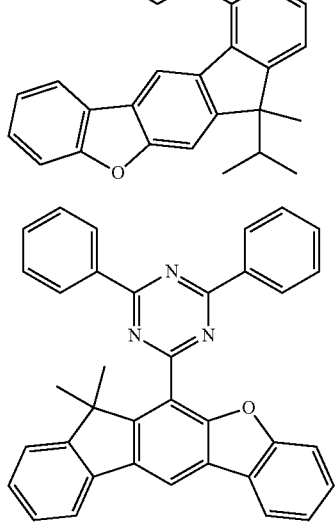
Compound E122
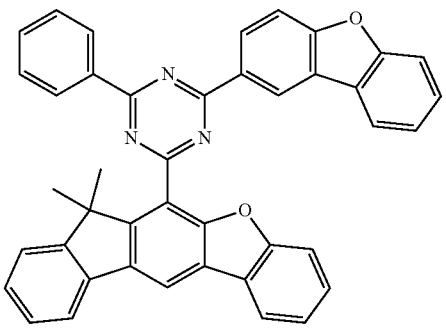
Compound E123
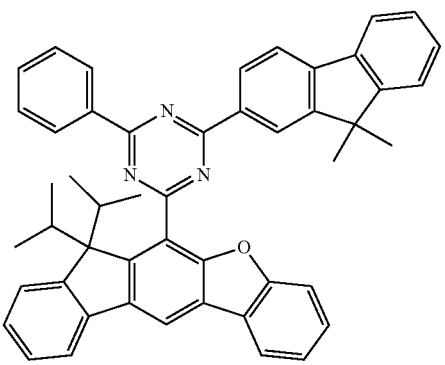
Compound E124
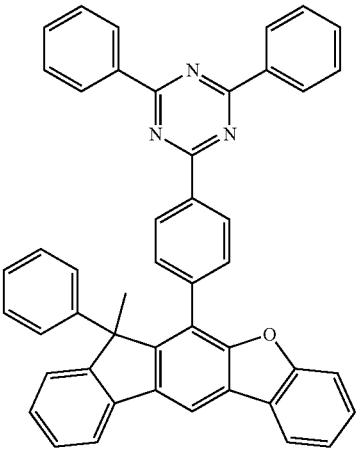
Compound E125
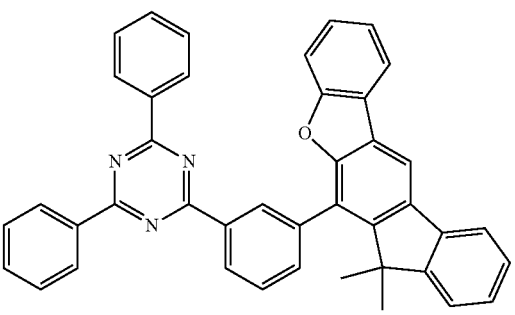

Compound E126
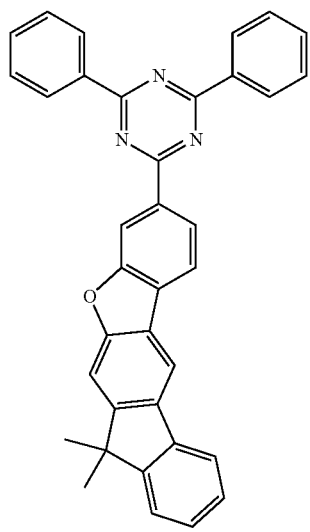
Compound E128
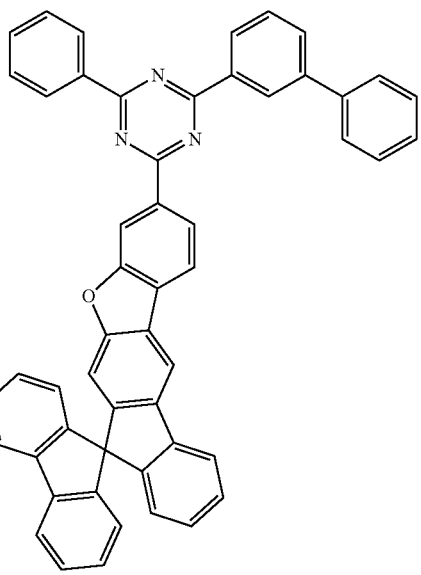
Compound E129
Compound E127
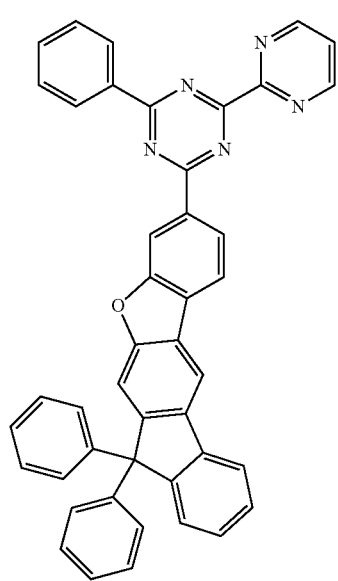
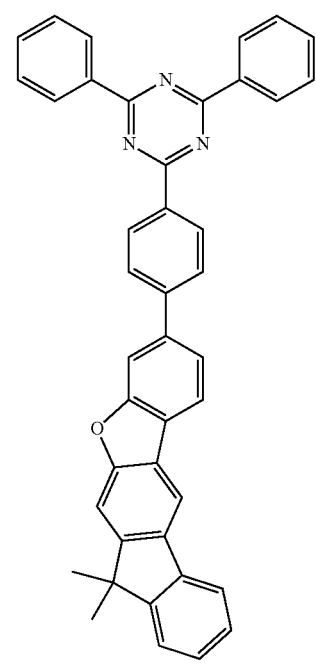
Compound E130
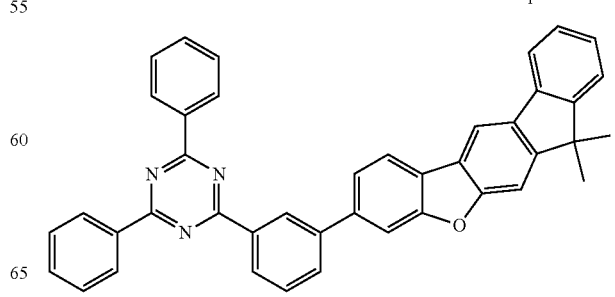

Compound E131
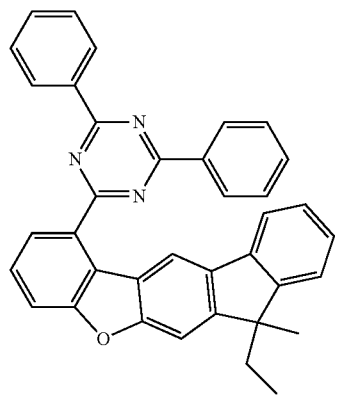
Compound E132
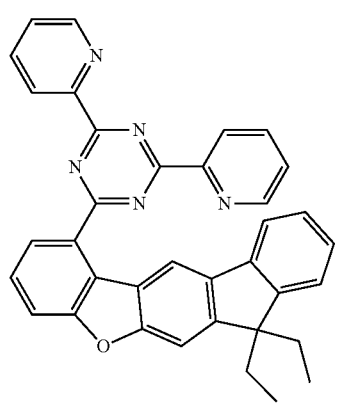
Compound E133
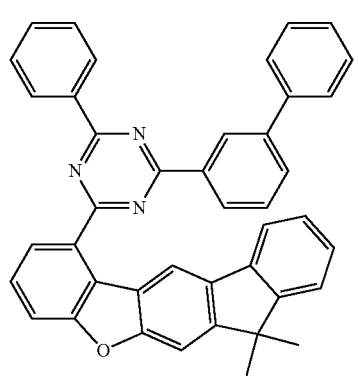
Compound E134
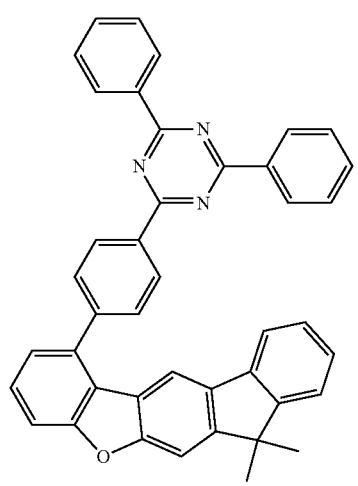
Compound E135
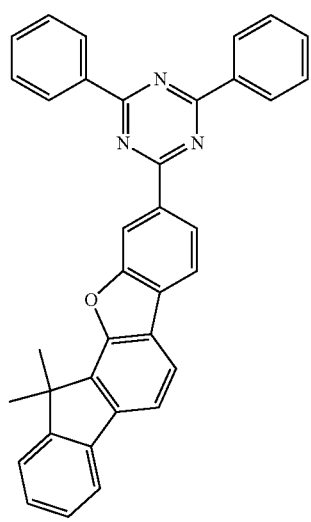
Compound E136
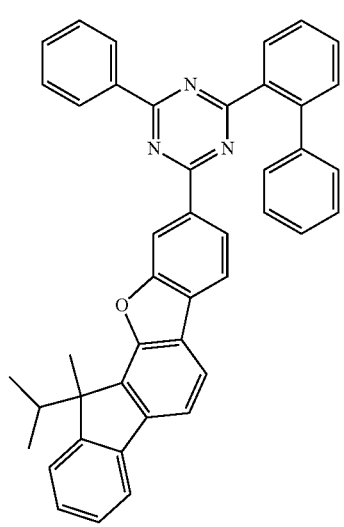
Compound E137
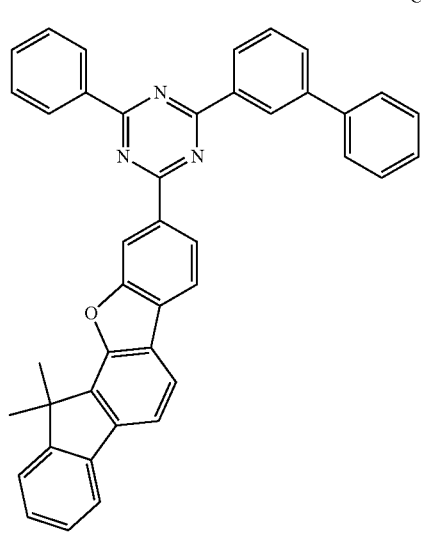

Compound E138
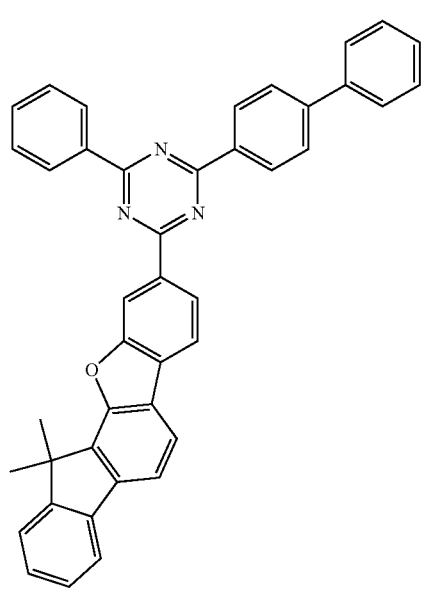
Compound E140
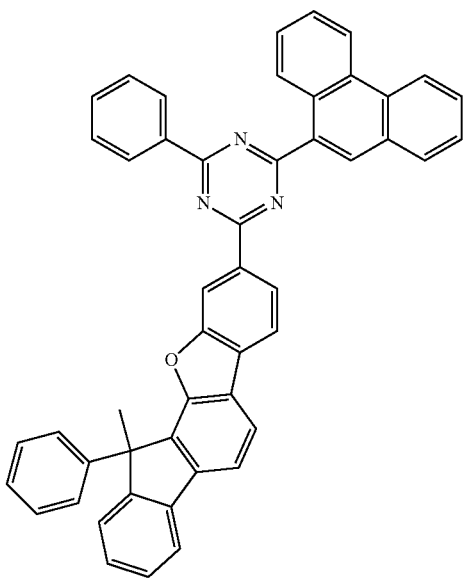
Compound E139
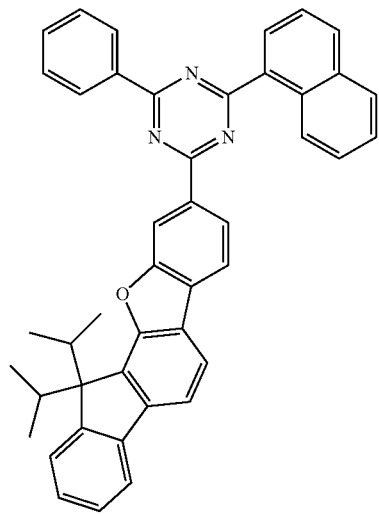
Compound E141
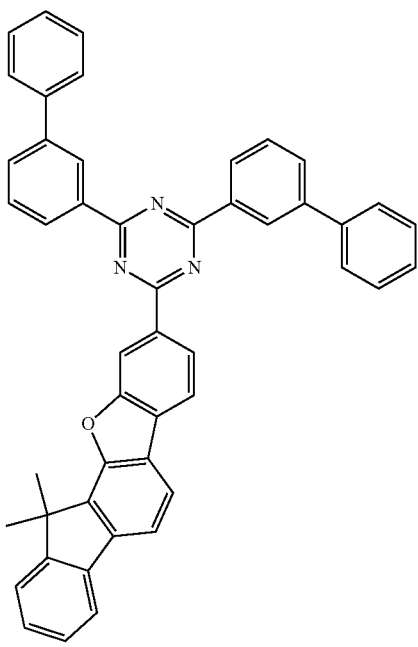

Compound E142
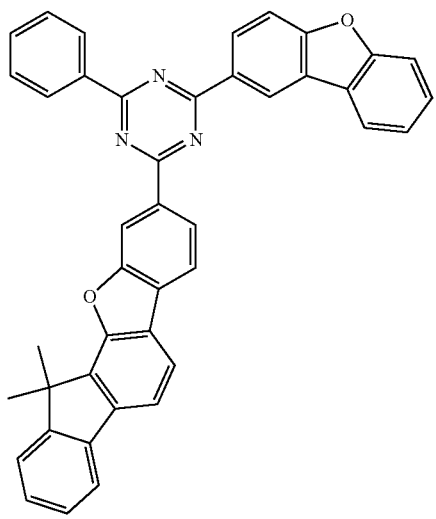
Compound E144
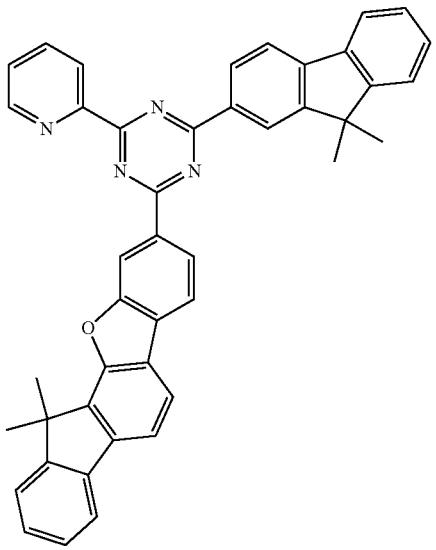
Compound E143
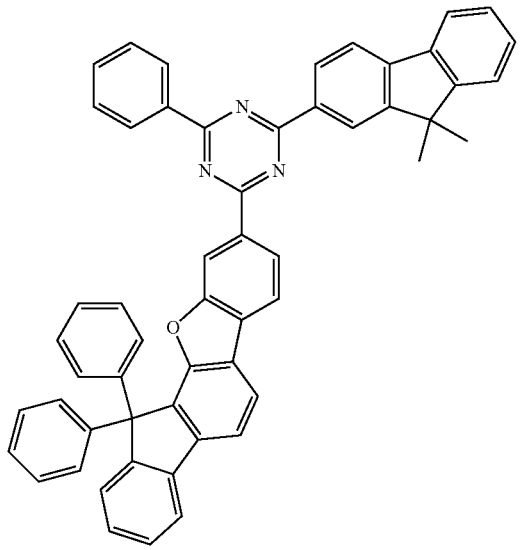
Compound E145
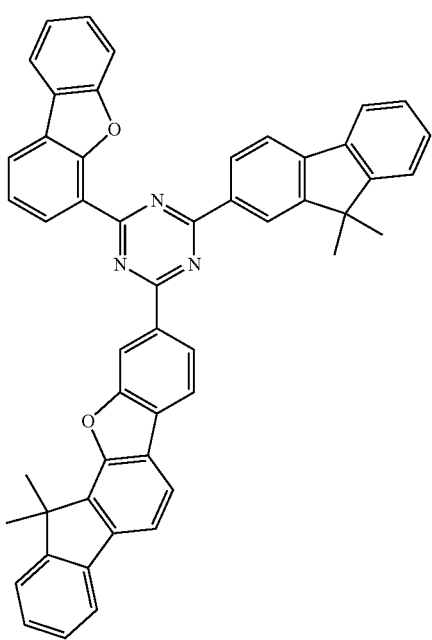

Compound E146
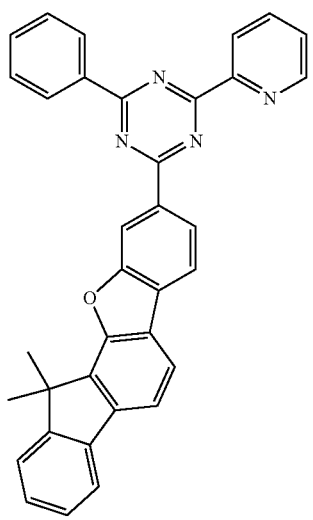
Compound E147
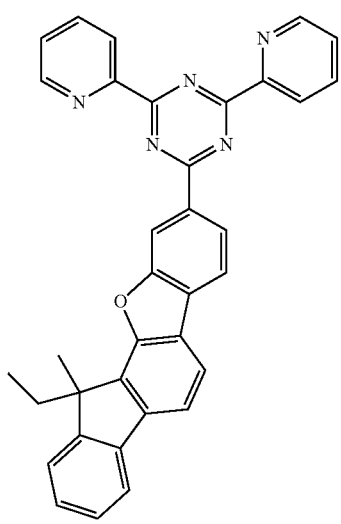
Compound E148
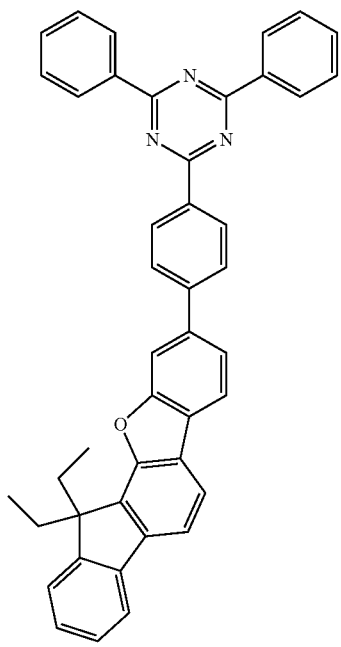
Compound E149
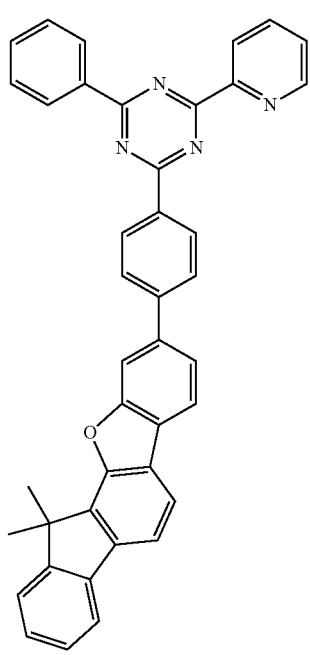
Compound E150
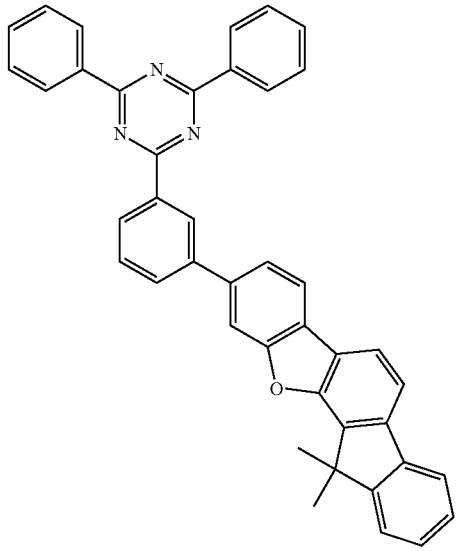

Compound E151
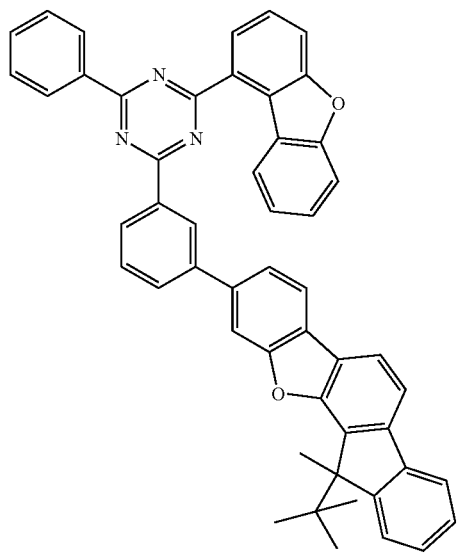
Compound E152
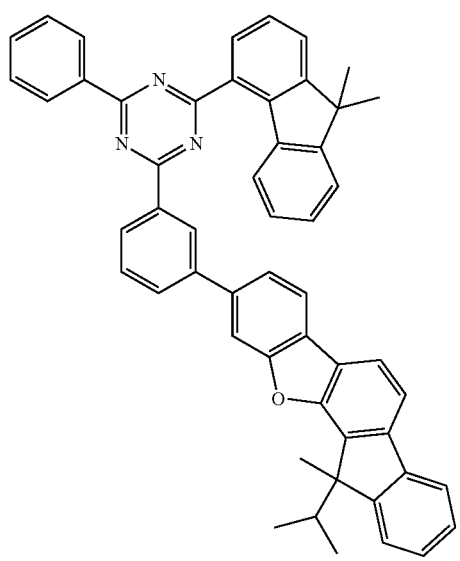
Compound E153
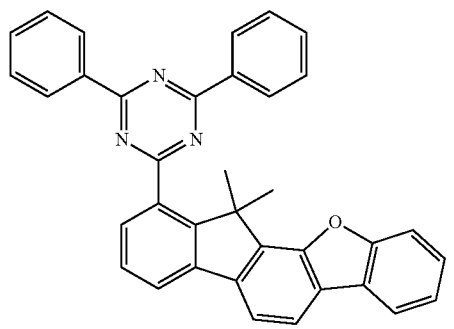
Compound E154
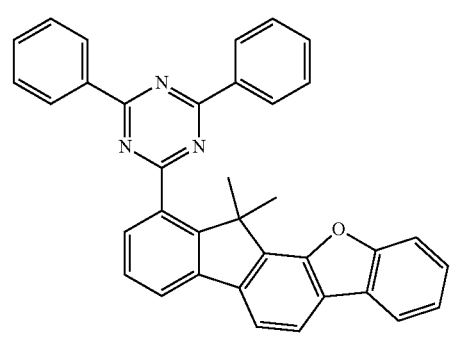
Compound E155
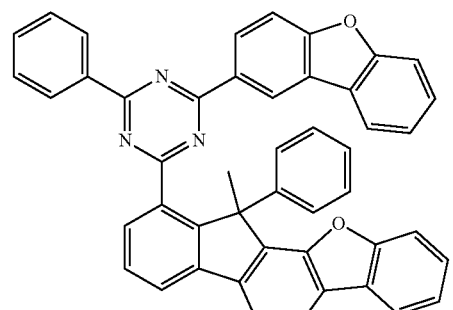
Compound E156
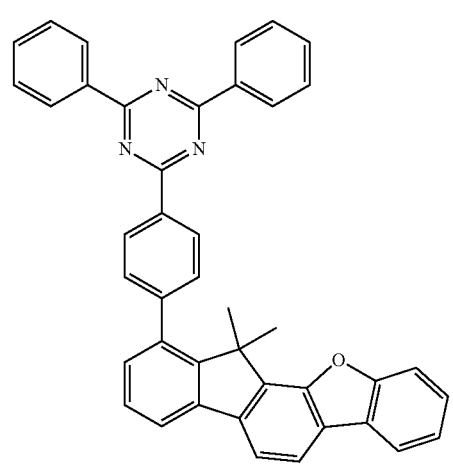
Compound E157
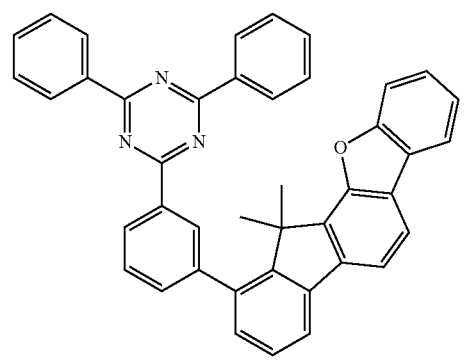

Compound E158
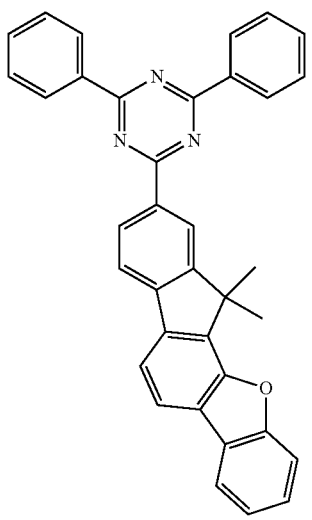
Compound E159
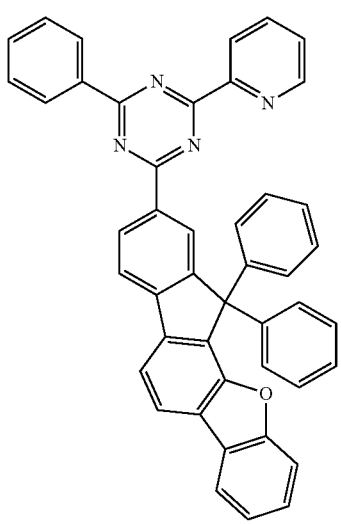
Compound E160
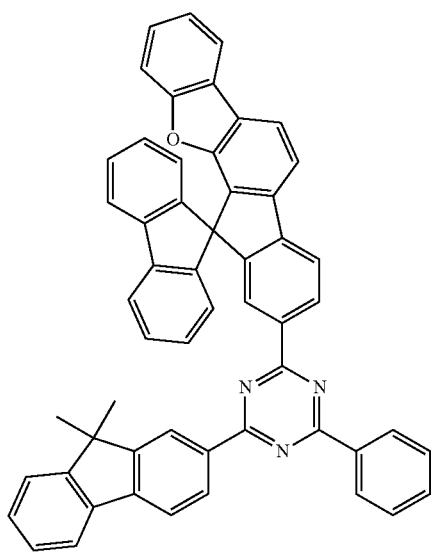
Compound E161
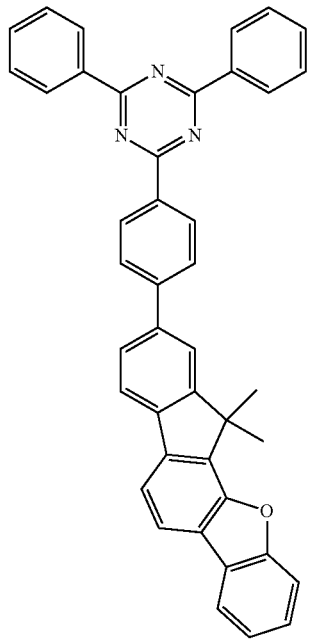
Compound E162
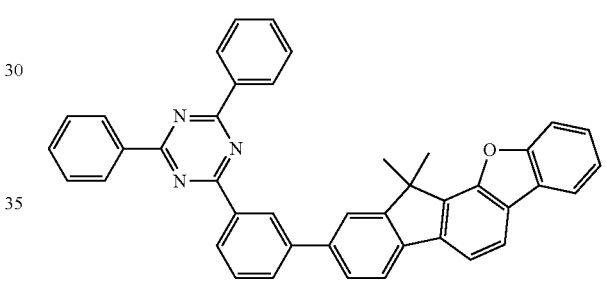
Compound E163
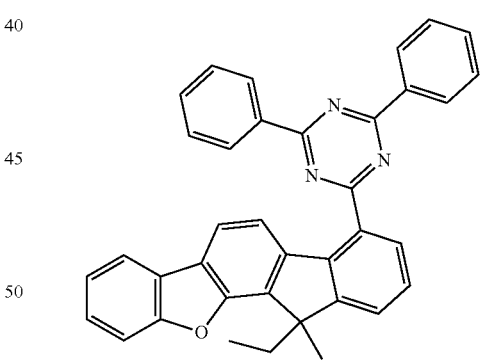
Compound E164
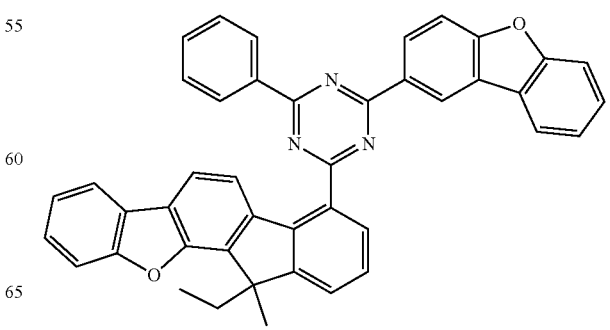

Compound E165
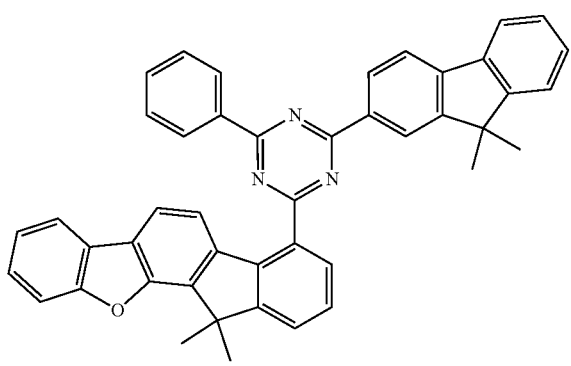
Compound E166
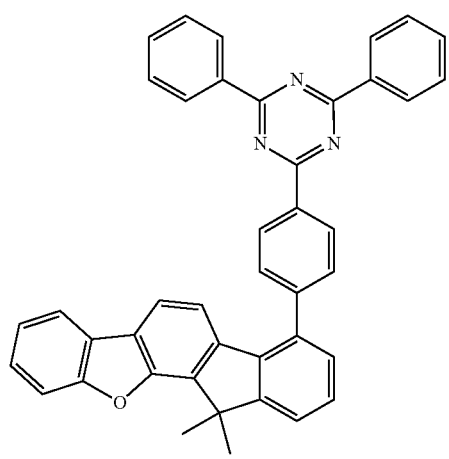
Compound E167
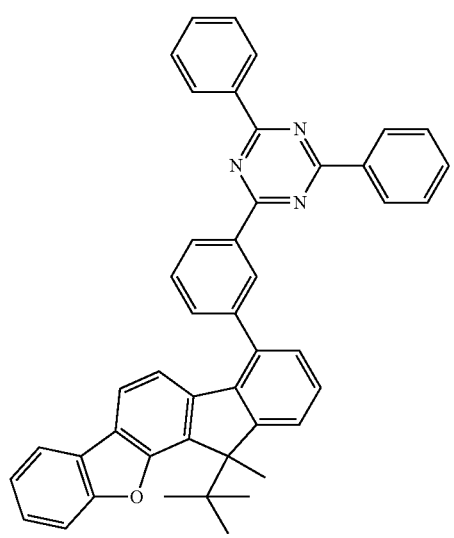
Compound E168
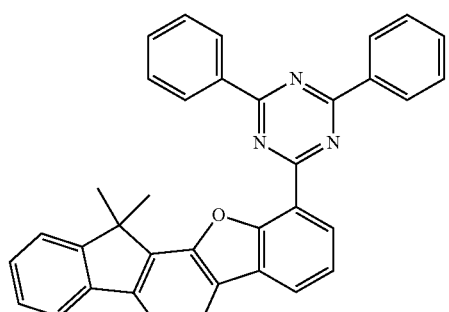
Compound E169
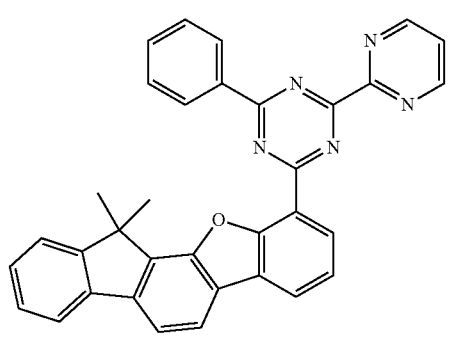
Compound E170
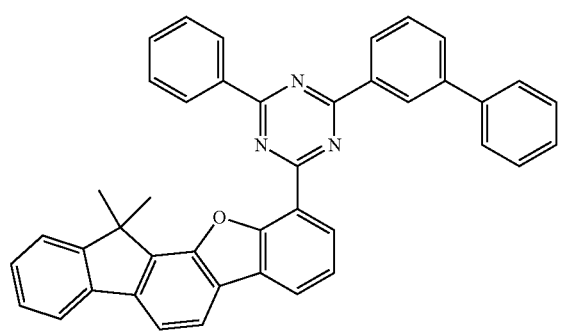
Compound E171
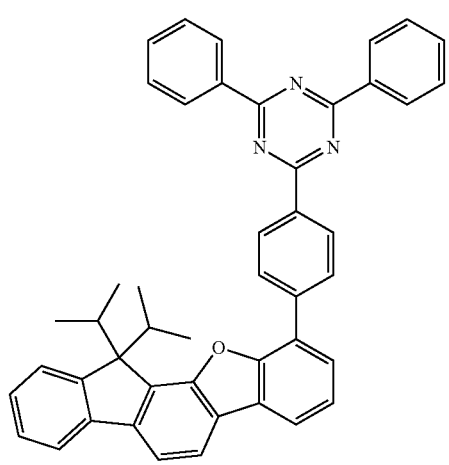

Compound E172
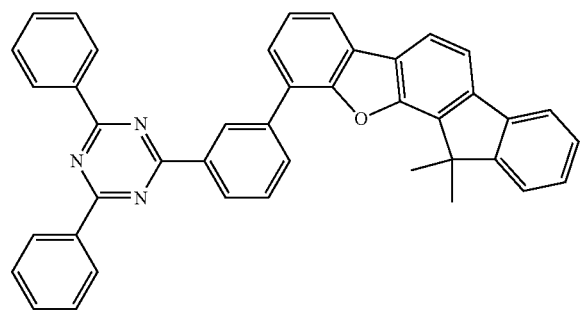
Compound E175
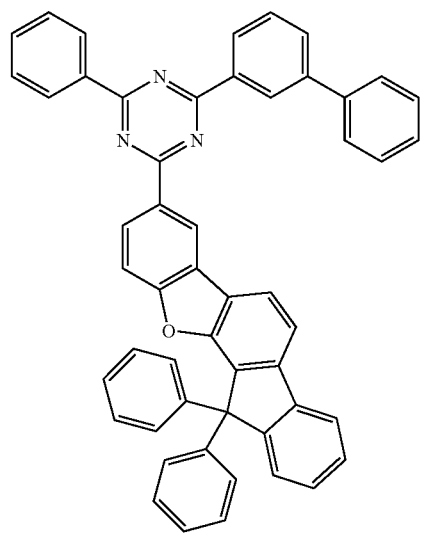
Compound E173
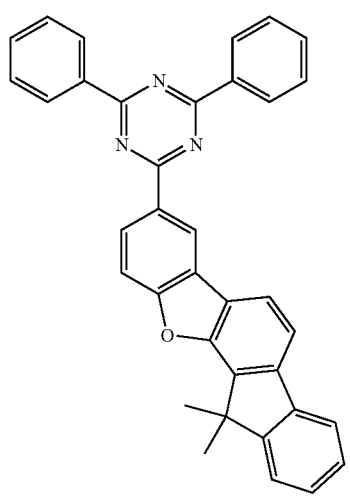
Compound E176
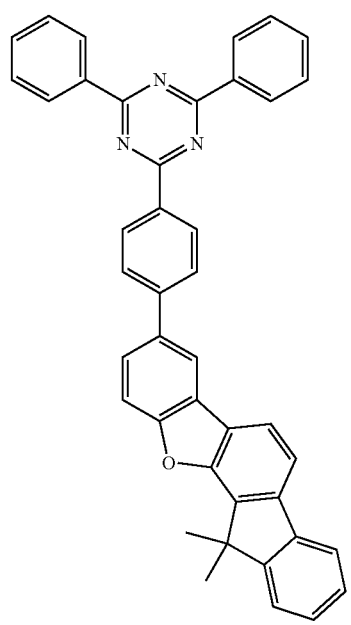
Compound E174
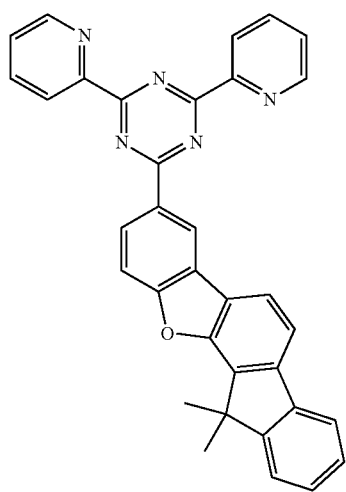
Compound E177
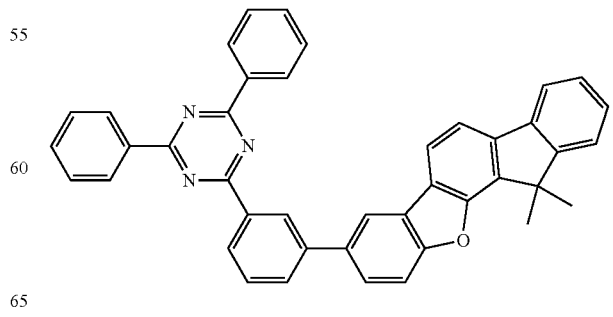

Compound E178
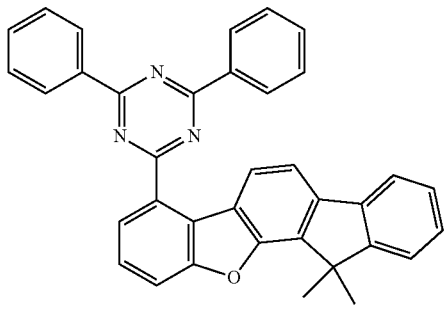
Compound E179
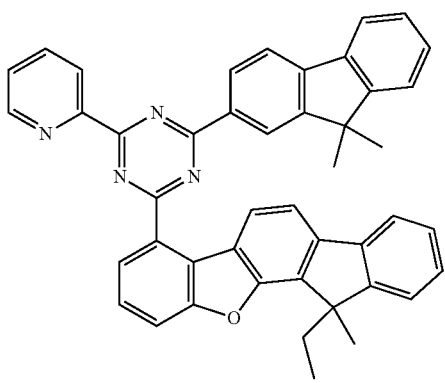
Compound E180
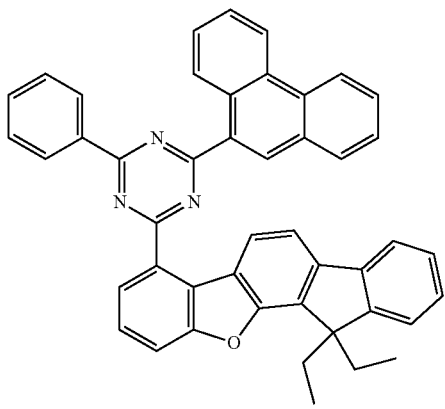
Compound E181
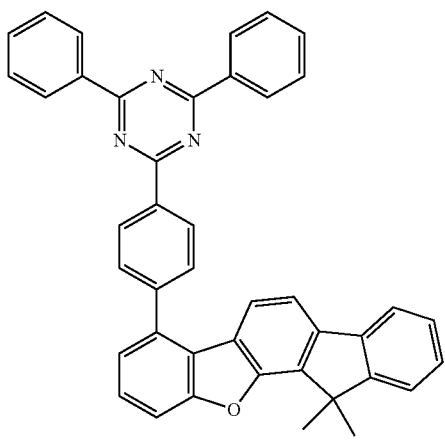
Compound E182
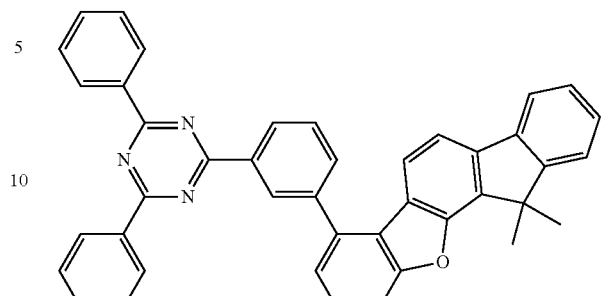
Compound E183
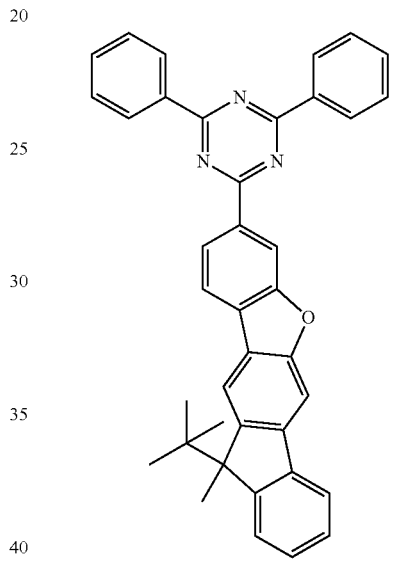
Compound E184

Compound E185
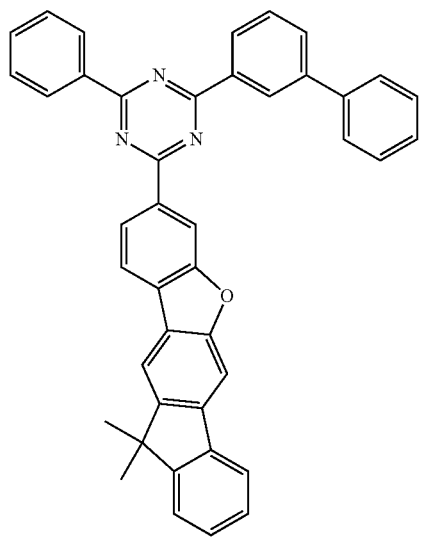
Compound E186
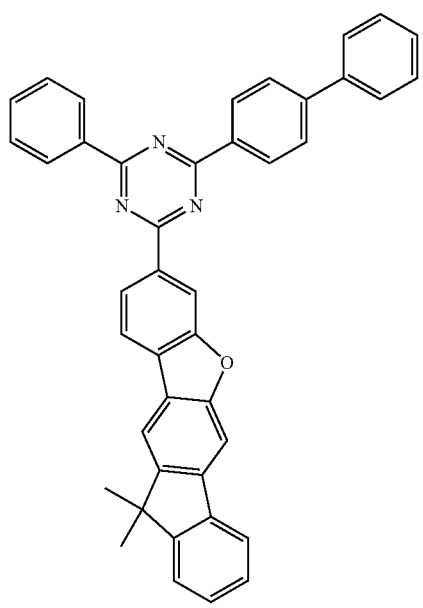
Compound E187
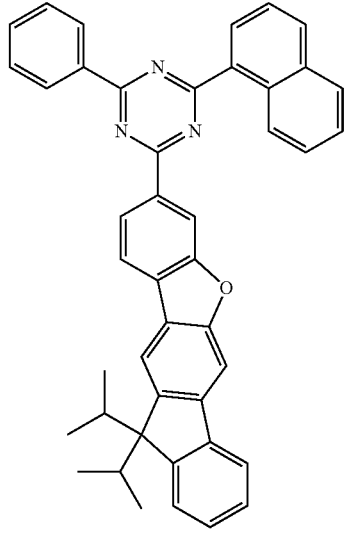
Compound E188
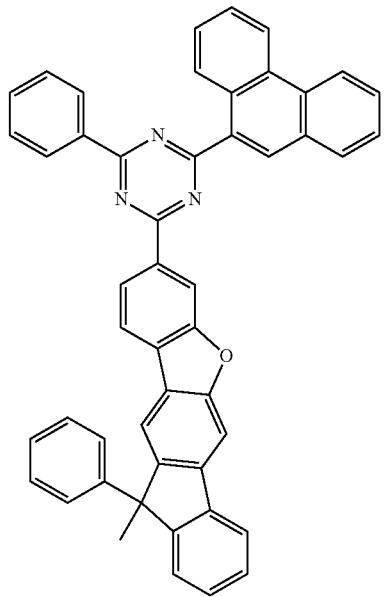

Compound E189
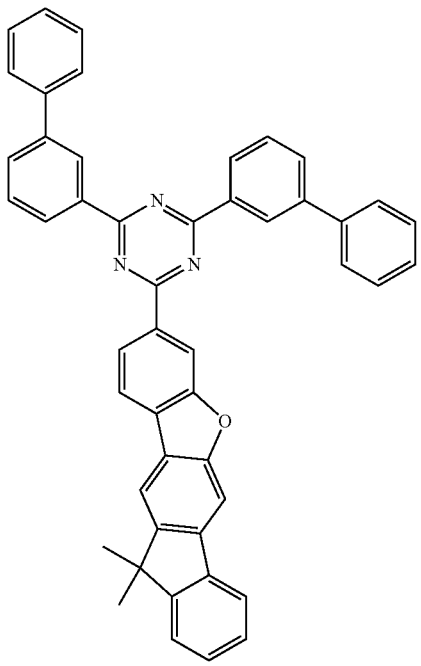
Compound E190
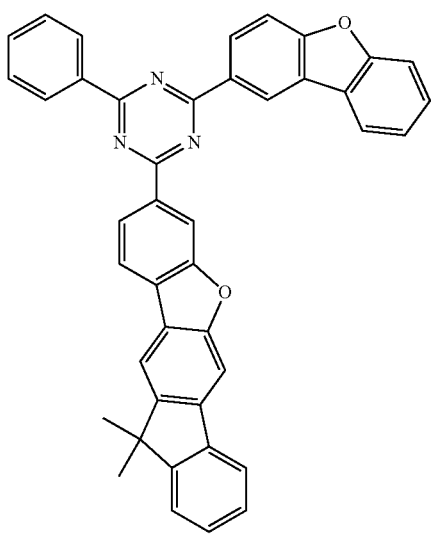
Compound E191
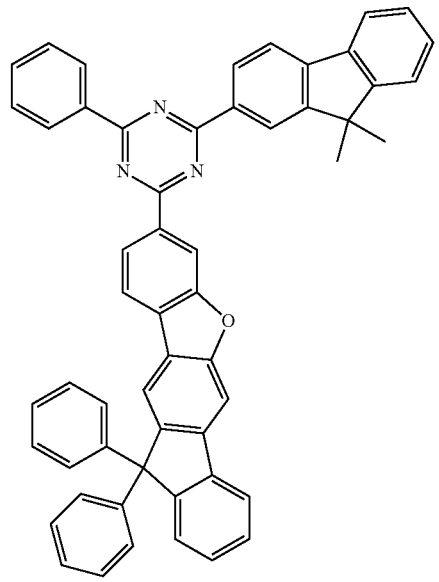
Compound E192
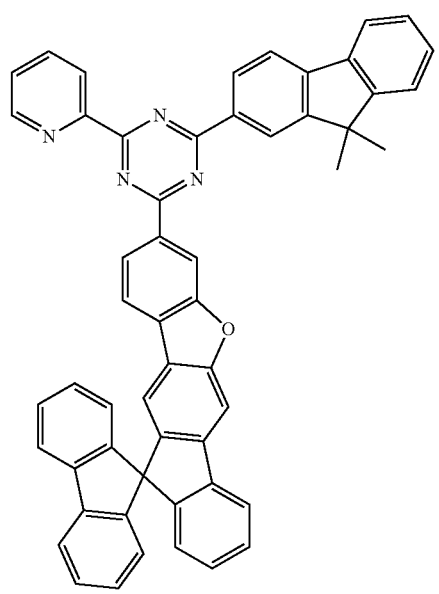

Compound E193
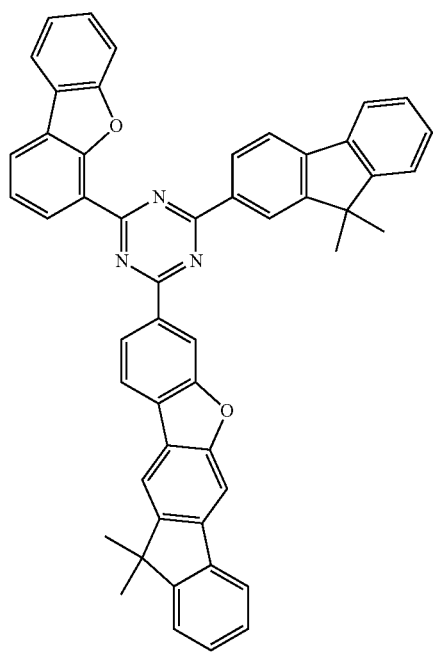
Compound E195
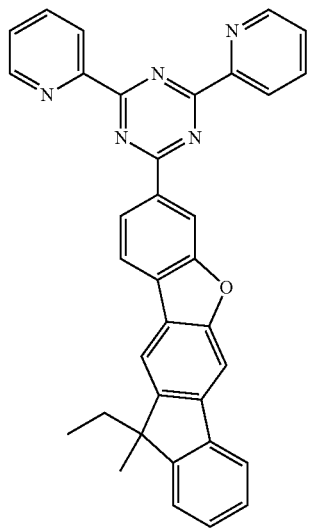
Compound E194
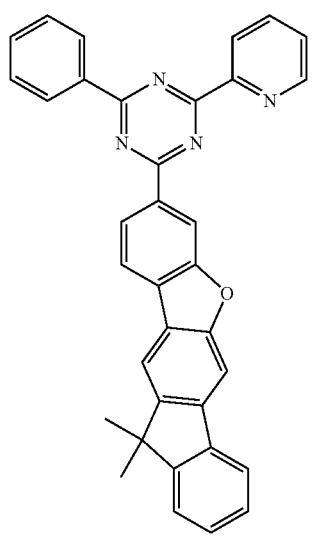
Compound E196
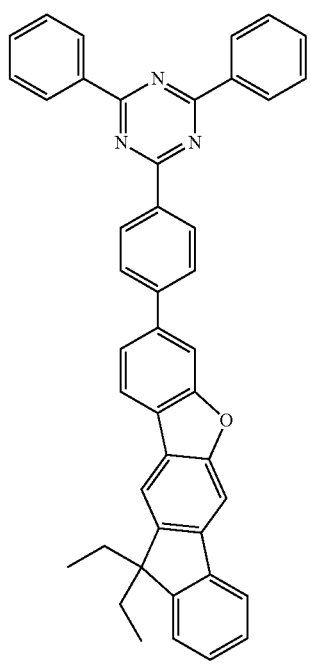

Compound E197
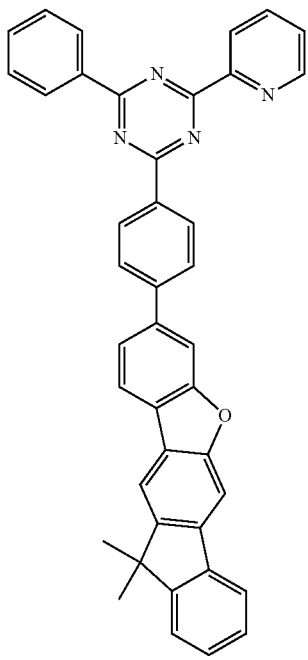
Compound E200
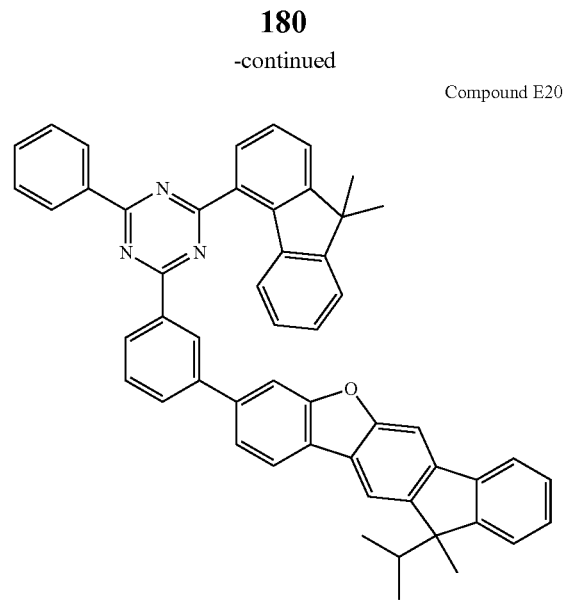
Compound E198
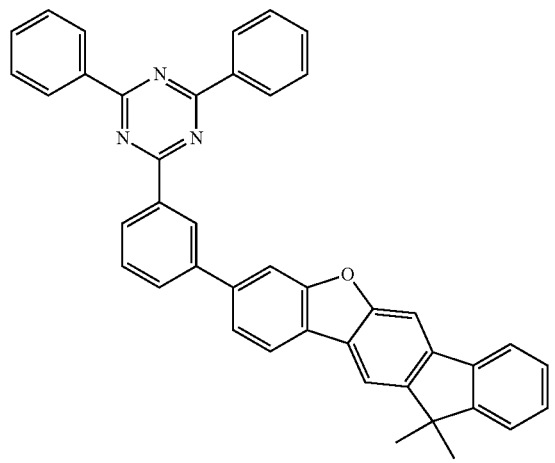
Compound E201
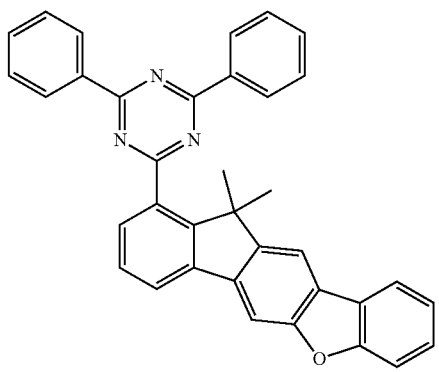
Compound E199
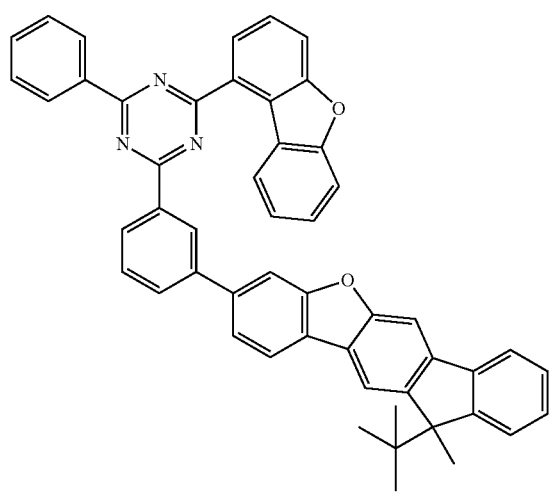
Compound E202
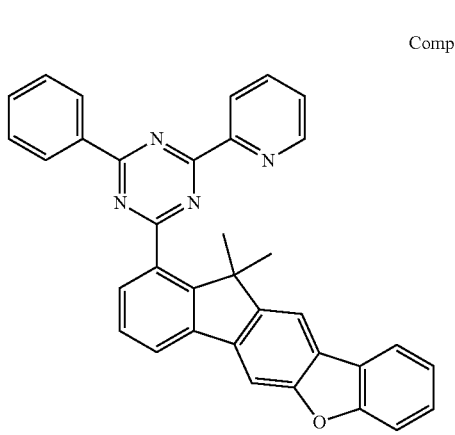

Compound E203
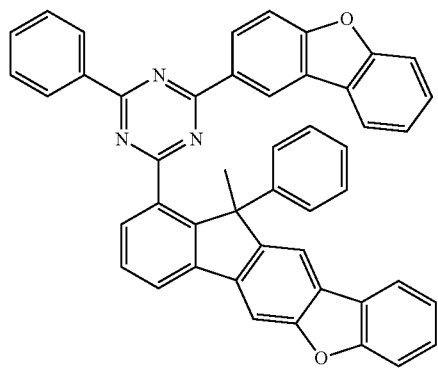
Compound E204
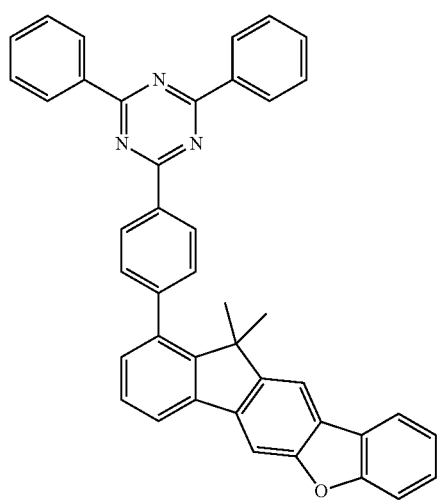
Compound E205
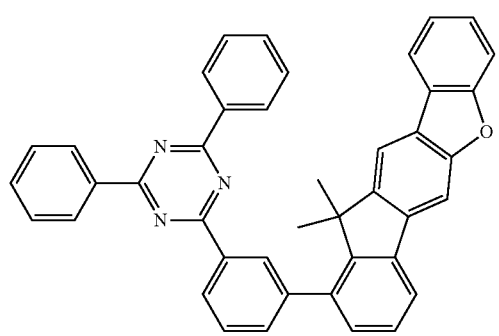
Compound E206
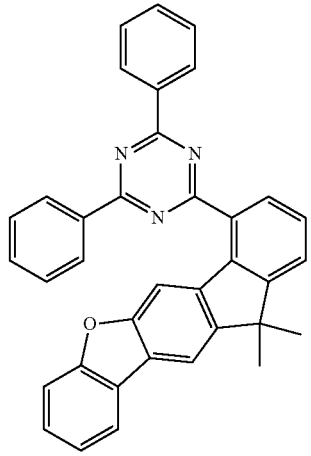
Compound E207
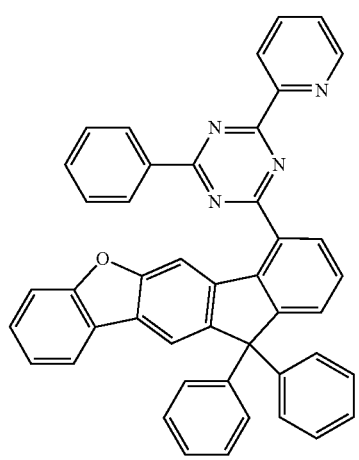
Compound E208
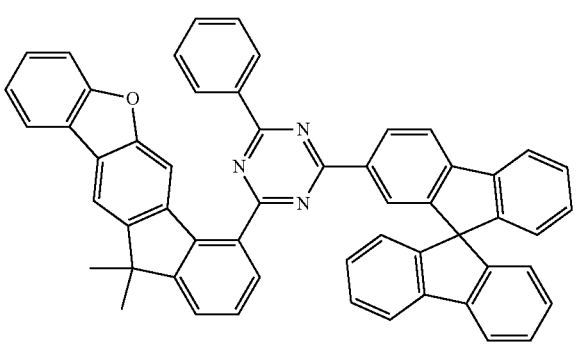

Compound E209
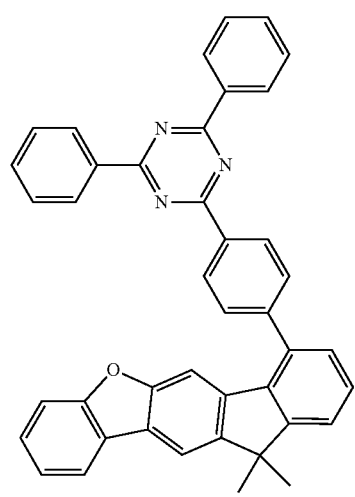
Compound E210
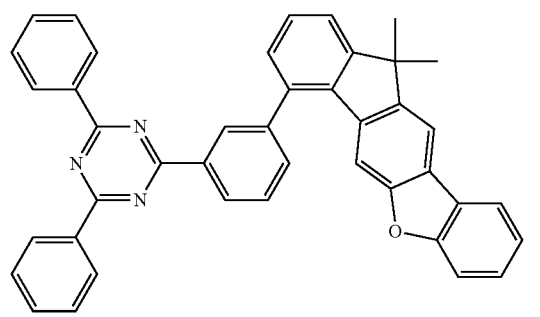
Compound E211
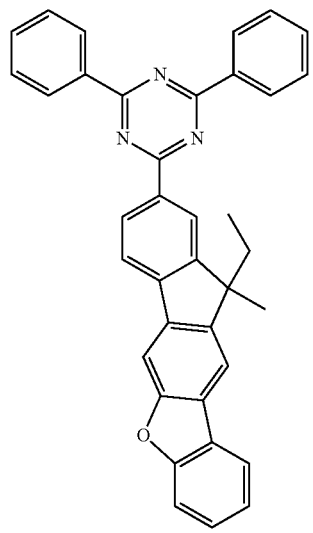
Compound E212
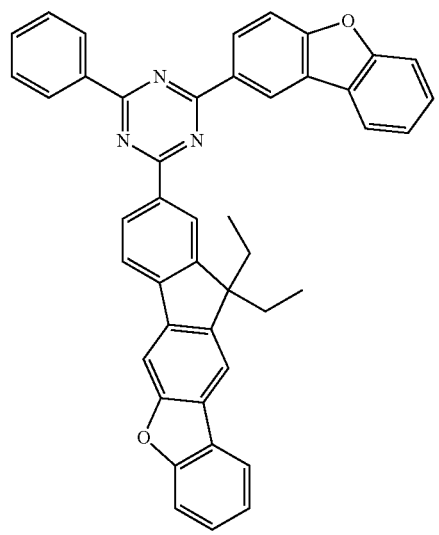
Compound E213
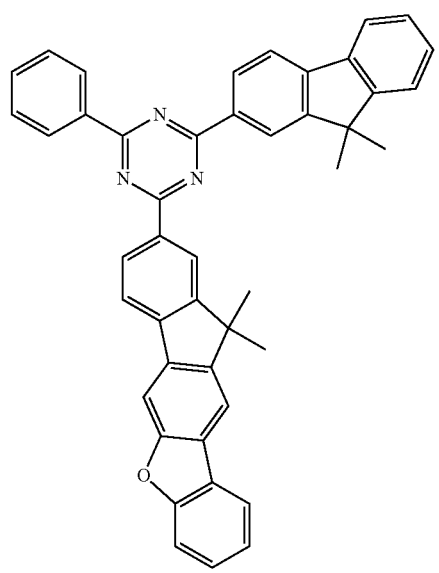

Compound E214
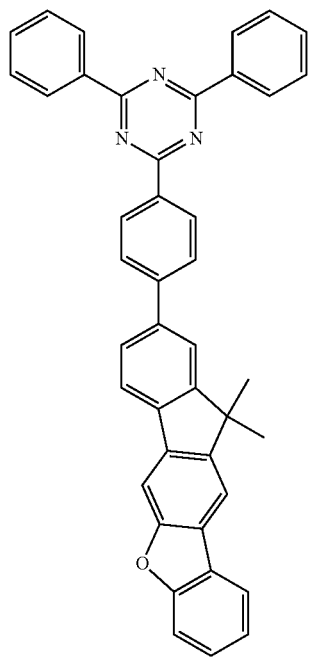
Compound E215
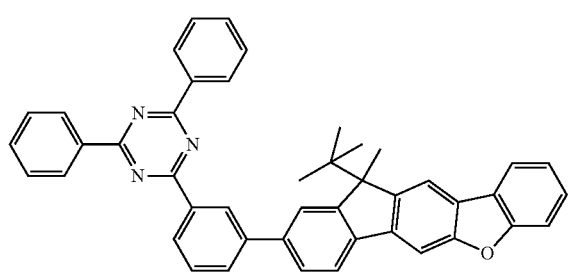
Compound E216
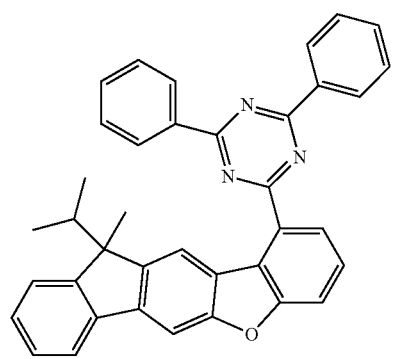
Compound E217
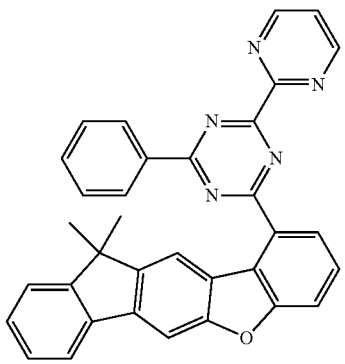
Compound E218
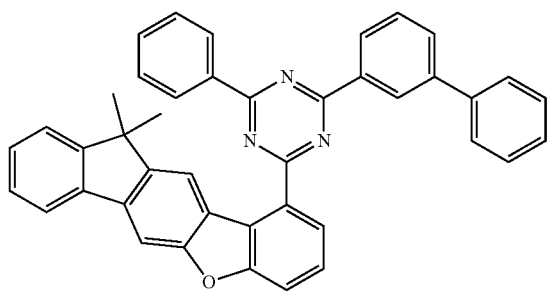
Compound E219
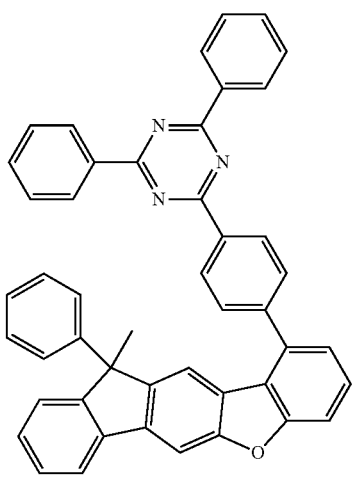
Compound E220
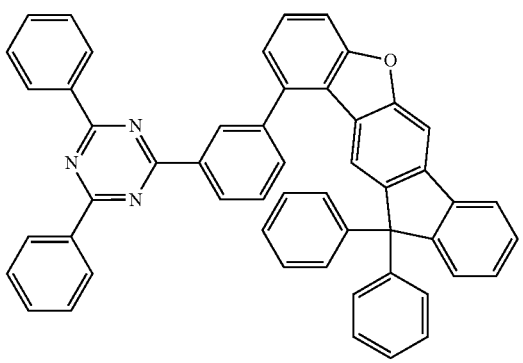

Compound E221
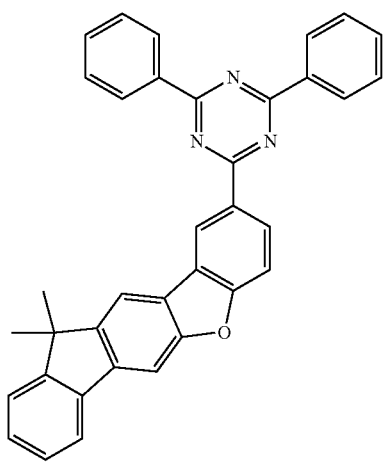
Compound E222
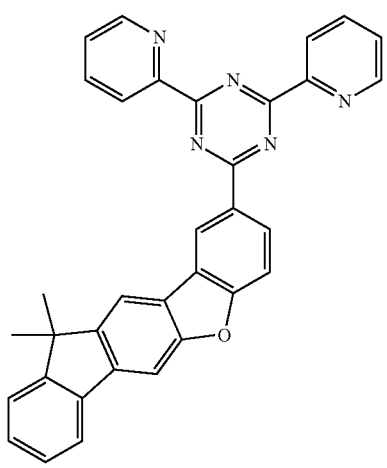
Compound E223
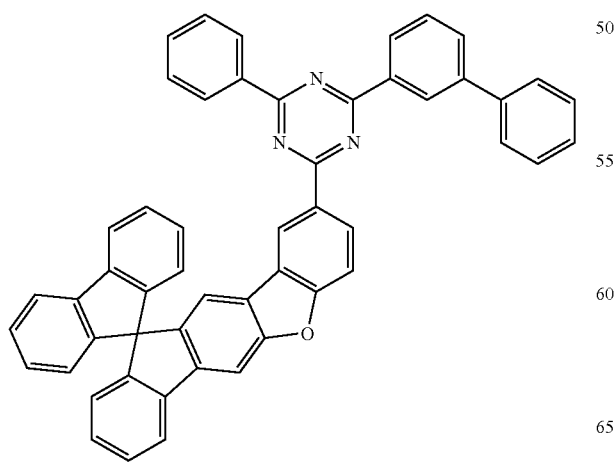
Compound E224
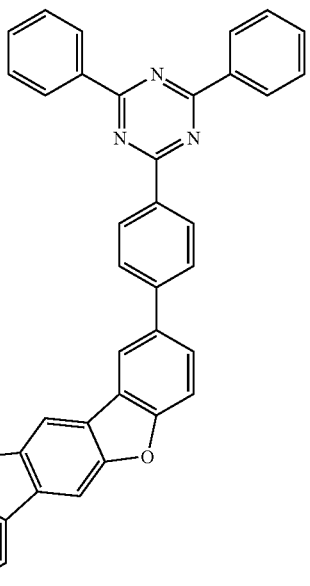
Compound E225
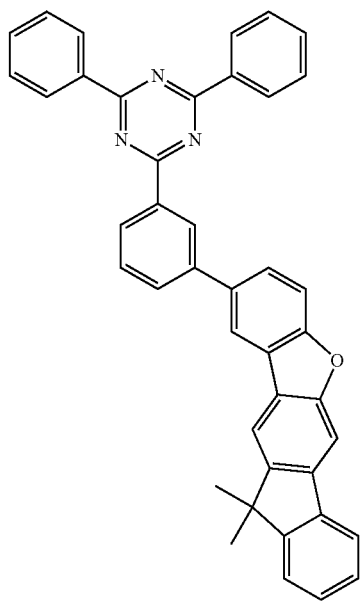
Compound E226
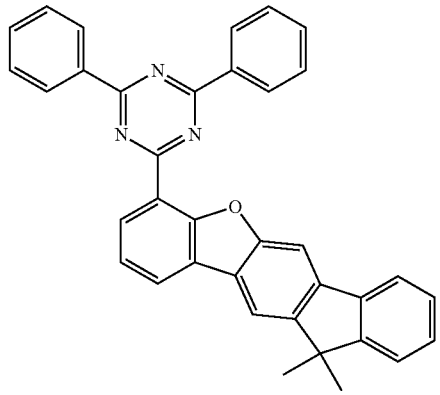

Compound E227
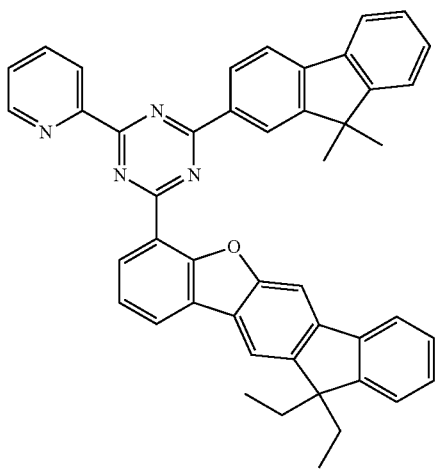
Compound E228
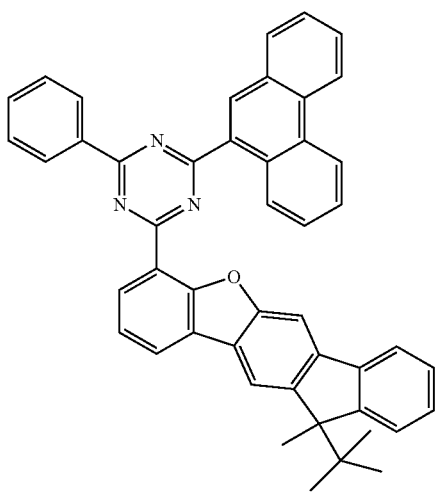
Compound E229
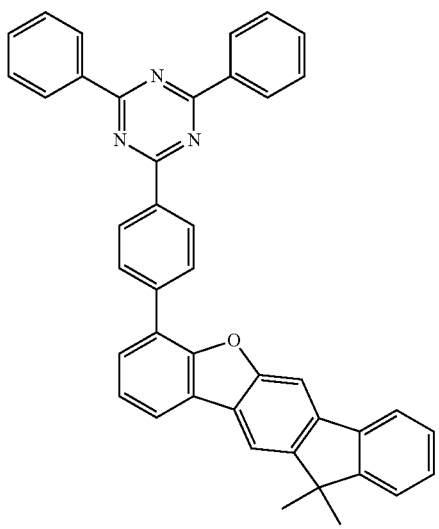
Compound E230
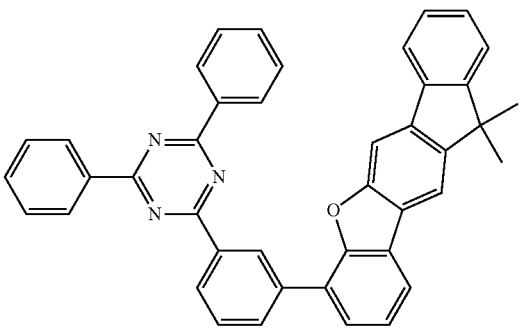
Compound E231
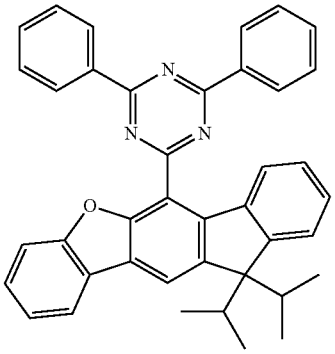
Compound E232
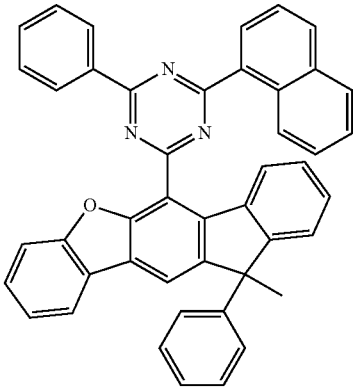
Compound E233
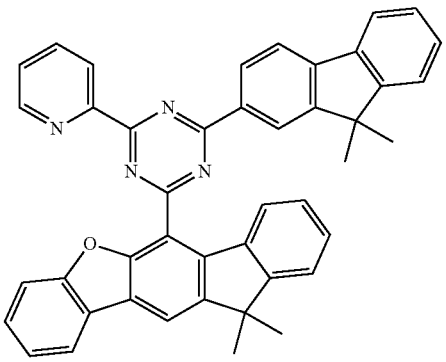

Compound E234
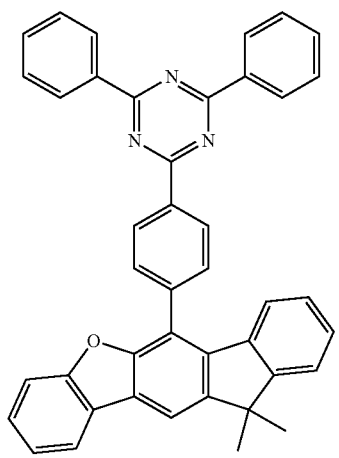
Compound E238
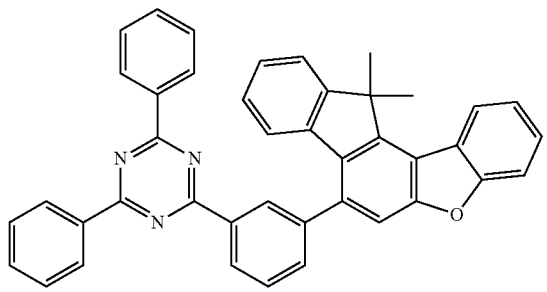
Compound E235
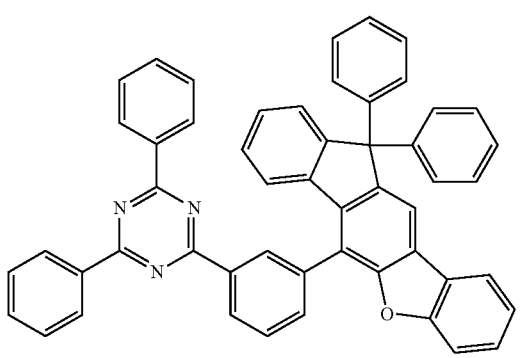
Compound E239
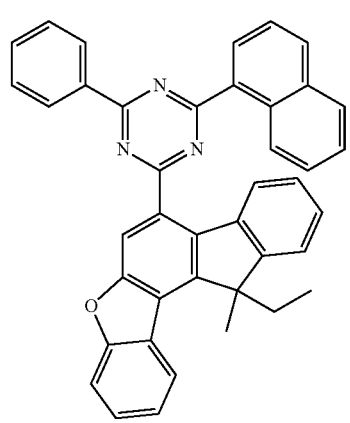
Compound E236
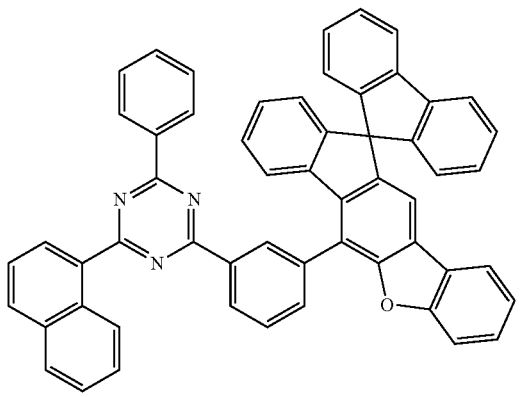
Compound E237
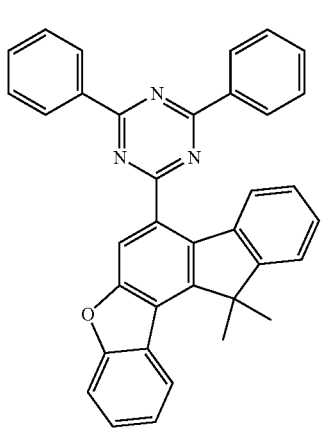
Compound E240
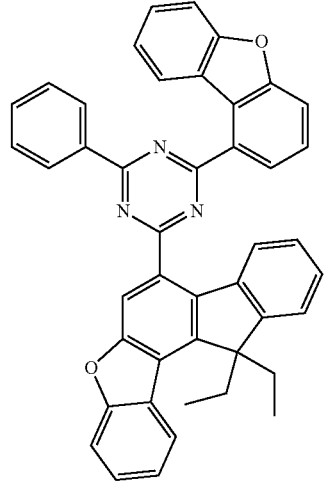

Compound E241
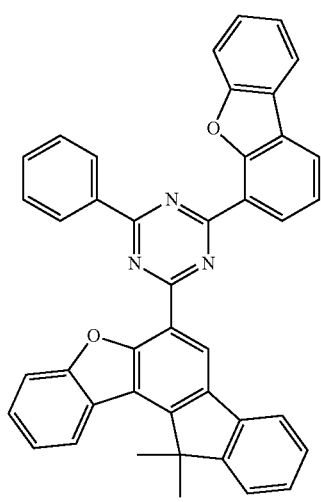
Compound E242
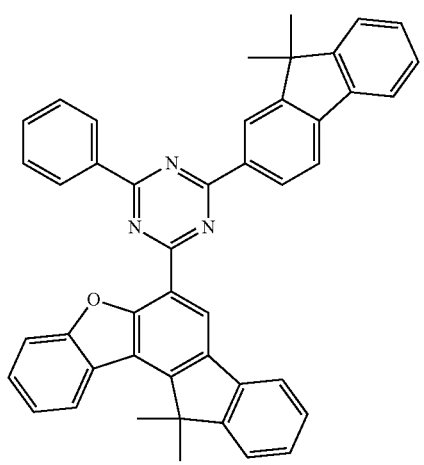
Compound E243
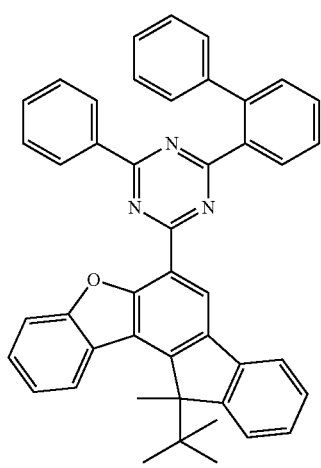
Compound E244
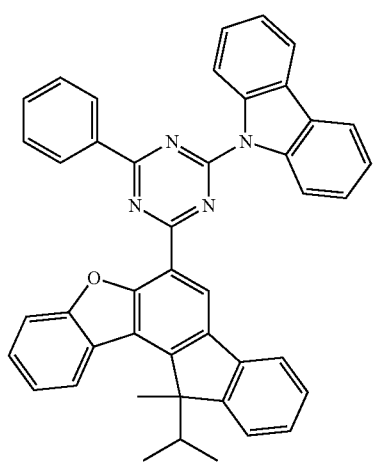
Compound E245
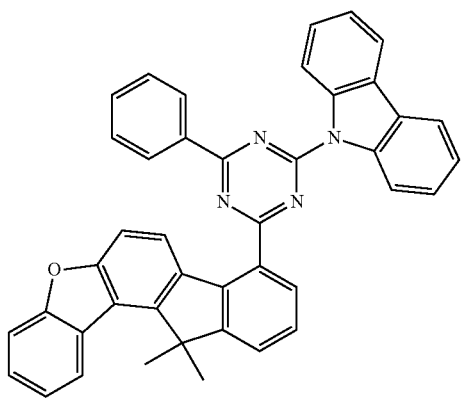
Compound E246
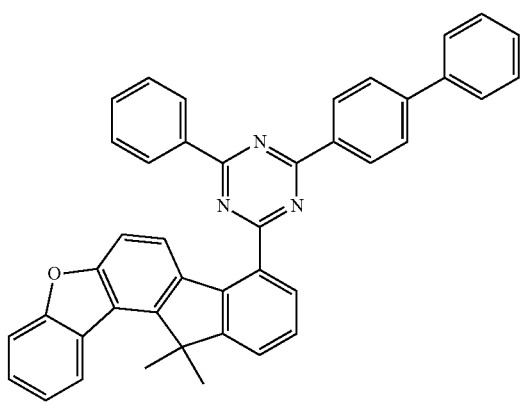

Compound E247
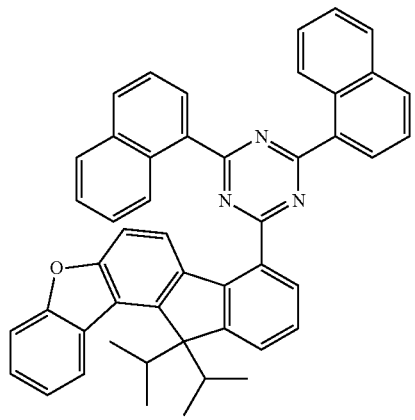
Compound E250
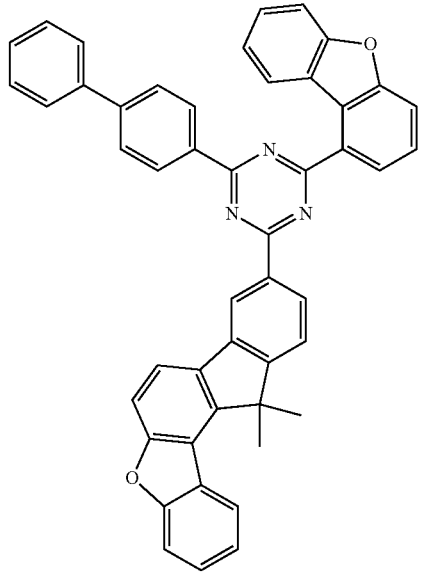
Compound E248
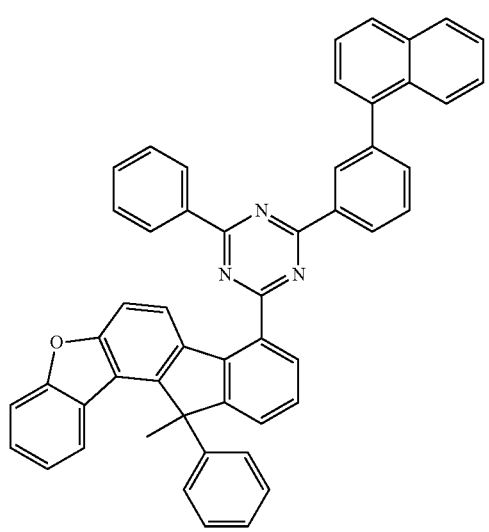
Compound E249
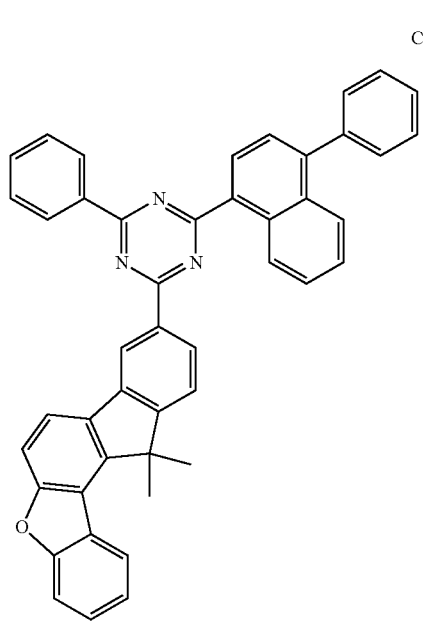
Compound E251
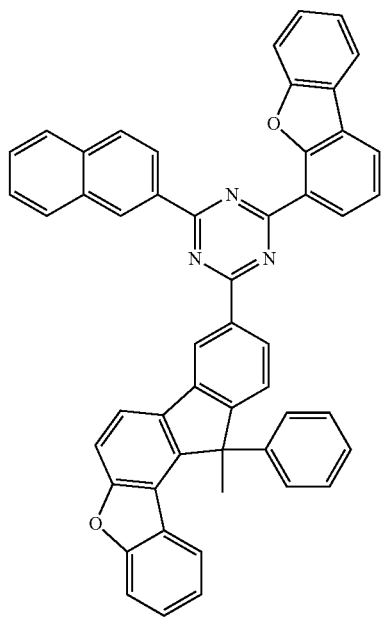

Compound E252
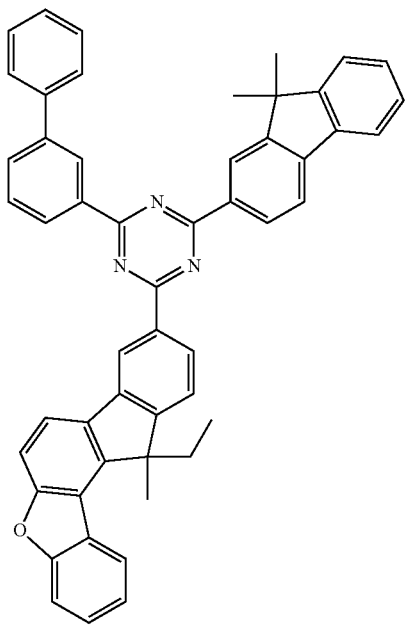
Compound E253
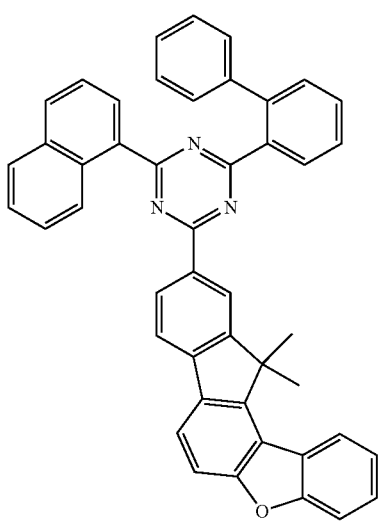
Compound E254
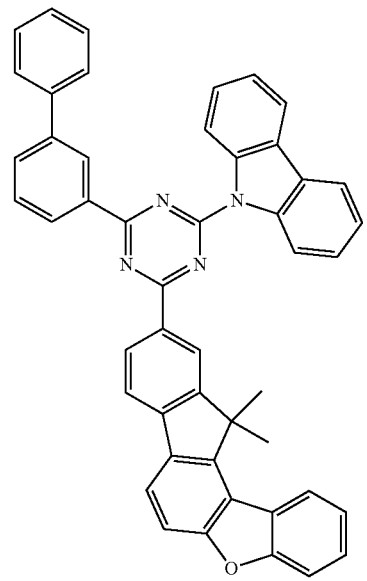
Compound E255
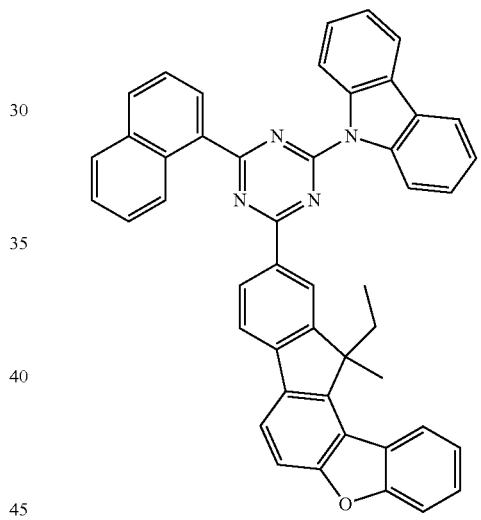
Compound E256
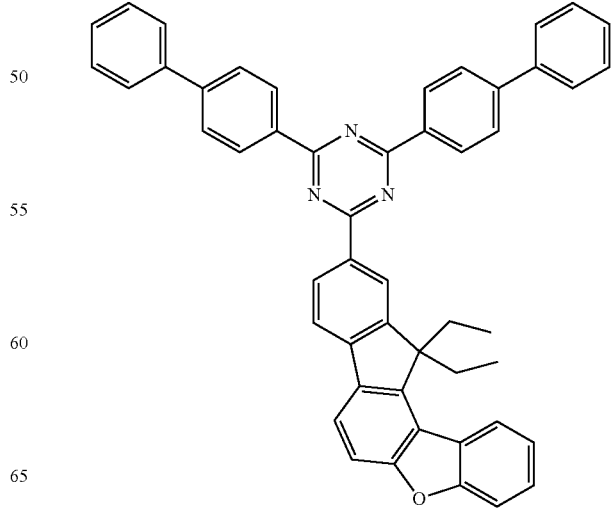

-continued
Compound E257
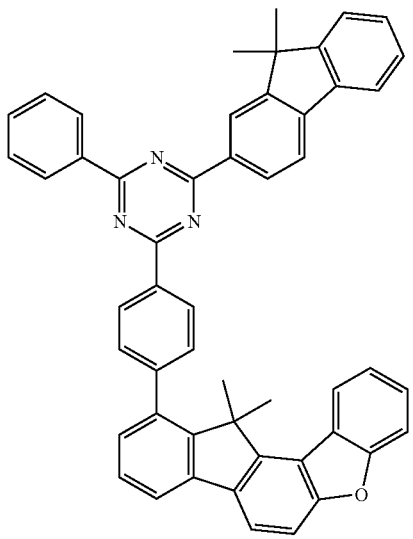
Compound E258
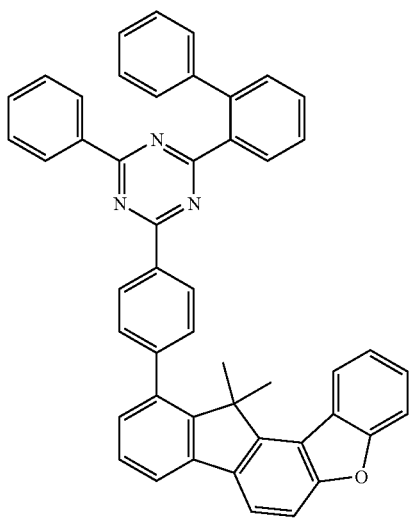
Compound E259
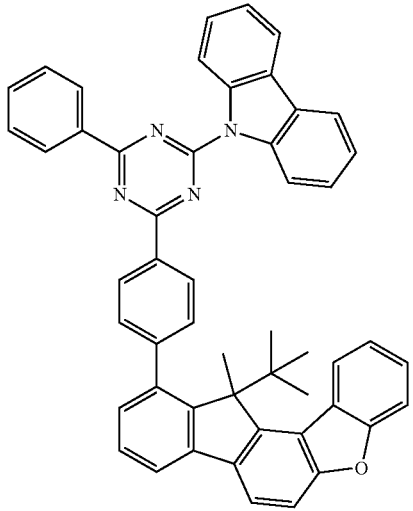
-continued
Compound E260
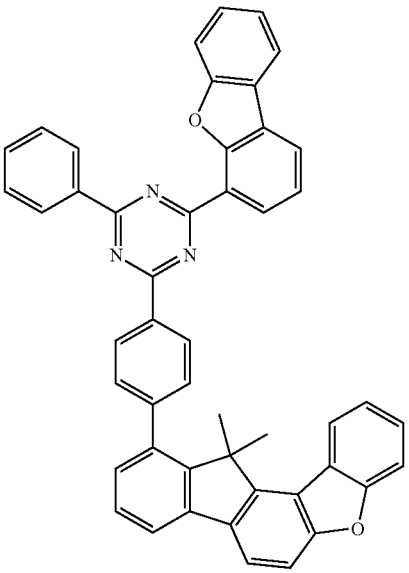
Compound E261
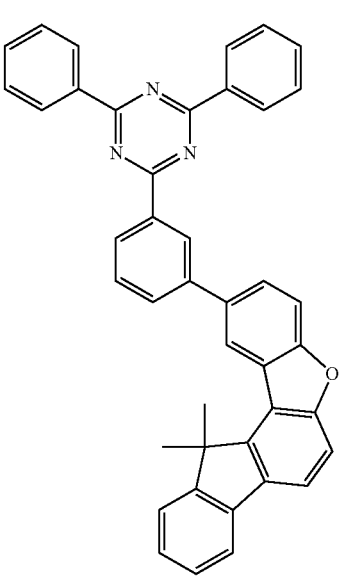

Compound E262
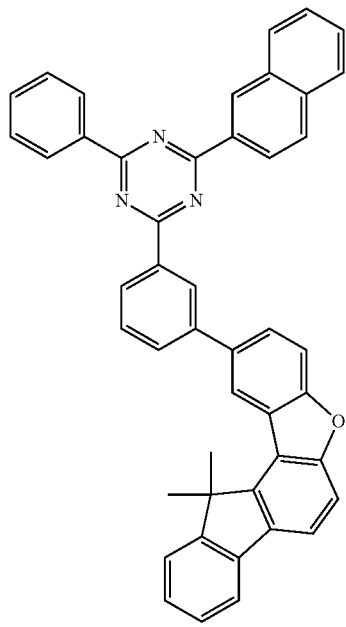
Compound E263
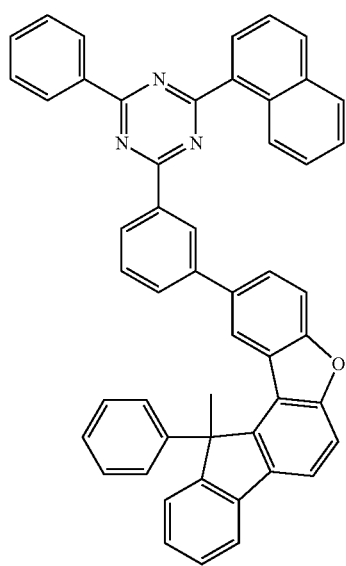
Compound E264
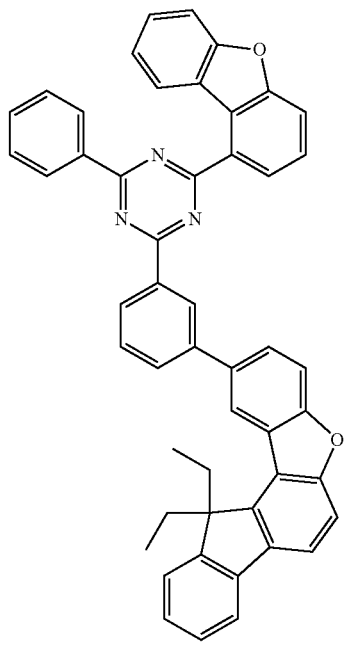
Compound E265
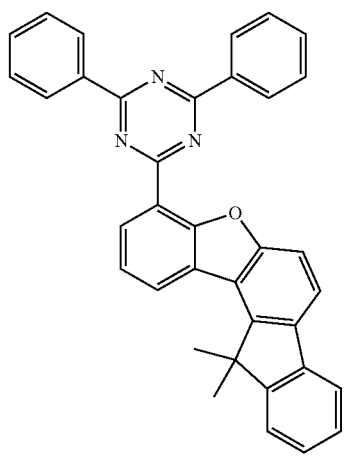
Compound E266
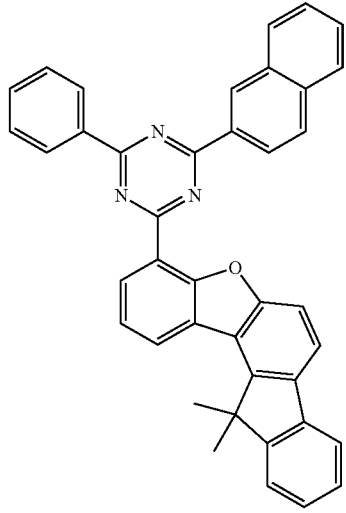

Compound E267
Compound E268
Compound E269
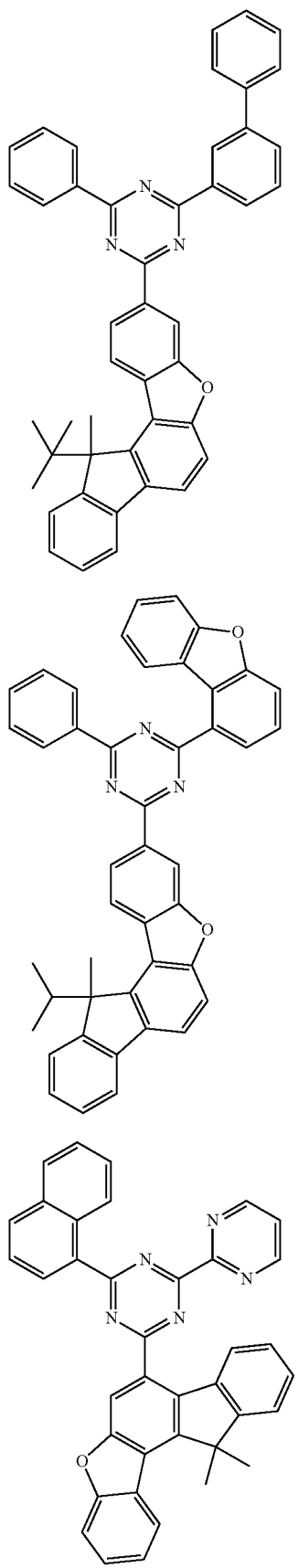
Compound E270
Compound E271
Compound E272
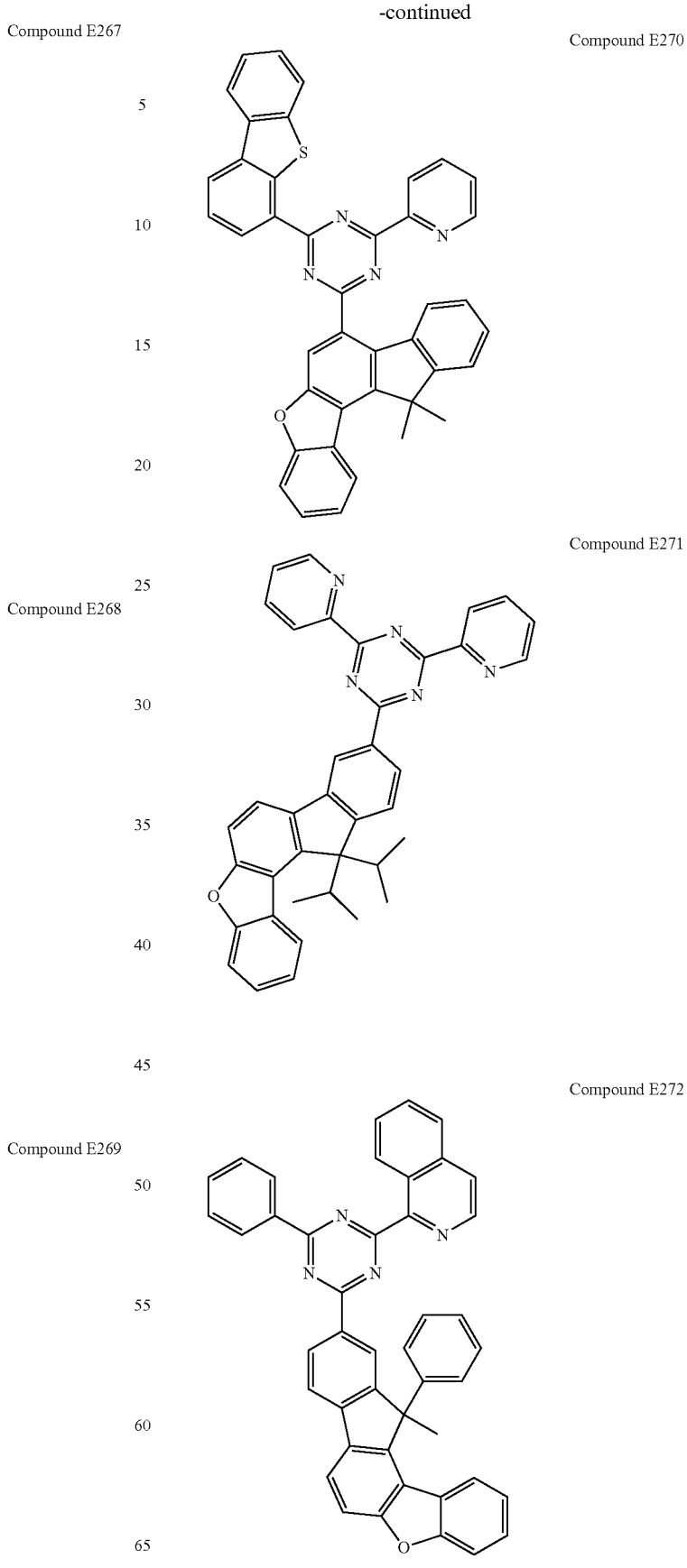

Compound E273
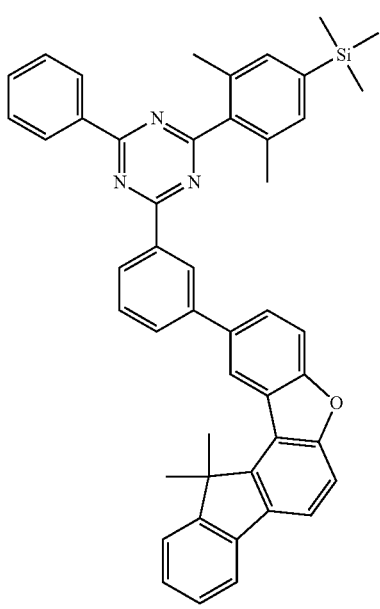
Compound E274
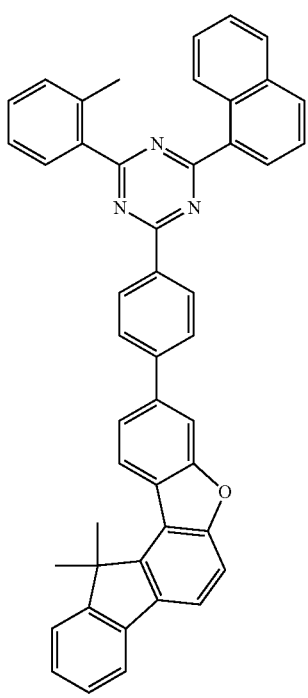
Compound E275
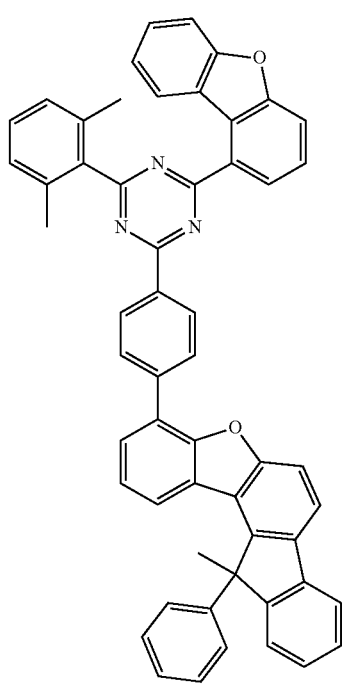
Compound E276
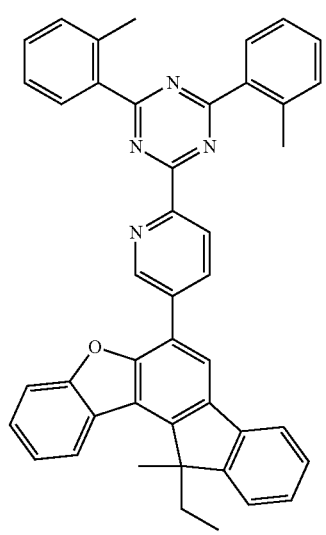
Compound E277
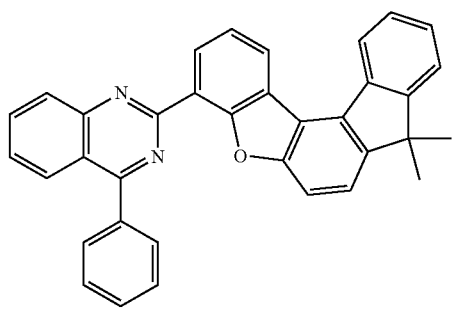

Compound E278
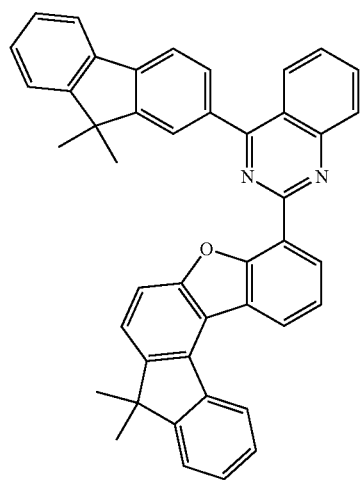
Compound E281
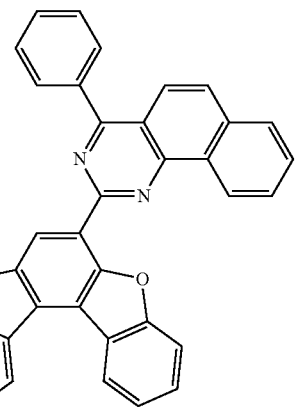
Compound E279
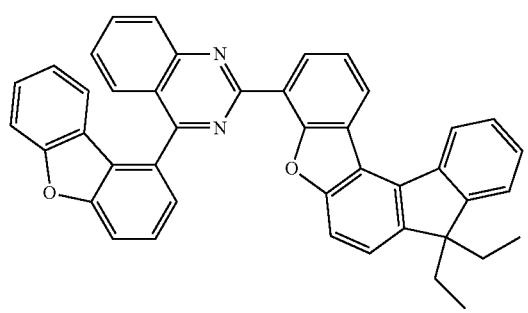
Compound E282
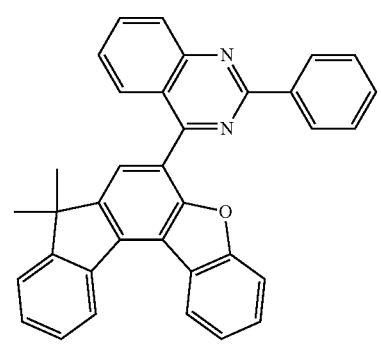
Compound E283
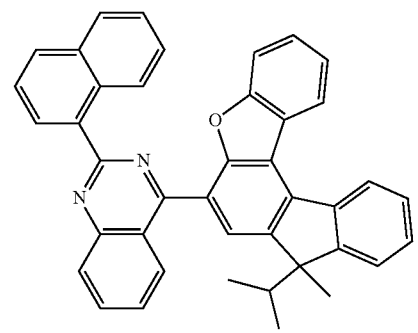
Compound E280
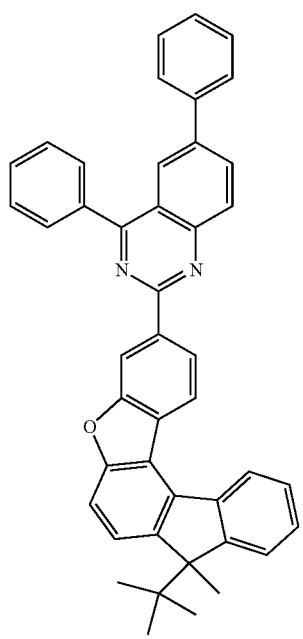
Compound E284
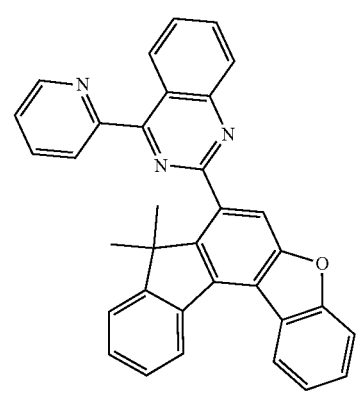

Compound E285
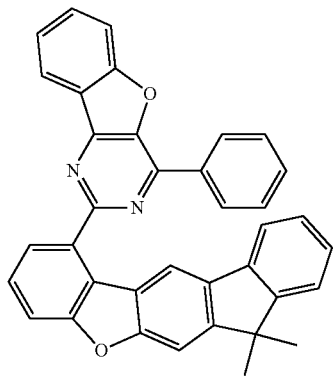
Compound E288
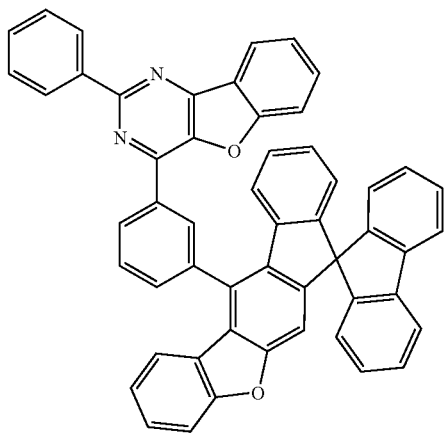
Compound E286
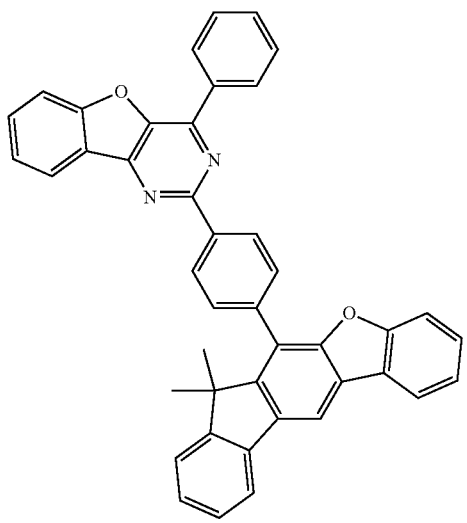
Compound E289
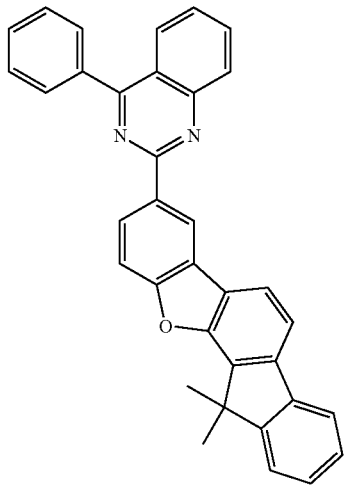
Compound E287
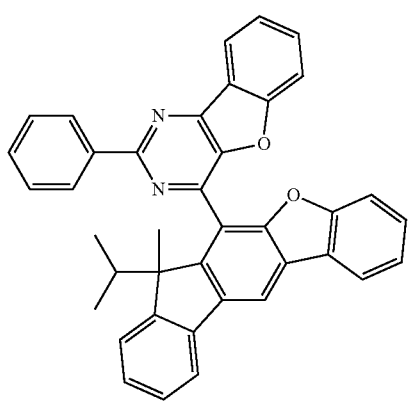
Compound E290
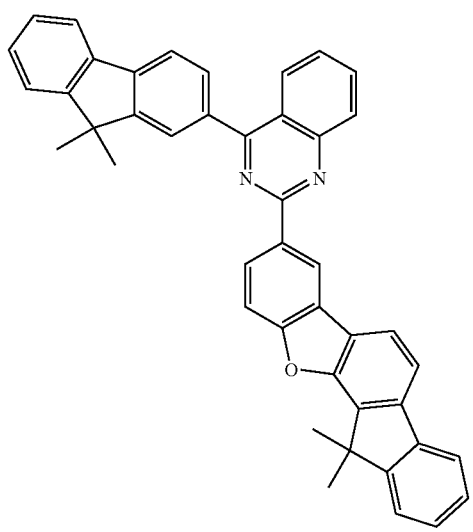

Compound E291
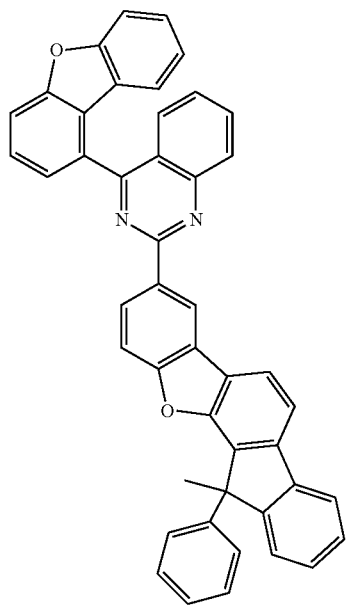
Compound E292
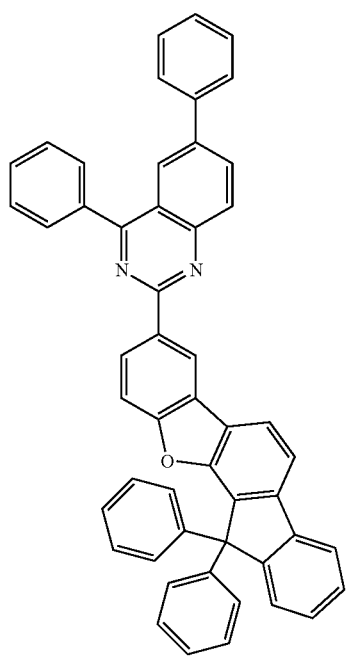
Compound E293
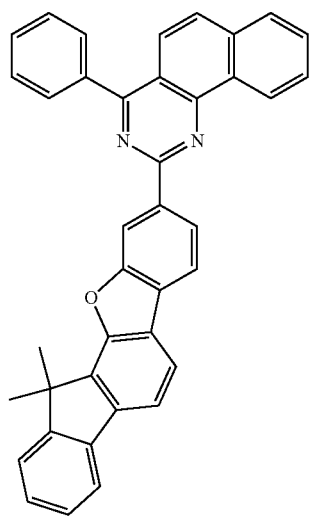
Compound E294
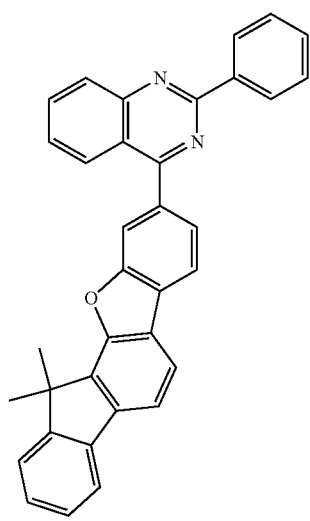
Compound E295
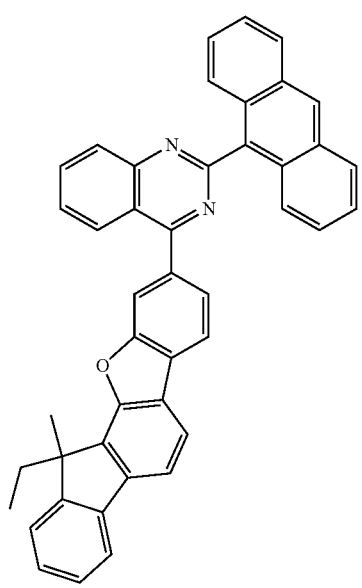

Compound E296
Compound E297
Compound E298
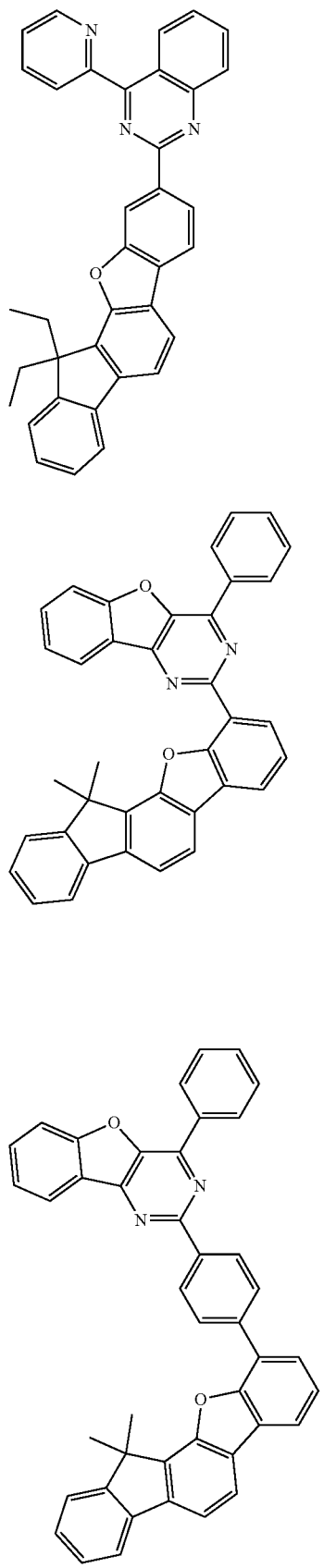
Compound E299
Compound E300
Compound E301
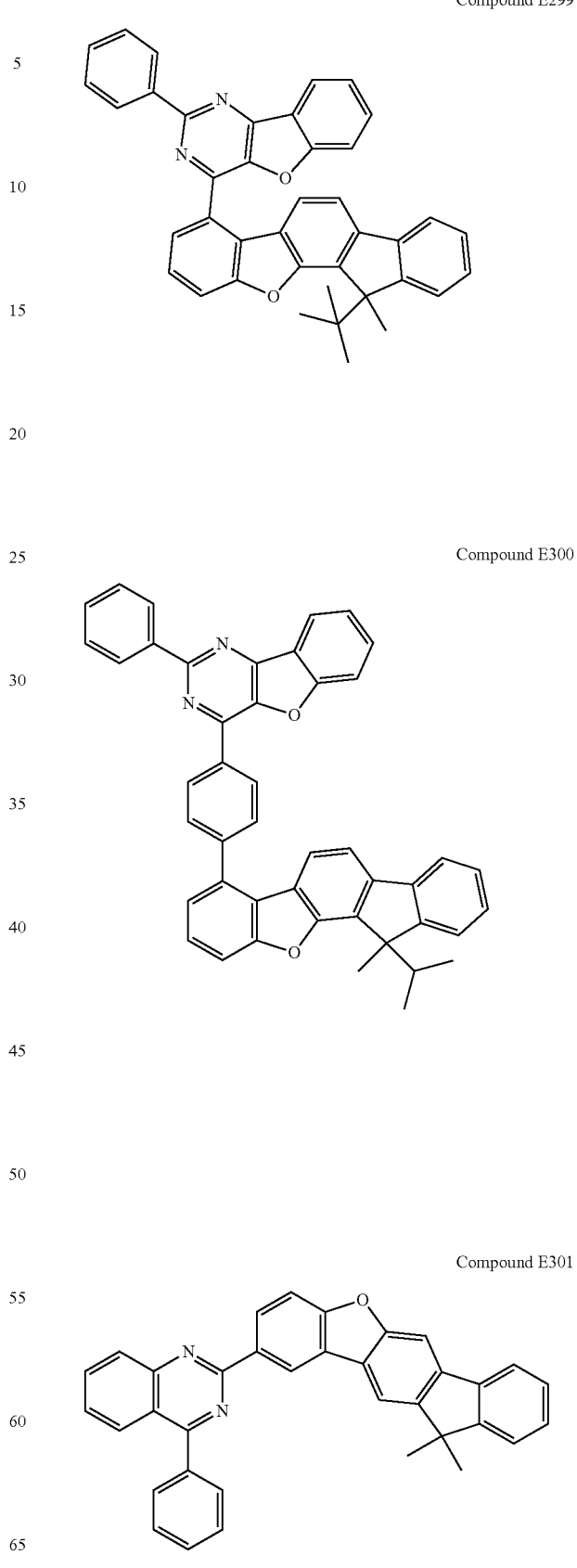

-continued
Compound E302
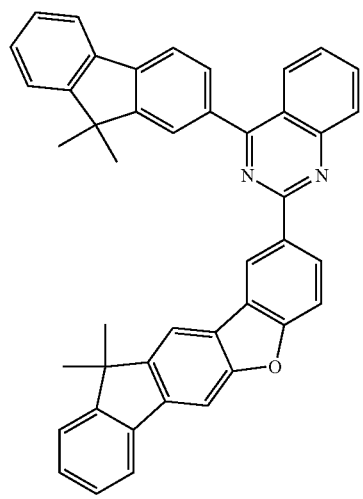
Compound E303
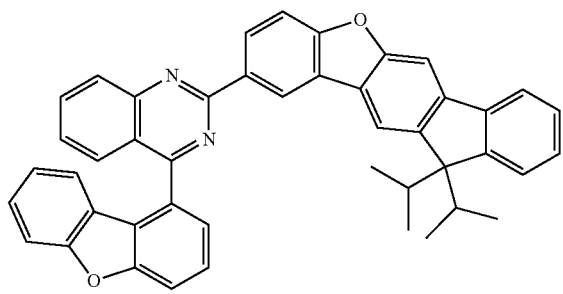
Compound E304
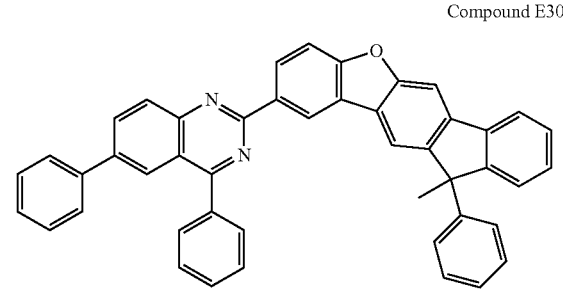
Compound E305
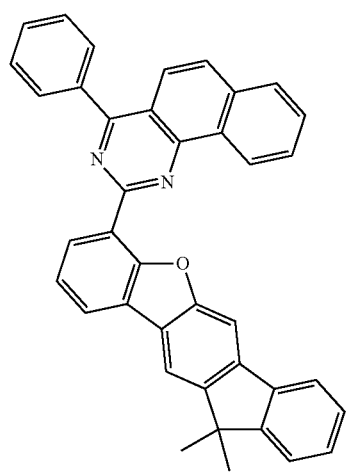
-continued
Compound E306
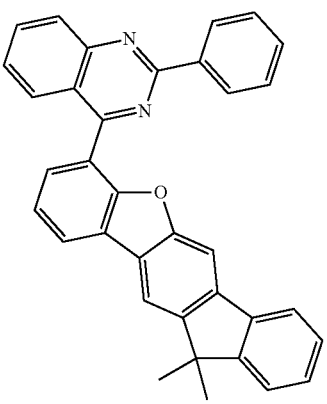
Compound E307
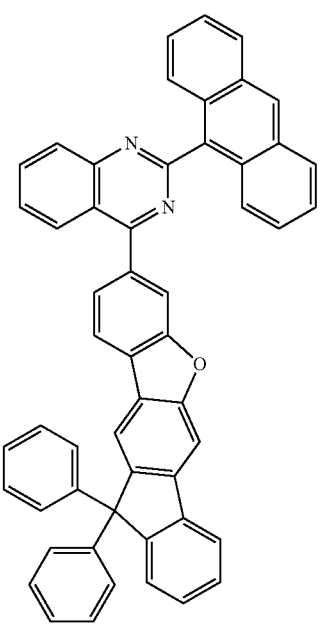
Compound E308
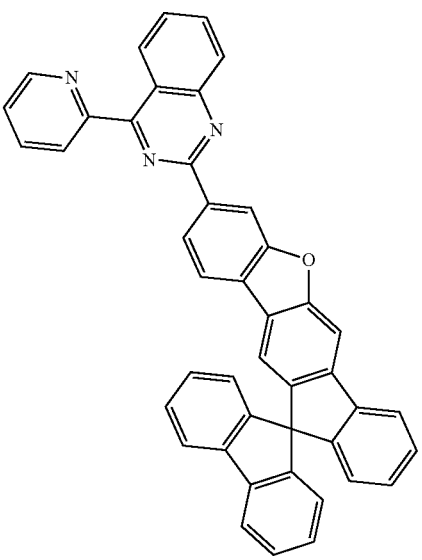

Compound E309
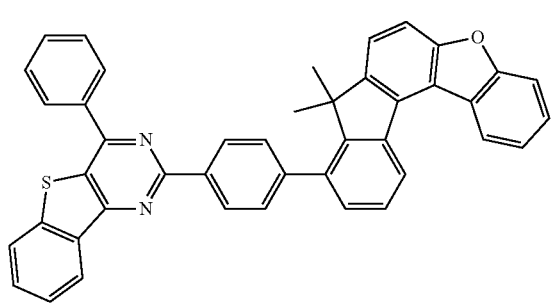
Compound E310
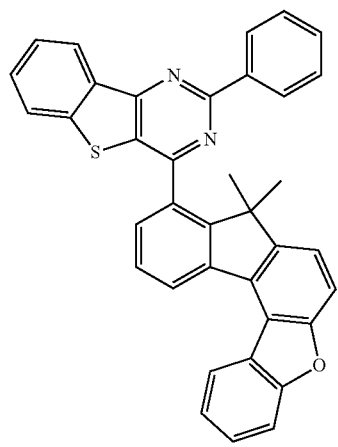
Compound E311
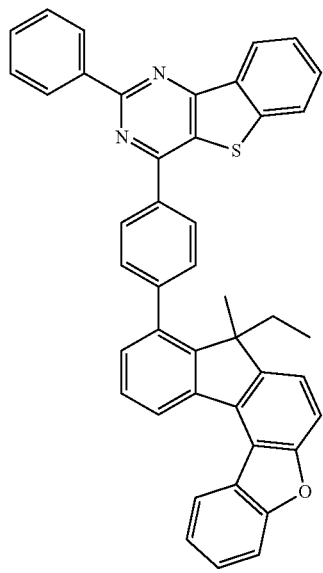
Compound E312
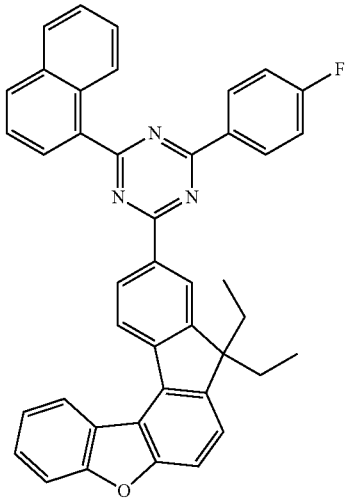
Compound E313
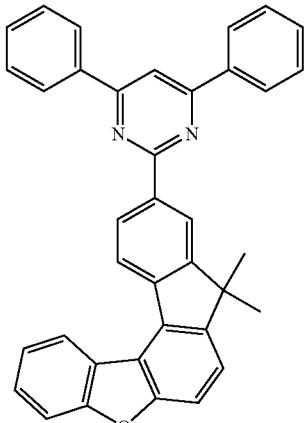
Compound E314
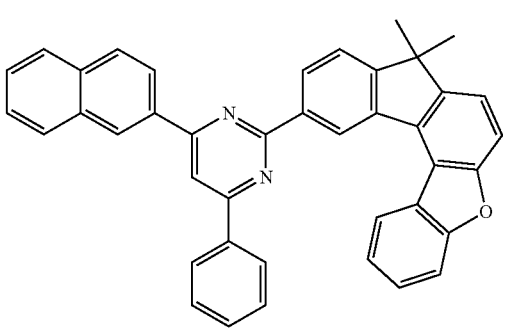

Compound E315
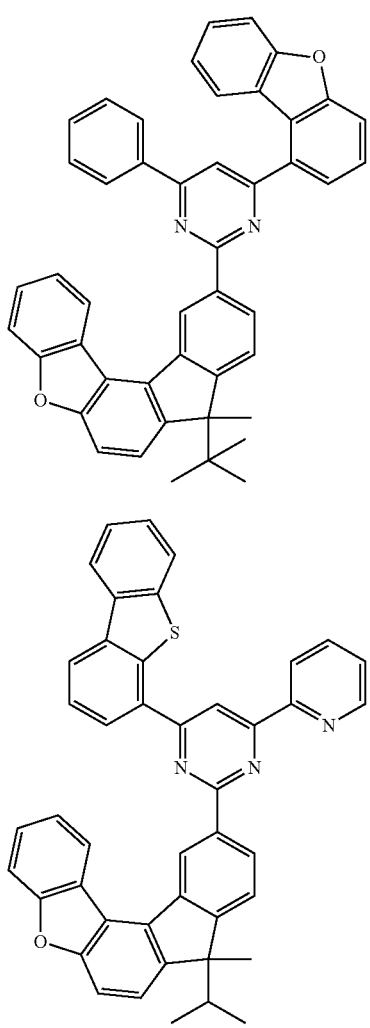
Compound E318
Compound E319
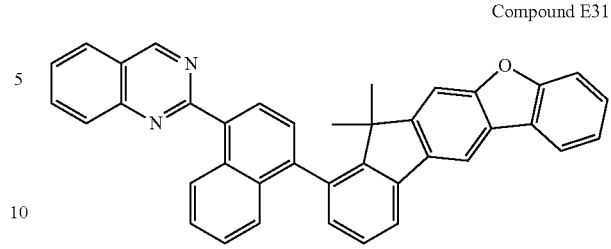
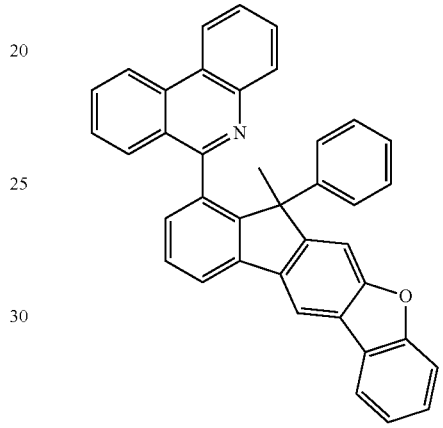
Compound E316
Compound E317
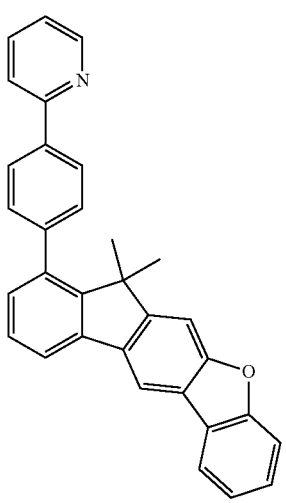
Compound E320
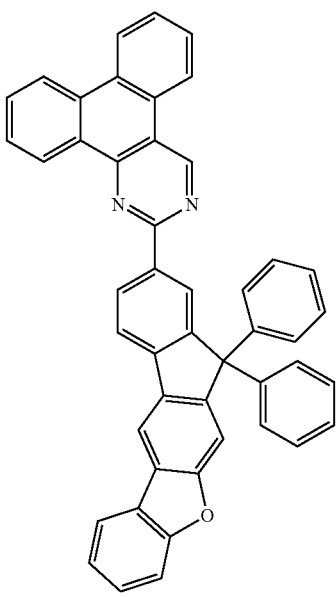

Compound E321
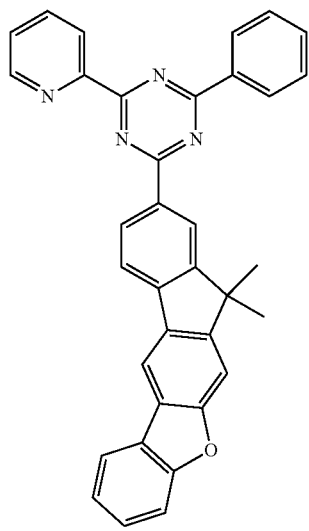
Compound E324
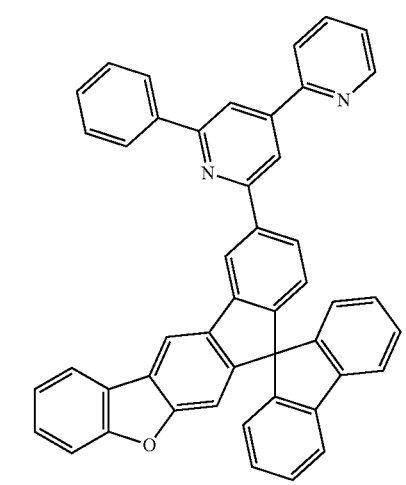
Compound E322
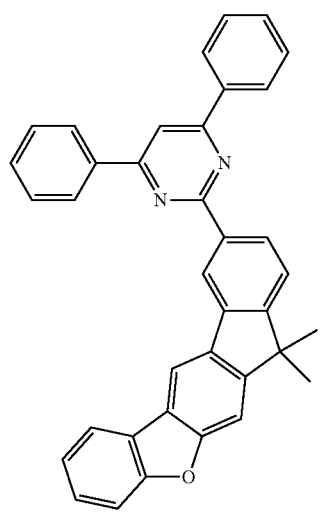
Compound E325
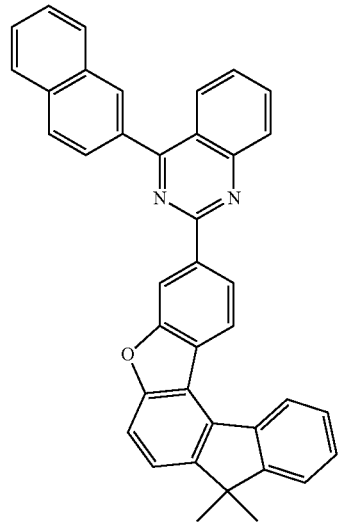
Compound E323
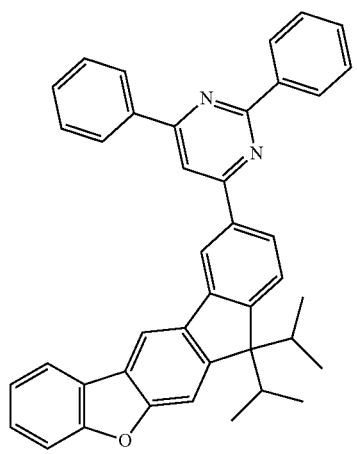
Compound E326
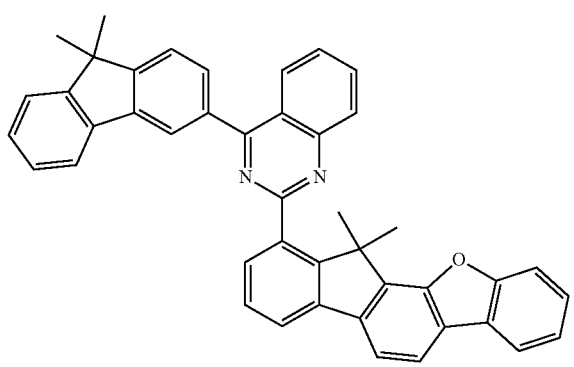

Compound E327
Compound E328
Compound E329
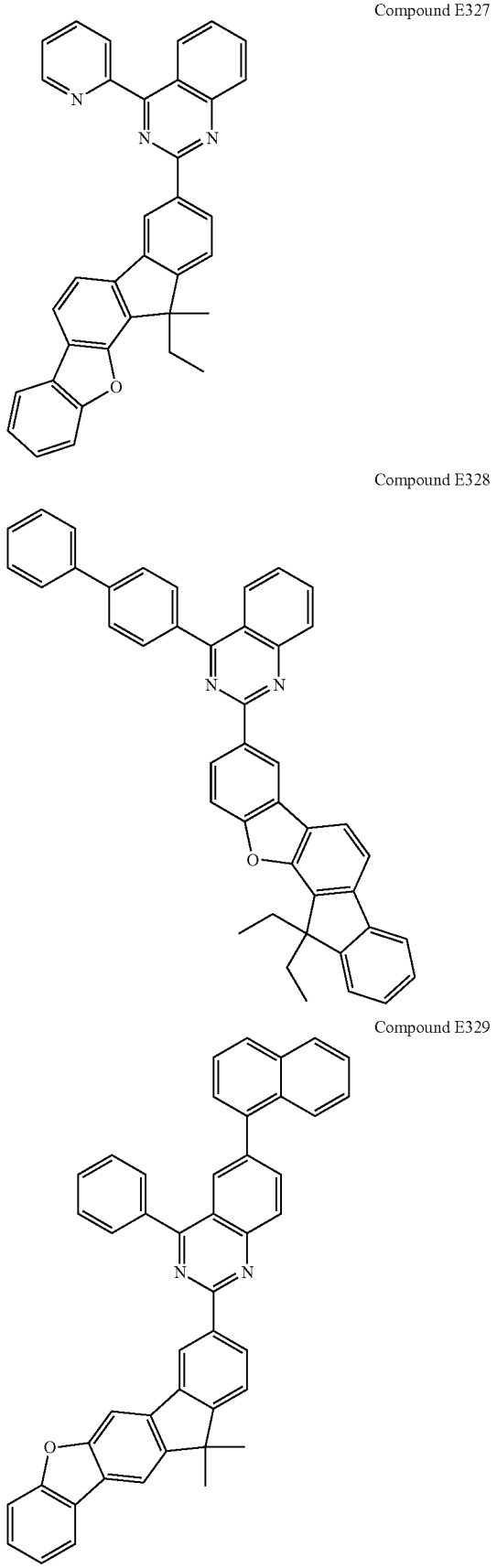
Compound E330
Compound E331
Compound E332
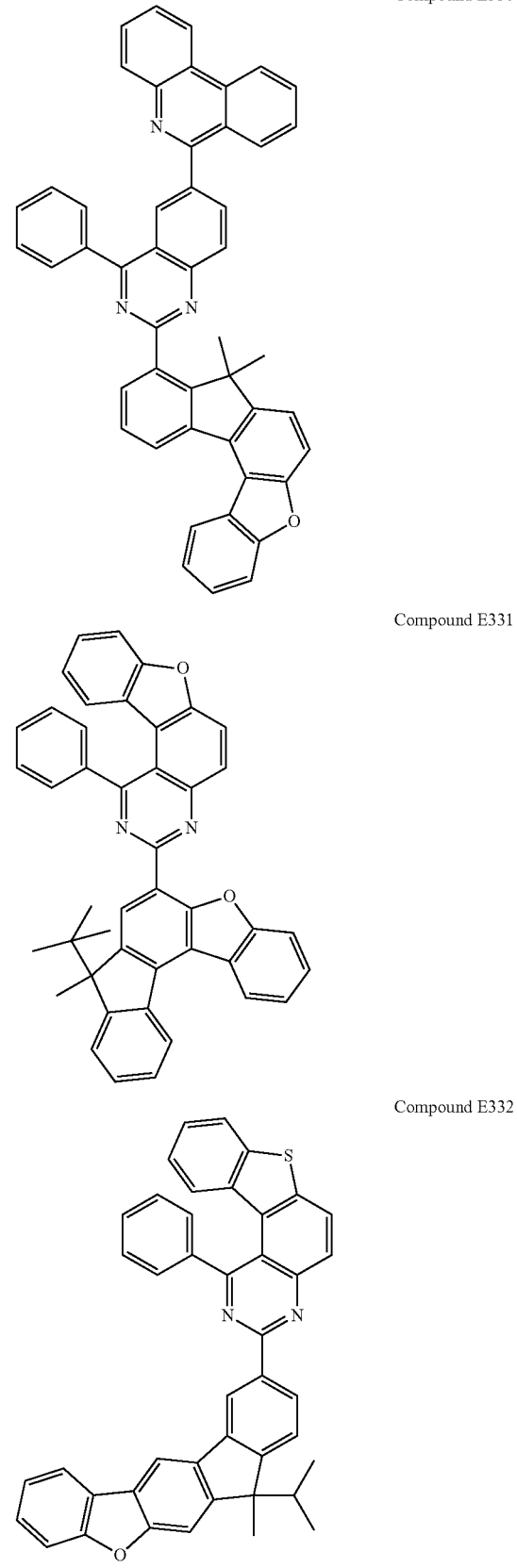

Compound E333
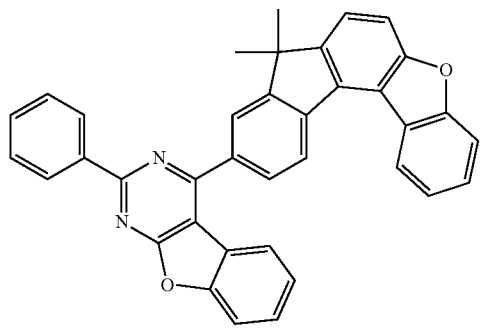
Compound E334
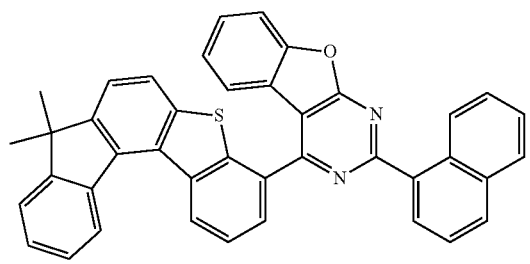
Compound E335
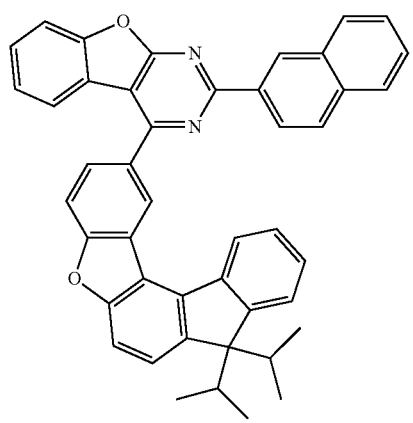
Compound E336
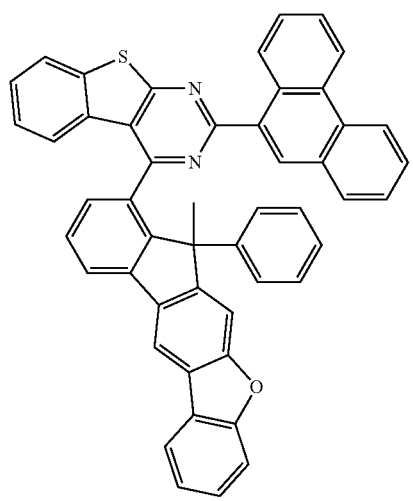
Compound E337
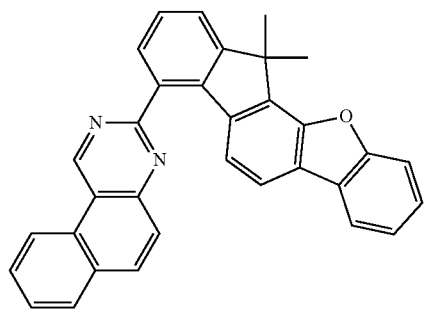
Compound E338
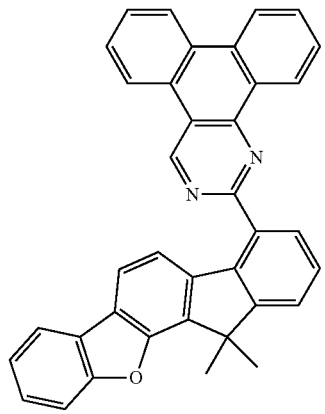
Compound E339
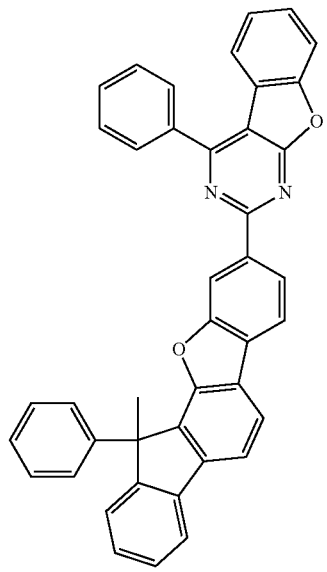

Compound E340
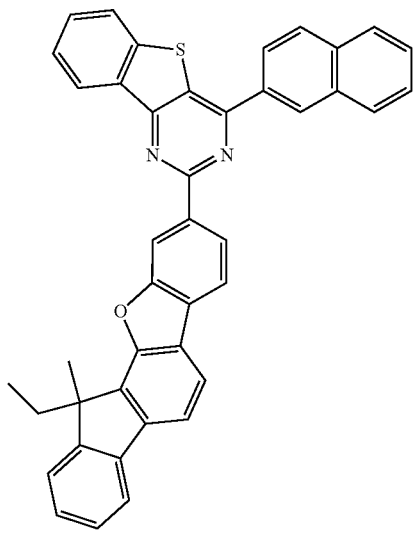
Compound E341
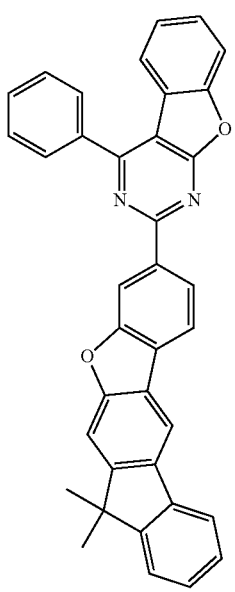
Compound E342
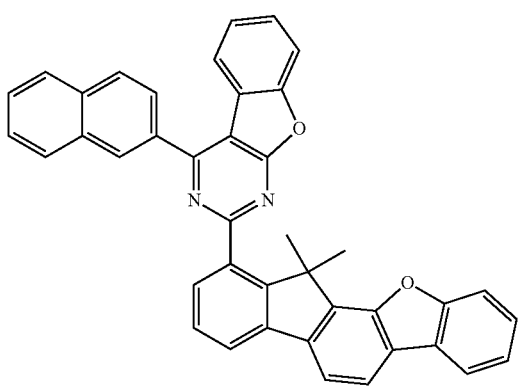
Compound E343
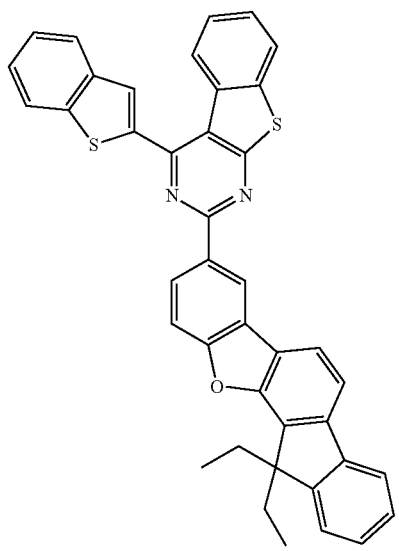
Compound E344
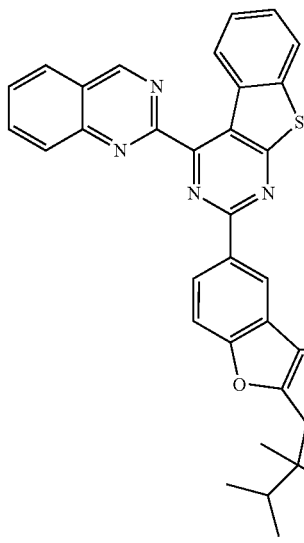
Compound E345
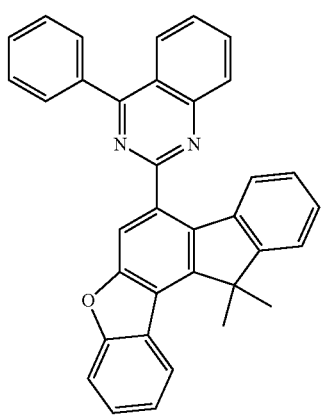

Compound E346
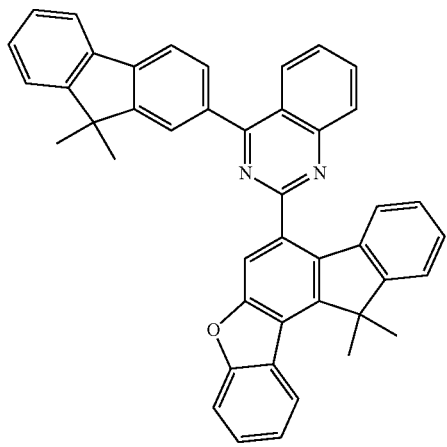
Compound E347
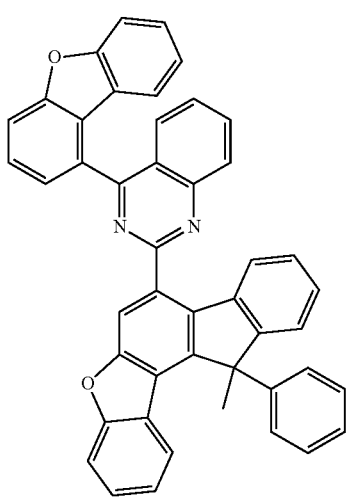
Compound E348
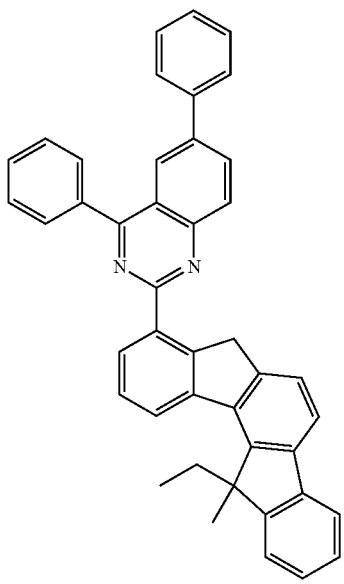
Compound E349
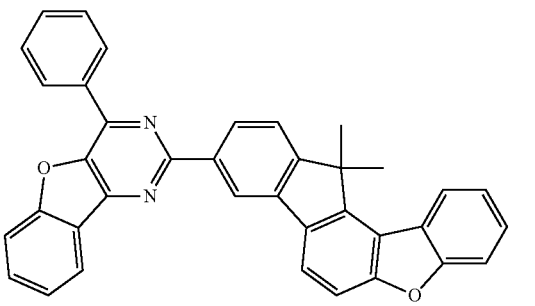
Compound E350
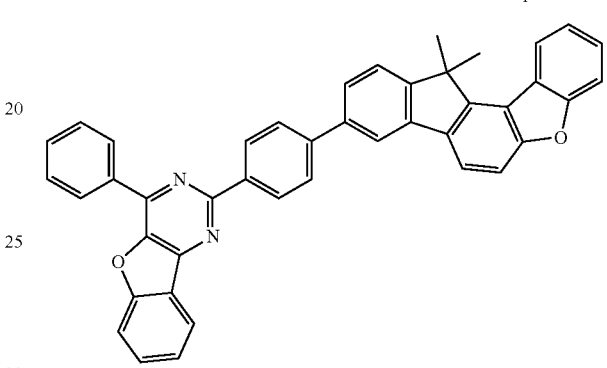
Compound E351
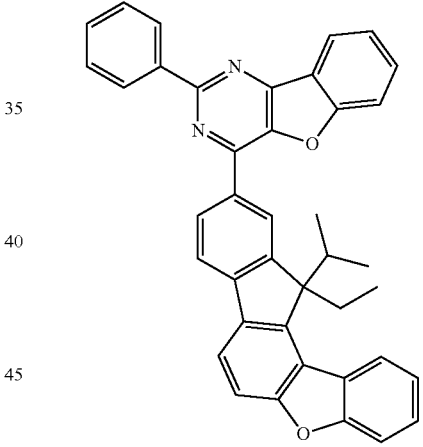
Compound E352
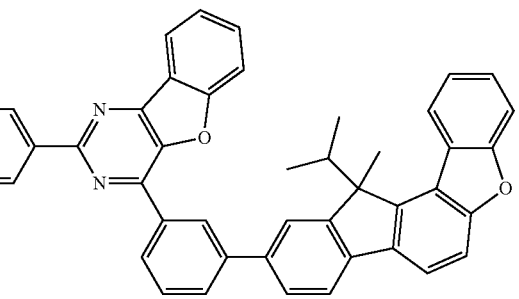

Compound E353
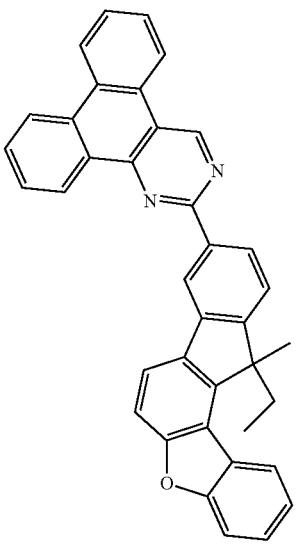
Compound E354
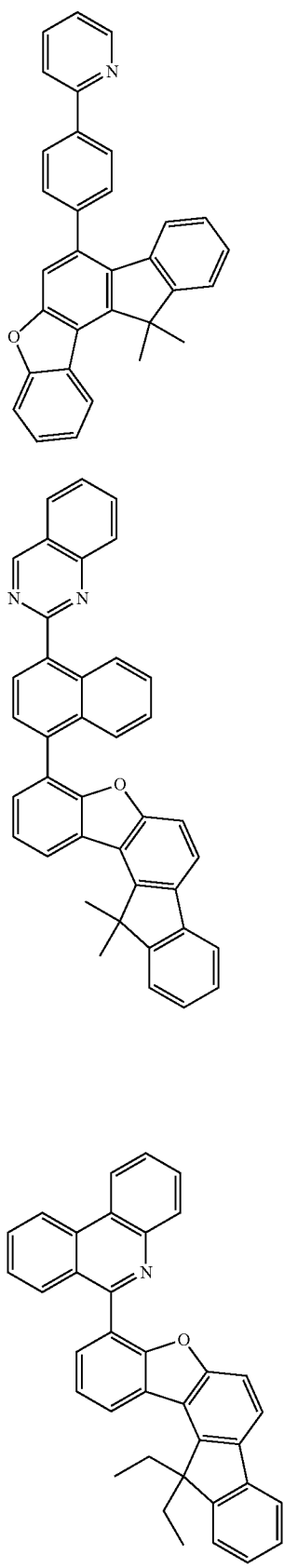
Compound E355
Compound E356
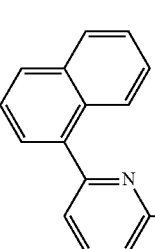
Compound E357
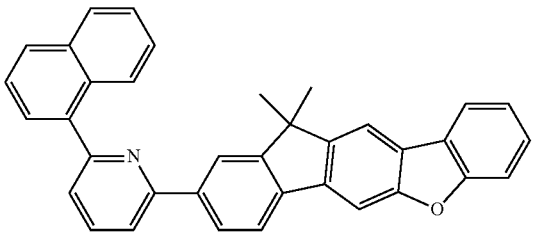
Compound E358
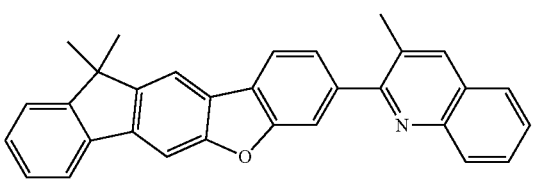
Compound E359
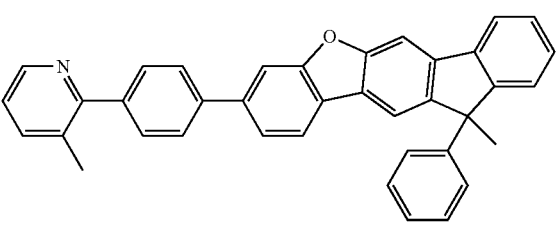
Compound E360
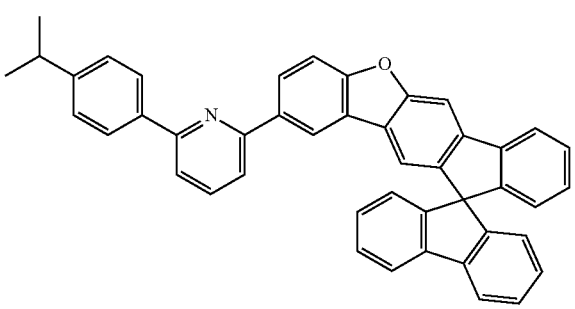

Compound E361
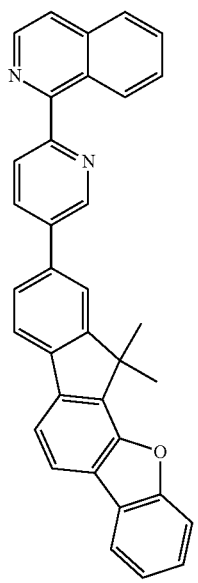
Compound E363
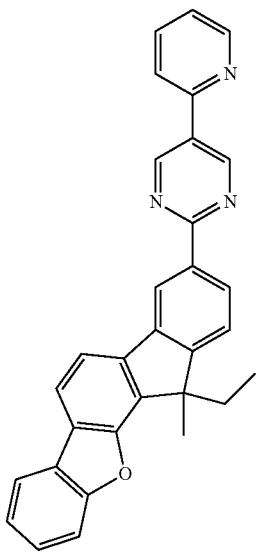
Compound E364
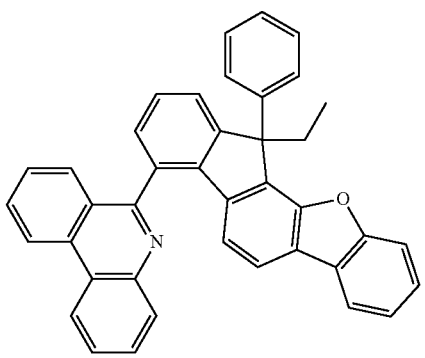
Compound E362
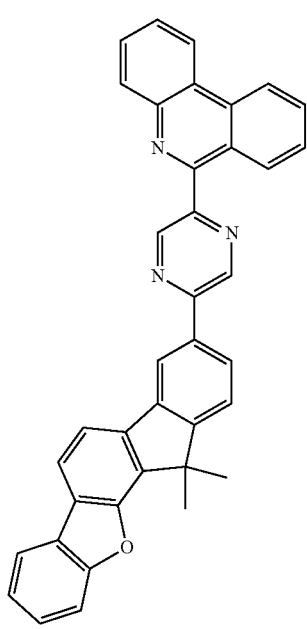
Compound E365
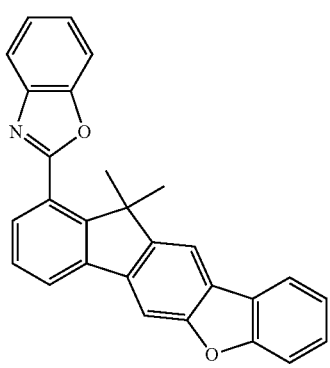
Compound E366

-continued
Compound E367
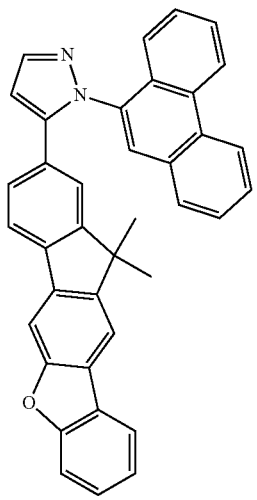
Compound E368
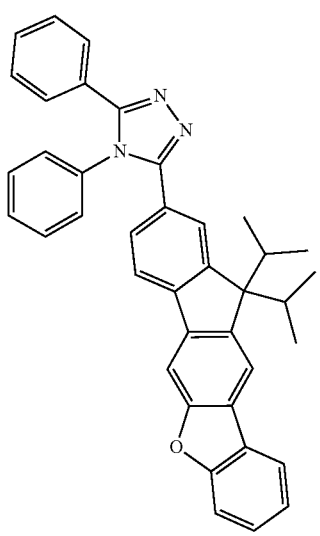
Compound E369
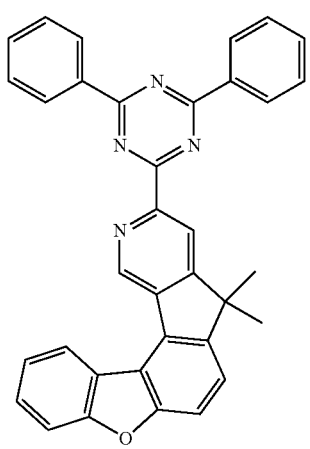
-continued
Compound E370
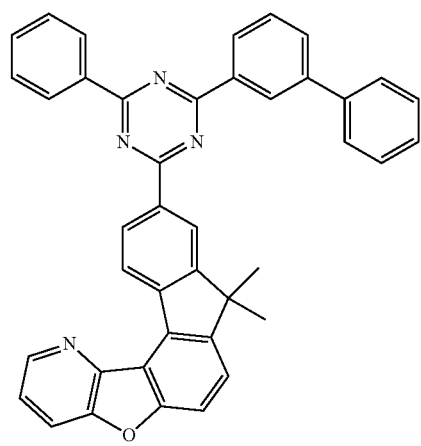
Compound E371
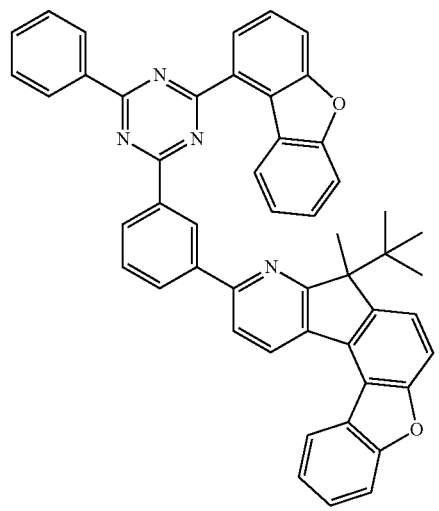
Compound E372
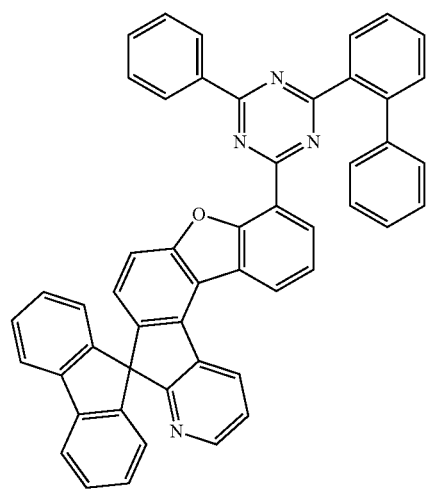

Compound E373
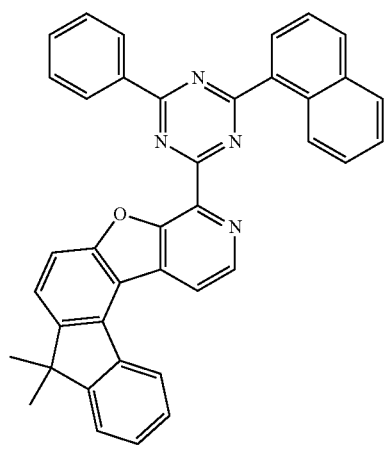
Compound E374
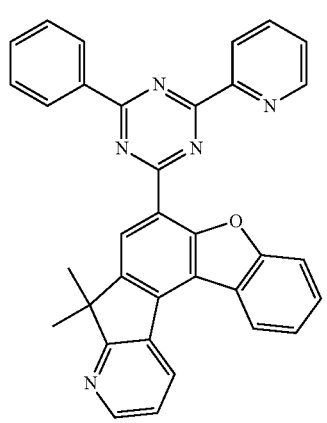
Compound E375
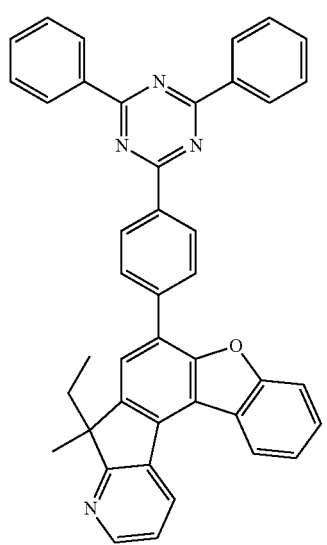
Compound E376
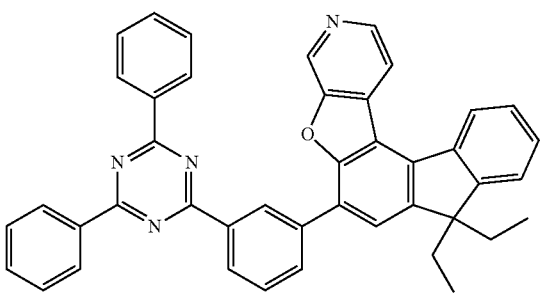
Compound E377
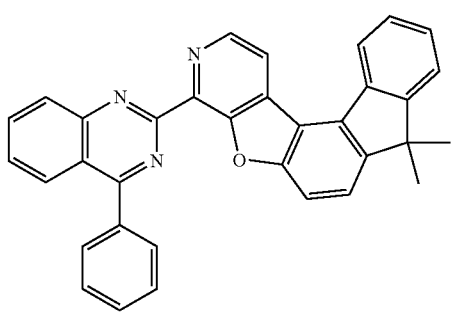
Compound E378
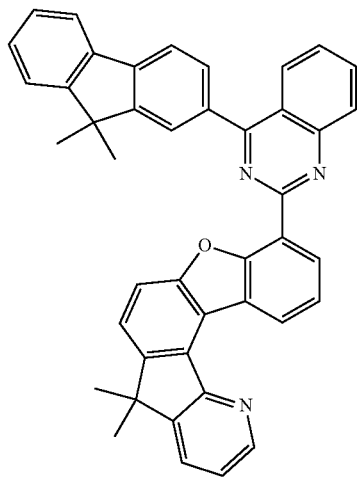
Compound E379
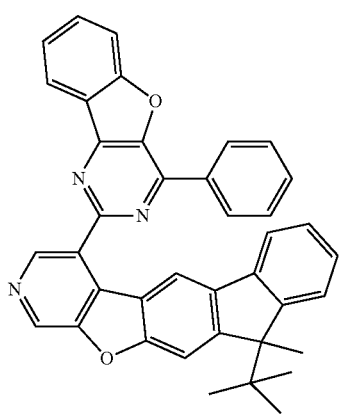

Compound E380
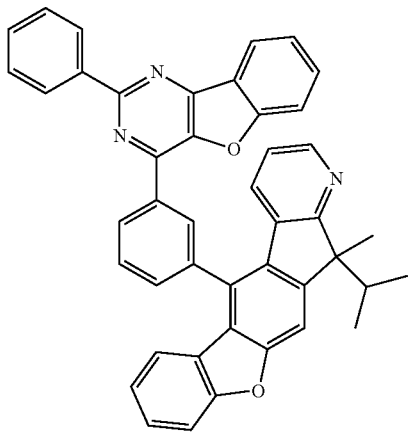
Compound E381
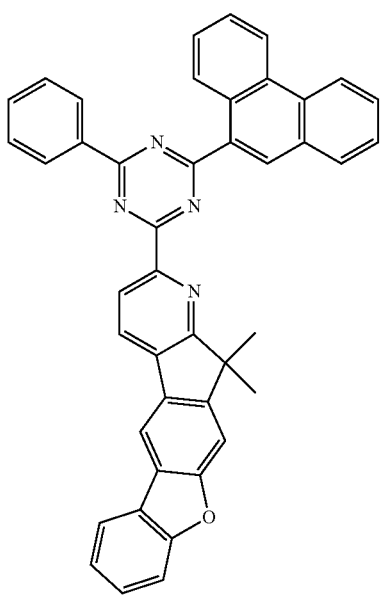
Compound E382
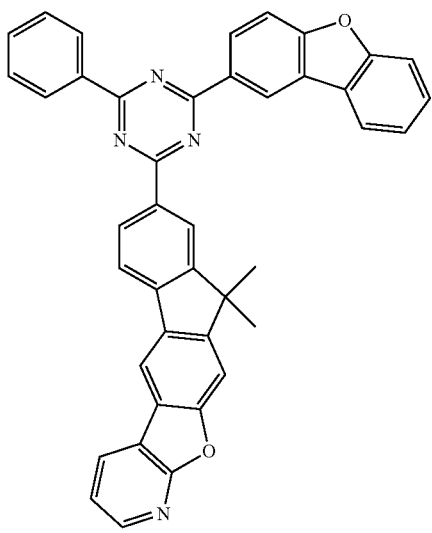
Compound E383
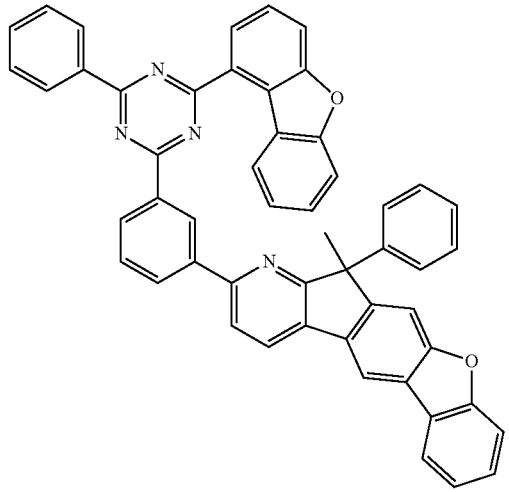
Compound E384
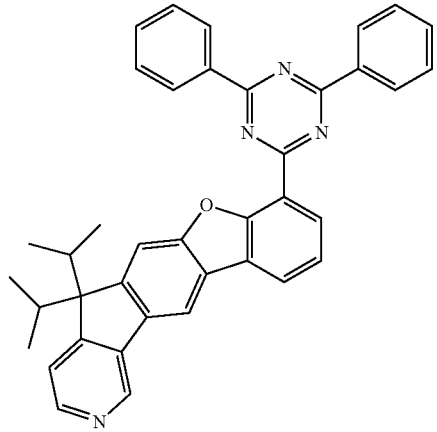
Compound E385
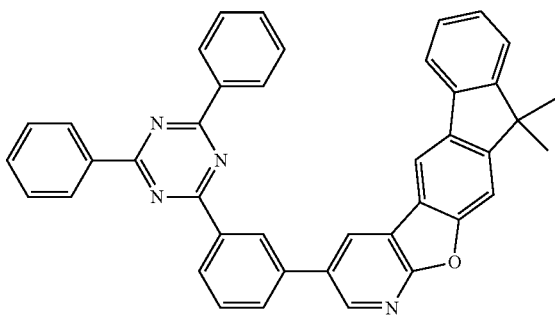

Compound E386
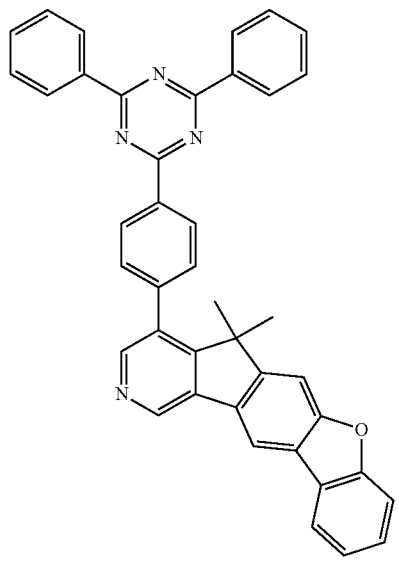
Compound E387
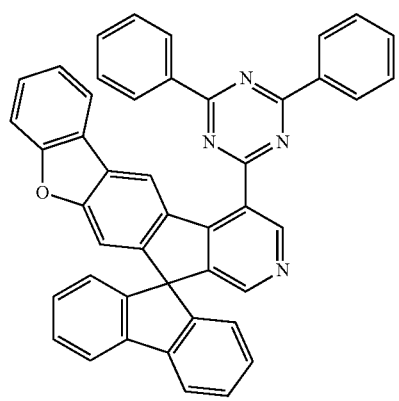
Compound E388
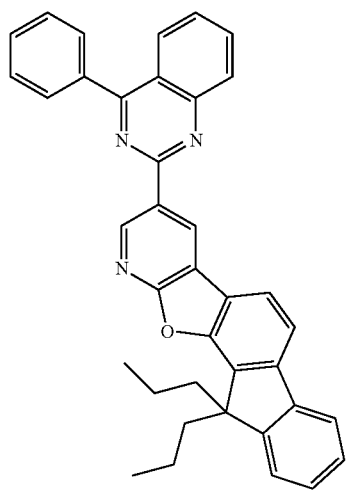
Compound E389
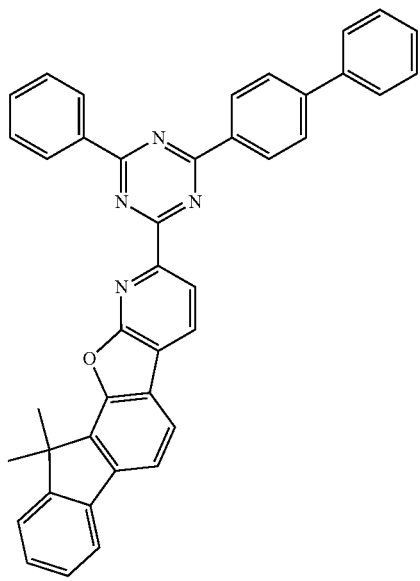
Compound E390
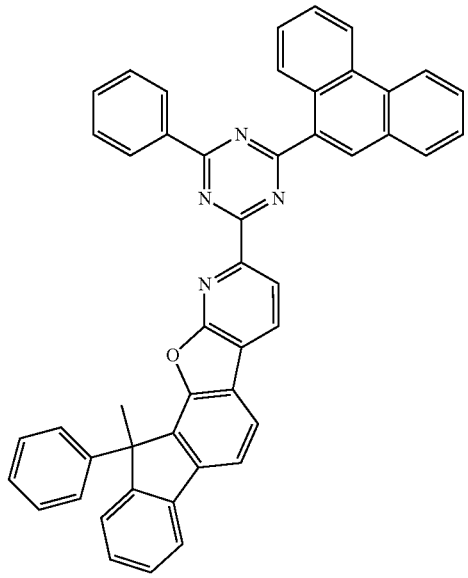
Compound E391
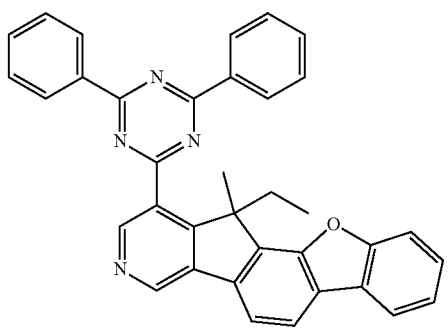

Compound E392
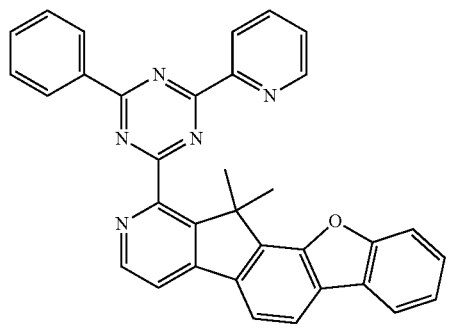
Compound E393
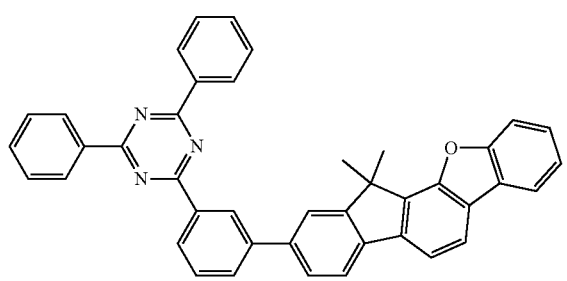
Compound E394
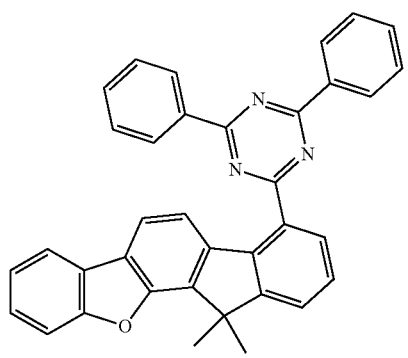
Compound E395
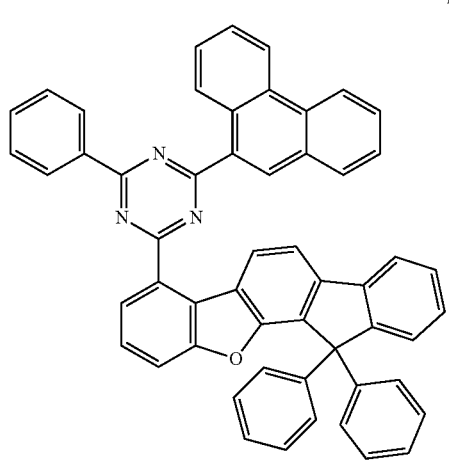
Compound E396
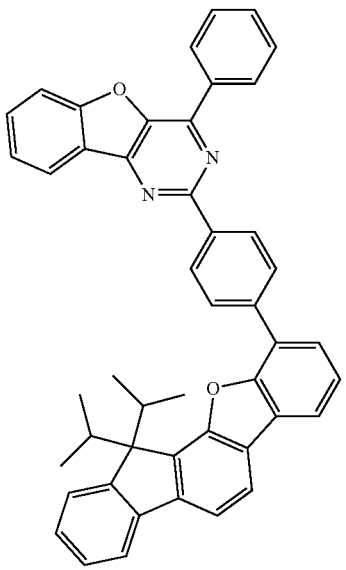
Compound E397
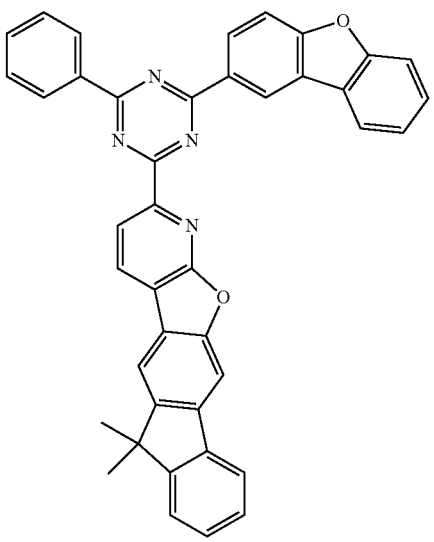
Compound E398
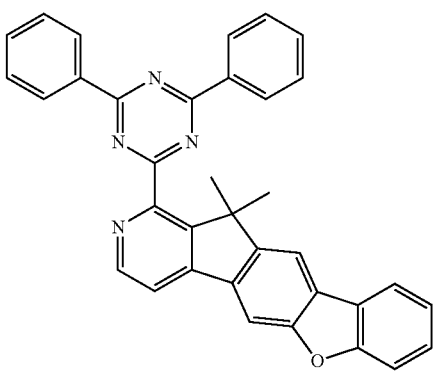

Compound E399
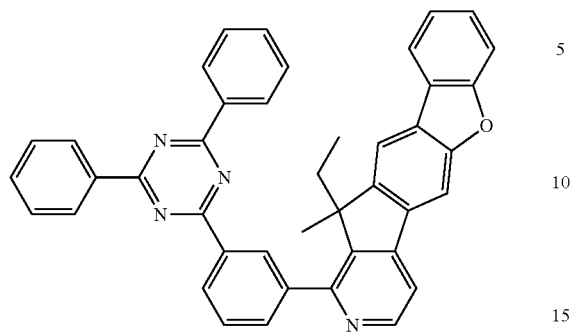
Compound E400
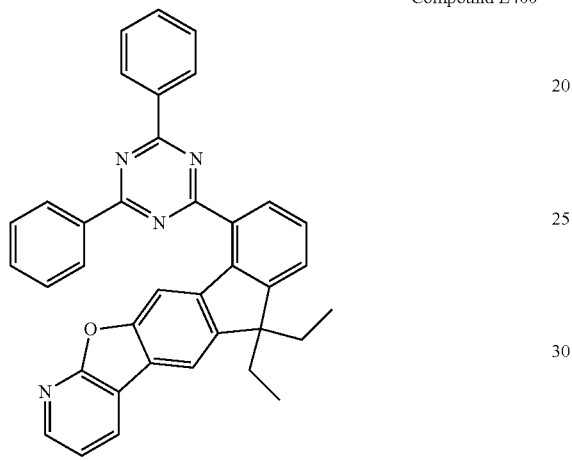
Compound E401
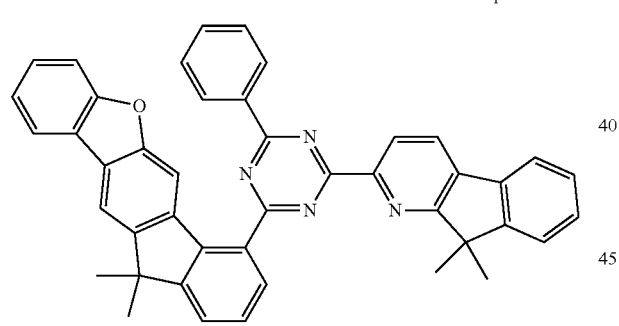
Compound E402
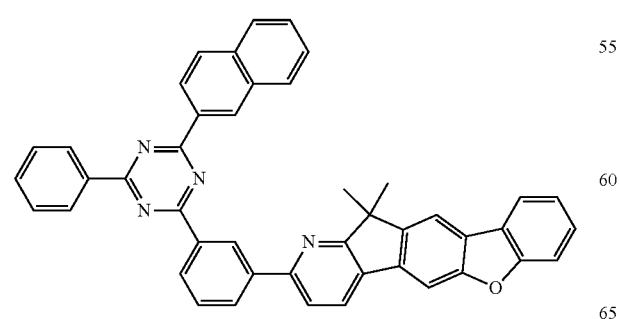
Compound E403
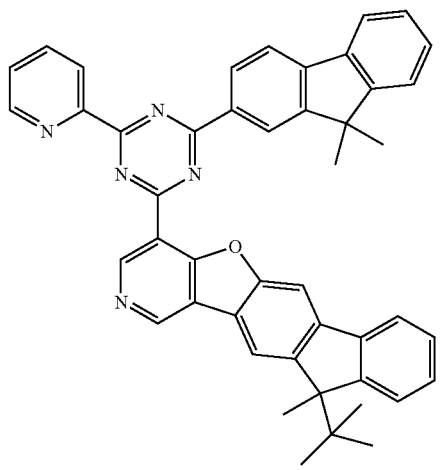
Compound E404
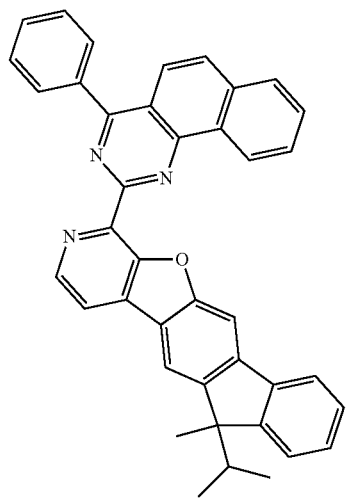
Compound E405
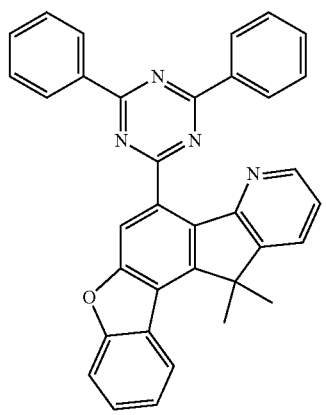

Compound E406
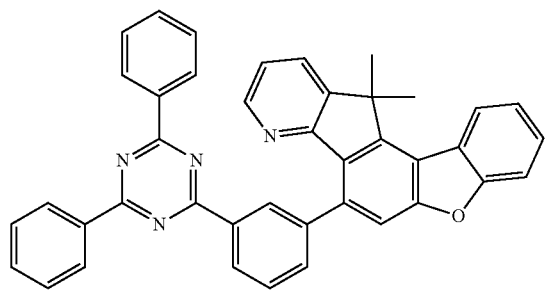
Compound E407
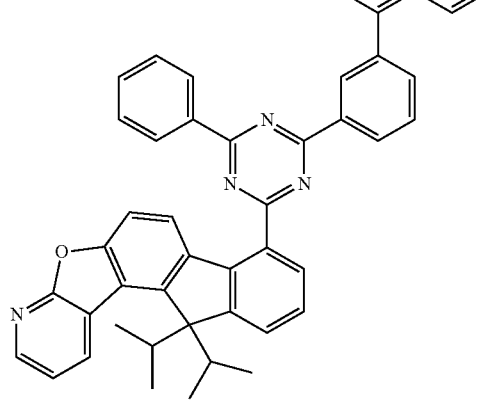
Compound E408
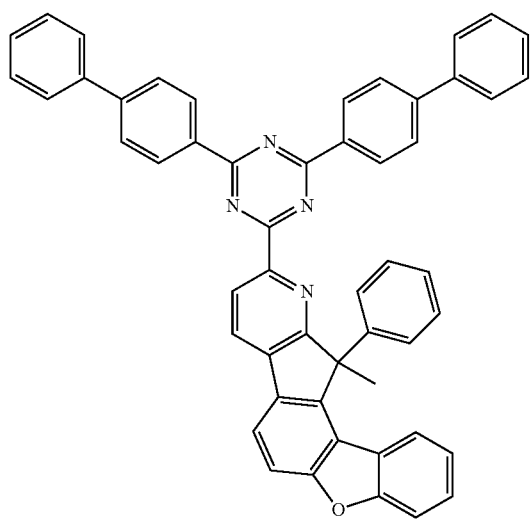
Compound E409
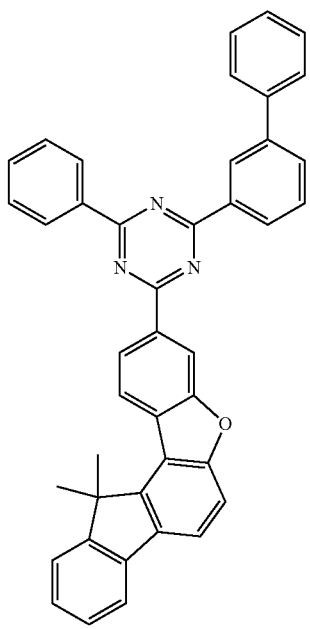
Compound E410
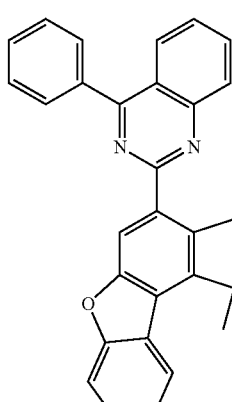
Compound E411
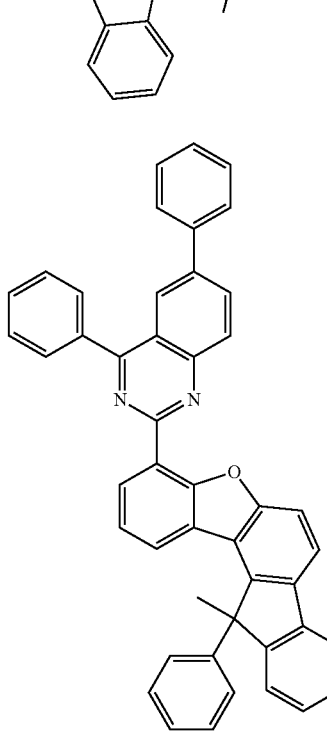

Compound E412

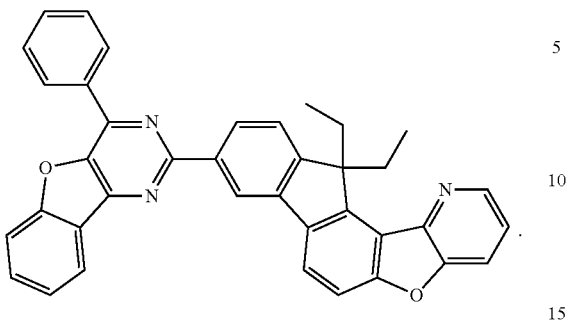

11. An organic light emitting device comprising a first electrode, a second electrode opposite to the first electrode, and at least one organic layer interposed between the first and second electrodes wherein the organic layer comprises the compound according to claim 10.

12. The organic light emitting device according to claim 11, wherein the organic layer further comprises a light emitting layer comprising a phosphorescent dopant compound.

13. An organic light emitting device comprising a first electrode, a second electrode opposite to the first electrode, and at least one organic layer interposed between the first and second electrodes wherein the organic layer comprises (a) the compound according to claim 10 as a first compound and (b) a second compound represented by Formula 2:

$$HAr_3-(L)_n-HAr_4 \quad (2)$$

wherein L represents a linker and is a single bond or is selected from substituted or unsubstituted $C_1$-$C_{30}$ alkylene groups, substituted or unsubstituted $C_2$-$C_{30}$ alkenylene groups, substituted or unsubstituted $C_2$-$C_{30}$ alkynylene groups, substituted or unsubstituted $C_2$-$C_{30}$ cycloalkylene groups, substituted or unsubstituted $C_2$-$C_{30}$ heterocycloalkylene groups, substituted or unsubstituted $C_6$-$C_{30}$ arylene groups, and substituted or unsubstituted $C_2$-$C_{30}$ heteroarylene groups, n is an integer from 1 to 3, provided that when n is equal to or greater than 2, the plurality of L groups are identical to or different from each other, $HAr_3$ is selected from the following structures:

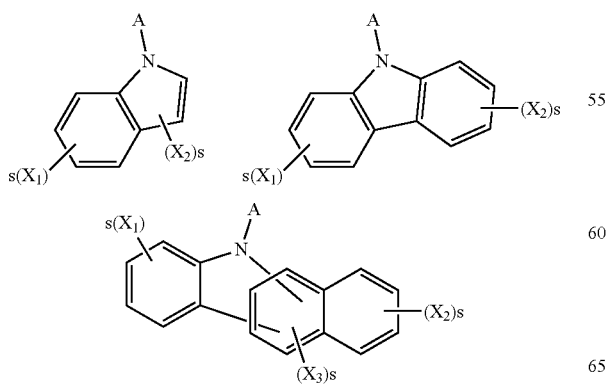

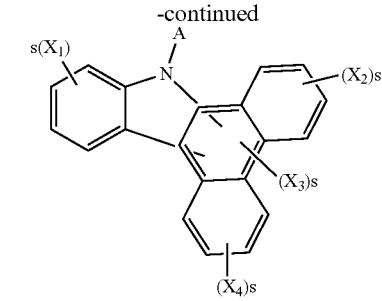

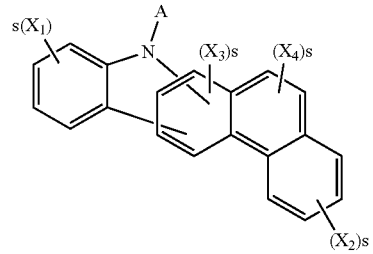

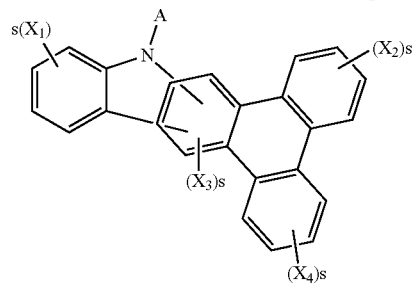

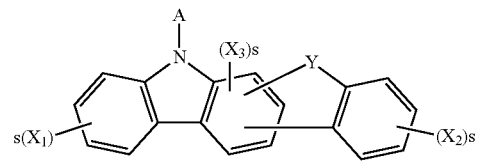

wherein Y is selected from N—$R_1$, $CR_2R_3$, $SiR_4R_5$, $GeR_6R_7$, O, S, and Se, $X_1$ to $X_4$ are each independently selected from hydrogen, deuterium, substituted or unsubstituted $C_1$-$C_{30}$ alkyl groups, substituted or unsubstituted $C_2$-$C_{30}$ alkenyl groups, substituted or unsubstituted $C_2$-$C_{30}$ cycloalkyl groups, substituted or unsubstituted $C_5$-$C_{30}$ cycloalkenyl groups, substituted or unsubstituted $C_1$-$C_{30}$ alkoxy groups, substituted or unsubstituted $C_6$-$C_{30}$ aryloxy groups, substituted or unsubstituted $C_1$-$C_{30}$ alkylthioxy groups, substituted or unsubstituted $C_5$-$C_{30}$ arylthioxy groups, substituted or unsubstituted $C_1$-$C_{30}$ alkylamine groups, substituted or unsubstituted $C_5$-$C_{30}$ arylamine groups, substituted or unsubstituted $C_5$-$C_{50}$ aryl groups, substituted or unsubstituted $C_3$-$C_{50}$ heteroaryl groups containing O, N or S as a heteroatom, substituted or unsubstituted silyl groups, substituted or unsubstituted germanium groups, substituted or unsubstituted boron groups, substituted or unsubstituted aluminum groups, a carbonyl group, a phosphoryl group, an amino group, a nitrile group, a hydroxyl group, a nitro group, halogen groups, a selenium group, a tellurium group, an amide group, and an ester group, with the proviso that $X_1$ to $X_4$ together with an adjacent group optionally forms an aliphatic, aromatic, heteroaliphatic or heteroaromatic fused ring and one of $X_1$ to $X_4$ is linked to L, s is an integer from 1 to 4, and A and $R_1$ to $R_7$ are each independently selected from hydrogen, deuterium, halogen atoms, a cyano group, substituted or unsubstituted $C_1$-$C_{20}$ alkyl groups, substituted or unsubstituted $C_3$-$C_{20}$ cycloalkyl groups, substituted or unsubstituted $C_1$-$C_{20}$ alkoxy groups, substituted or unsubstituted $C_6$-$C_{30}$ aryloxy groups, substituted or unsubstituted $C_1$-$C_{20}$ alkylthio groups, substituted or unsubstituted $C_6$-$C_{30}$ arylthio groups, substituted or unsubstituted $C_3$-$C_{50}$ alkylsilyl groups, substituted or unsubstituted $C_6$-$C_{50}$ arylsilyl groups, substituted or unsubstituted $C_6$-$C_{30}$ aromatic hydrocarbon groups, and substituted or unsubstituted $C_5$-$C_{30}$ heterocyclic groups, and $HAr_4$ is selected from the following structures:

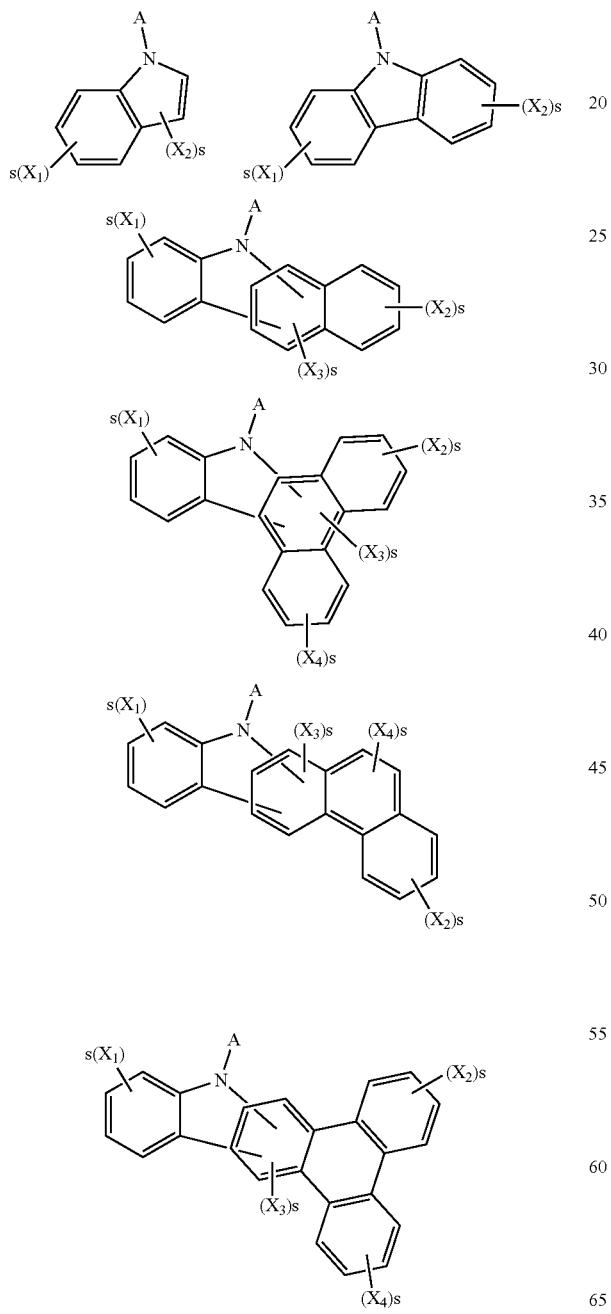

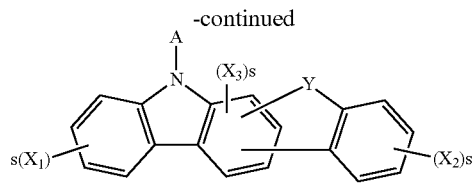

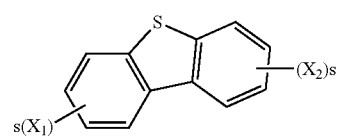

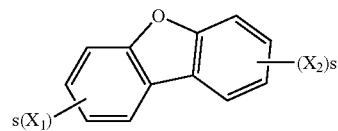

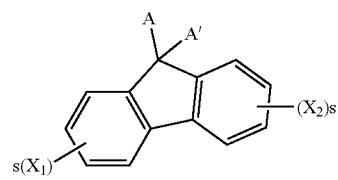

wherein Y, $X_1$ to $X_4$, s, A, and $R_1$ to $R_7$ are as defined above and A' has the same meaning as A and $R_1$ to $R_7$.

14. The organic light emitting device according to claim 13, wherein each of A, A', $X_1$ to $X_4$, $R_1$ to $R_7$, $HAr_3$, $HAr_4$, and L is further substituted with one or more substituents selected from $C_1$-$C_{60}$ alkyl groups, $C_5$-$C_{60}$ heteroaryl groups, $C_3$-$C_{60}$ cycloalkyl groups, $C_6$-$C_{60}$ aryl groups, $C_1$-$C_{60}$ alkoxy groups, $C_6$-$C_{30}$ aryloxy groups, $C_1$-$C_{20}$ alkylamino groups, $C_1$-$C_{20}$ alkylsilyl groups, $C_6$-$C_{30}$ arylsilyl groups, $C_1$-$C_{50}$ arylalkylamino groups, $C_2$-$C_{60}$ alkenyl groups, a cyano group, halogen groups, and deuterium.

15. The organic light emitting device according to claim 13, wherein the organic layer comprises further a light emitting layer, a hole transport layer between the light emitting layer and the first electrode, and an electron transport layer between the light emitting layer and the second electrode and wherein the light emitting layer comprises the first compound according to claim 10 and the second compound represented by Formula 2.

16. The organic light emitting device according to claim 15, wherein the light emitting layer further comprises a phosphorescent dopant compound.

17. The organic light emitting device according to claim 16, wherein the first compound, the second compound, and the dopant compound are mixed in a weight ratio of 1:0.01-99:0.01-15.

18. The organic light emitting device according to claim 13, wherein the second compound represented by Formula 2 is selected from Compounds H1 to H148:

Compound H1
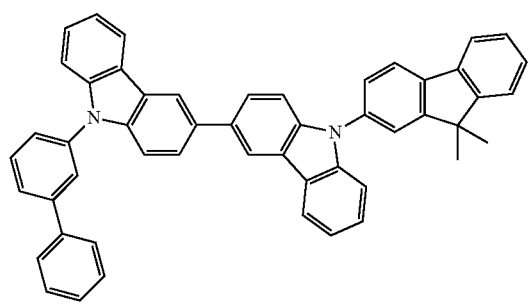
Compound H2
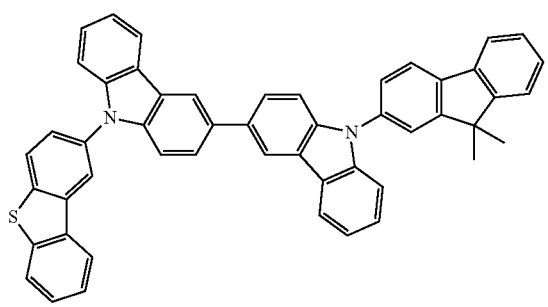
Compound H3
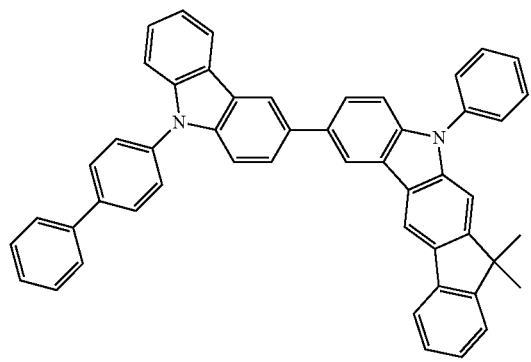
Compound H4
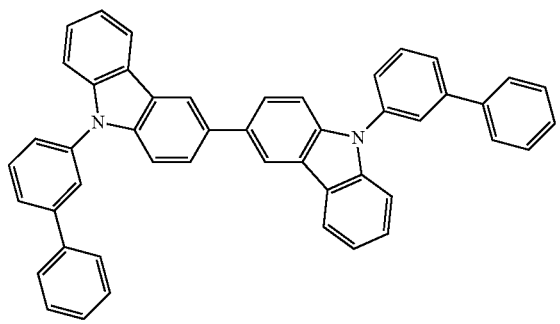
Compound H5
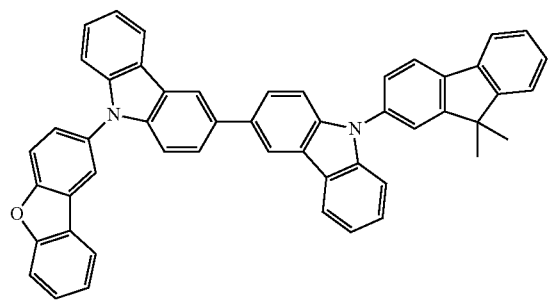
Compound H6
Compound H7
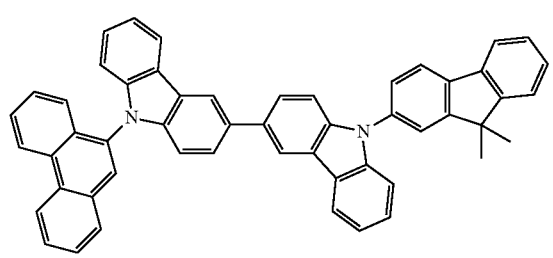
Compound H8
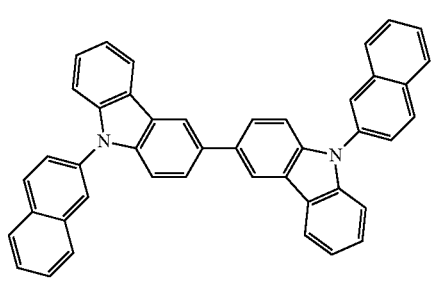

Compound H9
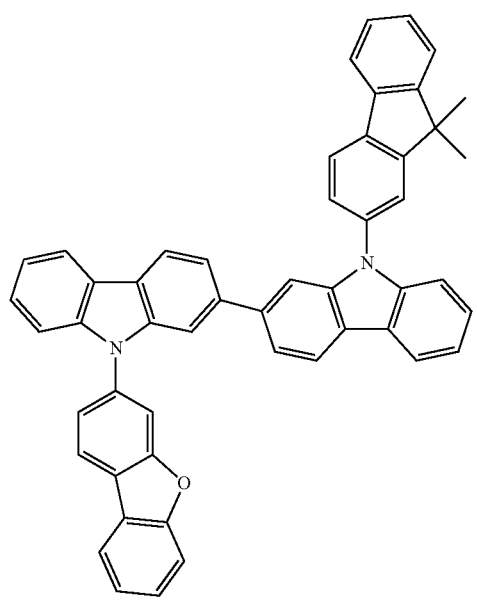
Compound H10
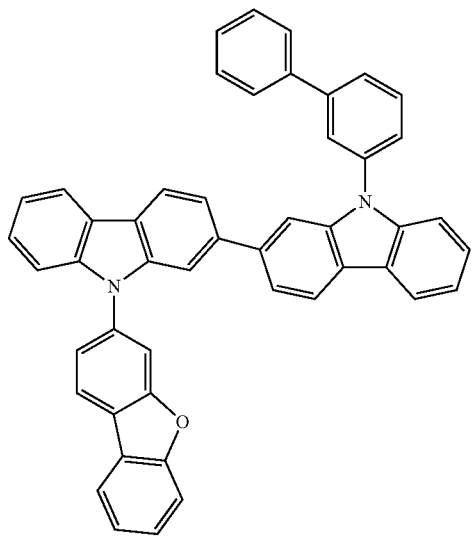
Compound H11
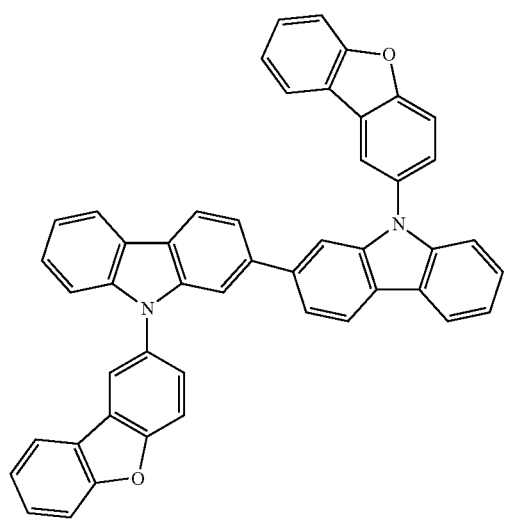
Compound H12
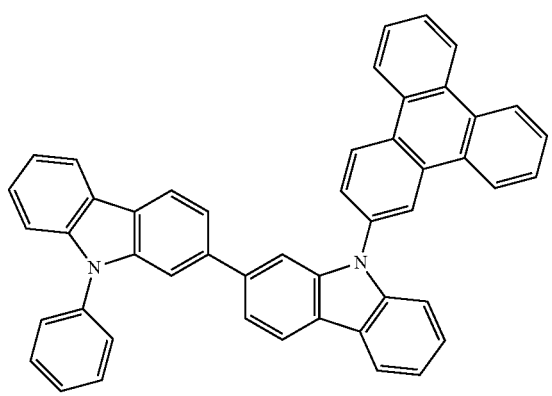

-continued
Compound H13
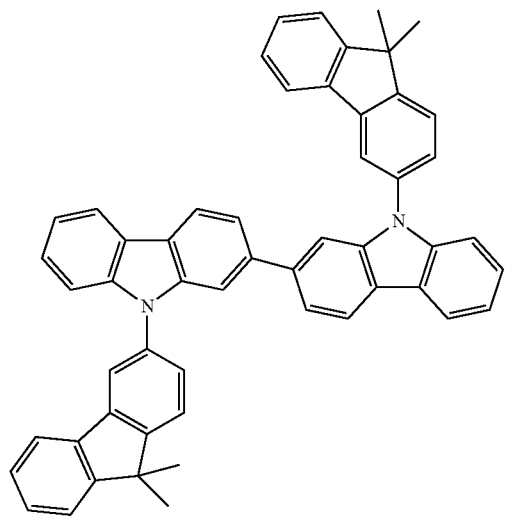
Compound H14
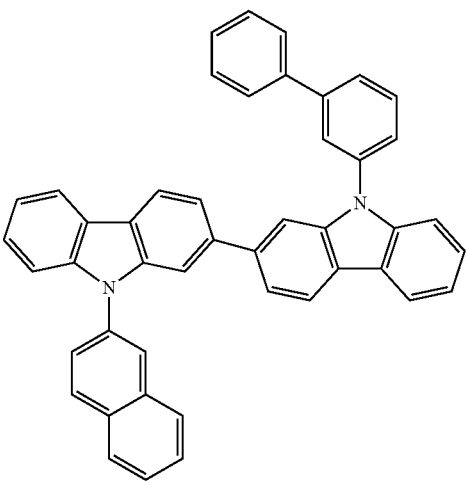
Compound H15
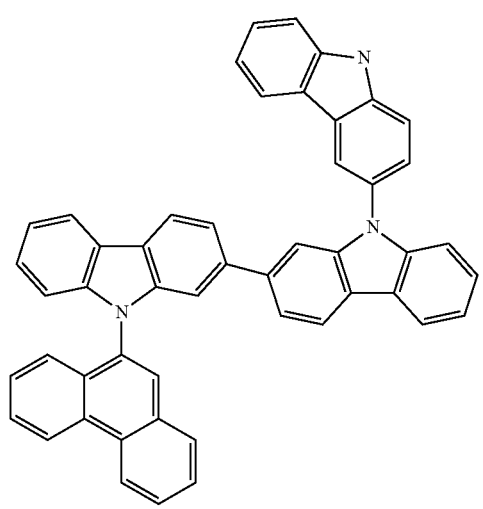
Compound H16
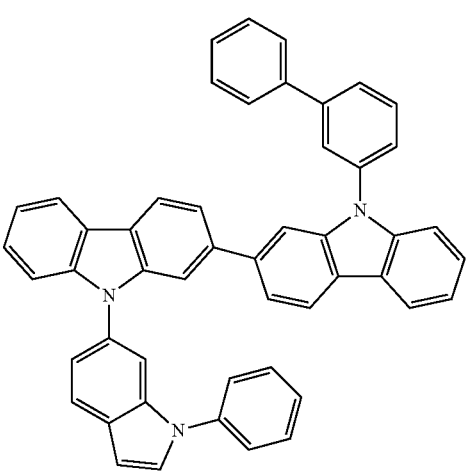
Compound H17
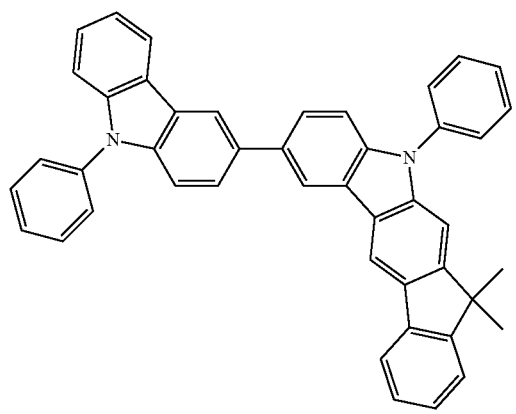
Compound H18
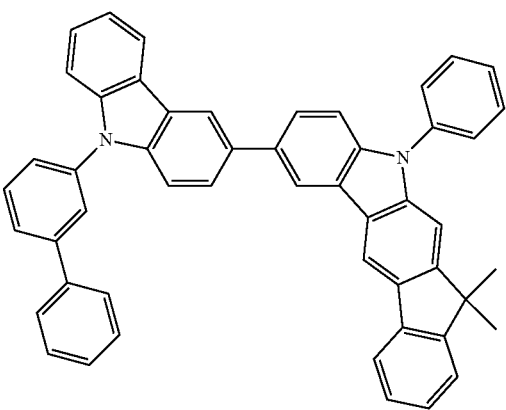

-continued
Compound H19
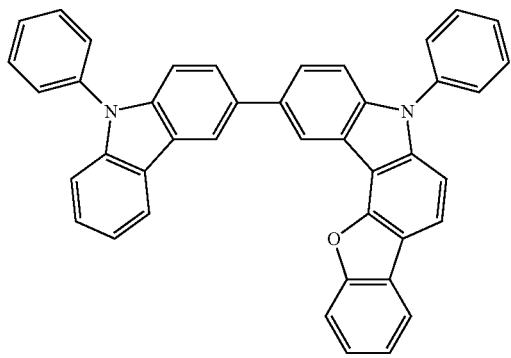
Compound H20
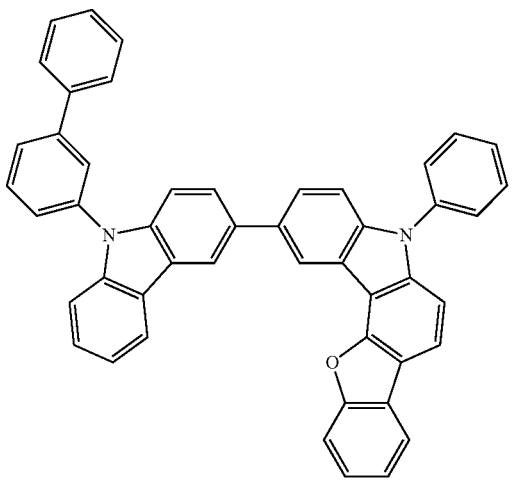
Compound H21
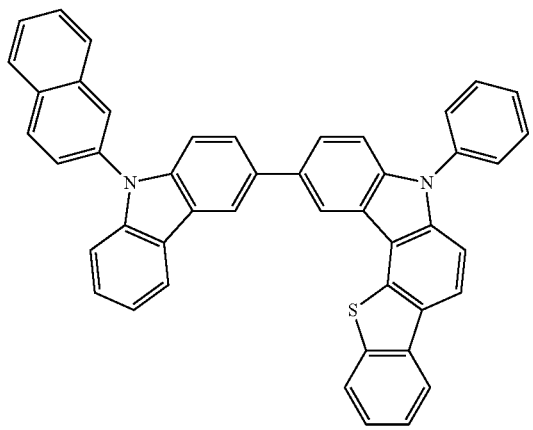
Compound H22
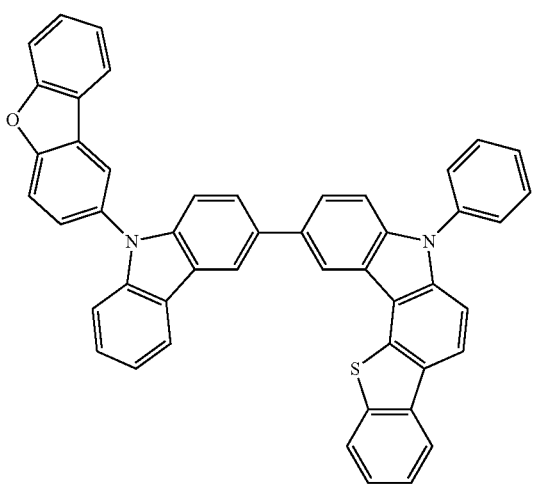
Compound H23
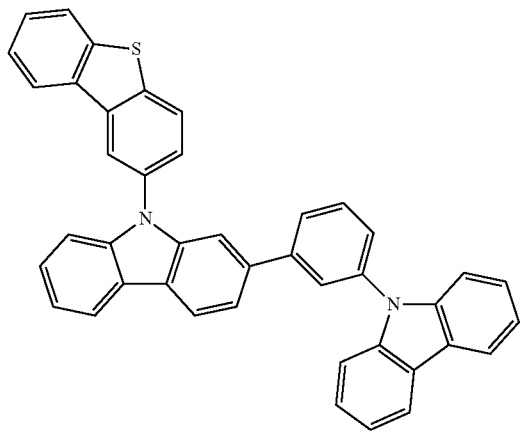
Compound H24
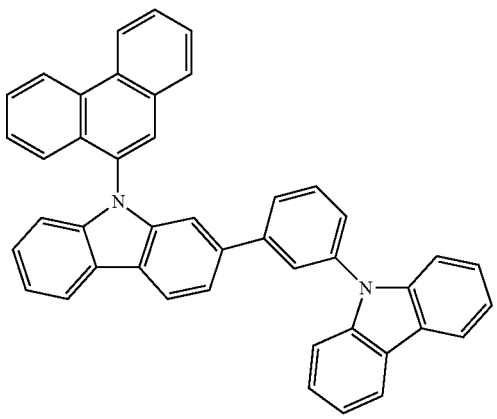

-continued
Compound H25
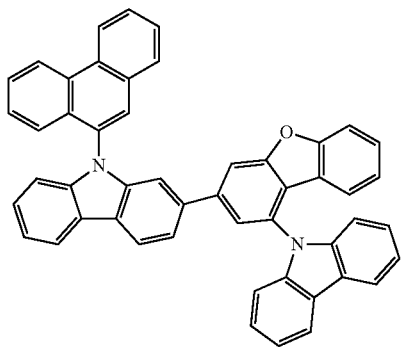
Compound H26
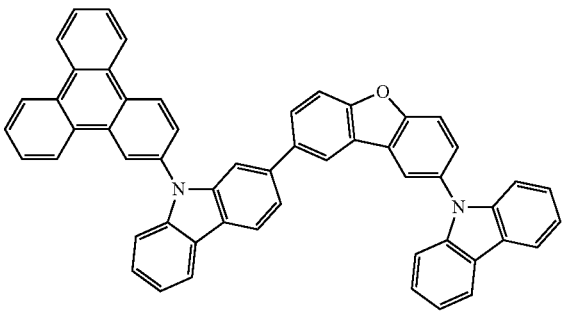
Compound H27
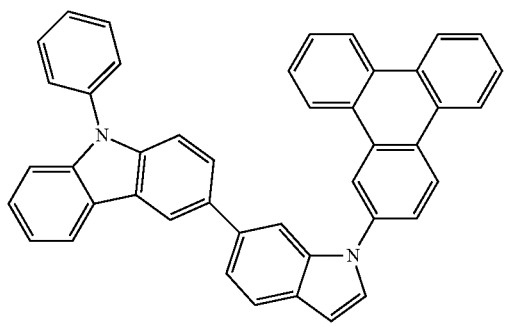
Compound H28
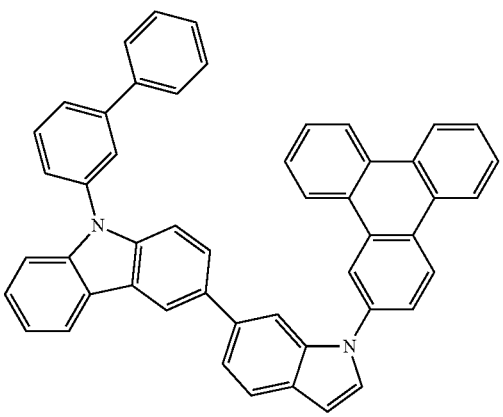
Compound H29
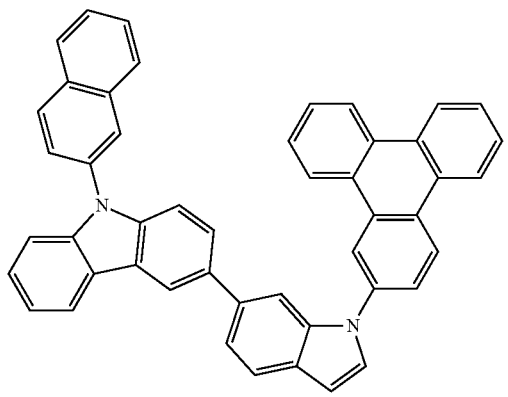
Compound H30
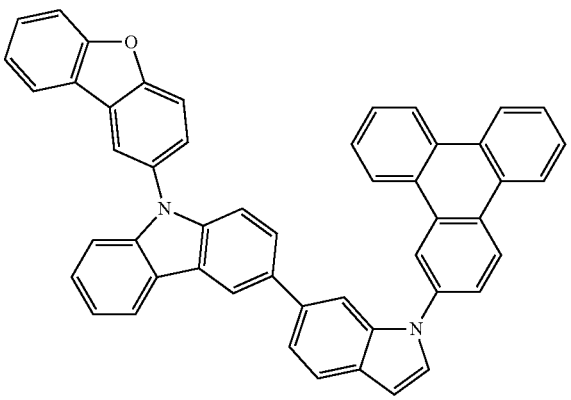
Compound H31
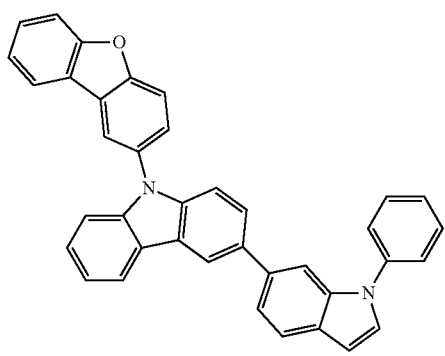
Compound H32
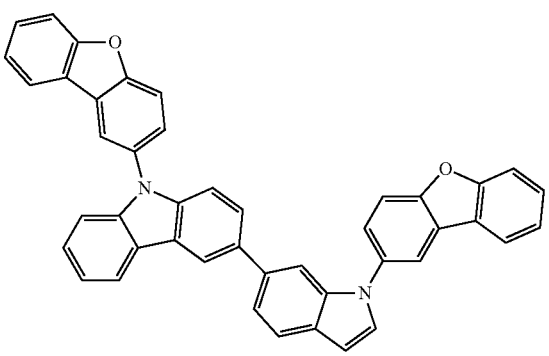

-continued
Compound H33
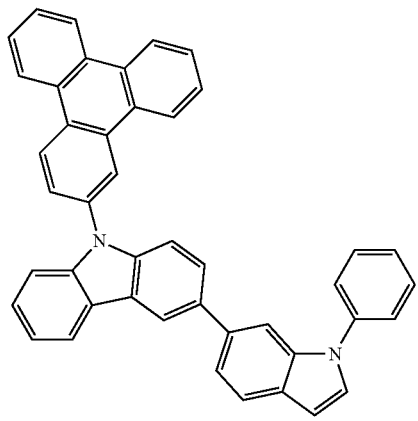
Compound H34
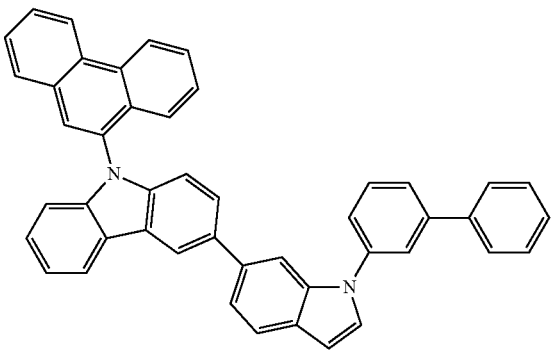
Compound H35
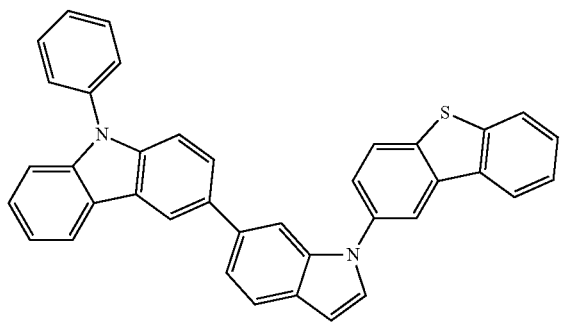
Compound H36
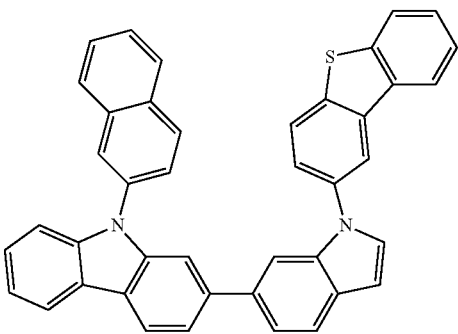
Compound H37
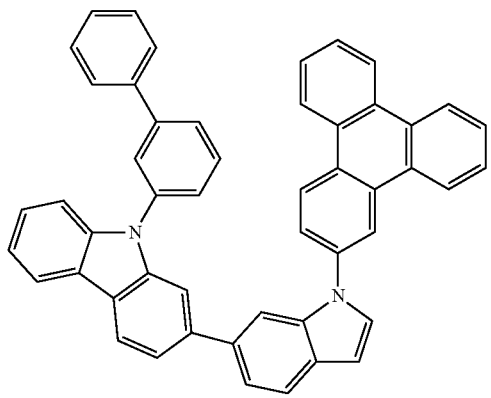
Compound H38
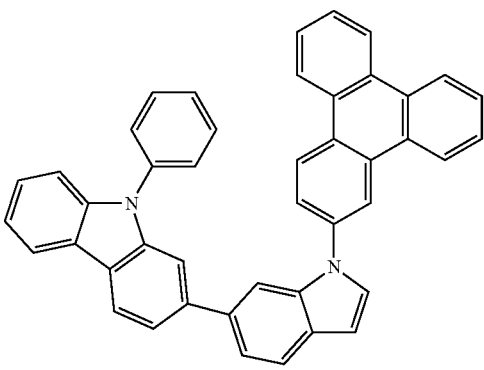
Compound H39
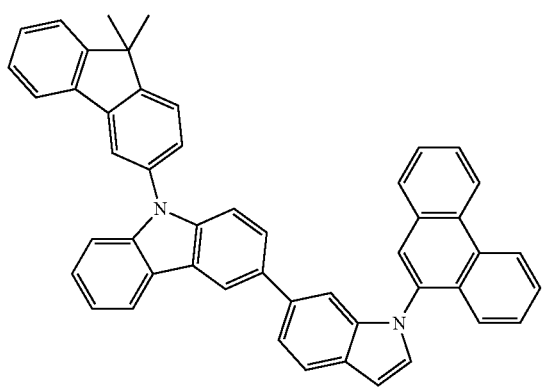
Compound H40
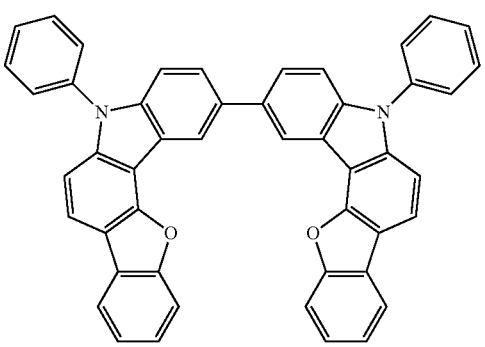

-continued
Compound H41
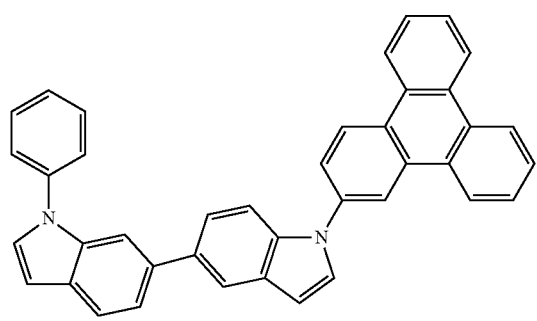
Compound H42
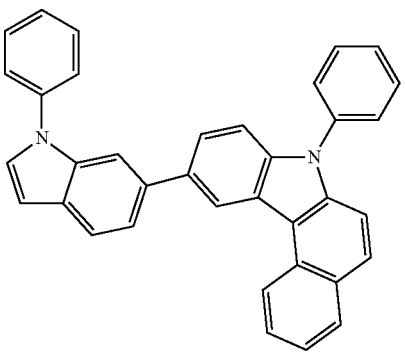
Compound H43
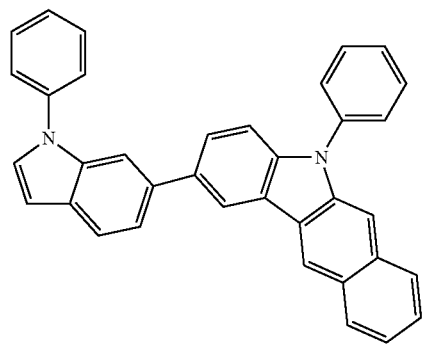
Compound H44
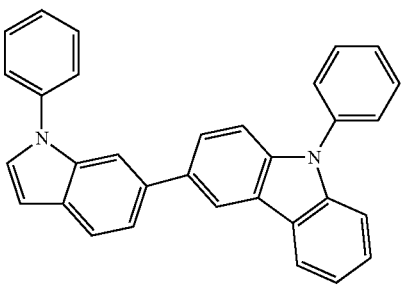
Compound H45
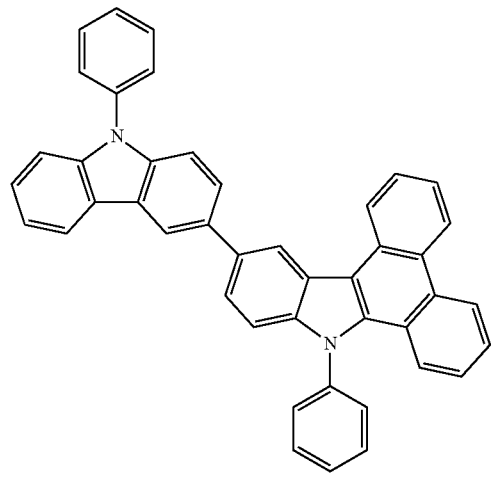
Compound H46
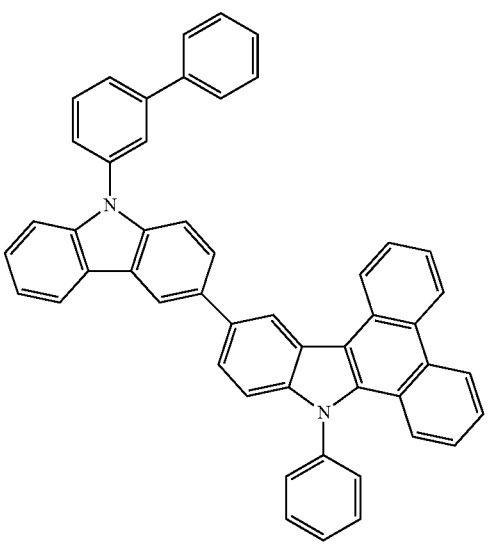

-continued
Compound H47
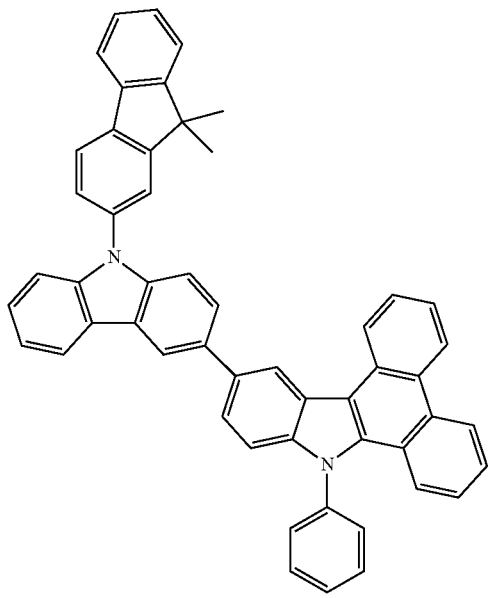
Compound H48
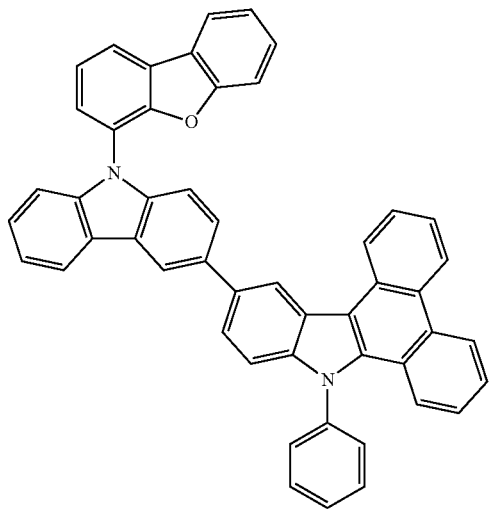
Compound H49
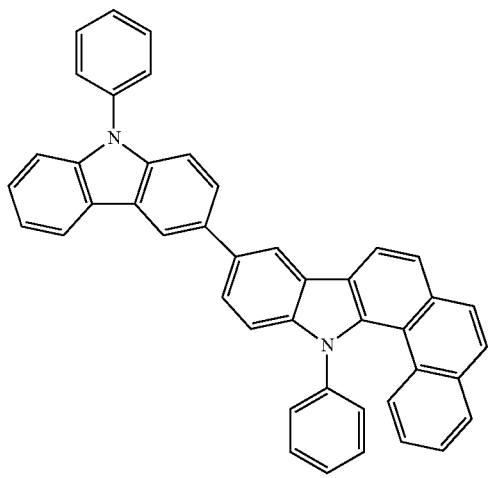
Compound H50
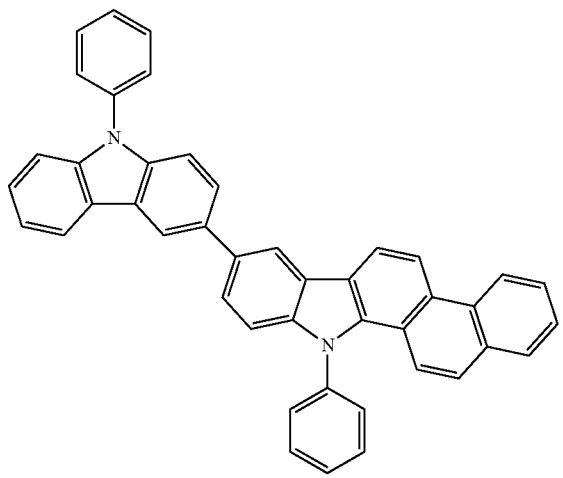
Compound H51
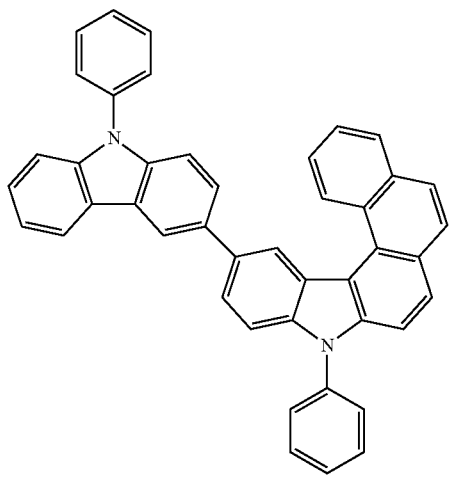
Compound H52
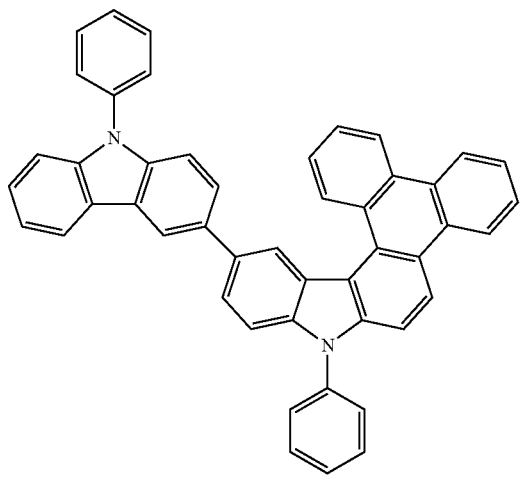

-continued
Compound H53
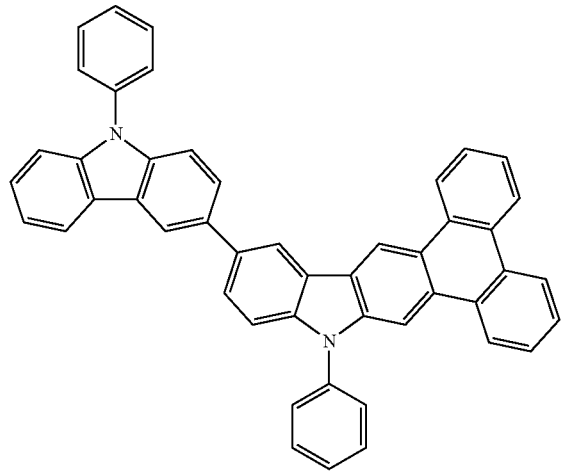
Compound H54
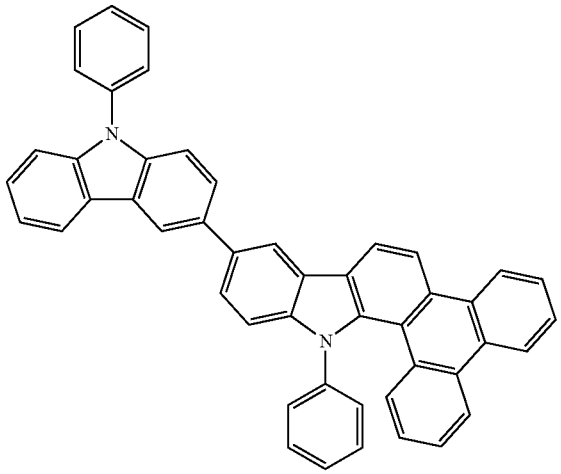
Compound H55
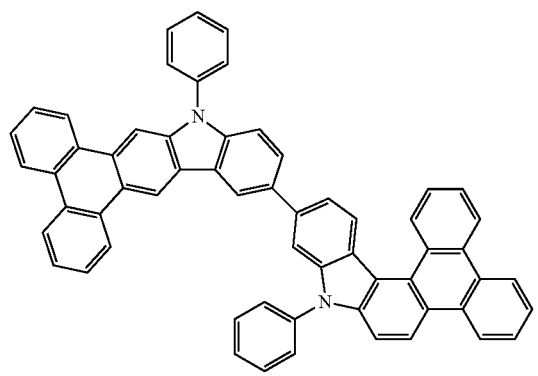
Compound H56
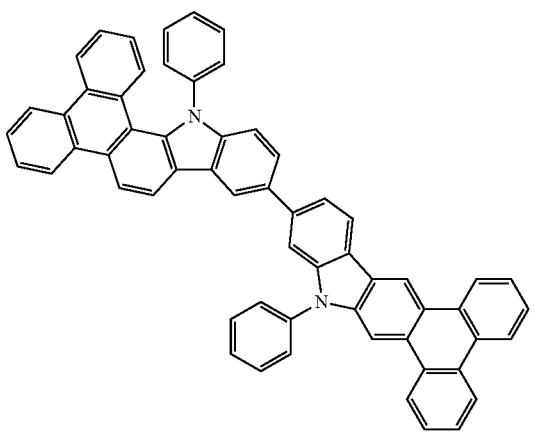
Compound H57
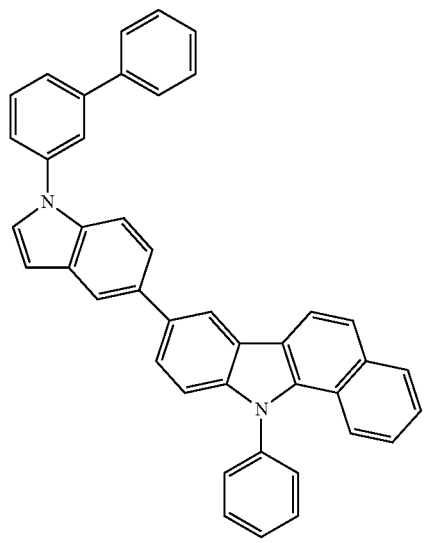
Compound H58
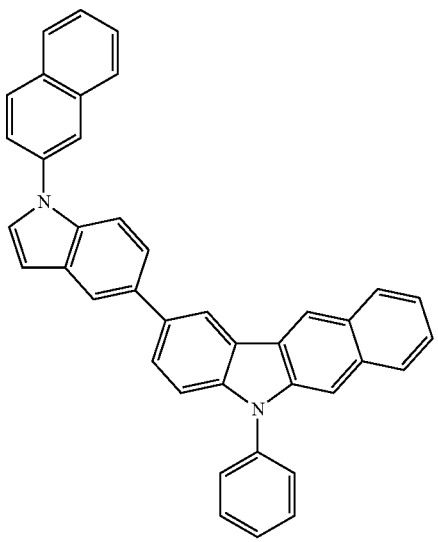

-continued
Compound H59
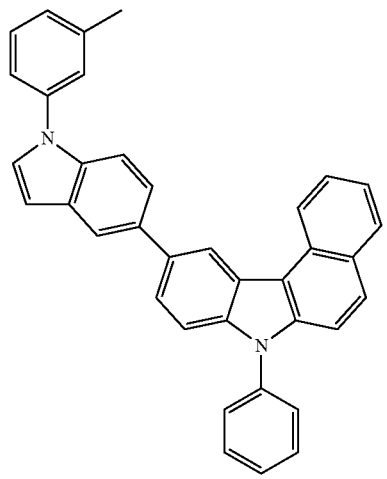
Compound H60
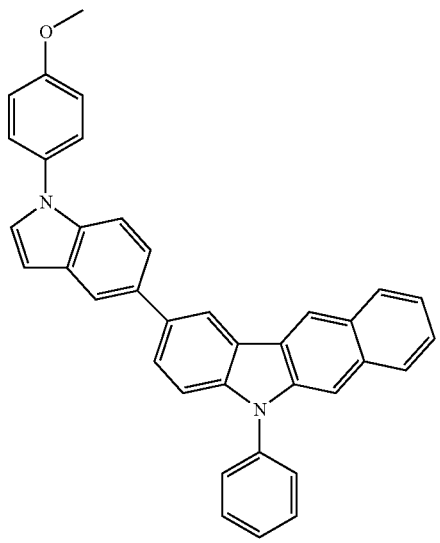
Compound H61
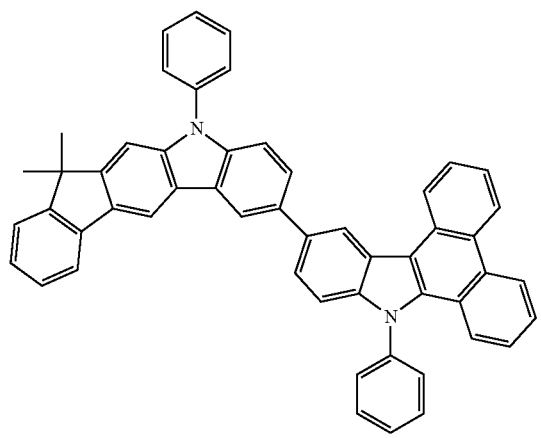
Compound H62
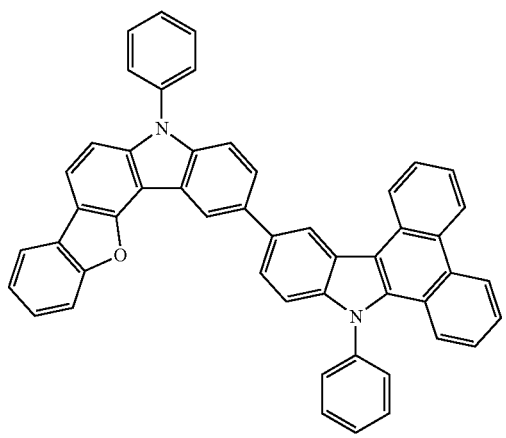
Compound H63
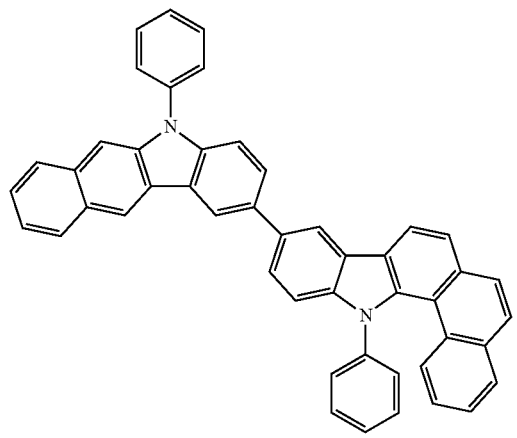
Compound H64
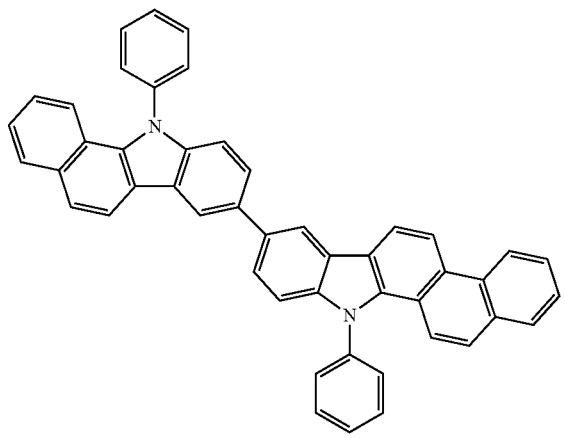

-continued
Compound H65
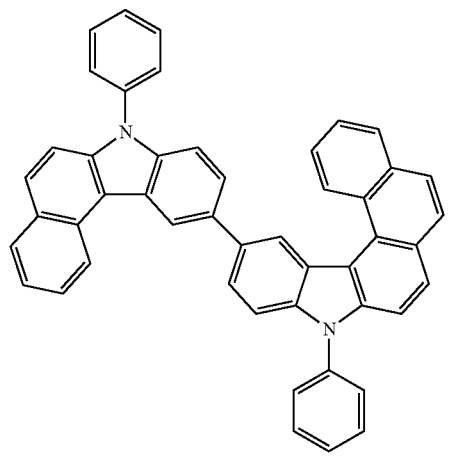
Compound H66
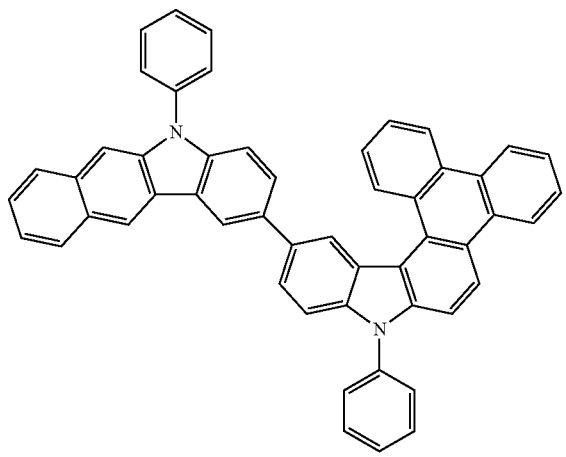
Compound H67
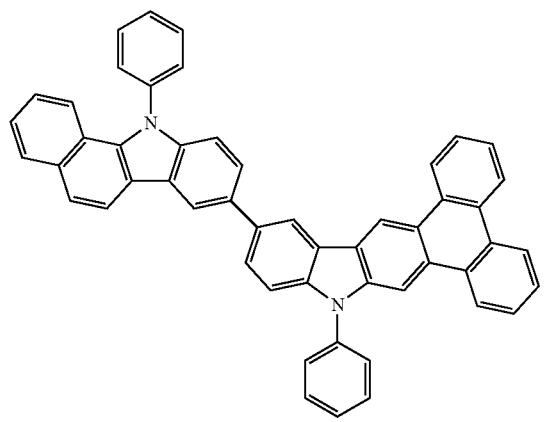
Compound H68
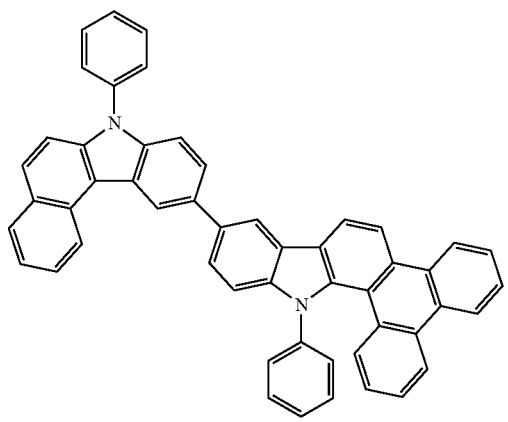
Compound H69
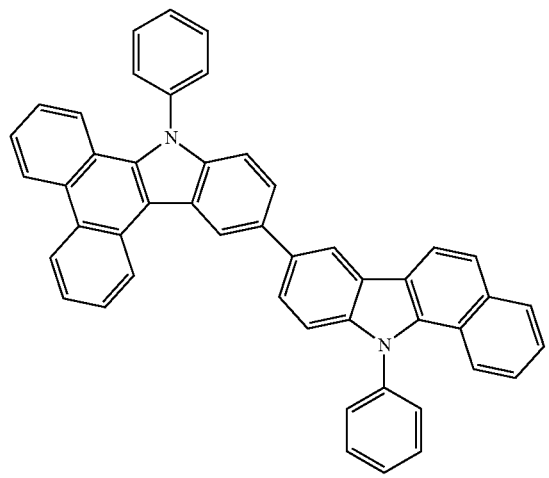
Compound H70
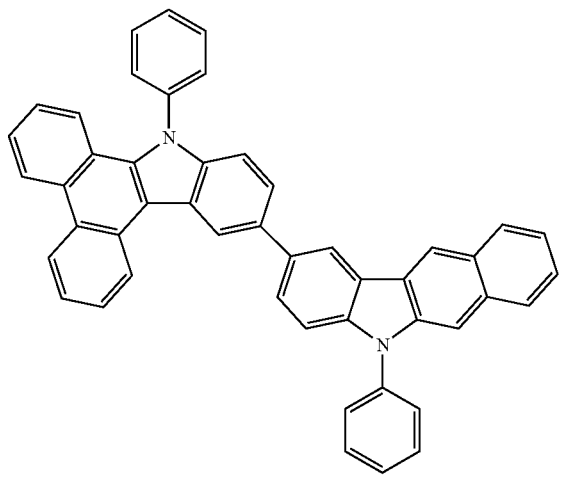

-continued
Compound H71
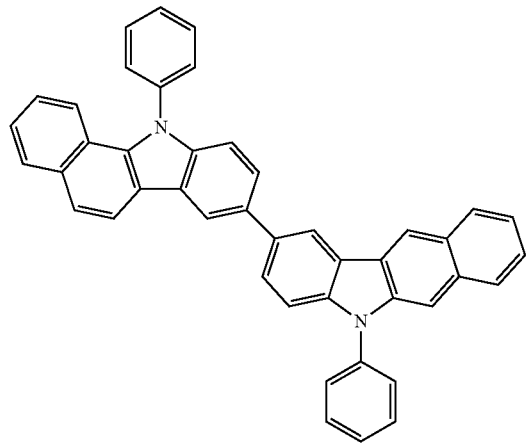
Compound H72
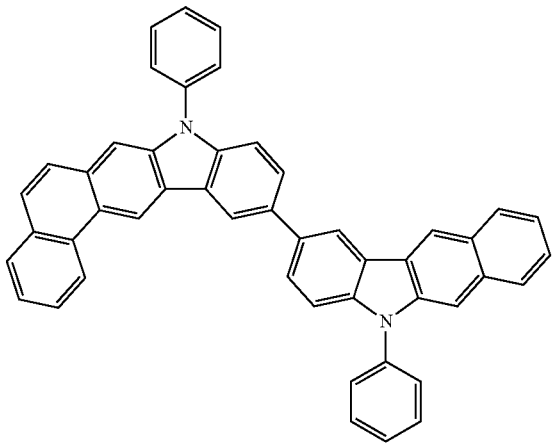
Compound H73
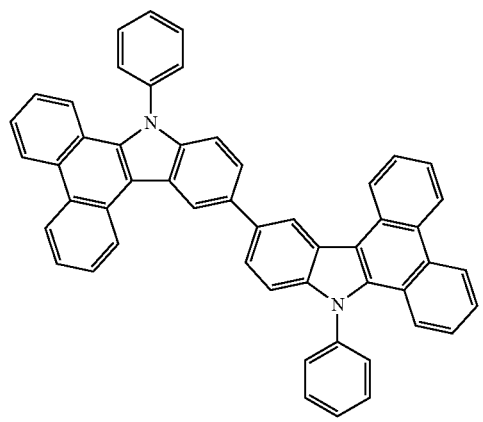
Compound H74
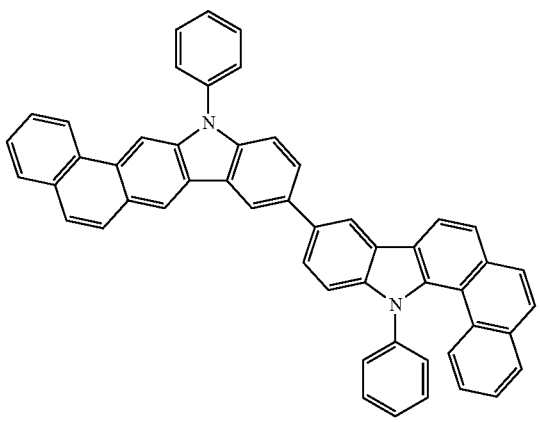
Compound H75
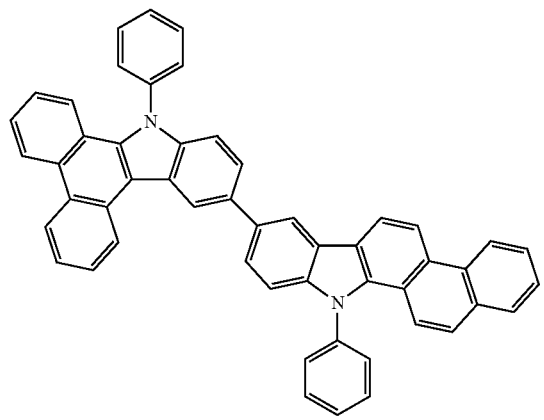
Compound H76
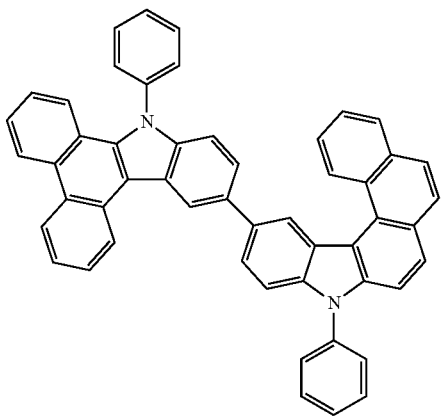

-continued
Compound H77
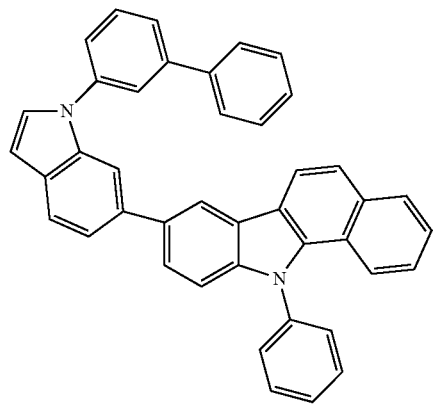
Compound H78
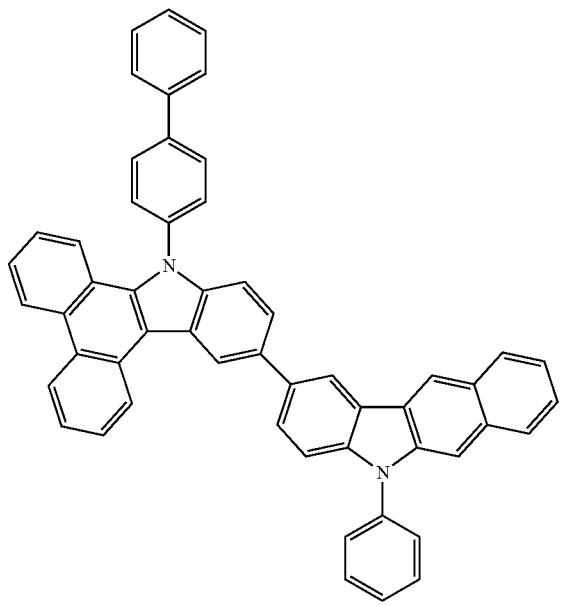
Compound H79
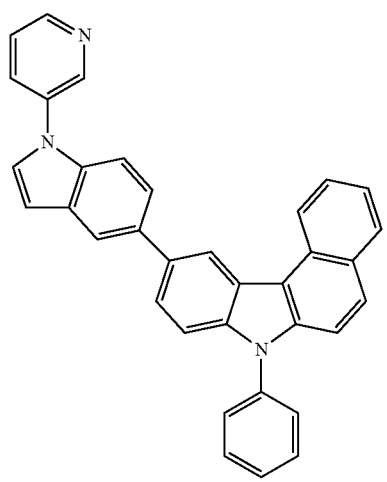
Compound H80
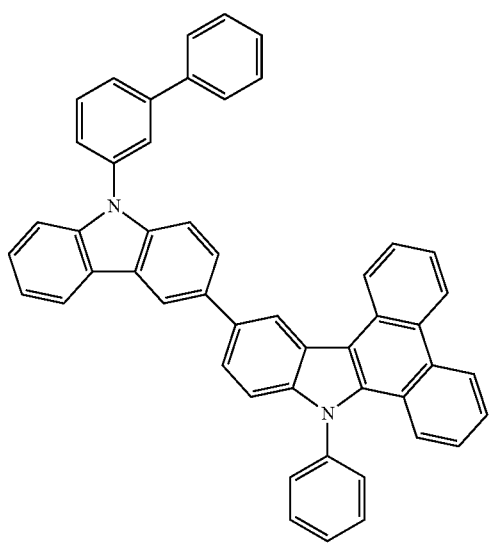
Compound H81
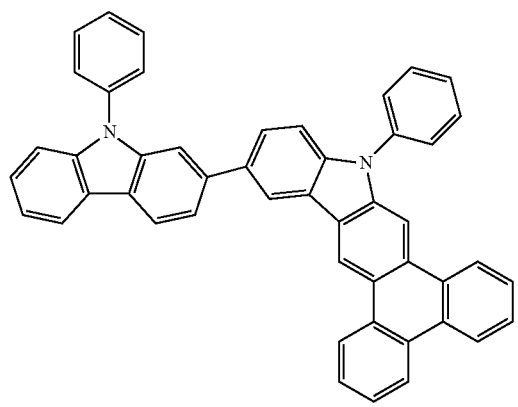
Compound H82
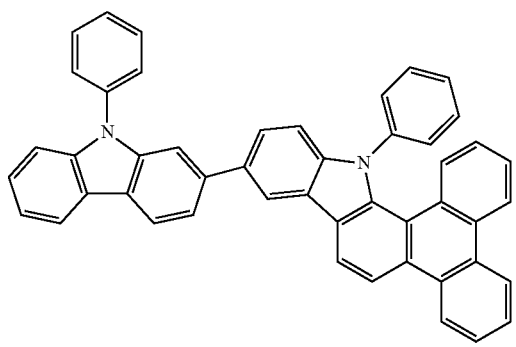

-continued
Compound H83
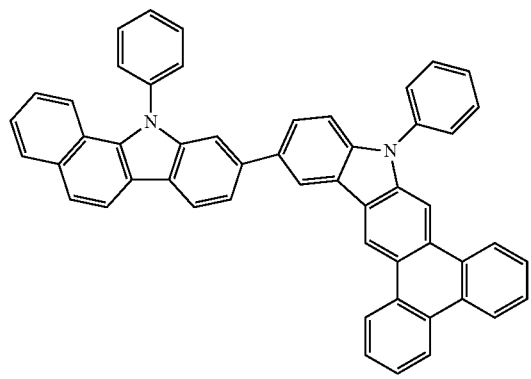
Compound H84
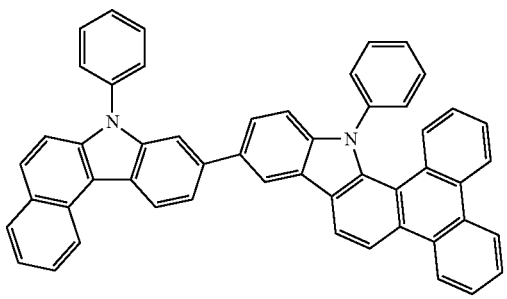
Compound H85
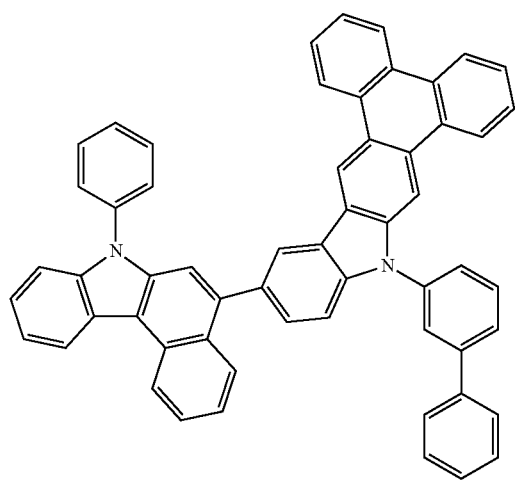
Compound H86
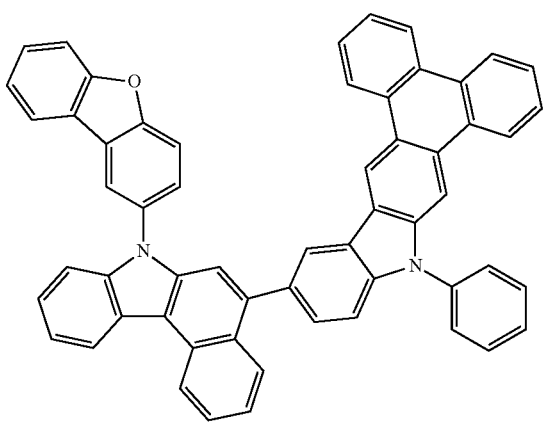
Compound H87
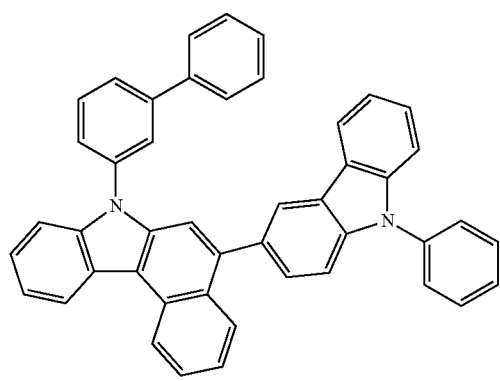
Compound H88
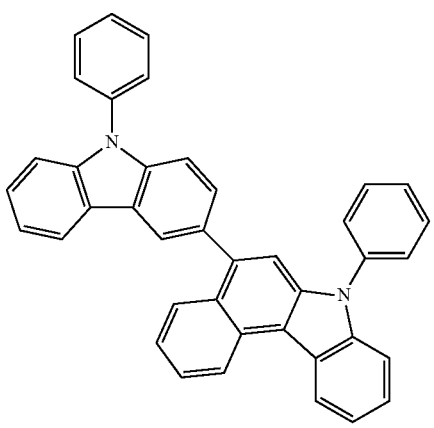

-continued
Compound H89
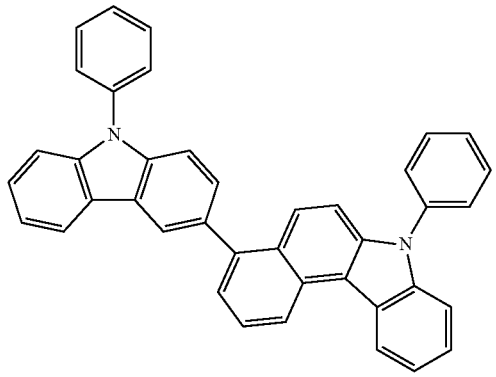
Compound H90
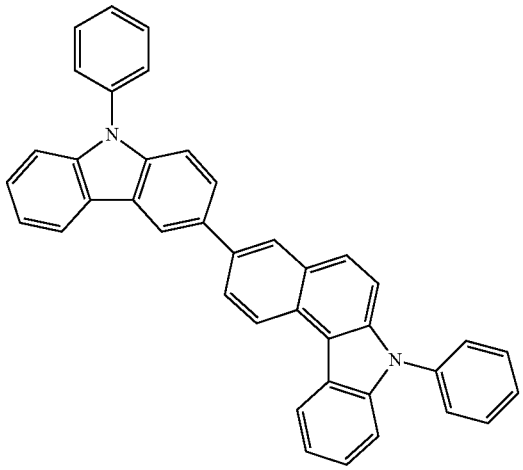
Compound H91
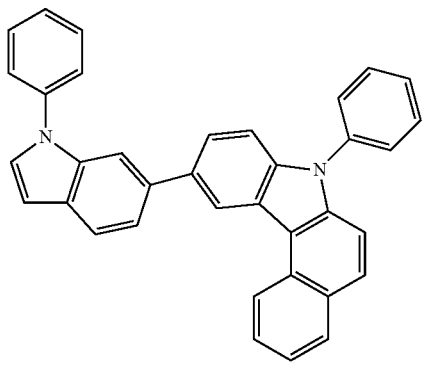
Compound H92
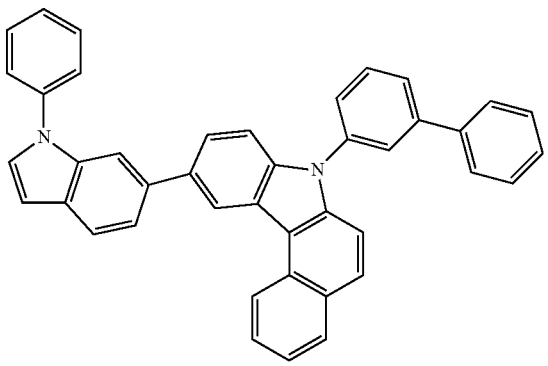
Compound H93
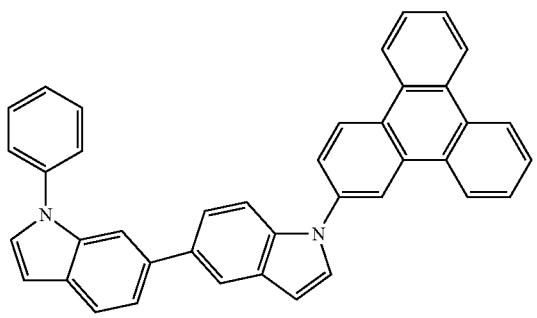
Compound H94
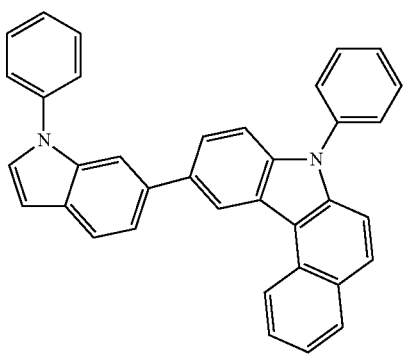
Compound H95
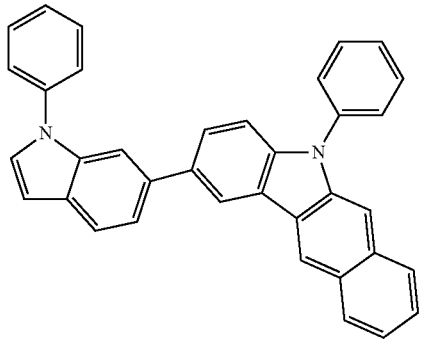
Compound H96
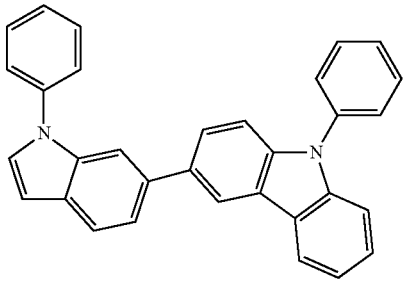

-continued
Compound H97
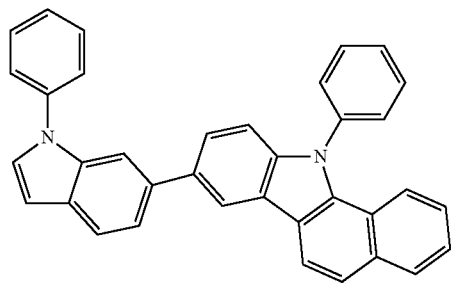
Compound H98
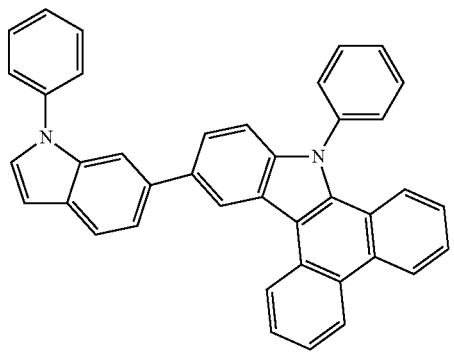
Compound H99
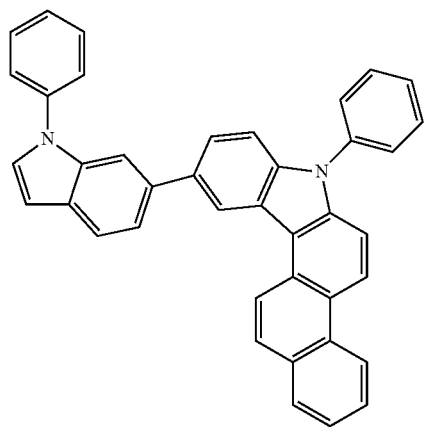
Compound H100
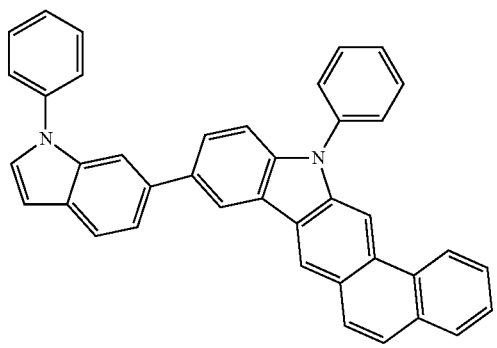
Compound H101
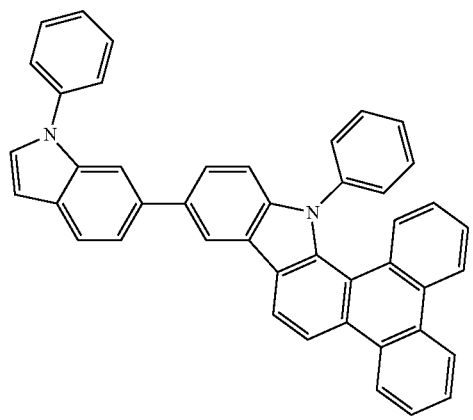
Compound H102
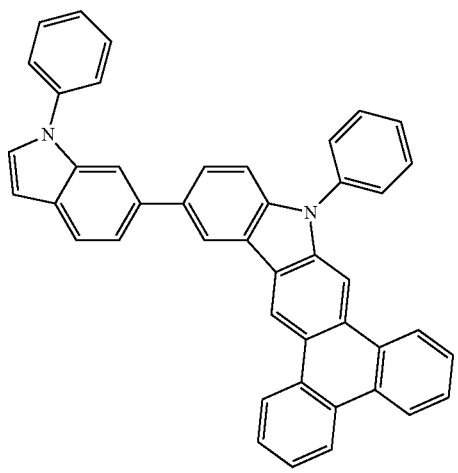

-continued
Compound H103
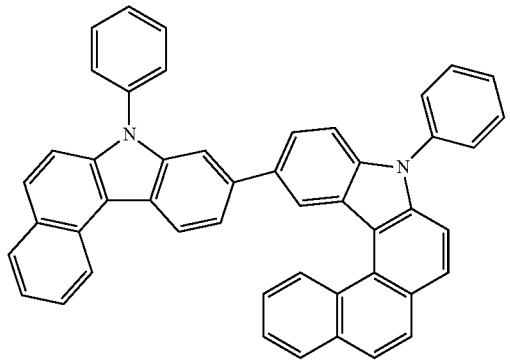
Compound H104
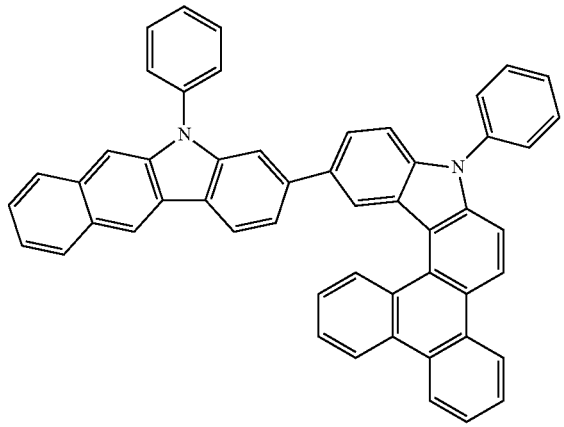
Compound H105
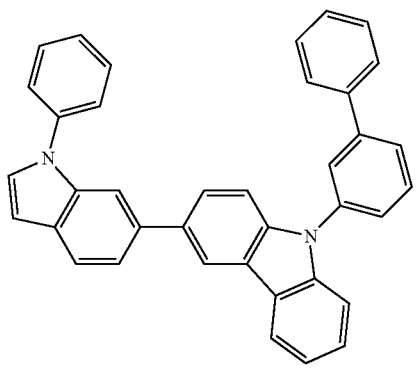
Compound H106
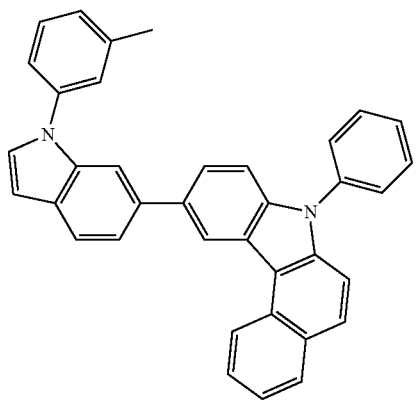
Compound H107
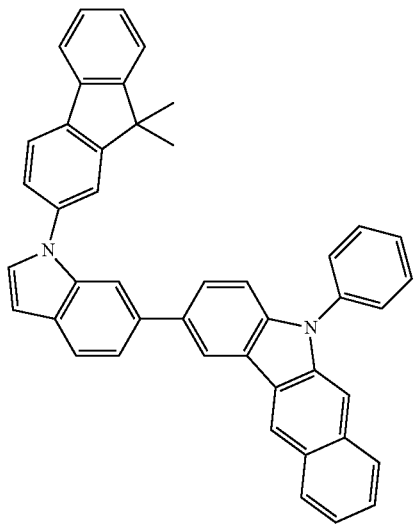
Compound H108
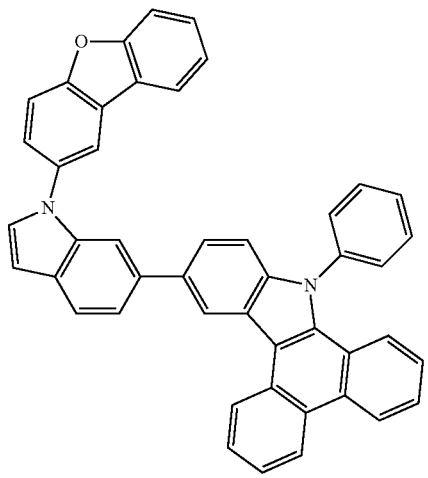

-continued
Compound H109
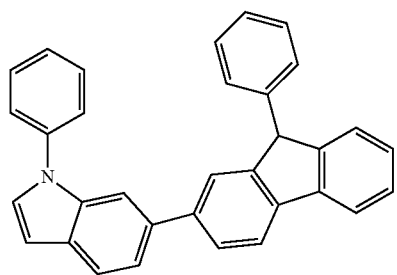
Compound H110
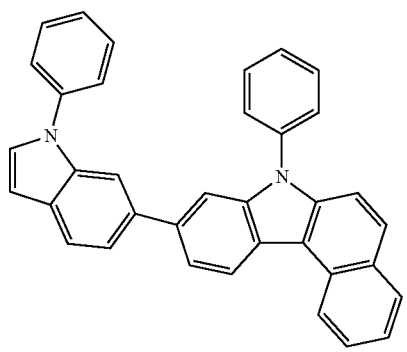
Compound H111
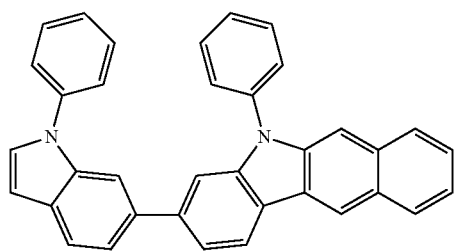
Compound H112
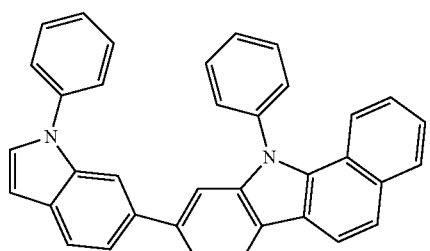
Compound H113
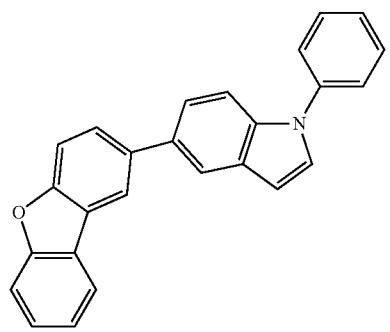
Compound H114
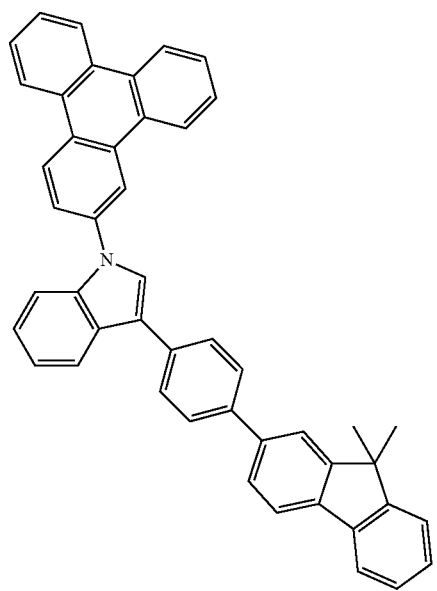

-continued
Compound H115
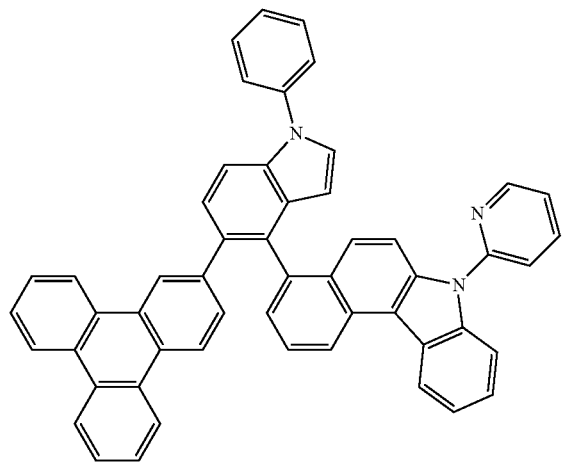
Compound H116
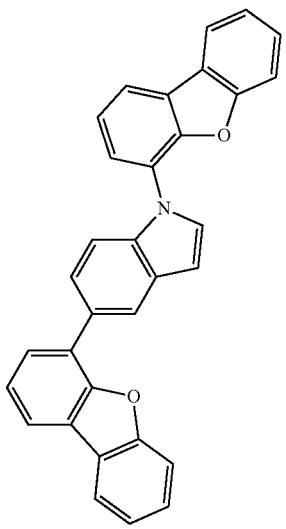
Compound H117
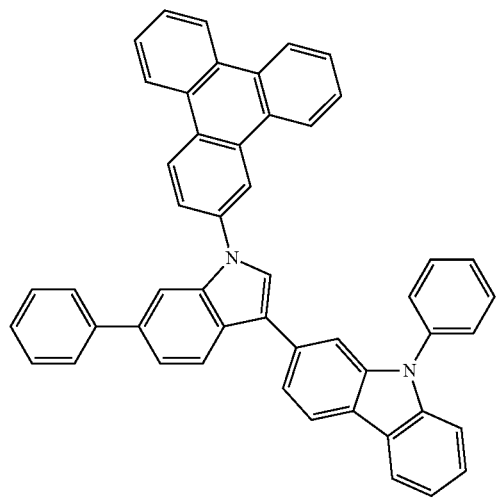
Compound H118
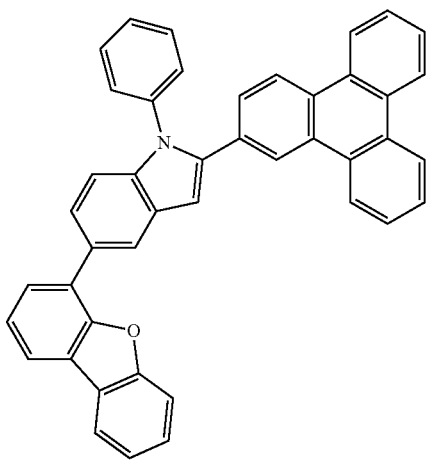
Compound H119
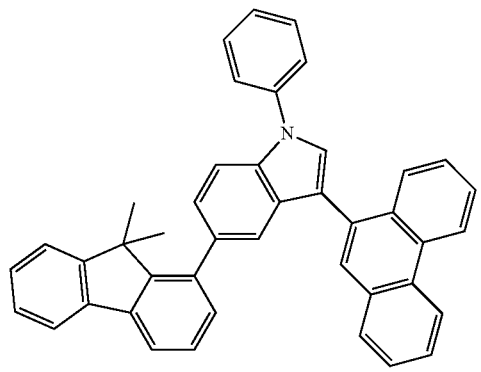
Compound H120
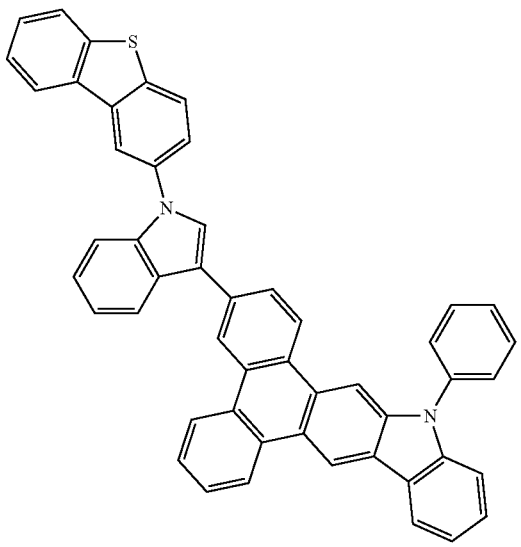

Compound H121
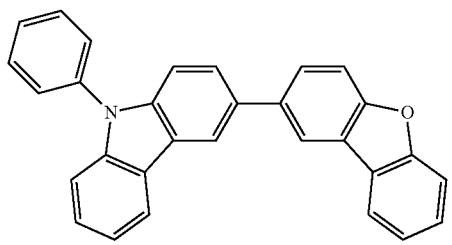
Compound H122
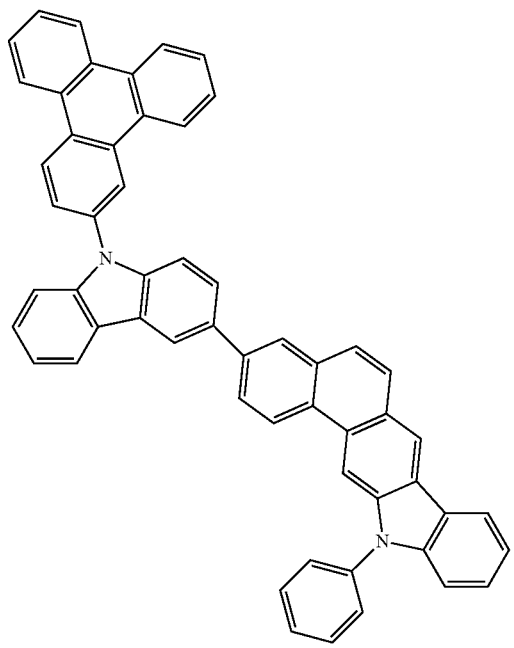
Compound H123
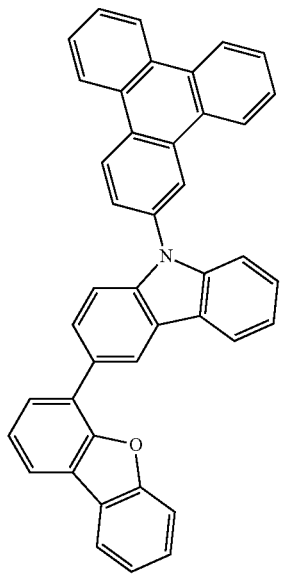
Compound H124
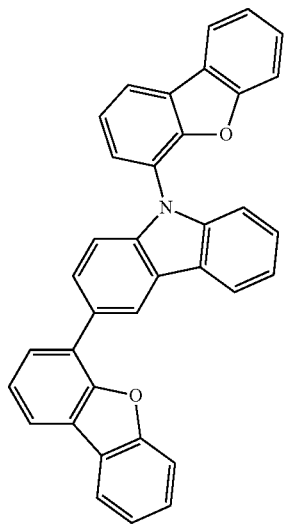

-continued
Compound H125
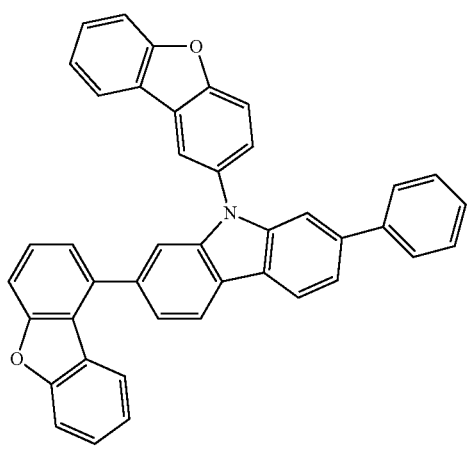
Compound H126
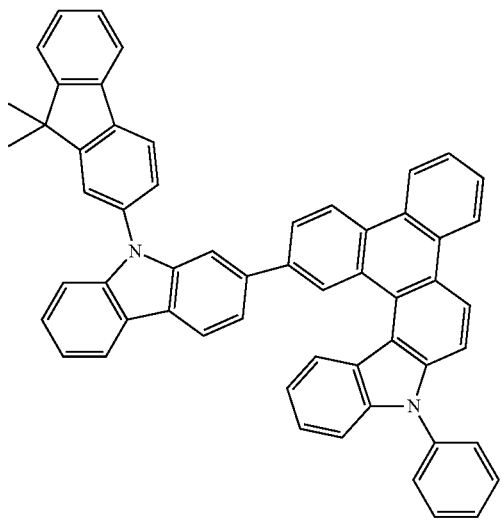
Compound H127
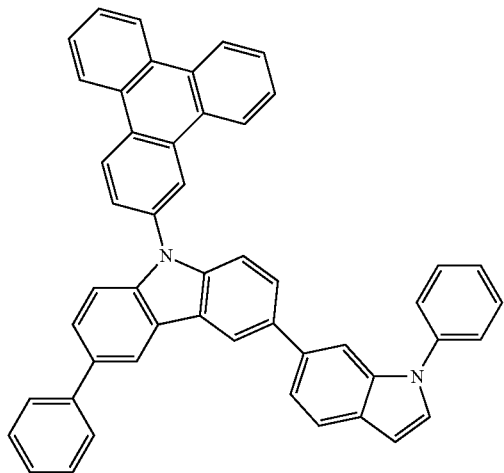
Compound H128
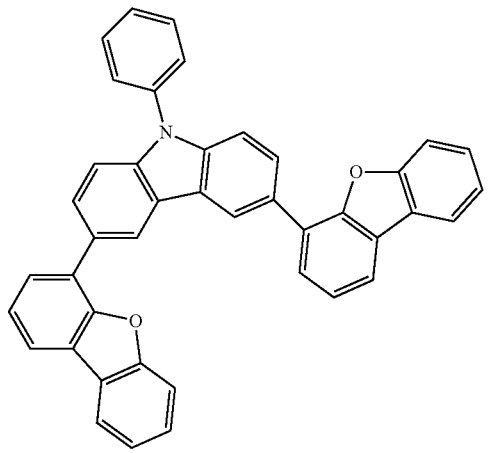

-continued
Compound H129
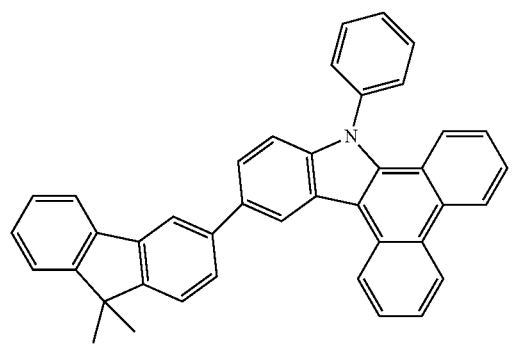
Compound H130
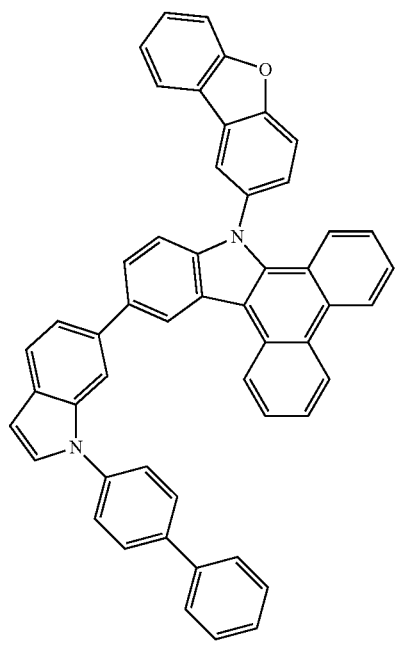
Compound H131
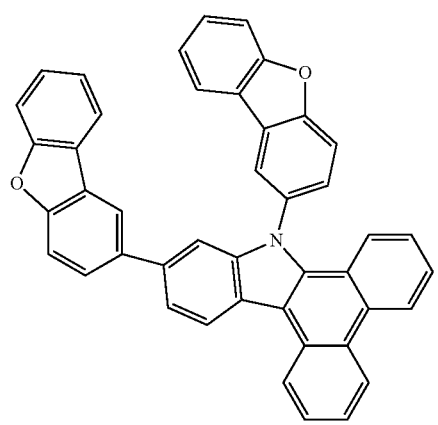
Compound H132
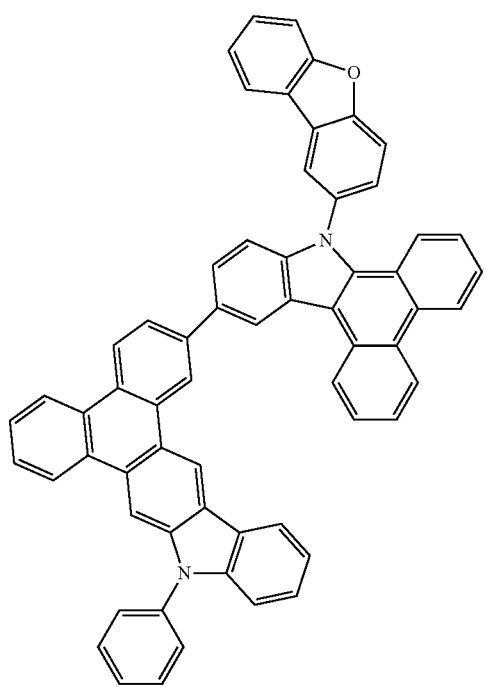

-continued
Compound H133
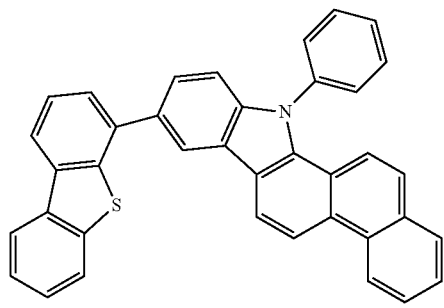
Compound H134
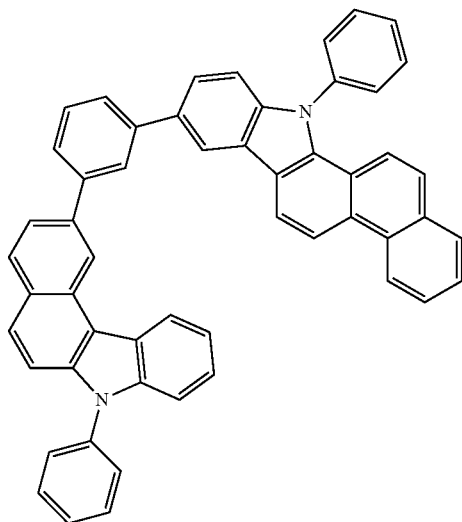
Compound H135
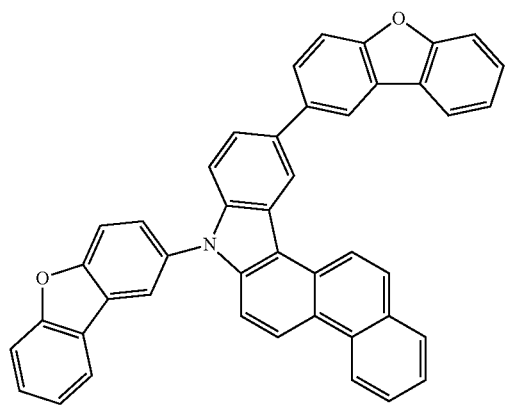
Compound H136
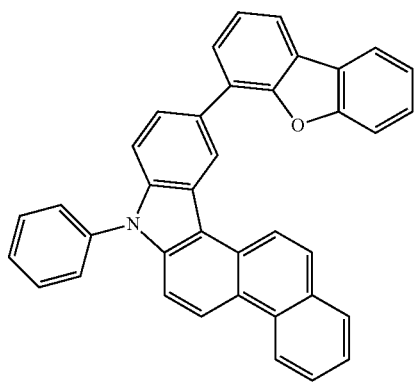
Compound H137
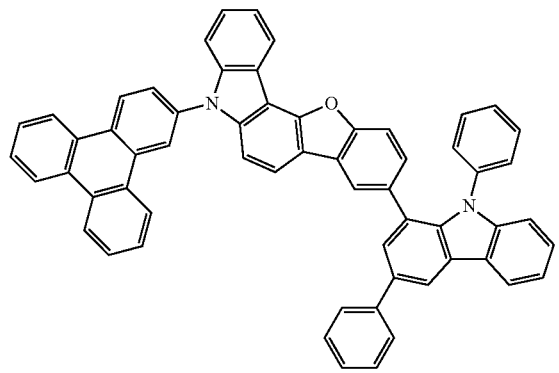
Compound H138
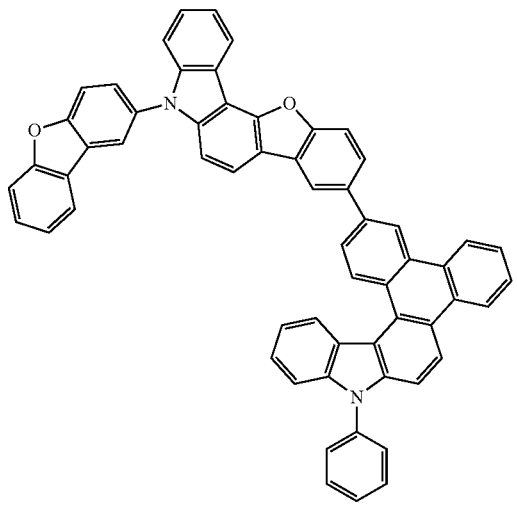

Compound H139
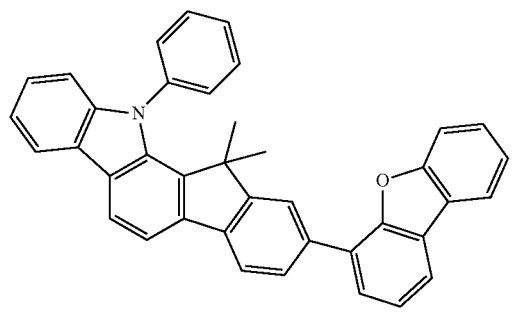
Compound H140
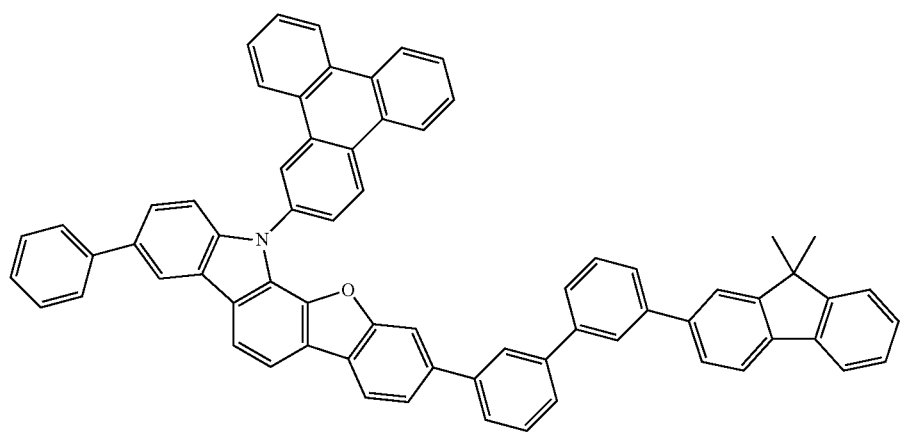
Compound H141
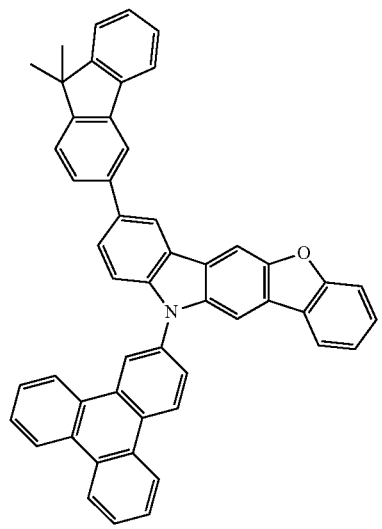
Compound H142
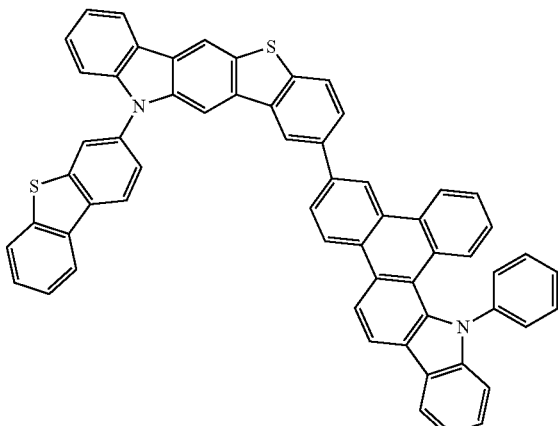
Compound H143
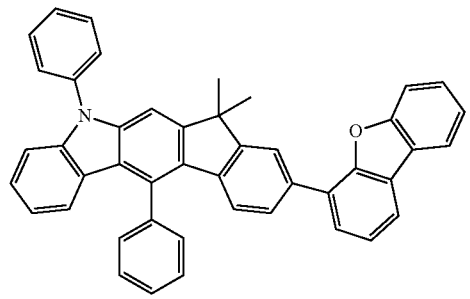
Compound H144
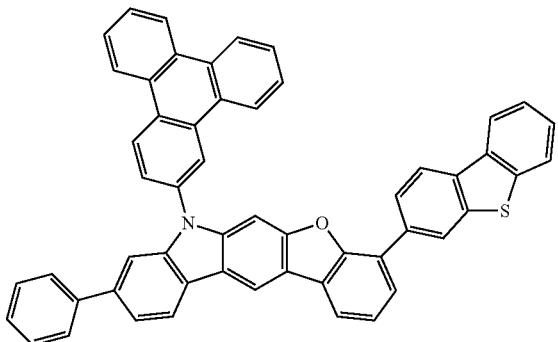

Compound H145

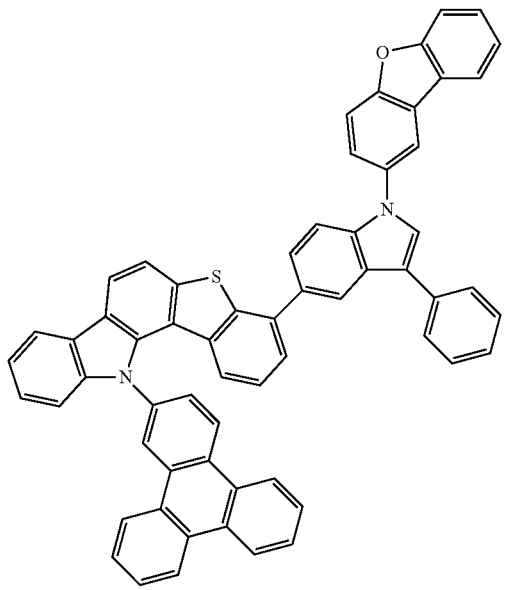

Compound H146

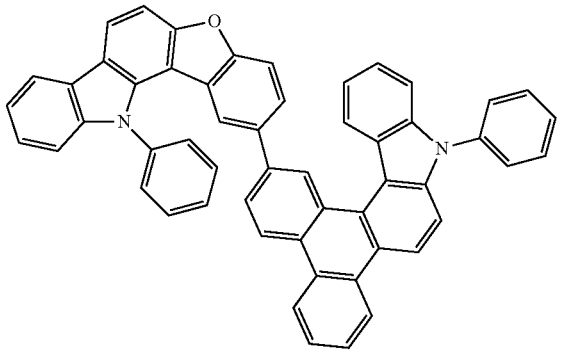

Compound H147

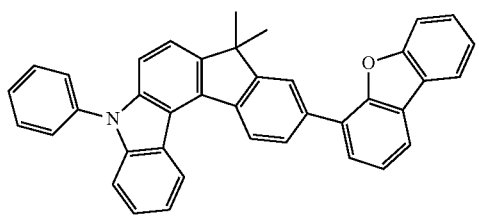

Compound H148

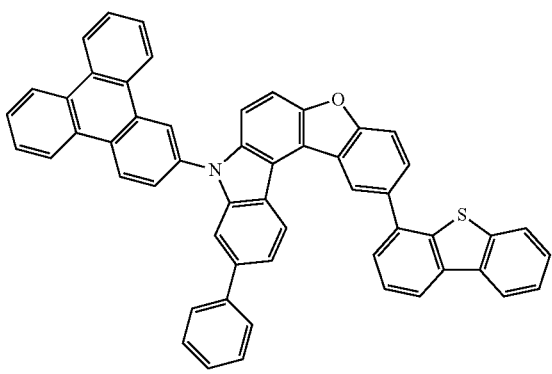

19. An organic light emitting compound represented by Formula 1:

$$HAr_1—(L)_n—HAr_2 \quad (1)$$

wherein L represents a linker and is a single bond or is selected from substituted or unsubstituted $C_1$-$C_{30}$ alkylene groups, substituted or unsubstituted $C_2$-$C_{30}$ alkenylene groups, substituted or unsubstituted $C_2$-$C_{30}$ alkynylene groups, substituted or unsubstituted $C_2$-$C_{30}$ cycloalkylene groups, substituted or unsubstituted $C_2$-$C_{30}$ heterocycloalkylene groups, substituted or unsubstituted $C_6$-$C_{30}$ arylene groups, and substituted or unsubstituted $C_2$-$C_{30}$ heteroarylene groups, n is an integer from 1 to 3, provided that when n is equal to or greater than 2, the plurality of L groups are identical to or different from each other, $HAr_1$, is the following structure 2:

Structure 2

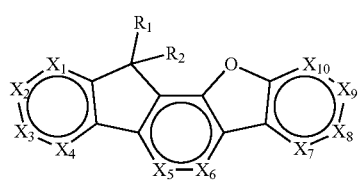

wherein $X_1$ to $X_{10}$ are identical to or different from each other and are each independently $CR_3$ or N, $R_1$ to $R_3$ are identical to or different from each other and are each independently selected from a hydrogen atom, a deuterium atom, substituted or unsubstituted $C_1$-$C_{30}$ alkyl groups, substituted or unsubstituted $C_2$-$C_{30}$ alkenyl groups, substituted or unsubstituted $C_2$-$C_{30}$ alkynyl groups, substituted or unsubstituted $C_3$-$C_{30}$ cycloalkyl groups, substituted or unsubstituted $C_2$-$C_{30}$ heterocycloalkyl groups, substituted or unsubstituted $C_5$-$C_{30}$ cycloalkenyl groups, substituted or unsubstituted $C_1$-$C_{30}$ alkoxy groups, substituted or unsubstituted $C_6$-$C_{30}$ aryloxy groups, substituted or unsubstituted $C_1$-$C_{30}$ alkylthioxy groups, substituted or unsubstituted $C_6$-$C_{30}$ arylthioxy groups, substituted or unsubstituted $C_1$-$C_{30}$ alkylamine groups, substituted or unsubstituted $C_6$-$C_{30}$ arylamine groups, substituted or unsubstituted $C_6$-$C_{50}$ aryl groups, substituted or unsubstituted $C_3$-$C_{50}$ heteroaryl groups containing O, N or S as a heteroatom, substituted or unsubstituted $C_1$-$C_{24}$ alkylsilyl groups, substituted or unsubstituted $C_6$-$C_{24}$ arylsilyl groups, substituted or unsubstituted germanium groups, substituted or unsubstituted boron groups, substituted or unsubstituted aluminum groups, a carbonyl group, a phosphoryl group, an amino group, a thiol group, a cyano group, a hydroxyl group, a nitro group, halogen groups, a selenium group, a tellurium group, an amide group, an ether group, and an ester group, with the proviso that one of $X_1$ to $X_{10}$ is a carbon atom linked to L, and $HAr_2$ is selected from the following structures:

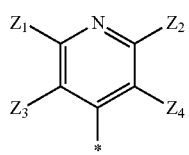

D5

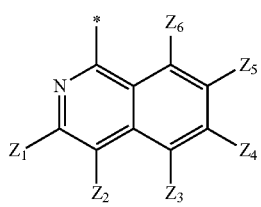

D6

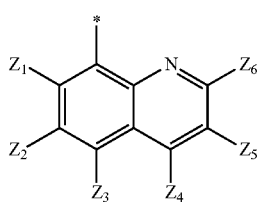

D7

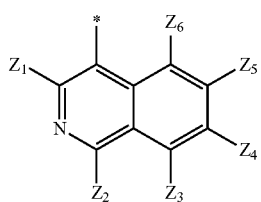

D8

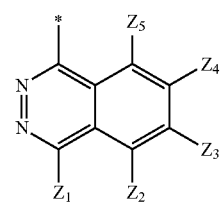

D9

-continued

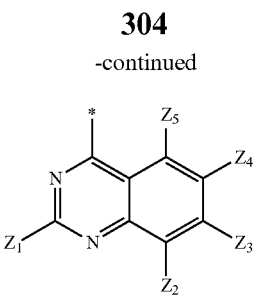

D10

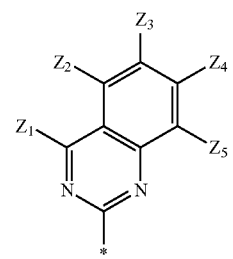

D11

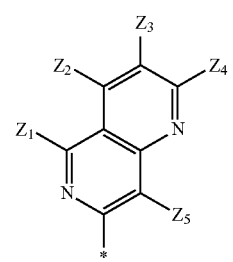

D12

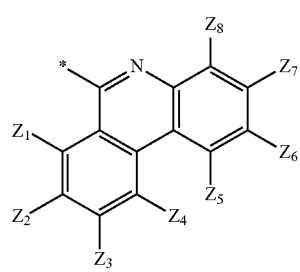

D13

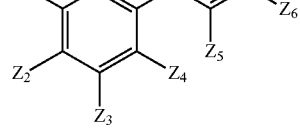

D14

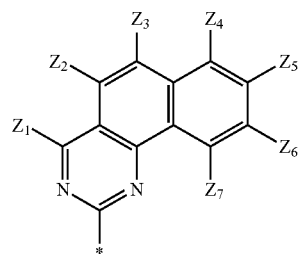

D15

-continued
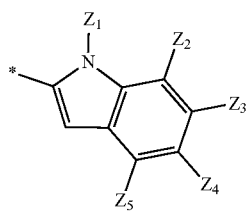D16
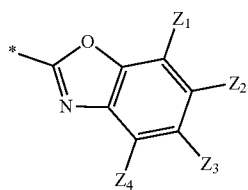D17
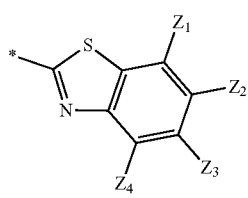D18
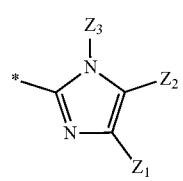D19
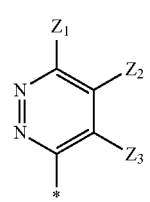D20
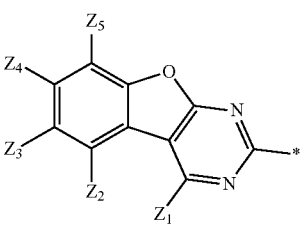D21
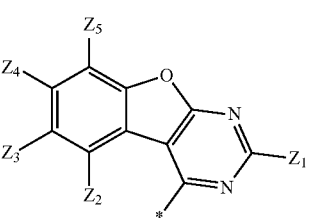D22
-continued
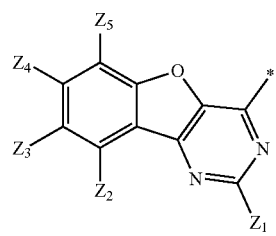D23
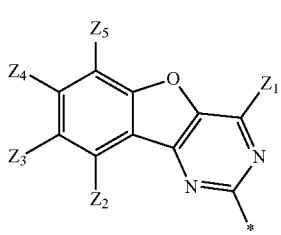D24
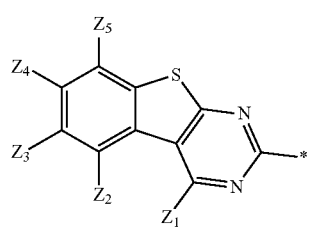D25
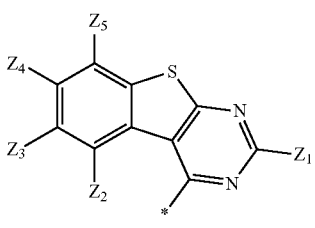D26
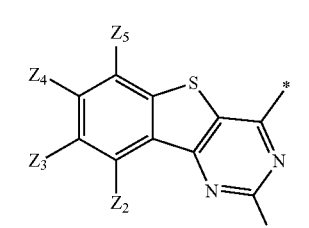D27
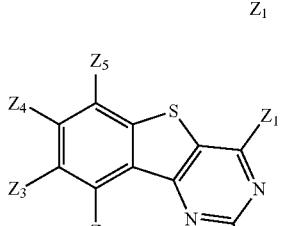D28
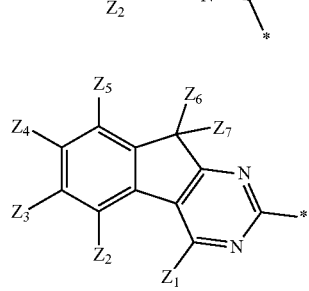D29

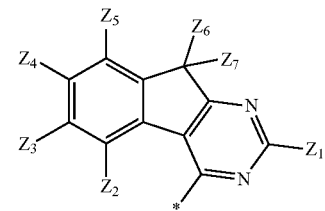
D30

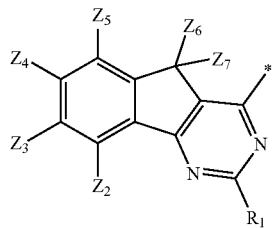
D31

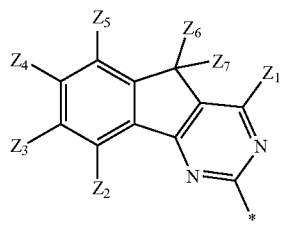
D32

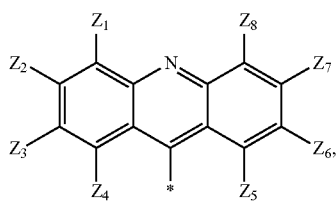
D33 and wherein $Z_1$ to $Z_9$ are identical to or different from each other and have the same meanings as $R_1$ to $R_3$ and the asterisk (*) represents a site at which $HAr_2$ is linked to L.

20. An organic light emitting compound represented by Formula 1:

$$HAr_1-(L)_n-HAr_2 \quad (1)$$

wherein L represents a linker and is a single bond or is selected from substituted or unsubstituted $C_1$-$C_{30}$ alkylene groups, substituted or unsubstituted $C_2$-$C_{30}$ alkenylene groups, substituted or unsubstituted $C_2$-$C_{30}$ alkynylene groups, substituted or unsubstituted $C_2$-$C_{30}$ cycloalkylene groups, substituted or unsubstituted $C_2$-$C_{30}$ heterocycloalkylene groups, substituted or unsubstituted $C_6$-$C_{30}$ arylene groups, and substituted or unsubstituted $C_2$-$C_{30}$ heteroarylene groups, n is an integer from 1 to 3, provided that when n is equal to or greater than 2, the plurality of L groups are identical to or different from each other, $HAr_1$, is selected from a group consisting of the following structures 1 and 4:

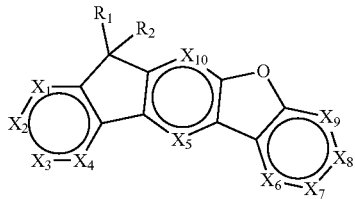
Structure 1

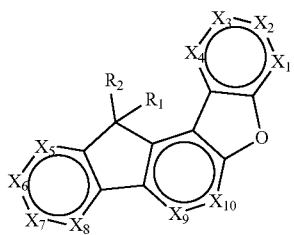
Structure 4 wherein $X_1$ to $X_{10}$ are identical to or different from each other and are each independently $CR_3$ or N, $R_1$ to $R_3$ are identical to or different from each other and are each independently selected from a hydrogen atom, a deuterium atom, substituted or unsubstituted $C_1$-$C_{30}$ alkyl groups, substituted or unsubstituted $C_2$-$C_{30}$ alkenyl groups, substituted or unsubstituted $C_2$-$C_{30}$ alkynyl groups, substituted or unsubstituted $C_2$-$C_{30}$ cycloalkyl groups, substituted or unsubstituted $C_2$-$C_{30}$ heterocycloalkyl groups, substituted or unsubstituted $C_5$-$C_{30}$ cycloalkenyl groups, substituted or unsubstituted $C_1$-$C_{30}$ alkoxy groups, substituted or unsubstituted $C_6$-$C_{30}$ aryloxy groups, substituted or unsubstituted $C_1$-$C_{30}$ alkylthioxy groups, substituted or unsubstituted $C_6$-$C_{30}$ arylthioxy groups, substituted or unsubstituted $C_1$-$C_{30}$ alkylamine groups, substituted or unsubstituted $C_6$-$C_{30}$ arylamine groups, substituted or unsubstituted $C_6$-$C_{50}$ aryl groups, substituted or unsubstituted $C_3$-$C_{50}$ heteroaryl groups containing O, N or S as a heteroatom, substituted or unsubstituted $C_1$-$C_{24}$ alkylsilyl groups, substituted or unsubstituted $C_6$-$C_{24}$ arylsilyl groups, substituted or unsubstituted germanium groups, substituted or unsubstituted boron groups, substituted or unsubstituted aluminum groups, a carbonyl group, a phosphoryl group, an amino group, a thiol group, a cyano group, a hydroxyl group, a nitro group, halogen groups, a selenium group, a tellurium group, an amide group, an ether group, and an ester group, with the proviso that one of $X_1$ to $X_{10}$ is a carbon atom linked to L, and $HAr_2$ is selected from the following structures:

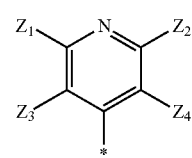
D5

-continued
D6
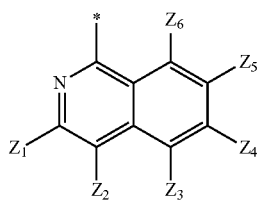
D7
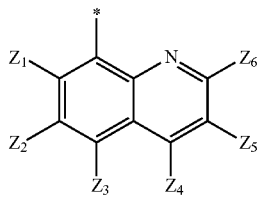
D8
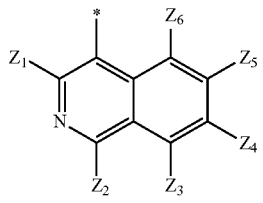
D9
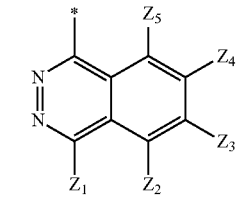
D10
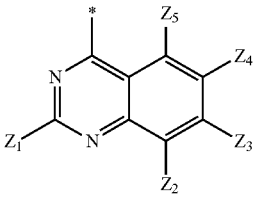
D11
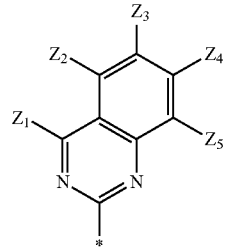
D12
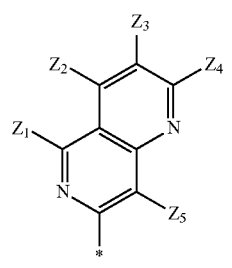
-continued
D13
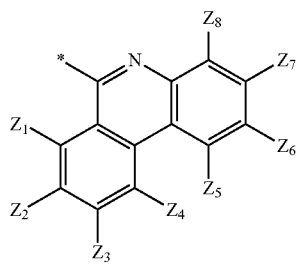
D14
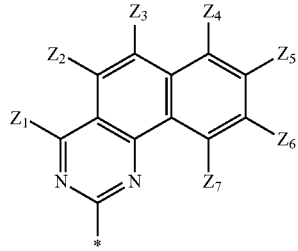
D15
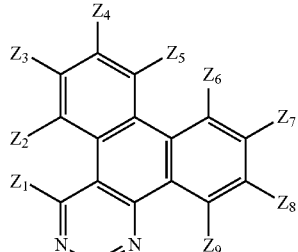
D16
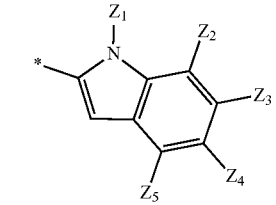
D17
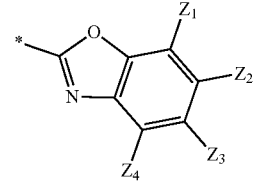
D18
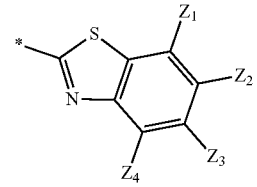
D19
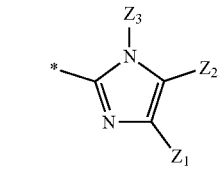

| | |
|---|---|
| 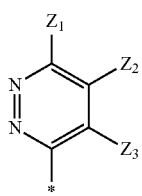 D20 | 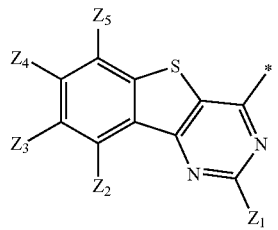 D27 |
| 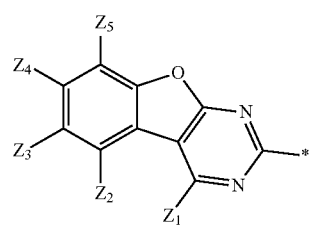 D21 | 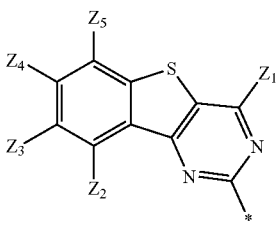 D28 |
| 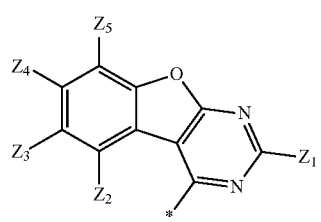 D22 | 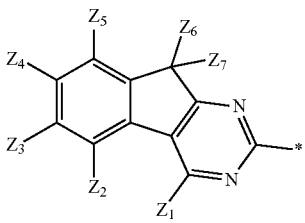 D29 |
| 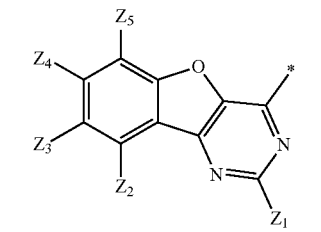 D23 | 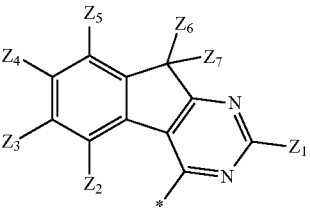 D30 |
| 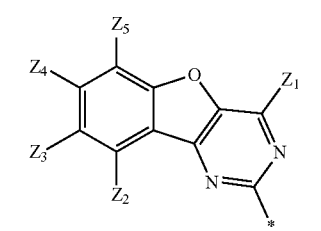 D24 | 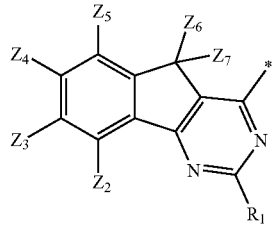 D31 |
| 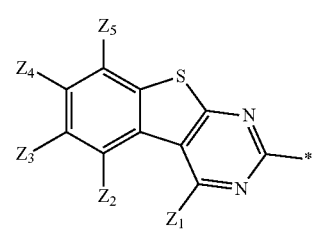 D25 | 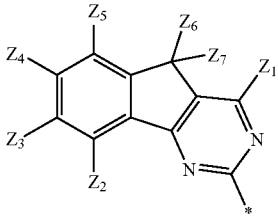 D32 |
| 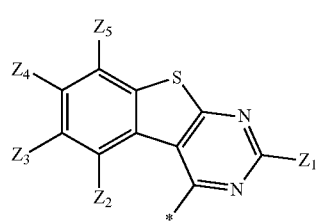 D26 | 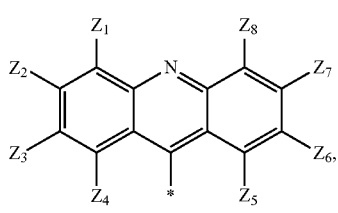 D33 | and
wherein $Z_1$ to $Z_9$ are identical to or different from each other and have the same meanings as $R_1$ to $R_3$ and the asterisk (*) represents a site at which $HAr_2$ is linked to L.

* * * * *